United States Patent
Yoshizaki et al.

(10) Patent No.: US 11,723,272 B2
(45) Date of Patent: Aug. 8, 2023

(54) ORGANIC ELECTROLUMINESCENCE ELEMENT AND ELECTRONIC DEVICE

(71) Applicant: IDEMITSU KOSAN CO., LTD., Tokyo (JP)

(72) Inventors: Kei Yoshizaki, Sodegaura (JP); Ryota Takahashi, Sodegaura (JP); Toshinari Ogiwara, Sodegaura (JP); Yuichiro Kawamura, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 597 days.

(21) Appl. No.: 16/640,412

(22) PCT Filed: Aug. 17, 2018

(86) PCT No.: PCT/JP2018/030572
§ 371 (c)(1),
(2) Date: Feb. 20, 2020

(87) PCT Pub. No.: WO2019/039414
PCT Pub. Date: Feb. 28, 2019

(65) Prior Publication Data
US 2020/0365812 A1 Nov. 19, 2020

(30) Foreign Application Priority Data
Aug. 21, 2017 (JP) .................... 2017-158937

(51) Int. Cl.
*H10K 85/60* (2023.01)
*H10K 50/11* (2023.01)
(Continued)

(52) U.S. Cl.
CPC ......... *H10K 85/6574* (2023.02); *C09K 11/06* (2013.01); *H10K 50/11* (2023.02);
(Continued)

(58) Field of Classification Search
CPC ............ H01L 51/0073; H01L 51/0072; H01L 51/5016; H01L 21/5024; H01L 51/5072;
(Continued)

(56) References Cited

U.S. PATENT DOCUMENTS

2016/0149139 A1* 5/2016 Xia et al. ............ H01L 51/0054
257/40
2016/0268516 A1* 9/2016 Tanaka et al. ...... H01L 51/0072
257/40
(Continued)

FOREIGN PATENT DOCUMENTS

CN 105556696 A 5/2016
CN 106046006 A 10/2016
(Continued)

OTHER PUBLICATIONS

International Preliminary Report on Patentability dated Feb. 25, 2020 for corresponding International Patent Application No. PCT/JP2018/030572.
(Continued)

*Primary Examiner* — Thinh T Nguyen
(74) *Attorney, Agent, or Firm* — Foley & Lardner LLP

(57) ABSTRACT

An organic electroluminescence device includes: an anode; an emitting layer; and a cathode. The emitting layer contains a first compound and a second compound, the first compound being a delayed fluorescent compound, the second compound being a compound represented by a formula (2).
(Continued)

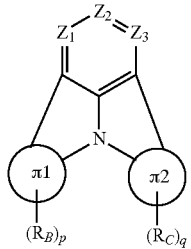

21 Claims, 5 Drawing Sheets

(51) Int. Cl.
H10K 50/12 (2023.01)
C09K 11/06 (2006.01)
H10K 101/10 (2023.01)
H10K 50/15 (2023.01)
H10K 50/16 (2023.01)
H10K 50/17 (2023.01)

(52) U.S. Cl.
CPC ........... *H10K 50/12* (2023.02); *H10K 85/636* (2023.02); *H10K 85/6572* (2023.02); *H10K 50/15* (2023.02); *H10K 50/16* (2023.02); *H10K 50/171* (2023.02); *H10K 2101/10* (2023.02)

(58) Field of Classification Search
CPC ............... H10K 85/6574; H10K 50/12; H10K 2101/10; H10K 85/6572; H10K 50/171; H10K 50/15
USPC ....................................... 257/40; 438/82, 99
See application file for complete search history.

(56) References Cited

U.S. PATENT DOCUMENTS

2016/0293853 A1* 10/2016 Zeng et al. ......... H01L 51/0072
 257/40
2016/0293854 A1 10/2016 Zeng et al.
2016/0293855 A1 10/2016 Zeng et al.
2016/0293856 A1 10/2016 Ji et al.
2016/0301014 A1 10/2016 Kawamura et al.

FOREIGN PATENT DOCUMENTS

| JP | 2017-099276 A | * | 2/2015 | ......... H01L 51/0072 |
| JP | 2017-092276 A | | 5/2017 | |
| WO | WO-2012/108878 A1 | | 8/2012 | |
| WO | WO-2012/153780 A1 | | 11/2012 | |
| WO | WO-2013/038650 A1 | | 3/2013 | |
| WO | WO-2015/022987 A1 | | 2/2015 | |
| WO | WO-2017/138755 A1 | | 8/2017 | |

OTHER PUBLICATIONS

Chinese Office Action issued in connection with CN Appl. Ser. No. 201880053889.6 dated Oct. 8, 2022 (without English translation).
Adachi, "Yuki Hando-tai no Debaisu Bussei (Device Physics of Organic Semiconductors)", Kodansha, published on Apr. 1, 2012, §10.9, pp. 261-268.
Nakanotani et al., "High-efficiency organic light-emitting diodes with fluorescent emitters", Nature Communications, 2014, pp. 1-7, vol. 5, No. 4016, 2014 Macmillan Publishers Limited.
Uoyama et al., "Highly efficient organic light-emitting diodes from delayed fluorescence", Nature, Dec. 2012, pp. 234-240, vol. 492, 2012 Macmillan Publishers Limited.
International Searching Authority, "International Search Report," issued in connection with International Patent Application No. PCT/JP2018/030572, dated Nov. 20, 2018.
International Searching Authority, "Written Opinion" issued in connection with International patent Application No. PCT/JP2018/030572, dated Nov. 20, 2018.

* cited by examiner

ORGANIC ELECTROLUMINESCENCE ELEMENT AND ELECTRONIC DEVICE

CROSS-REFERENCE TO RELATED APPLICATIONS

The present application claims priority under 37 U.S.C. § 371 to International Patent Application No. PCT/JP2018/030572, filed Aug. 17, 2018, which claims priority to and the benefit of Japanese Patent Application No. 2017-158937, filed on Aug. 21, 2017. The contents of these applications are hereby incorporated by reference in their entireties.

TECHNICAL FIELD

The present invention relates to an organic electroluminescence device and an electronic device.

BACKGROUND ART

When a voltage is applied to an organic electroluminescence device (hereinafter, occasionally referred to as "organic EL device"), holes are injected from an anode and electrons are injected from a cathode into an emitting layer. The injected electrons and holes are recombined in the emitting layer to form excitons. Specifically, according to the electron spin statistics theory, singlet excitons and triplet excitons are generated at a ratio of 25%:75%.

A fluorescent organic EL device with emission caused by singlet excitons, which has been applied to a full-color display for a mobile phone, TV and the like, is inferred to exhibit an internal quantum efficiency of 25% at a maximum. It is thus desired for a fluorescent organic EL device to use triplet excitons in addition to singlet excitons to cause a further efficient emission from the organic EL device.

In view of the above, a highly efficient fluorescent organic EL device using delayed fluorescence has been studied.

For instance, a TADF (Thermally Activated Delayed Fluorescence) mechanism has been studied. The TADF mechanism uses a phenomenon where inverse intersystem crossing from triplet excitons to singlet excitons thermally occurs when a material having a small energy difference ($\Delta ST$) between singlet energy level and triplet energy level is used. The details of the thermally activated delayed fluorescence are described in, for instance, ADACHI, Chihaya, ed. (Apr. 1, 2012), "Yuki Hando-tai no Debaisu Bussei (Device Physics of Organic Semiconductors)", Kodansha, pp. 261-268. An organic EL device using such a TADF mechanism is disclosed in, for instance, Non-Patent Literature 1.

The organic EL device disclosed in Non-Patent Literature 1 includes an emitting layer containing a TADF compound as an assist dopant, a perylene derivative (TBPe; 2,5,8,11-tetra-tert-butylperylene) as an emitting material, and DPEPO (bis-(2-(diphenylphosphino)phenyl)ether oxide) as a host material. The emitting layer emits blue light.

CITATION LIST

Non-Patent Literature

Non-Patent Literature 1: Hajime Nakanotani et al, "High-efficiency organic light-emitting diodes with fluorescent emitters", NATURE COMMUNICATIONS, 5, 4016, 2014

SUMMARY OF THE INVENTION

Problems to be Solved by the Invention

The organic electroluminescence device disclosed in Non-Patent Literature 1, which uses a TADF compound as a host material and a perylene derivative (compound TBPe) as an emitting material, surely emits blue light. However, it is desired that a full width at half maximum should be further narrowed.

An object of the invention is to provide an organic electroluminescence device capable of narrowing a full width at half maximum and an electronic device including the organic electroluminescence device.

Means for Solving the Problems

An organic electroluminescence device according to an aspect of the invention includes: an anode; an emitting layer; and a cathode, in which the emitting layer contains a first compound and a second compound, the first compound is a delayed fluorescent compound, and the second compound is represented by a formula (2).

[Formula 1]

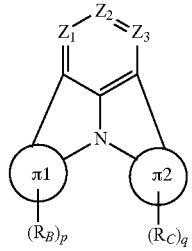

(2)

In the formula (2):
$Z_1$ is $CR_1$ or a nitrogen atom;
$Z_2$ is $CR_2$ or a nitrogen atom;
$Z_3$ is $CR_3$ or a nitrogen atom;
π1 and π2 are each independently a cyclic structure selected from the group consisting of a substituted or unsubstituted aromatic hydrocarbon ring having 6 to 50 ring carbon atoms, and a substituted or unsubstituted aromatic heterocyclic ring having 5 to 50 ring atoms;
$R_1$ to $R_3$, $R_B$ and $R_C$ each independently represent a hydrogen atom or a substituent, $R_1$ to $R_3$, $R_B$, and $R_C$ as the substituent being each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms;

$R_1$ and $R_2$ are mutually bonded to form a cyclic structure or are not mutually bonded to form no cyclic structure;

$R_2$ and $R_3$ are mutually bonded to form a cyclic structure or are not mutually bonded to form no cyclic structure;

adjacent $R_B$ are mutually bonded to form a cyclic structure or are not mutually bonded to form no cyclic structure;

adjacent $R_C$ are mutually bonded to form a cyclic structure or are not mutually bonded to form no cyclic structure;

$R_{101}$ to $R_{105}$ are each independently a hydrogen atom or a substituent;

$R_{101}$ to $R_{105}$ serving as the substituents are each independently a group selected from the group consisting of a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, and a substituted or unsubstituted heteroaryl group having 5 to 50 ring atoms; and p and q are each independently an integer in a range from 1 to 4.

According to another aspect of the invention, an electronic device including the organic electroluminescence device according to the above aspect of the invention is provided.

According to the above aspects of the invention, an organic electroluminescence device capable of narrowing a full width at half maximum and an electronic device including the organic electroluminescence device can be provided.

DESCRIPTION OF EMBODIMENT(S)

Organic EL Device
Device Arrangement of Organic EL Device

Arrangement(s) of an organic EL device according to an exemplary embodiment will be described below.

The organic EL device in the exemplary embodiment includes a pair of electrodes and an organic layer between the pair of electrodes. The organic layer includes at least one layer formed of an organic compound. Alternatively, the organic layer includes a plurality of layers each formed of an organic compound. The organic layer may further include an inorganic compound. In the organic EL device of the exemplary embodiment, at least one of the organic layers is an emitting layer. Specifically, for instance, the organic layer may consist of a single emitting layer, or may include layers usable in a typical organic EL device. The layer(s) usable for the organic EL device is not particularly limited but is at least one layer selected from the group consisting of a hole injecting layer, a hole transporting layer, an electron injecting layer, an electron transporting layer, and a blocking layer.

Typical device arrangements of an organic EL device include the following arrangements (a) to (f) and the like:

(a) anode/emitting layer/cathode;

(b) anode/hole injecting•transporting layer/emitting layer/cathode;

(c) anode/emitting layer/electron injecting•transporting layer/cathode;

(d) anode/hole injecting•transporting layer/emitting layer/electron injecting•transporting layer/cathode;

(e) anode/hole injecting•transporting layer/emitting layer/blocking layer/electron injecting•transporting layer/cathode; and (f) anode/hole injecting•transporting layer/blocking layer/emitting layer/blocking layer/electron injecting•transporting layer/cathode.

The arrangement (d) is preferably used among the above arrangements. However, the arrangement of the invention is not limited to the above arrangements. It should be noted that the above-described "emitting layer" is an organic layer having an emission function. The above-described "hole injecting•transporting layer" means "at least one of a hole injecting layer and a hole transporting layer." The above-described "electron injecting•transporting layer" means at least one of an electron injecting layer and an electron transporting layer." When the organic EL device includes the hole injecting layer and the hole transporting layer, the hole injecting layer is preferably provided between the hole transporting layer and the anode. When the organic EL device includes the electron injecting layer and the electron transporting layer, the electron injecting layer is preferably provided between the electron transporting layer and the cathode. The hole injecting layer, the hole transporting layer, the electron transporting layer and the electron injecting layer may each consist of a single layer or a plurality of layers.

Figure 1:
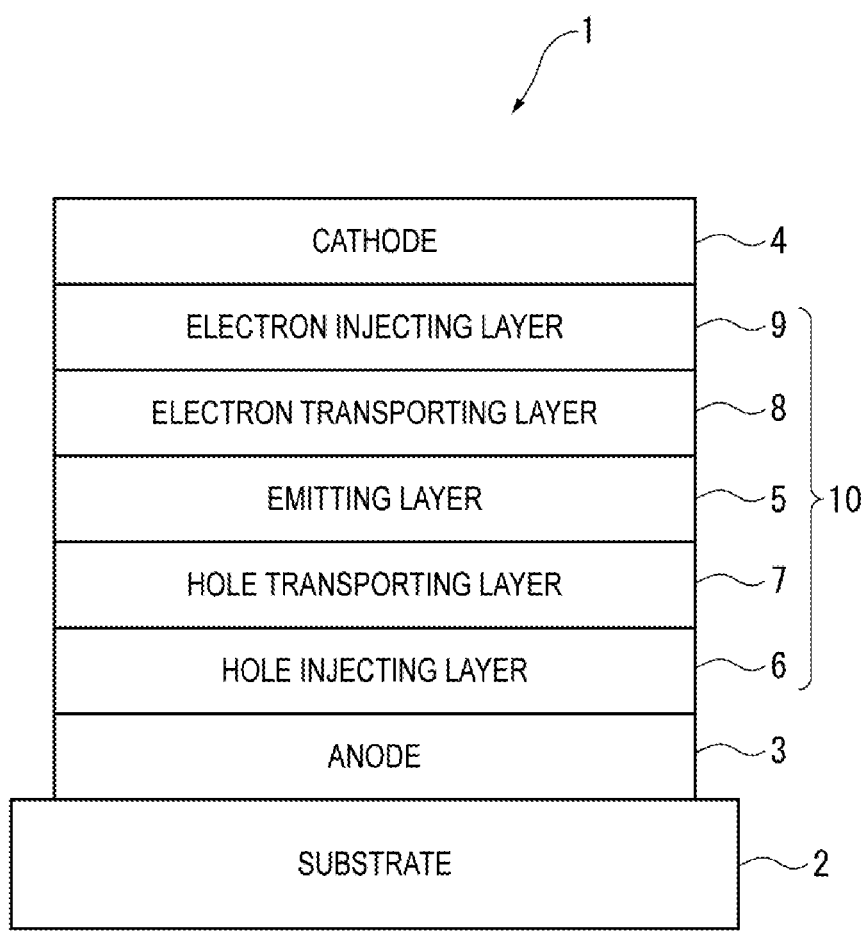
FIG. 1 schematically shows an exemplary arrangement of an organic electroluminescence device according to a first exemplary embodiment of the invention.

FIG. 1 schematically shows an arrangement of the organic EL device of the exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, an emitting layer 5, an electron transporting layer 8, and an electron injecting layer 9. The organic layer 10 includes the hole injecting layer 6, the hole transporting layer 7, the emitting layer 5, the electron transporting layer 8, and the electron injecting layer 9, which are sequentially laminated on the anode 3.

Emitting Layer

The emitting layer 5 of the organic EL device 1 contains a first compound and a second compound. The emitting layer 5 may contain a metal complex. It is also preferable that the emitting layer 5 contains no phosphorescent heavy metal complex. Examples of the heavy metal complex include iridium complex, osmium complex, and platinum complex. The emitting layer 5 may also preferably contain no metal complex.

The first compound is also preferably a host material (occasionally referred to as a matrix material). The second compound is also preferably a dopant material (occasionally referred to as a guest material, emitter, or luminescent material).

First Compound

The first compound is a delayed fluorescent compound. It is preferable that the first compound is not a phosphorescent metal complex. Further, the first compound is preferably not a metal complex.

In the organic EL device of the first exemplary embodiment, the first compound is also preferably a compound represented by a formula (1) below.

[Formula 2]

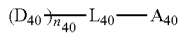
(1)

In the formula (1): $D_{40}$ is a group represented by a formula (1a) below;

$n_{40}$ is an integer in a range from 1 to 5;

a plurality of $D_{40}$ are mutually the same or different;

$L_{40}$ is a single bond or a linking group, $L_{40}$ as the linking group being selected from the group consisting of a substituted or unsubstituted aromatic hydrocarbon group having 6 to 30 ring carbon atoms, and a substituted or unsubstituted aromatic heterocyclic group having 5 to 30 ring atoms; and $A_{40}$ is a cyano group or a group represented by a formula (1b) below.

[Formula 3]

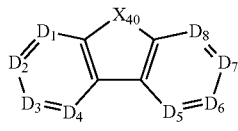
(1a)

[Formula 4]

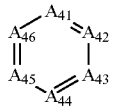
(1b)

In the formula (1a): $D_1$ to $D_8$ each independently represent a carbon atom bonded with $L_{40}$, or a carbon atom bonded with $R_{40x}$;

$R_{40x}$ is a hydrogen atom or a substituent;

a plurality of $R_{40x}$ are mutually the same or different;

$X_{40}$ represents an oxygen atom, a sulfur atom, a nitrogen atom bonded with $R_{41x}$, or a nitrogen atom bonded with $L_{40}$, and $R_{41x}$ is a hydrogen atom or a substituent, with a proviso that one of $D_1$ to $D_8$ is a carbon atom bonded with $L_{40}$, or $X_{40}$ is a nitrogen atom bonded with $L_{40}$.

In the formula (1b): $A_{41}$ to $A_{46}$ each independently represent a nitrogen atom, a carbon atom bonded with $L_{40}$, or a carbon atom bonded with $R_{42x}$;

$R_{42x}$ is a hydrogen atom or a substituent; and a plurality of $R_{42x}$ are mutually the same or different, with a proviso that one of $A_{41}$ to $A_{46}$ is a carbon atom bonded with $L_{40}$, and at least one of the rest of $A_{41}$ to $A_{46}$ is a nitrogen atom or a carbon atom bonded with a cyano group.

$R_{40x}$, $R_{41x}$, and $R_{42x}$ as the substituents are each independently selected from the group consisting of a fluorine atom, a cyano group, a substituted or unsubstituted alkyl group having 1 to 30 carbon atoms, a substituted or unsubstituted alkoxy group having 1 to 30 carbon atoms, a substituted or unsubstituted haloalkyl group having 1 to 30 carbon atoms, a substituted or unsubstituted haloalkoxy group having 1 to 30 carbon atoms, a substituted or unsubstituted alkylsilyl group having 1 to 10 carbon atoms, a substituted or unsubstituted arylsilyl group having 6 to 30 carbon atoms, a substituted or unsubstituted aryl group having 6 to 30 ring carbon atoms, and a substituted or unsubstituted heteroaryl group having 5 to 30 ring atoms.

In the formula (1a), when one of $D_1$ to $D_8$ is a carbon atom bonded with $L_{40}$, $X_{40}$ is an oxygen atom, a sulfur atom, or a nitrogen atom bonded with $R_{41x}$.

In the formula (1a), when $X_{40}$ is a nitrogen atom bonded with $L_{40}$, $D_1$ to $D_8$ are carbon atoms bonded with $R_{40x}$, $R_{40x}$ is a hydrogen atom or a substituent, a plurality of $R_{40x}$ being mutually the same or different.

In the first exemplary embodiment, the first compound is also preferably a compound represented by a formula (1A) below.

[Formula 5]

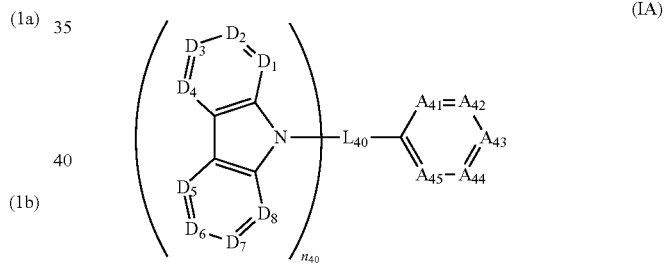
(1A)

In the formula (1A), $D_1$ to $D_8$ each independently represent a carbon atom bonded with $R_{40x}$, $R_{40x}$ is a hydrogen atom or a substituent;

$n_{40}$ is an integer in a range from 1 to 5;

a plurality of $R_{40x}$ are mutually the same or different;

$A_{41}$ to $A_{45}$ are each independently a nitrogen atom, or a carbon atom bonded with $R_{42x}$;

$R_{42x}$ is a hydrogen atom or a substituent;

a plurality of $R_{42x}$ are mutually the same or different;

one of $A_{41}$ to $A_{45}$ is a nitrogen atom or a carbon atom bonded with a cyano group;

$R_{40x}$ and $R_{42x}$ as the substituents each independently represent the same as described above; and $L_{40}$ is a single bond or a linking group, $L_{40}$ as the linking group representing the same as described above.

In the first exemplary embodiment, the first compound is also preferably a compound represented by a formula (1B) below.

[Formula 6]

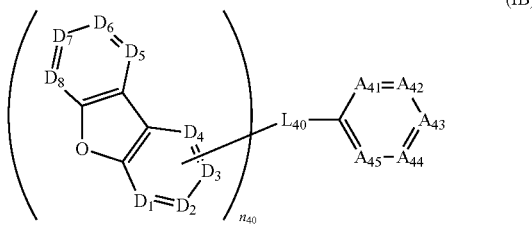

[Formula 7]

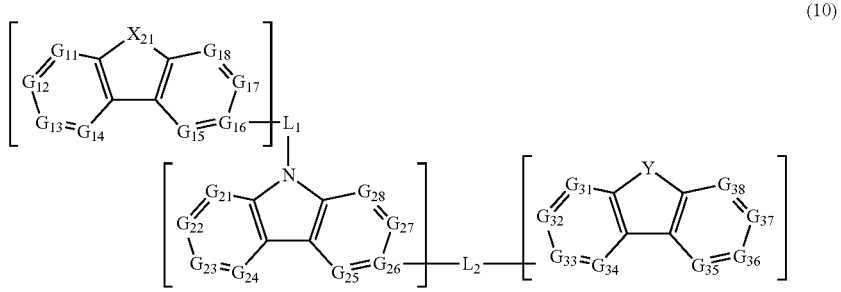

In the formula (1B): $D_1$ to $D_4$ each independently represent a carbon atom bonded with $L_{40}$, or a carbon atom bonded with $R_{40x}$, one of $D_1$ to $D_4$ is a carbon atom bonded with $L_{40}$, $D_5$ to $D_8$ each independently represent a carbon atom bonded with $R_{40x}$, $R_{40x}$ is a hydrogen atom or a substituent;

$n_{40}$ is an integer in a range from 1 to 5; a plurality of $R_{40x}$ are mutually the same or different;

$A_{41}$ to $A_{45}$ are each independently a nitrogen atom, or a carbon atom bonded with $R_{42x}$;

$R_{42x}$ is a hydrogen atom or a substituent;

a plurality of $R_{42x}$ are mutually the same or different;

with a proviso that one of $A_{41}$ to $A_{45}$ is a nitrogen atom or a carbon atom bonded with a cyano group;

$R_{40x}$ and $R_{42x}$ as the substituents each independently represent the same as described above; and $L_{40}$ is a single bond or a linking group, $L_{40}$ as the linking group representing the same as described above.

$n_{40}$ is preferably an integer in a range from 1 to 3, more preferably 1 or 2.

$L_{40}$ is preferably a linking group. $L_{40}$ as the linking group is preferably a substituted or unsubstituted aromatic hydrocarbon group having 6 to 30 ring carbon atoms, more preferably a substituted or unsubstituted aromatic hydrocarbon group having 6 to 10 ring carbon atoms, further preferably a substituted or unsubstituted phenylene group.

When the energy gap of the first compound is large, LUMO (Lowest Unoccupied Molecular Orbital) of the second compound becomes deeper (larger) than LUMO of the first compound. As a result, electrons are more likely to be trapped in the emitting layer by the first compound and the second compound, electron transportability of the emitting layer may be deteriorated. Consequently, more number of holes may be generated in the emitting layer, where the emitting region is localized near the electron injecting layer, thereby reducing the lifetime of the organic EL device.

Accordingly, it is preferable that the first compound is a compound having a small energy gap. In order to reduce the energy gap, it is preferable that the moiety represented by $A_{40}$ and the moiety represented by $D_{40}$ are bonded through $L_{40}$ as the linking group.

In the organic EL device of the first exemplary embodiment, the first compound is also preferably a compound represented by a formula (10) below.

In the formula (10): At least one of $G_{11}$ to $G_{18}$ represents a nitrogen atom, one of the rest of $G_{11}$ to $G_{18}$ represents a carbon atom bonded with $L_1$, and the rest of $G_{11}$ to $G_{18}$ represent $C(R_{1x})$.

It should be noted that "C(R)" herein represents a carbon atom bonded with R.

One of the $G_{21}$ to $G_{28}$ represents a carbon atom bonded with $L_2$, and the rest of $G_{21}$ to $G_{28}$ represent $C(R_{2x})$ or a nitrogen atom.

One of the $G_{31}$ to $G_{38}$ represents a carbon atom bonded with $L_2$, and the rest of $G_{31}$ to $G_{38}$ represent $C(R_{3x})$ or a nitrogen atom.

$R_{1x}$ to $R_{3x}$ are each independently a hydrogen atom or a substituent;

$R_{1x}$, $R_{2x}$, and $R_{3x}$ as the substituents are each independently selected from the group consisting of a substituted or unsubstituted alkyl group having 1 to 20 carbon atoms, a substituted or unsubstituted cycloalkyl group having 3 to 20 ring carbon atoms, a substituted or unsubstituted cycloalkoxy group having 3 to 20 ring carbon atoms, a substituted or unsubstituted alkoxy group having 1 to 20 carbon atoms, a substituted or unsubstituted aryl group having 6 to 18 ring carbon atoms, a substituted or unsubstituted heteroaryl group having 5 to 18 ring atoms, a substituted or unsubstituted aryloxy group having 6 to 18 ring carbon atoms, a substituted or unsubstituted amino group having 0 to 20 carbon atoms, a substituted or unsubstituted silyl group having 0 to 30 carbon atoms, a fluoro group, and a cyano group.

A plurality of $R_{1x}$ are mutually the same or different.

A plurality of $R_{2x}$ are mutually the same or different.

A plurality of $R_{3x}$ are mutually the same or different.

When $R_{1x}$, $R_{2x}$ and/or $R_{3x}$ have a substituent, the substituents for $R_{1x}$, $R_{2x}$ and/or $R_{3x}$ are each independently selected from the group consisting of an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, a heteroaryl group having 5 to 18 ring atoms, an aryloxy group having 6 to 18 ring carbon atoms, an amino group having 0 to 20 carbon atoms, a silyl group having 0 to 30 carbon atoms, a fluoro group, and a cyano group.

$X_{21}$ represents an oxygen atom, a sulfur atom, or —N($R_{4x}$)—.

$R_{4x}$ is a hydrogen atom or a substituent.

$R_{4x}$ as a substituent is a group selected from the group consisting of an alkyl group having 1 to 20 carbon atoms, a cycloalkyl group having 3 to 20 ring carbon atoms, an aryl group having 6 to 18 ring carbon atoms, and a heteroaryl group having 5 to 18 ring atoms.

$L_1$ is a single bond or a linking group.

$L_1$ as the linking group is a group selected from the group consisting of an alkylene group having 1 to 20 carbon atoms, a cycloalkylene group having 3 to 20 ring carbon atoms, an arylene group having 6 to 18 ring carbon atoms, and a heteroarylene group having 5 to 18 ring atoms.

$L_2$ is a single bond or a linking group.

$L_2$ as the linking group is selected from the group consisting of an alkylene group having 1 to 20 carbon atoms, a cycloalkylene group having 3 to 20 ring carbon atoms, an arylene group having 6 to 18 ring carbon atoms, a heteroarylene group having 5 to 18 ring atoms, a divalent linking group including a nitrogen atom, a divalent linking group including an oxygen atom, a divalent linking group including a silicon atom, a divalent linking group including a phosphorus atom, and a divalent linking group including a sulfur atom.

Y represents an oxygen atom, a sulfur atom, or —N(-$L_3$-$R_{5x}$)—.

$L_3$ is a single bond or a linking group.

$L_3$ as the linking group is selected from the group consisting of an alkylene group having 1 to 20 carbon atoms, a cycloalkylene group having 3 to 20 ring carbon atoms, an arylene group having 6 to 18 ring carbon atoms, and a heteroarylene group having 5 to 18 ring atoms.

$R_{5x}$ is a hydrogen atom or a substituent.

$R_{5x}$ as a substituent is a group selected from the group consisting of an alkyl group having 1 to 20 carbon atoms, a cycloalkyl group having 3 to 20 ring carbon atoms, an aryl group having 6 to 18 ring carbon atoms, and a heteroaryl group having 5 to 18 ring atoms.

When $X_{21}$ is an oxygen atom or a sulfur atom, only one of $G_{11}$ to $G_{18}$ represents a nitrogen atom. When $X_{21}$ is —N($R_{4x}$)—, Y represents —N(-$L_3$-$R_{5x}$)—, and $R_{2x}$ and $R_{3x}$ each represent a hydrogen atom.

In the formula (10), it is preferable that $X_{21}$ represents an oxygen atom or a sulfur atom.

In the formula (10), it is also preferable that $X_{21}$ represents —N($R_{4x}$)—.

In the formula (10), it is preferable that $G_{16}$ represents a carbon atom bonded with $L_1$.

In the formula (10), it is preferable that $G_{26}$ and $G_{33}$ each represent a carbon atom bonded with $L_2$.

In the organic EL device of the first exemplary embodiment, the first compound is also preferably a compound represented by a formula (10A) below.

[Formula 8]

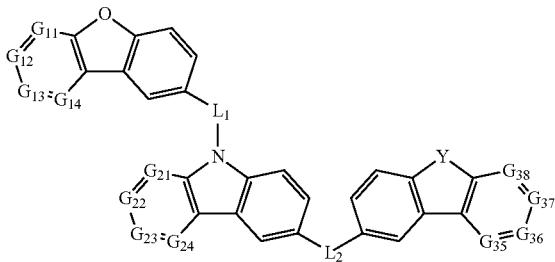

(10A)

In the formula (10A): One of the $G_{11}$ to $G_{14}$ represents a nitrogen atom, and the rest of $G_{11}$ to $G_{14}$ represent $C(R_{1x})$.

$G_{21}$ to $G_{24}$ represent $C(R_{2x})$ or a nitrogen atom.

$G_{35}$ to $G_{38}$ represent $C(R_{3x})$ or a nitrogen atom.

$R_{1x}$ to $R_{3x}$ are each independently a hydrogen atom or a substituent; $R_{1x}$, $R_{2x}$, and $R_{3x}$ as the substituents are each independently selected from the group consisting of an alkyl group having 1 to 20 carbon atoms, a cycloalkyl group having 3 to 20 ring carbon atoms, an aryl group having 6 to 18 ring carbon atoms, and a heteroaryl group having 5 to 18 ring atoms.

$L_1$ is a single bond or a linking group.

$L_1$ as the linking group is a group selected from the group consisting of an arylene group having 6 to 18 ring carbon atoms, and a heteroarylene group having 5 to 18 ring atoms.

$L_2$ is a single bond or a linking group.

$L_2$ as the linking group is selected from the group consisting of an arylene group having 6 to 18 ring carbon atoms, a heteroarylene group having 5 to 18 ring atoms, a divalent linking group including a nitrogen atom, a divalent linking group including an oxygen atom, a divalent linking group including a silicon atom, a divalent linking group including a phosphorus atom, and a divalent linking group including a sulfur atom.

Y represents an oxygen atom, a sulfur atom, or —N(-$L_3$-$R_{5x}$)—.

$L_3$ is a single bond or a linking group.

$L_3$ as the linking group is selected from the group consisting of an arylene group having 6 to 18 ring carbon atoms, and a heteroarylene group having 5 to 18 ring atoms.

$R_{5x}$ is a hydrogen atom or a substituent.

$R_{5x}$ as a substituent is a group selected from the group consisting of an alkyl group having 1 to 20 carbon atoms, a cycloalkyl group having 3 to 20 ring carbon atoms, an aryl group having 6 to 18 ring carbon atoms, and a heteroaryl group having 5 to 18 ring atoms.

Examples of the divalent linking group including a nitrogen atom include a group represented by a formula (11a) below.

Examples of the divalent linking group including an oxygen atom include a group represented by a formula (11b) below.

Examples of the divalent linking group including a silicon atom include a group represented by a formula (11c) below.

Examples of the divalent linking group including a phosphorus atom include a group represented by a formula (11d) and a formula (11e) below.

Examples of the divalent linking group including a sulfur atom include a group represented by a formula (11f) and a formula (11g) below.

[Formula 9]

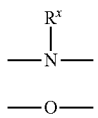
(11a)

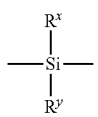
(11b)

(11c)

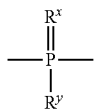
(11d)

(11e)

(11f)

(11g)

In the formulae (11a) to (11g): $R^x$, $R^y$, and $R^z$ each independently represent a hydrogen atom or a substituent, $R^x$, $R^y$, and $R^z$ as the substituents are each independently selected from the group consisting of a substituted or unsubstituted alkyl group having 1 to 20 carbon atoms, a substituted or unsubstituted cycloalkyl group having 3 to 20 ring carbon atoms, a substituted or unsubstituted cycloalkoxy group having 3 to 20 ring carbon atoms, a substituted or unsubstituted alkoxy group having 1 to 20 carbon atoms, a substituted or unsubstituted aryl group having 6 to 18 ring carbon atoms, a substituted or unsubstituted heteroaryl group having 5 to 18 ring atoms, a substituted or unsubstituted aryloxy group having 6 to 18 ring carbon atoms, a substituted or unsubstituted amino group having 0 to 20 carbon atoms, a substituted or unsubstituted silyl group having 0 to 30 carbon atoms, a fluoro group, and a cyano group.

$R^{x'}$ in the formula (11e) is an oxygen atom.

$L_2$ is preferably a group represented by the formula (11d), (11f) or (11e).

In the compound represented by the formula (10) or the formula (10A), it is preferable that at least one of Rex represents a substituted or unsubstituted carbazolyl group, a substituted or unsubstituted dibenzofuranyl group, or a substituted or unsubstituted dibenzothienyl group.

In the formulae (10) and (10A), it is preferable that $G_{14}$ is a nitrogen atom.

In the formulae (10) and (10A), it is preferable that Y represents $—N(-L_3-R_{5x})—$, and $R_{5x}$ represents a heteroaryl group represented by a formula (11) below.

[Formula 10]

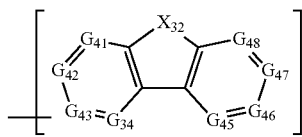
(11)

In the formula (11): One of the $G_{41}$ to $G_{48}$ represents a carbon atom bonded with $L_3$, and the rest of $G_{41}$ to $G_{48}$ represent $C(R_{6x})$.

$R_{6x}$ is a hydrogen atom or a substituent.

R6x as a substituent is selected from the group consisting of a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted cycloalkoxy group having 3 to 20 ring carbon atoms, a substituted or unsubstituted aryl group having 6 to 18 ring carbon atoms, a substituted or unsubstituted heteroaryl group having 5 to 18 ring atoms, a substituted or unsubstituted aryloxy group having 6 to 18 ring carbon atoms, a substituted or unsubstituted amino group having 0 to 20 carbon atoms, a substituted or unsubstituted silyl group having 0 to 30 carbon atoms, a fluoro group, and a cyano group.

A plurality of $R_{6x}$ are mutually the same or different.

When $R_{6x}$ has a substituent, the substituent of $R_{6x}$ is at least one substituent each independently selected from the group consisting of an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, a heteroaryl group having 5 to 18 ring atoms, an aryloxy group having 6 to 18 ring carbon atoms, an amino group having 0 to 20 carbon atoms, a silyl group having 0 to 20 carbon atoms, a fluoro group, and a cyano group.

$X_{32}$ represents an oxygen atom, a sulfur atom, or $—N(R_{7x})—$.

$R_{7x}$ is a hydrogen atom or a substituent.

$R_{7x}$ as a substituent is selected from the group consisting of an alkyl group having 1 to 20 carbon atoms, a cycloalkyl group having 3 to 20 ring carbon atoms, an aryl group having 6 to 18 ring carbon atoms, and a heteroaryl group having 5 to 18 ring atoms.

In the formulae (10) and (10A), it is preferable that Y is an oxygen atom or a sulfur atom.

In the formulae (10) and (10A), it is preferable that $L_1$ represents a single bond, or a linking group selected from the group consisting of an arylene group having 6 to 18 ring carbon atoms, and a heteroarylene group having 5 to 18 ring atoms.

In the formulae (10) and (10A), it is preferable that $L_1$ represents a linking group selected from the group consisting of an arylene group having 6 to 18 ring carbon atoms, and a heteroarylene group having 5 to 18 ring atoms.

It is preferable that the heteroarylene group having 5 to 18 ring atoms for $L_1$ in the formula (10) or the formula (10A) is not a divalent group of dibenzofuran or a divalent group of dibenzothiophene.

In the formulae (10) and (10A), it is preferable that $L_1$ represents a phenylene group.

In the formulae (10) and (10A), it is preferable that $L_2$ is selected from the group consisting of an alkylene group having 1 to 20 carbon atoms, a cycloalkylene group having 3 to 20 ring carbon atoms, a divalent linking group including an oxygen atom, a divalent linking group including a silicon atom, a divalent linking group including a phosphorus atom, and a divalent linking group including a sulfur atom.

In the formulae (10) and (10A), it is also preferable that $L_2$ represents a single bond.

In the formulae (10) and (10A), it is preferable that, when Y represents —N(-$L_3$-$R_{5X}$)— and $R_{5X}$ represents a heteroaryl group represented by the formula (11), at least one of $G_{31}$ to $G_{38}$ and $G_{41}$ to $G_{48}$ represents a nitrogen atom.

In the organic EL device of the first exemplary embodiment, the first compound is also preferably a compound represented by a formula (100) below.

[Formula 11]

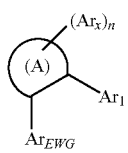

(100)

In the formula (100), $A_{r1}$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and a group represented by any one of formulae (12a) to (12j) below.

$Ar_{EWG}$ is a group selected from the group consisting of a cyano group, a substituted or unsubstituted heteroaryl group having 5 to 30 ring atoms including one or more nitrogen atoms in a ring, and an aryl group having 6 to 30 ring carbon atoms substituted by at least one cyano group.

$Ar_X$ is each independently a hydrogen atom or a substituent.

$Ar_X$ as the substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, a group represented by a formula (12a) below, a group represented by a formula (12b) below, a group represented by a formula (12c) below, a group represented by a formula (12d) below, a group represented by a formula (12e) below, a group represented by a formula (12f) below, a group represented by a formula (12g) below, a group represented by a formula (12h) below, a group represented by a formula (12i) below, and a group represented by a formula (12j) below.

n represents an integer in a range from 0 to 5.

When n is 2 or more, a plurality of $Ar_X$ may be mutually the same or different.

The ring (A) is a five-membered ring, a six-membered ring, or a seven-membered ring.

At least one of $Ar_1$ and $Ar_X$ is a group selected from the group consisting of groups represented by formulae (12a) to (12j) below.

[Formula 12]

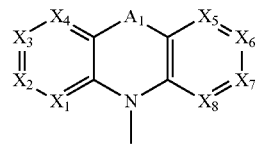

(12a)

[Formula 13]

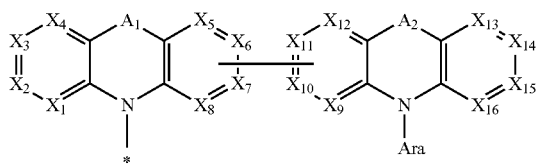

(12b)

[Formula 14]

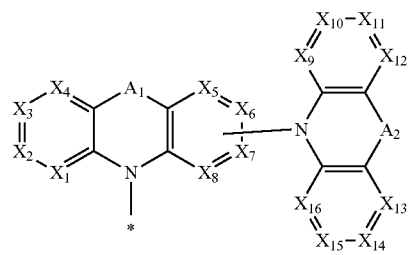

(12c)

[Formula 15]

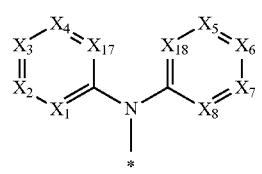

(12d)

[Formula 16]

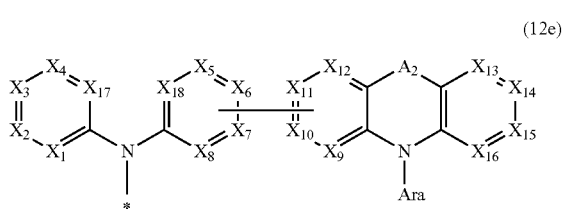

(12e)

[Formula 17]

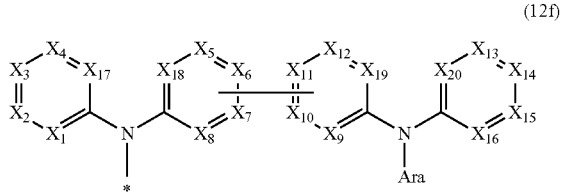

(12f)

-continued

[Formula 18]

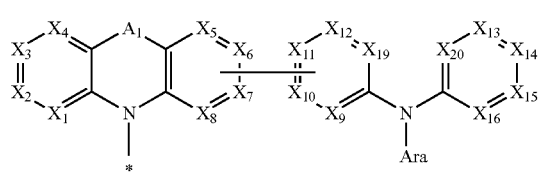

(12g)

[Formula 19]

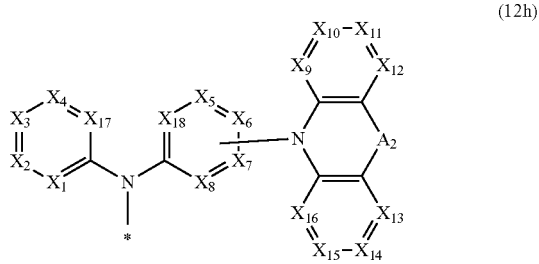

(12h)

[Formula 20]

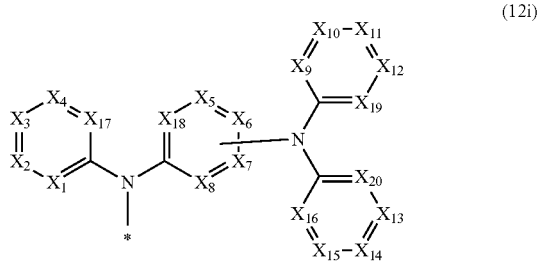

(12i)

[Formula 21]

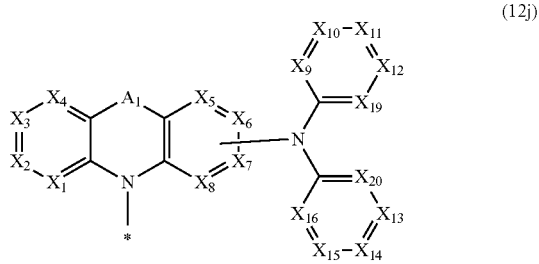

(12j)

In the formulae (12a) to (12j): $X_1$ to $X_{20}$ are each independently a nitrogen atom or C—$R_{300}$;

with a proviso that, in the formula (12b), one of $X_5$ to $X_8$ is a carbon atom bonded with one of $X_9$ to $X_{12}$, and one of $X_9$ to $X_{12}$ is a carbon atom bonded with one of $X_5$ to $X_8$; in the formula (12c), one of one of $X_5$ to $X_8$ is a carbon atom bonded with a nitrogen atom in the six-membered ring of the fused ring including $X_9$ to $X_{12}$, $X_{13}$ to $X_{16}$ and $A_2$; in the formula (12e), one of $X_5$ to $X_8$ and $X_{18}$ is a carbon atom bonded with one of $X_9$ to $X_{12}$, and one of $X_9$ to $X_{12}$ is a carbon atom bonded with one of $X_5$ to $X_8$ and $X_{18}$, in the formula (12f), one of $X_5$ to $X_8$ and $X_{18}$ is a carbon atom bonded with one of $X_9$ to $X_{12}$ and $X_{19}$ and one of $X_9$ to $X_{12}$ and $X_{19}$ is a carbon atom bonded with one of $X_5$ to $X_8$ and $X_{18}$, in the formula (12g), one of $X_5$ to $X_8$ is a carbon atom bonded with one of $X_9$ to $X_{12}$ and $X_{19}$, and one of $X_9$ to $X_{12}$ and $X_{19}$ is a carbon atom bonded with one of $X_5$ to $X_8$; in the formula (12h), one of $X_5$ to $X_8$ and $X_{18}$ is a carbon atom bonded with the nitrogen atom in the six-membered ring of the fused ring including $X_9$ to $X_{12}$, $X_{13}$ to $X_{16}$ and $A_2$; in the formula (12i), one of $X_5$ to $X_8$ and $X_{18}$ is a carbon atom bonded with the nitrogen atom connecting the ring including $X_9$ to $X_{12}$ and $X_{19}$ and the ring including $X_{13}$ to $X_{16}$ and $X_{20}$; and in the formula (12j), one of $X_5$ to $X_8$ is a carbon atom bonded with the nitrogen atom connecting the ring including $X_9$ to $X_{12}$ and $X_{19}$ and the ring including $X_{13}$ to $X_{16}$ and $X_{20}$.

$R_{300}$ is each independently a hydrogen atom or a substituent.

$R_{300}$ as the substituent is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;

a plurality of $R_{300}$ as the substituents are mutually the same or different; and the plurality of $R_{300}$ as the substituents are mutually directly bonded to form a ring, are bonded through a hetero atom to form a ring, or are not bonded.

$A_1$ and $A_2$ are each independently a single bond, an oxygen atom, a sulfur atom, $C(R_{301})(R_{302})$, $Si(R_{303})(R_{304})$, C(=O), S(=O), $SO_2$, or $N(R_{305})$.

$R_{301}$ to $R_{305}$ are each independently a hydrogen atom or a substituent.

$R_{301}$ to $R_{305}$ as the substituents are each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; and Ara is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group.

In the organic EL device of the first exemplary embodiment, the first compound is also preferably a compound represented by a formula (101) below.

[Formula 22]

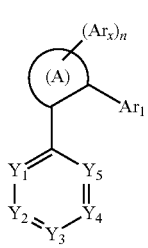

(101)

In the formula (101): $Y_1$ to $Y_5$ are each independently a nitrogen atom, C—CN, or C—$R_{310}$; with a proviso that at least one of $Y_1$ to $Y_5$ is a nitrogen atom or C—CN.

$R_{310}$ is each independently a hydrogen atom or a substituent.

$R_{310}$ as the substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

$Ar_1$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, the group represented by the formula (12a), the group represented by the formula (12b), and the group represented by the formula (12c).

$Ar_X$ is each independently a hydrogen atom or a substituent.

$Ar_X$ as the substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, the group represented by the formula (12a), the group represented by the formula (12b), and the group represented by the formula (12c).

n represents an integer in a range from 0 to 5.

When n is 2 or more, a plurality of $Ar_X$ are mutually the same or different.

The ring (A) is a five-membered ring, a six-membered ring, or a seven-membered ring.

At least one of $Ar_1$ and $Ar_X$ is a group selected from the group consisting of groups represented by the formulae (12a) to (12c).

It is preferable in the formula (101) that at least one of $Y_1$, $Y_3$, and $Y_5$ is a nitrogen atom.

It is preferable in the formula (101) that $Y_1$, $Y_3$, and $Y_5$ are nitrogen atoms and $Y_2$ and $Y_4$ are C—$R_{310}$.

In the organic EL device of the first exemplary embodiment, the first compound is also preferably a compound represented by a formula (102) below.

[Formula 23]

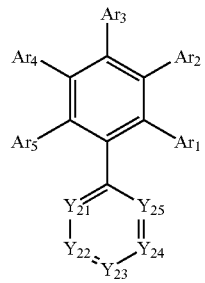

(102)

In the formula (102), $Y_{21}$ to $Y_{25}$ are each independently a nitrogen atom, C—CN, or C—$R_{310}$, with a proviso that at least one of $Y_{21}$ to $Y_{25}$ is a nitrogen atom or C—CN.

$R_{310}$ is each independently a hydrogen atom or a substituent.

$R_{310}$ as the substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

$Ar_1$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, the group represented by the formula (12a), the group represented by the formula (12b), and the group represented by the formula (12c).

$Ar_2$ to $Ar_5$ are each independently a hydrogen atom or a substituent, and $Ar_2$ to $Ar_5$ serving as the substituents are each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, the group represented by the formula (12a), the group represented by the formula (12b), and the group represented by the formula (12c).

At least one of $Ar_1$ to $Ar_5$ is a group selected from the group consisting of groups represented by the formulae (12a) to (12c).

In the organic EL device of the first exemplary embodiment, the first compound is also preferably a compound represented by a formula (103), (104) or (105) below.

[Formula 24]

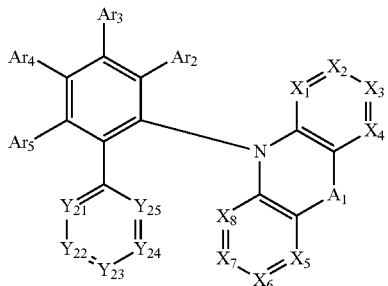
(103)

[Formula 25]

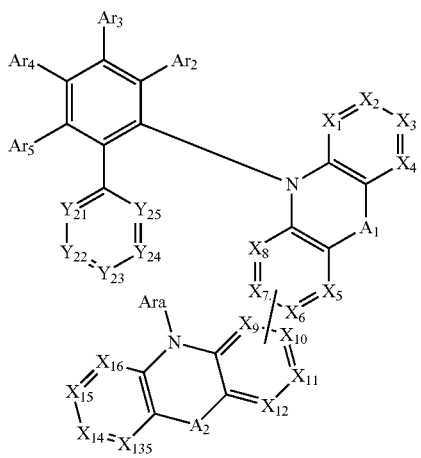
(104)

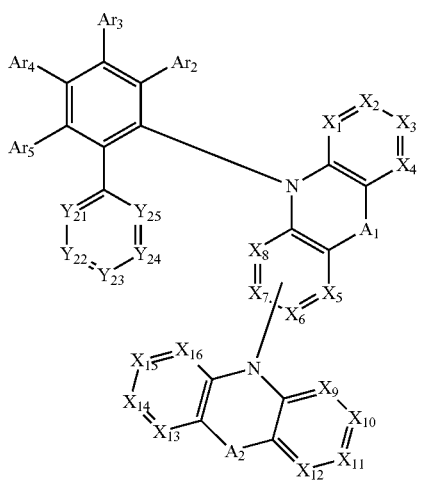
(105)

In the formulae (103) to (105), $Y_{21}$ to $Y_{25}$, $Ar_2$ to $Ar_5$, $X_1$ to $X_{16}$, $A_1$, $A_2$, and Ara represent the same as above-described $Y_{21}$ to $Y_{25}$, $Ar_2$ to $Ar_5$, $X_1$ to $X_{16}$, $A_1$, $A_2$, and Ara, respectively.

In the organic EL device of the first exemplary embodiment, the first compound is also preferably a compound represented by a formula (106), (107) or (108) below.

[Formula 26]

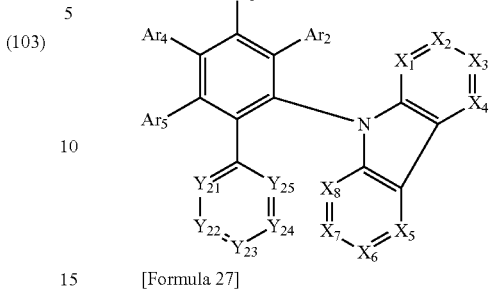
(106)

[Formula 27]

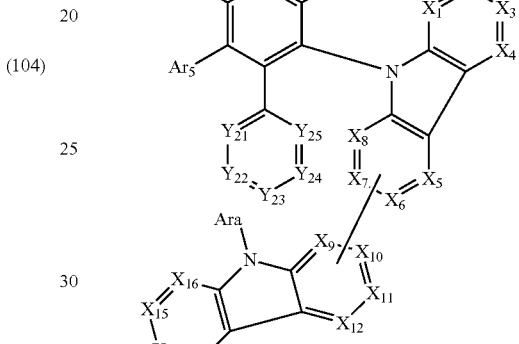
(107)

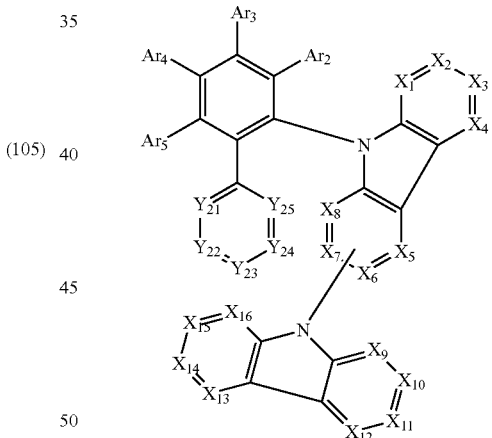
(108)

In the formulae (106) to (108), $Y_{21}$ to $Y_{25}$, $Ar_2$ to $Ar_5$, $X_1$ to $X_{16}$, and Ara represent the same as above-described $Y_{21}$ to $Y_{25}$, $Ar_2$ to $Ar_5$, $X_1$ to $X_{16}$, and Ara, respectively.

It is preferable that at least one of $Y_{21}$, $Y_{23}$, and $Y_{25}$ is a nitrogen atom.

It is also preferable that $Y_{21}$, $Y_{23}$, and $Y_{25}$ are nitrogen atoms and $Y_{22}$ and $Y_{24}$ are C—$R_{310}$.

It is also preferable that $Y_{21}$ and $Y_{23}$ are nitrogen atoms and $Y_{22}$, $Y_{24}$, and $Y_{25}$ are C—$R_{310}$.

It is also preferable that $Y_{21}$ and $Y_{25}$ are nitrogen atoms and $Y_{22}$, $Y_{23}$, and $Y_{24}$ are C—$R_{310}$.

In the organic EL device of the first exemplary embodiment, the first compound is also preferably a compound represented by a formula (120) below.

[Formula 28]

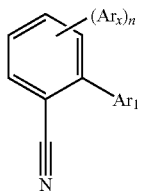

(120)

In the formula (120), $Ar_1$, $Ar_X$, and n represent the same as $Ar_1$, $Ar_X$, and n in the formula (100), respectively.

$Ar_1$ and $Ar_X$ in the formula (120) are each preferably a group represented by the formula (12a).

In the formula (120), n is preferably 3.

In the organic EL device of the first exemplary embodiment, the first compound is also preferably a compound represented by a formula (121) below.

[Formula 29]

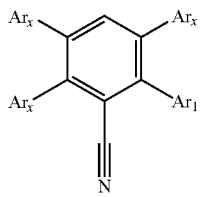

(121)

In the formula (121), $Ar_1$ and $Ar_X$ represent the same as $Ar_1$ and $Ar_X$ in the formula (100), respectively.

$Ar_1$ and $Ar_X$ in the formulae (120) and (121) are each preferably a group represented by the formula (12a).

It is preferable that $Ar_1$ and $Ar_X$ in the formula (121) are each a group represented by the formula (12a) and $A_1$ in the formula (12a) is a single bond.

The first compound of the first exemplary embodiment is also preferably a fluoranthene derivative.

Delayed Fluorescence

Delayed fluorescence (thermally activated delayed fluorescence) is explained in "Yuki Hando-tai no Debaisu Bussei (Device Physics of Organic Semiconductors)" (edited by ADACHI, Chihaya, published by Kodansha, on pages 261-268). This document describes that, when an energy difference $\Delta E_{13}$ between a singlet state and a triplet state of a fluorescent material can be decreased, in spite of a typical low transition probability, inverse energy transfer from the triplet state to the singlet state occurs at a high efficiency to express TADF (Thermally Activated Delayed Fluorescence). Further, a generating mechanism of delayed fluorescence is described in FIG. 10.38 in this document. The first compound in the exemplary embodiment is a compound emitting thermally activated delayed fluorescence ("thermally activated delayed fluorescent compound") to be generated by such a mechanism.

Delayed fluorescence can be observed by measuring transient PL (Photo Luminescence).

Behavior of delayed fluorescence can also be analyzed based on the decay curve obtained by measuring the transient PL. The transient PL measurement is a method for measuring reduction behavior (transitional property) of PL emission obtained after a sample is irradiated with pulse laser to be excited and then the irradiation of the pulse laser is stopped. PL emission using a TADF material is divided into an emission component from singlet excitons generated by the first PL excitation and an emission component from singlet excitons generated via triplet excitons. Lifetime of the singlet excitons initially generated in the PL excitation is very short at a nano-second order. Accordingly, the emission from the singlet excitons is rapidly reduced after pulse laser radiation.

On the other hand, since delayed fluorescence provides emission from singlet excitons generated through long-life triplet excitons, emission is gradually reduced. Thus, there is a large difference in time between the emission from the singlet excitons initially generated in the PL excitation and the emission from the singlet excitons derived from the triplet excitons. Accordingly, a luminous intensity derived from delayed fluorescence is obtainable.

Figure 2:
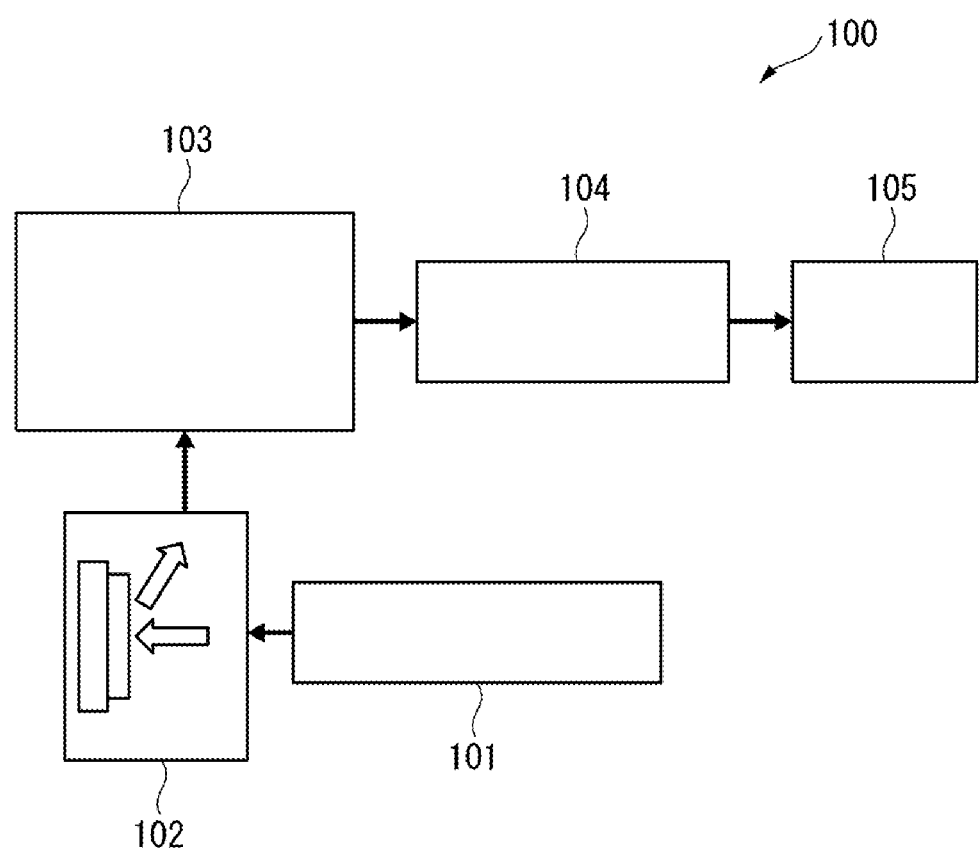
FIG. 2 schematically shows a device for measuring transient PL.

FIG. 2 schematically shows an exemplary device for measuring transient PL.

A transient PL measuring device 100 in the exemplary embodiment includes: a pulse laser 101 capable of radiating a light having a predetermined wavelength; a sample chamber 102 configured to house a measurement sample; a spectrometer 103 configured to divide a light radiated from the measurement sample; a streak camera 104 configured to provide a two-dimensional image; and a personal computer 105 configured to import and analyze the two-dimensional image. A device usable for the measurement of the transient PL is not limited to the device described in the exemplary embodiment.

The sample housed in the sample chamber 102 is obtained by forming a thin film, in which a matrix material is doped with a doping material at a concentration of 12 mass %, on the quartz substrate.

The thus-obtained thin film sample is housed in the sample chamber 102, and is irradiated with a pulse laser emitted from the pulse laser unit 101 to excite the doping material. Emission is extracted at 90 degrees angle relative to an irradiation direction of the excited light. The extracted emission is dispersed with the spectrometer 103 to form a two-dimensional image in the streak camera 104. As a result, the two-dimensional image expressed in coordinates of which ordinate axis indicates time and of which abscissa axis indicates a wavelength, in which a luminous point indicates a luminous intensity, can be obtained. If the two-dimensional image is cut out along a predetermined time axis, emission spectrum expressed in coordinates of which ordinate axis indicates a luminous intensity and of which abscissa axis indicates the wavelength can be obtained. If the two-dimensional image is cut out along a wavelength axis, a decay curve (transient PL) expressed in coordinates of which ordinate axis indicates a logarithm of the luminous intensity and of which abscissa axis indicates time can be obtained.

For instance, using a reference compound H1 below as the matrix material and a reference compound D1 as the doping material, a thin film sample A was prepared as described above and the transitional PL was measured.

[Formula 30]

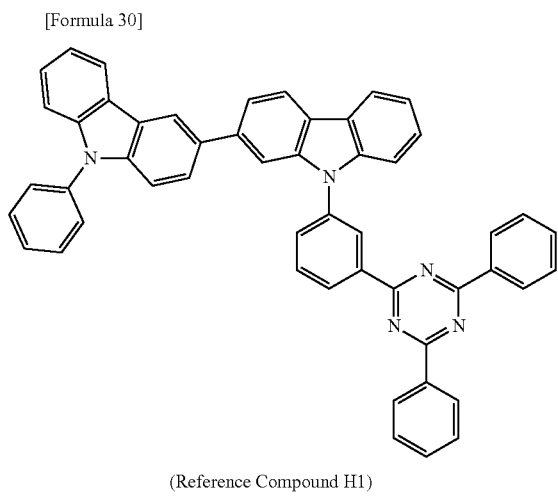

(Reference Compound H1)

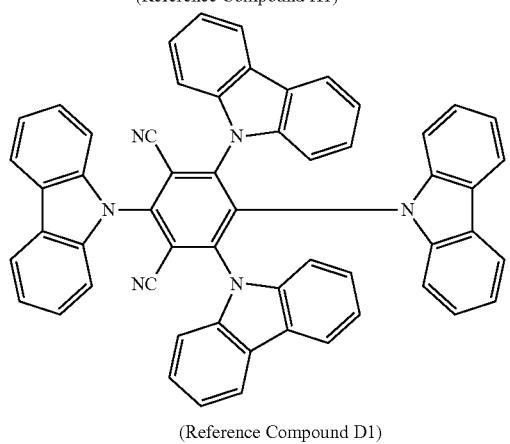

(Reference Compound D1)

Herein, the decay curve was analyzed using the above-described thin film samples A and B. The thin film sample B was prepared as described above, using a reference compound H2 below as the matrix material and the reference compound D1 as the doping material.

Figure 3:
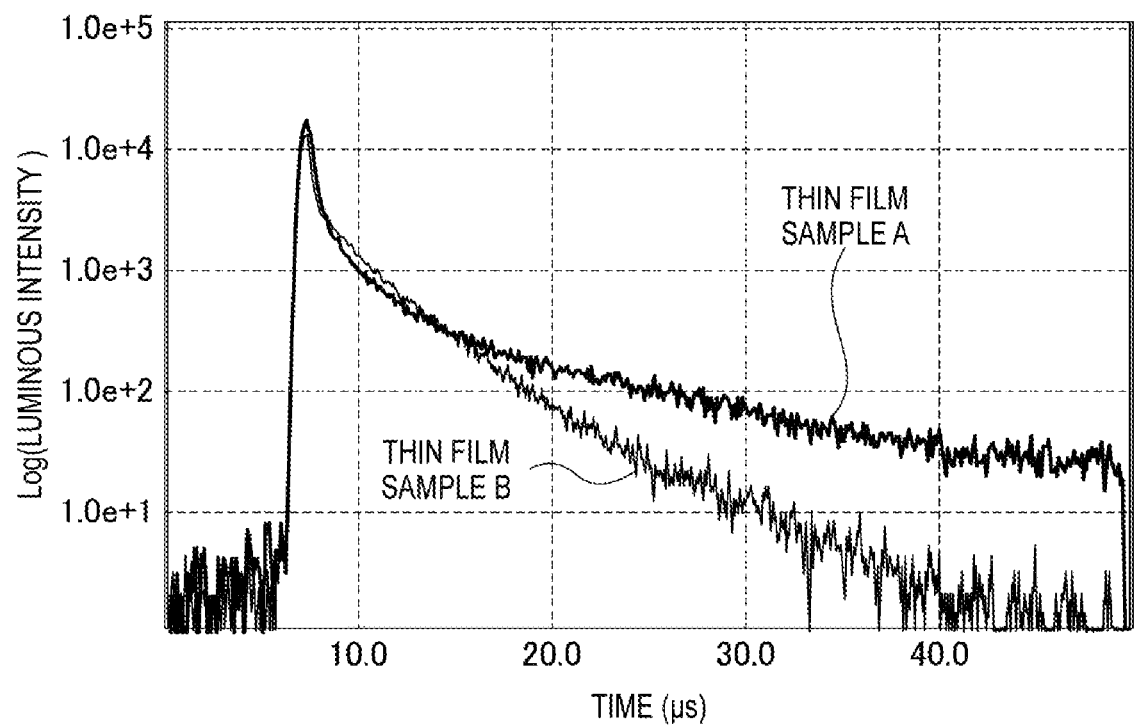
FIG. 3 shows examples of a transient PL decay curve.

FIG. 3 shows a decay curve obtained from the measured transitional PL of the thin film samples A and B.

[Formula 31]

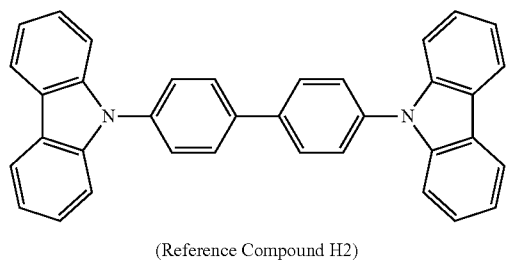

(Reference Compound H2)

An emission decay curve expressed in coordinates of which ordinate axis indicates a luminous intensity and of which abscissa axis indicates time can be obtained by measuring the transient PL as described above. Based on the emission decay curve, a fluorescence intensity ratio between fluorescence in the single state generated by light excitation and the delayed fluorescence in the singlet state generated by the inverse energy transfer through the triplet state can be estimated. In a delayed fluorescent material, a ratio of the intensity of the slowly decaying delayed fluorescence to the intensity of the promptly decaying fluorescence is relatively large.

In the first exemplary embodiment, the luminescence amount of the delayed fluorescence can be obtained using the device shown in FIG. 2. Emission from the first compound includes: Prompt emission observed immediately when the excited state is achieved by exciting the first compound with a pulse beam (i.e., a beam emitted from a pulse laser unit) having an absorbable wavelength; and Delayed emission observed not immediately when but after the excited state is achieved. In the first exemplary embodiment, an amount of Delay Emission is preferably 5% or more based on an amount of Prompt Emission. Specifically, provided that the amount of Prompt emission is denoted by $X_P$ and the amount of Delay emission is denoted by $X_D$, it is preferable that a value of $X_D/X_P$ is 0.05 or more.

The amount of Prompt emission and the amount of Delay emission can be obtained according to the same method as a method described in "Nature 492, 234-238, 2012." The amount of Prompt emission and the amount of Delayed emission may be calculated using a device different from one described in the above Reference Literature.

For instance, a sample usable for measuring the delayed fluorescence may be prepared by co-depositing the first compound and a compound TH-2 below on a quartz substrate at a ratio of the first compound being 12 mass % to form a 100-nm-thick thin film.

[Formula 32]

TH-2

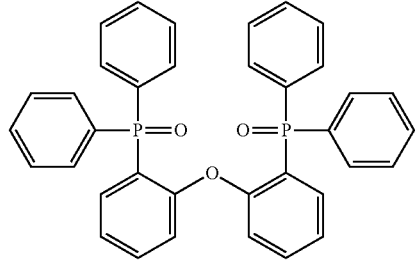

Specific examples of the first compound of the first exemplary embodiment are shown below. It should be noted that the first compound according to the invention is not limited to these specific examples.

[Formula 33]

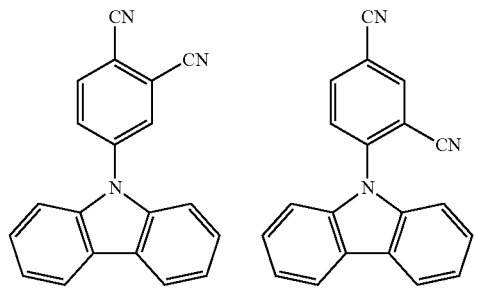

[Formula 34]
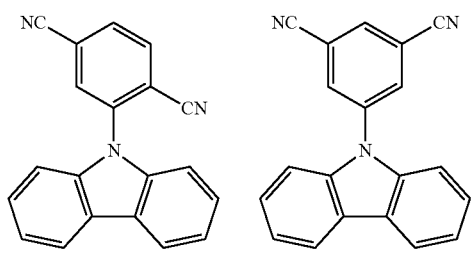
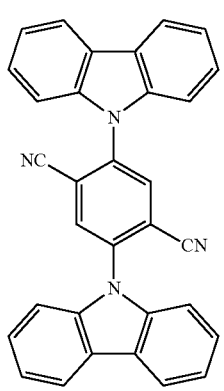
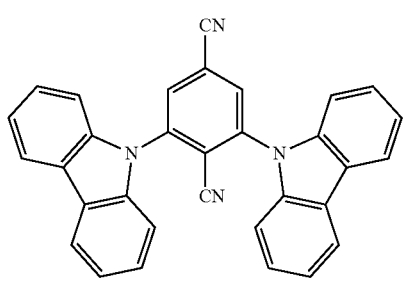
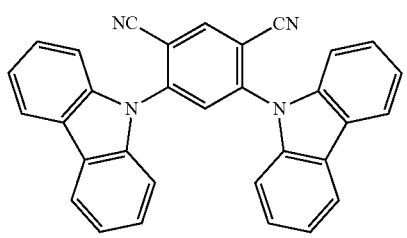
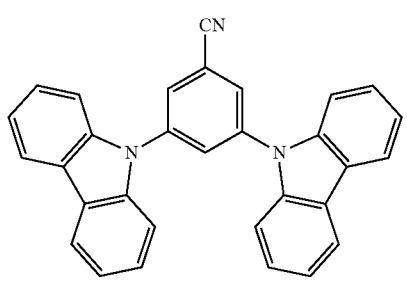
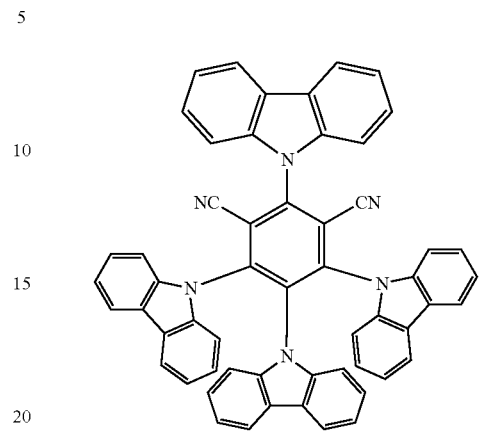
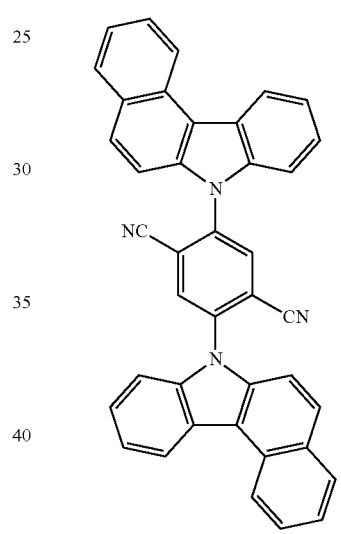
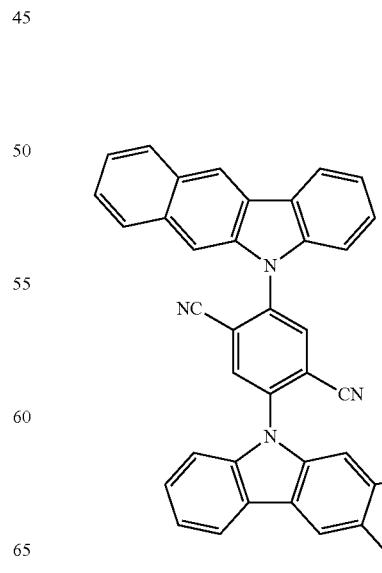

-continued
[Formula 35]
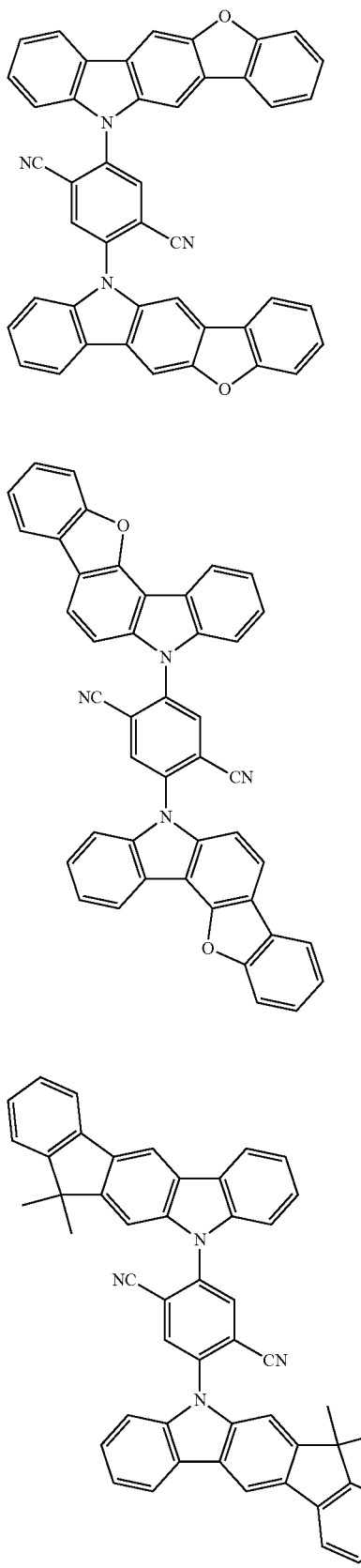
[Formula 36]
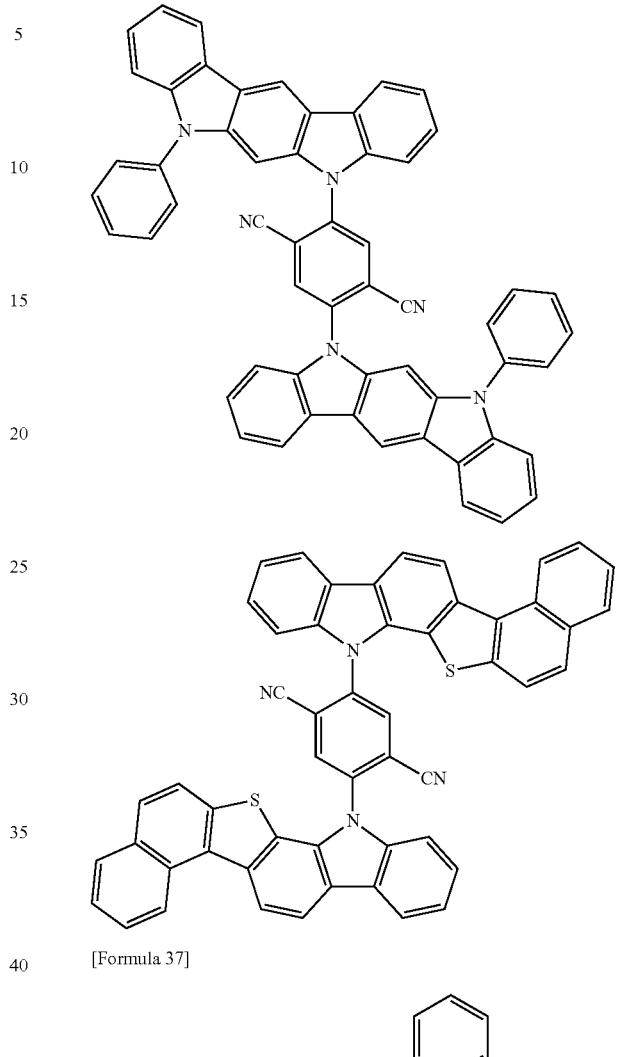
[Formula 37]
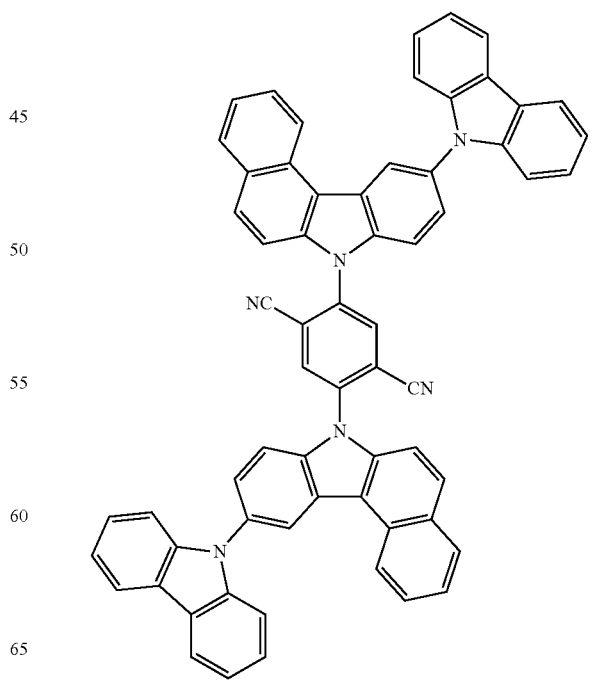

-continued

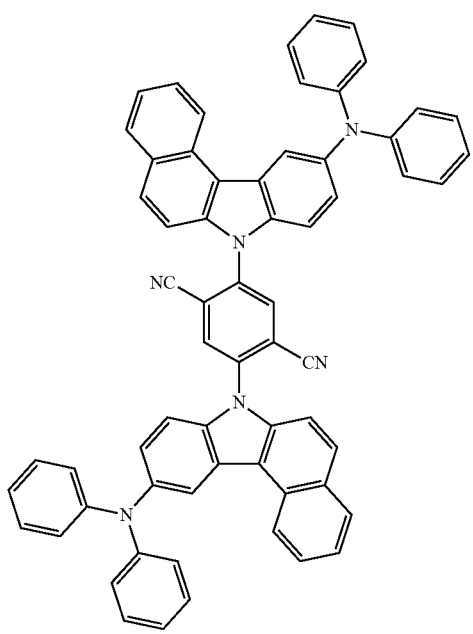

[Formula 38]

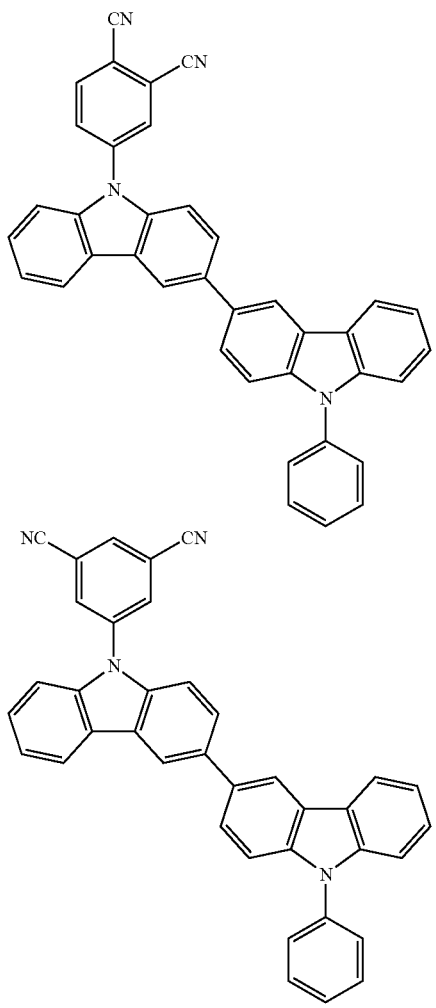

-continued

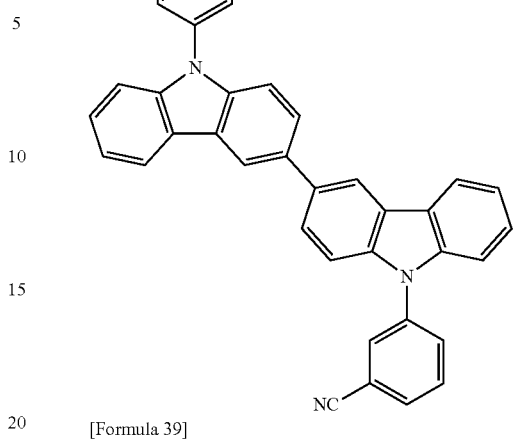

[Formula 39]

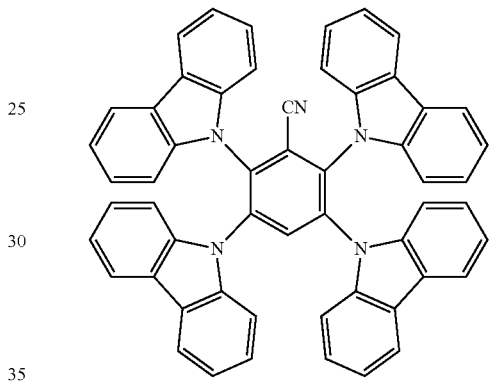

Second Compound

The second compound is represented by a formula (2) below.

[Formula 40]

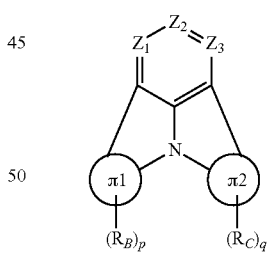

(2)

In the formula (2):
$Z_1$ is $CR_1$ or a nitrogen atom;
$Z_2$ is $CR_2$ or a nitrogen atom;
$Z_3$ is $CR_3$ or a nitrogen atom;
π1 and π2 are each independently a cyclic structure selected from the group consisting of a substituted or unsubstituted aromatic hydrocarbon ring having 6 to 50 ring carbon atoms, and a substituted or unsubstituted aromatic heterocyclic ring having 5 to 50 ring atoms;
$R_1$ to $R_3$, $R_B$ and $R_C$ each independently represent a hydrogen atom or a substituent; $R_1$ to $R_3$, $R_B$, and $R_C$ as the substituent being each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms;

$R_1$ and $R_2$ are mutually bonded to form a cyclic structure or are not mutually bonded to form no cyclic structure; $R_2$ and $R_3$ are mutually bonded to form a cyclic structure or are not mutually bonded to form no cyclic structure;

adjacent $R_B$ are mutually bonded to form a cyclic structure or are not mutually bonded to form no cyclic structure;

adjacent $R_C$ are mutually bonded to form a cyclic structure or are not mutually bonded to form no cyclic structure;

$R_{101}$ to $R_{105}$ are each independently a hydrogen atom or a substituent; $R_{101}$ to $R_{105}$ as the substituents are each independently a group selected from the group consisting of a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, and a substituted or unsubstituted heteroaryl group having 5 to 50 ring atoms; and p and q are each independently an integer in a range from 1 to 4.

π1 and π2 are each an aromatic hydrocarbon ring having 6 to 50 (preferably 6 to 24, more preferably 6 to 18) ring carbon atoms, or an aromatic heterocycle having 5 to 50 (preferably 5 to 24, more preferably 5 to 13) ring atoms.

$R_B$ in the formula (2) is bonded with one of carbon atoms of the aromatic hydrocarbon ring of π1 or one of atoms of the aromatic heterocycle of π1.

$R_C$ in the formula (2) is bonded with one of carbon atoms of the aromatic hydrocarbon ring of π2 or one of atoms of the aromatic heterocycle of π2.

Specific examples of the above aromatic hydrocarbon ring having 6 to 50 ring carbon atoms include a benzene ring, naphthalene ring, anthracene ring, benzoanthracene ring, phenanthrene ring, benzophenanthrene ring, fluorene ring, benzofluorene ring, dibenzofluorene ring, picene ring, tetracene ring, pentacene ring, pyrene ring, chrysene ring, benzochrysene ring, s-indacene ring, as-indacene ring, fluoranthene ring, benzofluoranthene ring, triphenylene ring, benzotriphenylene ring, perylene ring, coronene ring, and dibenzoanthracene ring.

Specific examples of the aromatic heterocycle having 5 to 50 ring atoms include pyrrole ring, pyrazole ring, isoindole ring, benzofuran ring, benzothiophene ring, isobenzofuran ring, dibenzothiophene ring, isoquinoline ring, cinnoline ring, quinoxaline ring, phenanthridine ring, phenanthroline ring, pyridine ring, pyrazine ring, pyrimidine ring, pyridazine ring, triazine ring, imidazopyridine ring, indole ring, indazole ring, benzimidazole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazole ring, thiadiazole ring, benzothiazole ring, triazole ring, imidazole ring, benzoimidazole ring, pyrane ring, dibenzofuran ring, benzo[c]dibenzofuran ring, purine ring, and acridine ring.

In the organic EL device of the first exemplary embodiment, the second compound is preferably a compound represented by a formula (20) below.

[Formula 41]

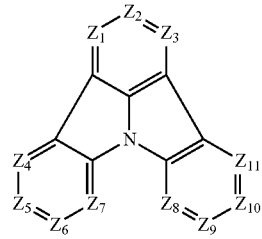

(20)

In the formula (20): $Z_4$ is $CR_4$ or a nitrogen atom;
$Z_5$ is $CR_5$ or a nitrogen atom;
$Z_6$ is $CR_6$ or a nitrogen atom;
$Z_7$ is $CR_7$ or a nitrogen atom;
$Z_8$ is $CR_8$ or a nitrogen atom;
$Z_9$ is $CR_9$ or a nitrogen atom;
$Z_{10}$ is $CR_{10}$ or a nitrogen atom;
$Z_{11}$ is $CR_{11}$ or a nitrogen atom;

$R_4$ to $R_{11}$ are each independently a hydrogen atom or a substituent; and $R_4$ to $R_{11}$ as the substituents are each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms.

$R_4$ and $R_5$ are mutually bonded to form a cyclic structure or are not mutually bonded to form no cyclic structure.

$R_5$ and $R_6$ are mutually bonded to form a cyclic structure or are not mutually bonded to form no cyclic structure.

$R_6$ and $R_7$ are mutually bonded to form a cyclic structure or are not mutually bonded to form no cyclic structure.

$R_8$ and $R_9$ are mutually bonded to form a cyclic structure or are not mutually bonded to form no cyclic structure.

$R_9$ and $R_{10}$ are mutually bonded to form a cyclic structure or are not mutually bonded to form no cyclic structure.

$R_{10}$ and $R_{11}$ are mutually bonded to form a cyclic structure or are not mutually bonded to form no cyclic structure.

$Z_1$ to $Z_3$, $R_1$ to $R_3$, and $R_{101}$ to $R_{105}$ represent the same as $Z_1$ to $Z_3$, $R_1$ to $R_3$, and $R_{101}$ to $R_{105}$ in the formula (2), respectively.

In the organic EL device of the first exemplary embodiment, the second compound is also preferably a compound represented by a formula (200) below.

[Formula 42]

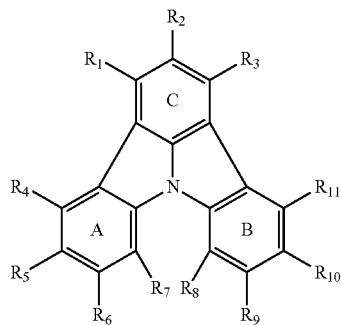

(200)

In the formula (200): in each of the pairs of $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$ (n represents an integer selected from 1, 2, 4 to 6, and 8 to 10) are mutually bonded to form a cyclic structure having three or more atoms (sometimes referred to as "three-or-more-atom cyclic structure) in combination with a carbon atom bonded with $R_n$ and a carbon atom bonded with $R_{n+1}$, or $R_n$ and $R_{n+1}$ are not mutually bonded to form no cyclic structure;

the three-or-more-atom cyclic structure includes, as the atom(s) of the cyclic structure, one or more atoms selected from a carbon atom, oxygen atom, sulfur atom, and nitrogen atom in addition to the carbon atom bonded with $R_n$ and the carbon atom bonded with $R_{n+1}$; and at least one atom of the three-or-more-atom cyclic structure that is bondable with an atom other than the rest of atoms of the cyclic structure has a hydrogen atom or a substituent $R_X$, the substituent $R_X$ being each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms.

Adjacent substituents $R_X$ are mutually bonded to form a cyclic structure or are not mutually bonded to form no cyclic structure. It should be noted that the number of the atoms of the three-or-more-atom cyclic structure does not include the number of atoms of the substituent $R_X$.

$R_1$ to $R_{11}$ that do not contribute to the formation of the three-or-more-atom cyclic structure represent the same as $R_1$ to $R_{11}$ in the formula (20).

$R_{101}$ to $R_{105}$ represent the same as $R_{101}$ to $R_{105}$ in the formula (20), respectively.

In this paragraph, the meaning of the phrase in the preceding paragraph "$R_n$ and $R_{n+1}$ (n representing an integer selected from 1, 2, 4 to 6, and 8 to 10) are mutually bonded to form a three-or-more-atom cyclic structure formed of atoms selected from a carbon atom, oxygen atom, sulfur atom, and nitrogen atom, in combination with two ring-forming carbon atoms with which $R_n$ and $R_{n+1}$ are bonded" will be described in detail.

$R_1$ to $R_{11}$ each represent a hydrogen atom, a substituent, or an atom or a plurality of mutually bonded atoms selected from the group consisting of a carbon atom, oxygen atom, sulfur atom, and nitrogen atom.

When $R_1$ to $R_{11}$ each represent an atom or a plurality of mutually bonded atoms selected from the group consisting of a carbon atom, oxygen atom, sulfur atom, and nitrogen atom, in each of the pairs of $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$ (n representing an integer selected from 1, 2, 4 to 6, and 8 to 10) are mutually bonded to form the three-or-more-atom cyclic structure formed of atoms selected from a carbon atom, oxygen atom, sulfur atom, and nitrogen atom, in combination with the two ring-forming carbon atom with which $R_n$ and $R_{n+1}$ are bonded.

The above phrase "$R_n$ and $R_{n+1}$ (n representing an integer selected from 1, 2, 4 to 6, and 8 to 10) are mutually bonded" means that one of atom(s) represented by $R_n$ and one of atom(s) represented by $R_{n+1}$ are mutually bonded. The term "one of atom(s) represented by $R_n$" means a single atom of $R_n$ when $R_n$ represents an atom or an atom at a terminal end of $R_n$ or an atom other than the atom at the terminal end of $R_n$ when $R_n$ represents a plurality of mutually bonded atoms. The same applies to the term "one of atom(s) represented by $R_{n+1}$."

Examples of the bonding include a single bond, double bond, or a bond having a bond order between 1 and 2. The same applies to the "bond" for $R_n$ and $R_{n+1}$ representing the plurality of mutually bonded atoms.

In each of two or more pairs selected from the pairs of $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$ of the organic EL device according to the first exemplary embodiment, it is preferable that $R_n$ and $R_{n+1}$ (n representing an integer selected from 1, 2, 4 to 6, and 8 to 10) are mutually bonded to form the three-or-more-atom cyclic structure in combination with the carbon atom bonded with $R_n$ and the carbon atom bonded with $R_{n+1}$.

In the organic EL device of the first exemplary embodiment, it is preferable that the second compound represented by the formula (2) includes two above-described cyclic structures (i.e. the three-or-more-atom cyclic structure formed by mutually bonding $R_n$ and $R_{n+1}$ (n representing an integer selected from 1, 2, 4 to 6, and 8 to 10) in each of the pairs of $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, the cyclic structure being formed of atoms selected from a carbon atom, oxygen atom, sulfur atom, and nitrogen atom, in combination with the two ring-forming carbon atoms with which $R_n$ and $R_{n+1}$ are bonded).

It is also preferable in the organic EL device of the first exemplary embodiment that the compound represented by the formula (200) includes three above-described cyclic structures. In this case, it is also preferable that each of the cyclic structures is present on corresponding one of the different benzene rings (i.e. the rings A, B, and C) of the main skeleton of the formula (200).

It is also preferable in the organic EL device of the first exemplary embodiment that the compound represented by the formula (200) includes four or more above-described cyclic structures.

In the organic EL device of the first exemplary embodiment, it is preferable that the pairs of $R_1$ and $R_2$ and $R_2$ and $R_3$ in the formula (200) do not simultaneously form the cyclic structure. It is preferable that the pairs of $R_4$ and $R_5$ and $R_5$ and $R_6$ do not simultaneously form the cyclic structure. It is preferable that the pairs of $R_5$ and $R_6$ and $R_6$ and $R_7$ do not simultaneously form the cyclic structure. It is preferable that the pairs of $R_8$ and $R_9$ and $R_9$ and $R_{10}$ do not simultaneously form the cyclic structure. It is preferable that the pairs of $R_9$ and $R_{10}$ and $R_{10}$ and $R_{11}$ do not simultaneously form the cyclic structure.

In the organic EL device of the exemplary embodiment, when two or more pairs of the above pairs form the cyclic structures, it is preferable that the pairs are selected so that two or three rings selected from the rings A, B, and C have the cyclic structure formed of atoms selected from the carbon atom, oxygen atom, sulfur atom, and nitrogen atom. When the two or three rings selected from the rings A, B, and C have two or more of the above-described cyclic structures, the cyclic structures may be the same or different.

In the organic EL device of the first exemplary embodiment, $R_1$ to $R_3$ of the compound represented by the formula (200) each represent a hydrogen atom or a substituent. It is preferable that $R_1$ to $R_3$ as the substituent each independently represent a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms.

In the formula (200), examples of the halogen atom represented by $R_1$ to $R_{11}$ include a fluorine atom, a chlorine atom, a bromine atom, and an iodine atom.

Examples of the alkyl group having 1 to 20 (preferably 1 to 10, more preferably 1 to 6) carbon atoms represented by $R_1$ to $R_{11}$ include a methyl group, ethyl group, n-propyl group, isopropyl group, n-butyl group, isobutyl group, s-butyl group, t-butyl group, pentyl group (including isomeric group thereof), hexyl group (including isomeric group thereof), heptyl group (including isomeric group thereof), octyl group (including isomeric group thereof), nonyl group (including isomeric group thereof), decyl group (including isomeric group thereof), undecyl group (including isomeric group thereof, and dodecyl group (including isomeric group thereof). Among the above, a methyl group, ethyl group, n-propyl group, isopropyl group, n-butyl group, isobutyl group, s-butyl group, t-butyl group, and pentyl group (all including isomeric group thereof) are preferable, a methyl group, ethyl group, n-propyl group, isopropyl group, n-butyl group, isobutyl group, s-butyl group, and t-butyl group are more preferable, and a methyl group, ethyl group, isopropyl group and t-butyl group are further preferable.

Examples of the alkenyl group having 1 to 20 (preferably 1 to 10, more preferably 1 to 6) carbon atoms represented by $R_1$ to $R_{11}$ include a vinyl group, 2-propenyl group, 2-butenyl group, 3-butenyl group, 4-pentenyl group, 2-methyl-2-propenyl group, 2-methyl-2-butenyl group, and 3-methyl-2-butenyl group.

Examples of the alkynyl group having 1 to 20 (preferably 1 to 10, more preferably 1 to 6) carbon atoms represented by $R_1$ to $R_{11}$ include a 2-propynyl group, 2-butynyl group, 3-butynyl group, 4-pentynyl group, 5-hexynyl group, 1-methyl-2-propynyl group, 1-methyl-2-butynyl group, and 1,1-dimethyl-2-propynyl group.

Examples of the cycloalkyl group having 3 to 20 (preferably 3 to 6, more preferably 5 or 6) ring carbon atoms represented by $R_1$ to $R_{11}$ include a cyclopropyl group, cyclobutyl group, cyclopentyl group, cyclohexyl group, cycloheptyl group, cyclooctyl group, and adamantyl group. Among the above, a cyclopentyl group or a cyclohexyl group is preferable.

Examples of the alkoxy group having 1 to 20 (preferably 1 to 10, more preferably 1 to 6) carbon atoms represented by $R_1$ to $R_{11}$ include an alkoxy group whose alkyl-group moiety is one of the examples of the alkyl group having 1 to 20 carbon atoms. Specific examples of preferable alkoxy group include an alkoxy group whose alkyl-group moiety is one of the preferable examples of the alkyl group having 1 to 50 carbon atoms. The same applies to more preferable specific examples and further preferable specific examples of alkoxy group.

Examples of the fluoroalkyl group having 1 to 20 (preferably 1 to 10, more preferably 1 to 6) carbon atoms represented by $R_1$ to $R_{11}$ include a fluoroalkyl group formed by substituting a hydrogen atom of the alkyl group of the examples with a fluorine atom. Examples of a preferable fluoroalkyl group include a group whose alkyl-group moiety before being substituted by a fluorine atom is one of the examples of the preferable alkyl group. The same applies to more preferable specific examples and further preferable specific examples of fluoroalkyl group.

Examples of the fluoroalkoxy group having 1 to 20 (preferably 1 to 10, more preferably 1 to 6) carbon atoms represented by $R_1$ to $R_{11}$ include a fluoroalkoxy group formed by substituting a hydrogen atom of the alkoxy group of the examples with a fluorine atom. Examples of a preferable fluoroalkoxy group include a group whose alkoxy-group moiety before being substituted by a fluorine atom is one of the examples of the preferable alkoxy group. The same applies to more preferable specific examples and further preferable specific examples of fluoroalkoxy group.

Examples of the aryloxy group having 6 to 50 (preferably 6 to 30, more preferably 6 to 24, further preferably 6 to 18) ring carbon atoms represented by $R_1$ to $R_{11}$ include a group whose aryl-group moiety is one of examples of later-described aryl group having 6 to 50 ring carbon atoms for $R_1$ to $R_{11}$. Specific examples of preferable aryloxy group is an aryloxy group whose aryl-group moiety is one of the preferable examples of the later-described aryl group having 6 to 50 ring carbon atoms. The same applies to more preferable specific examples and further preferable specific examples of aryloxy group.

Examples of the alkylthio group having 1 to 20 (preferably 1 to 10, more preferably 1 to 6) carbon atoms represented by $R_1$ to $R_{11}$ include an alkylthio group whose alkyl-group moiety is one of the examples of the alkyl group having 1 to 20 carbon atoms. Specific examples of preferable alkylthio group is an alkylthio group whose alkyl-group moiety is one of the preferable examples of the alkyl group. The same applies to more preferable specific examples and further preferable specific examples of alkylthio group.

Examples of the arylthio group having 6 to 50 (preferably 6 to 30, more preferably 6 to 24, further preferably 6 to 18) ring carbon atoms represented by $R_1$ to $R_{11}$ include a group whose aryl-group moiety is one of examples of the later-described aryl group having 6 to 50 ring carbon atoms for $R_1$ to $R_{11}$. Specific examples of preferable arylthio group is a group whose aryl-group moiety is one of the preferable examples of the later-described aryl group having 6 to 50 ring carbon atoms. The same applies to more preferable specific examples and further preferable specific examples of arylthio group.

Specific examples of the "group represented by —Si($R_{101}$)($R_{102}$)($R_{103}$)" represented by $R_1$ to $R_{11}$ include monoalkylsilyl group, dialkylsilyl group, and trialkylsilyl group; monoarylsilyl group, diarylsilyl group, and triarylsilyl group; and monoalkyldiarylsilyl group, and dialkylmonoarylsilyl group.

In these substituted silyl group, the number of carbon atoms of the alkyl-group moiety is preferably 1 to 20, more preferably 1 to 10, further preferably 1 to 6. The number of the ring carbon atoms of the aryl-group moiety is preferably 6 to 50, more preferably 6 to 30, further preferably 6 to 24, especially preferably 6 to 18.

Among the above, a trialkylsilyl group and a triarylsilyl group are preferable, and trimethylsilyl group, triethylsilyl group, triisopropylsilyl group, t-butyl dimethylsilyl group, triphenylsilyl group, and tritolylsilyl group are more preferable.

Specific examples of the "group represented by —N($R_{104}$)($R_{105}$)" represented by $R_1$ to $R_{11}$ include monoalkylamino group, dialkylamino group, monoarylamino group, diarylamino group, monoheteroarylamino group, diheteroarylamino group, monoalkylmonoarylamino group, monoalkylmonoheteroarylamino group, and monoarylmonoheteroarylamino group. The aryl-group moiety of the substituted amino group may be substituted by an alkyl group having 1 to 20 (preferably 1 to 10, more preferably 1 to 6) carbon atoms.

In the substituted amino group, the number of carbon atoms of the alkyl-group moiety is preferably 1 to 20, more preferably 1 to 10, further preferably 1 to 6. In the substituted amino group, the number of the ring carbon atoms of the aryl-group moiety is preferably 6 to 50, more preferably 6 to 30, further preferably 6 to 24, especially preferably 6 to 18. In the substituted amino group, the number of the ring carbon atoms of the heteroaryl-group moiety is preferably 5 to 50, more preferably 5 to 30, further preferably 5 to 18, especially preferably 5 to 13.

Among the above, dialkylamino group, diarylamino group, diheteroarylamino group, and monoarylmonoheteroarylamino group are preferable, dimethylamino group, diethylamino group, diisopropylamino group, diphenylamino group, bis(alkyl-substituted phenyl)amino group, and bis(aryl-substituted phenyl)amino group are more preferable.

Specific examples of the alkyl-group moiety include the specific examples of the alkyl group having 1 to 20 carbon atoms. Specific examples of preferable alkyl-group moiety include the preferable examples of the alkyl group having 1 to 20 carbon atoms. The same applies to more preferable specific examples and further preferable specific examples of alkyl-group moiety.

Specific examples of aryl-group moiety include the later-described specific examples of the aryl group having 6 to 50 ring carbon atoms. Specific examples of preferable aryl-group moiety includes the later-described preferable specific examples of the aryl group having 6 to 50 ring carbon atoms. The same applies to more preferable specific examples and further preferable specific examples of aryl-group moiety.

Specific examples of the heteroaryl-group moiety include the later-described specific examples of the heteroaryl group having 5 to 50 ring atoms. Specific examples of the preferable heteroaryl-group moiety include the later-described preferable specific examples of the heteroaryl group having 5 to 50 ring atoms. The same applies to more preferable specific examples and further preferable specific examples of heteroaryl-group moiety.

When a plurality of the groups represented by Si($R_{101}$)($R_{102}$)($R_{103}$) are present in the formula (200), the groups may be mutually the same or different. When a plurality of the groups represented by N($R_{104}$)($R_{105}$) are present in the formula (200), the groups may be mutually the same or different.

The aryl group having 6 to 50 (preferably 6 to 30, more preferably 6 to 24, further preferably 6 to 18) ring carbon atoms represented by $R_1$ to $R_{11}$ may be a fused ring or a non-fused ring. Examples of the aryl group include a phenyl group, biphenylyl group, terphenylyl group, naphthyl group, acenaphthylenyl group, anthryl group, benzoanthryl group, aceanthryl group, phenanthryl group, benzo[c]phenanthryl group, phenalenyl group, fluorenyl group, picenyl group, pentaphenyl group, pyrenyl group, chrysenyl group, benzo[g]chrysenyl group, s-indecenyl group, as-indecenyl group, fluoranthenyl group, benzo[k]fluoranthenyl group, triphenylenyl group, benzo[b]triphenylenyl group and perylenyl group. Among the above, a phenyl group, biphenylyl group, terphenylyl group, naphthyl group, anthryl group, pyrenyl group, and fluoranthenyl group are preferable, a phenyl group, biphenylyl group, and terphenylyl group are more preferable, and a phenyl group is further preferable.

The heteroaryl group having 5 to 50 (preferably 5 to 30, more preferably 5 to 18, especially preferably 5 to 13) ring atoms represented by $R_1$ to $R_{11}$ includes at least one, preferably 1 to 5, more preferably 1 to 4, further preferably 1 to 3 hetero atoms. Examples of the hetero atoms include nitrogen atom, sulfur atom and oxygen atom, among which nitrogen atom and oxygen atom are preferable.

Examples of the heteroaryl group include a pyrrolyl group, furyl group, thienyl group, pyridyl group, imidazopyridyl group, pyridazinyl group, pyrimidinyl group, pyrazinyl group, triazinyl group, imidazolyl group, oxazolyl group, thiazolyl group, pyrazolyl group, isoxazolyl group, isothiazolyl group, oxadiazolyl group, thiadiazole group, triazolyl group, tetrazolyl group, indolyl group, isoindolyl group, benzofuranyl group, isobenzofuranyl group, benzothienyl group, isobenzothienyl group, indolizinyl group, quinolizinyl group, quinolyl group, isoquinolyl group, cinnolyl group, phthalazinyl group, quinazolinyl group, quinoxalinyl group, benzimidazolyl group, benzoxazolyl group, benzothiazolyl group, indazolyl group, benzisoxazolyl group, benzisothiazolyl group, dibenzofuranyl group, dibenzothienyl group, carbazolyl group, 9-phenylcarbazolyl group, phenanthridinyl group, acridinyl group, phenanthrolinyl group, phenazinyl group, phenothiazinyl group, phenoxazinyl group and xanthenyl group. Among the above, a pyridyl group, imidazopyridyl group, pyridazinyl group, pyrimidinyl group, pyrazinyl group, triazinyl group, benzimidazolyl group, dibenzofuranyl group, dibenzothienyl group, carbazolyl group, 9-phenylcarbazolyl group, phenanthrolinyl group, and quinazolinyl group are preferable.

Examples of the halogen atom, cyano group, substituted or unsubstituted alkyl group having 1 to 20 carbon atoms, substituted or unsubstituted alkenyl group having 1 to 20 carbon atoms, substituted or unsubstituted alkynyl group having 1 to 20 carbon atoms, substituted or unsubstituted cycloalkyl group having 3 to 20 ring carbon atoms, amino group, substituted or unsubstituted alkoxy group having 1 to 20 carbon atoms, substituted or unsubstituted fluoroalkyl group having 1 to 20 carbon atoms, substituted or unsubstituted fluoroalkoxy group having 1 to 20 carbon atoms, substituted or unsubstituted aryloxy group having 6 to 50 ring carbon atoms, substituted or unsubstituted alkylthio group having 1 to 20 carbon atoms, substituted or unsubstituted arylthio group having 6 to 50 ring carbon atoms, group represented by —Si($R_{101}$)($R_{102}$)($R_{103}$), group represented by —N($R_{104}$)($R_{105}$), substituted or unsubstituted aryl group having 6 to 50 ring carbon atoms, or substituted or unsubstituted heteroaryl group having 5 to 50 ring atoms, which serves as the substituent for the three-or-more-atom cyclic structure formed of atoms selected from a carbon atom, oxygen atom, sulfur atom, and nitrogen atom in combination of the two ring-forming carbon atoms with which $R_n$ and $R_{n+1}$ are bonded in the formula (200), are the same as the specific examples of the respective groups for $R_1$ to $R_{11}$. Preferable number of carbon atoms or number of atoms and preferable groups are also the same. Examples of the substituent include a substituted or unsubstituted alkyl group having 1 to 20 carbon atoms and a substituted or unsubstituted aryl group having 6 to 50 ring carbon atoms.

In the formula (200), the three-or-more-atom cyclic structure formed of atoms selected from a carbon atom, oxygen atom, sulfur atom, and nitrogen atom in combination with two ring-forming carbon atoms with which $R_n$ and $R_{n+1}$ are bonded is, though not specifically limited, preferably a ring having 3 to 7 atoms, more preferably 5 or 6 atoms.

Further, in the organic EL device of the first exemplary embodiment, the three-or-more-atom cyclic structure is also preferably any one of cyclic structures selected from formulae (2a) to (2g) or any one of groups selected from the formulae (2h) to (2j) below.

[Formula 43]

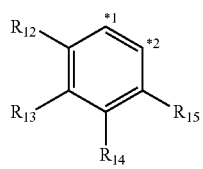

(2a)

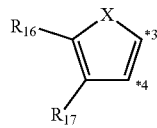

(2b)

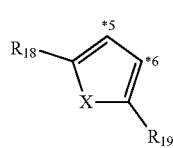

(2c)

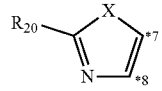

(2d)

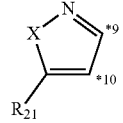

(2e)

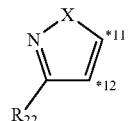

(2f)

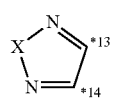

(2g)

In the formulae (2a) to (2g), one of *1 and *2, one of *3 and *4, one of *5 and *6, one of *7 and *8, one of *9 and *10, one of *11 and *12, and one of *13 and *14 are each a carbon atom bonded with $R_n$, and the other of *1 and *2, the other of *3 and *4, the other of *5 and *6, the other of *7 and *8, the other of *9 and *10, the other of *11 and *12, and the other of *13 and *14 are each a carbon atom bonded with $R_{n+1}$.

The ring-forming carbon atom bonded with $R_n$ may be either one of the two ring-forming carbon atoms represented by each of *1 and *2, *3 and *4, *5 and *6, *7 and *8, *9 and *10, *11 and *12, and *13 and *14.

In the formulae (2b) to (2g), X is each independently selected from the group consisting of C($R_{23}$)($R_{24}$), N$R_{25}$, an oxygen atom, and a sulfur atom.

$R_{12}$ to $R_{25}$ are each independently a hydrogen atom or a substituent, and $R_{12}$ to $R_{25}$ as the substituents are each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms.

$R_{12}$ and $R_{13}$ are mutually bonded to form a cyclic structure or are not mutually bonded to form no cyclic structure.

$R_{13}$ and $R_{14}$ are mutually bonded to form a cyclic structure or are not mutually bonded to form no cyclic structure.

$R_{14}$ and $R_{15}$ are mutually bonded to form a cyclic structure or are not mutually bonded to form no cyclic structure.

$R_{16}$ and $R_{17}$ are mutually bonded to form a cyclic structure or are not mutually bonded to form no cyclic structure.

$R_{23}$ and $R_{24}$ are mutually bonded to form a cyclic structure or are not mutually bonded to form no cyclic structure.

$R_{101}$ to $R_{105}$ represent the same as $R_{101}$ to $R_{105}$ in the formula (200), respectively.

Examples, specific example and preferable examples of $R_{12}$ to $R_{25}$ are the same as those of $R_1$ to $R_{11}$ in the formula (200).

[Formula 44]

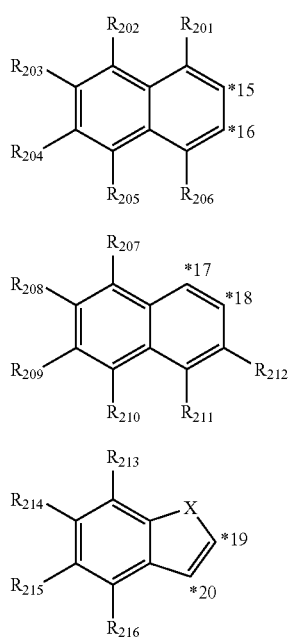

In the formulae (2h) to (2j), *15 and *16, *17 and *18, and *19 and *20 each represent the ring-forming carbon atoms before being bonded with $R_n$ and $R_{n+1}$, the ring-forming carbon atom bonded with $R_n$ may be either one of the two ring-forming carbon atoms represented by each of *1 and *2, and *3 and *4.

$R_{201}$ to $R_{216}$ represent the same as the above-described $R_{12}$ to $R_{25}$. X represents the same as the above-described X.

Adjacent ones of $R_{201}$ to $R_{216}$ may be mutually bonded to form a cyclic structure.

Examples, specific example and preferable examples of $R_{23}$ to $R_{25}$ and $R_{201}$ to $R_{216}$ included in X are the same as those of $R_1$ to $R_{11}$ in the formula (200).

In the organic EL device of the first exemplary embodiment, it is preferable that at least one of $R_2$, $R_4$, $R_5$, $R_{10}$, and $R_{11}$ (preferably one of $R_2$, $R_5$ and $R_{10}$, more preferably $R_2$) in the formula (200) is a group not involved in the formation of the three-or-more-atom cyclic structure, and is selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$) ($R_{101}$ to $R_{103}$ representing the same as $R_{101}$ to $R_{103}$ in the formula (200), respectively), a group represented by —N($R_{104}$)($R_{105}$) ($R_{104}$ and $R_{105}$ representing the same as $R_{104}$ and $R_{105}$ in the formula (200), respectively), a substituted or unsubstituted aryl group having 6 to 50 ring carbon atoms, and a substituted or unsubstituted heteroaryl group having 5 to 50 ring atoms.

Specific examples, preferable number of carbon atoms and preferable number of atoms of these groups are the same as described for $R_1$ to $R_{11}$.

It is preferable that (i) when a three-or-more-atom cyclic structure is formed of atoms selected from a carbon atom, oxygen atom, sulfur atom, and nitrogen atom in combination with the two ring-forming carbon atoms with which $R_n$ and $R_{n+1}$ are bonded, the substituent $R_X$ of the cyclic structure, (ii) $R_1$ to $R_{11}$ not involved in the formation of the three-or-more-atom cyclic structure in the formula (200), and (iii) $R_{12}$ to $R_{22}$, and $R_{201}$ to $R_{216}$ in the formulae (2a) to (2j) are each independently a hydrogen atom or a group selected from the group consisting of a substituted or unsubstituted alkyl group having 1 to 20 carbon atoms, a group represented by —N($R_{104}$)($R_{105}$) ($R_{104}$ and $R_{105}$ representing the same as $R_{104}$ and $R_{105}$ in the formula (200), respectively), a substituted or unsubstituted aryl group having 6 to 50 ring carbon atoms, a substituted or unsubstituted heteroaryl group having 5 to 50 ring atoms, a group represented by a formula (s-1) below, a group represented by a formula (s-2) below, a group represented by a formula (s-3) below, and a group represented by a formula (s-4) below.

[Formula 45]

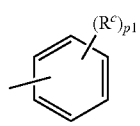  (s-1)

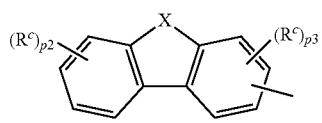  (s-2)

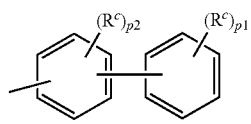  (s-3)

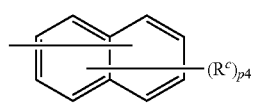  (s-4)

In the formulae (s-1) to (s-4): $R_C$ is each independently a hydrogen atom or a substituent;

$R^c$ as the substituent is each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms;

p1 is 5;

p2 is 4;

p3 is 3;

p4 is 7; and $R_{101}$ to $R_{105}$ represent the same as $R_{101}$ to $R_{105}$ in the formula (200), respectively.

In the formula (s-2), X represents the same as X in the formulae (2b) to (2g).

Examples, specific example and preferable examples of $R_{23}$ to $R_{25}$ and $R^c$ included in X are the same as those of $R_1$ to $R_{11}$ in the formula (200).

The compound represented by the formula (200) is preferably a compound represented by one of formulae (201) to (206), more preferably a compound represented by one of the formulae (201) to (204), further preferably a compound represented by one of the formulae (201) and (204).

[Formula 46]

(201)

(202)

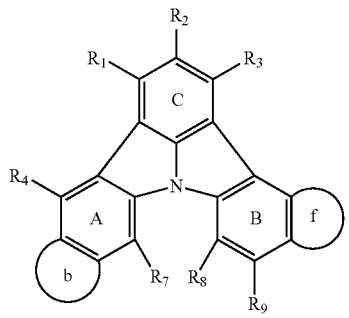

(203)

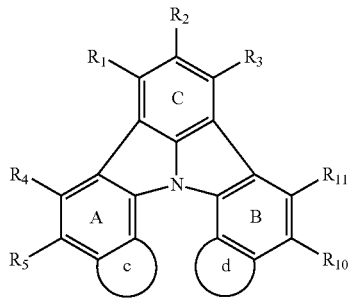

(204)

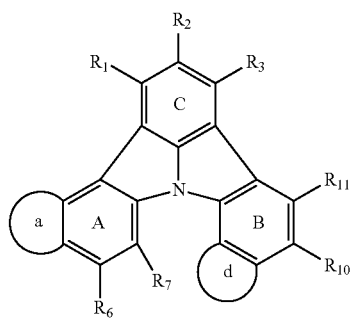

(205)

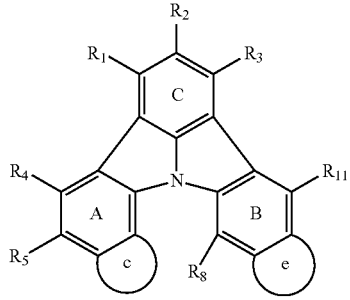

(206)

In the formulae (201) to (206), $R_1$ to $R_{11}$ represent the same as described above. Specific examples, preferable number of carbon atoms, number of atoms, and preferable groups are also the same as described above. The rings a to f are each independently the three-or-more-atom cyclic structure. The rings a to f each independently include one or more substituents Ry or are unsubstituted, the substituents Ry being mutually bonded to form a cyclic structure or not mutually bonded to form no cyclic structure. The substituent Ry is the same as the substituent represented by $R_1$ to $R_{11}$. It should be noted that the number of the atoms of the three-or-more-atom cyclic structure does not include the number of atoms of the additional substituent Ry.

In the formulae (201) to (206), the three-or-more-atom cyclic structure formed of atoms selected from a carbon atom, oxygen atom, sulfur atom, and nitrogen atom, which is represented by the rings a to f, is, though not specifically limited, preferably a ring having 3 to 7 atoms, more preferably 5 or 6 atoms. Further, in the formulae (201) to (206), the three-or-more-atom cyclic structure is also preferably any one of rings selected from the formulae (2a) to (2g) and any one of groups selected from the formulae (2h) to (2j).

In the formulae (201) to (206), specific examples of the additional substituent Ry are the same as the groups described in $R_1$ to $R_{11}$. Specific examples, preferable number of carbon atoms, number of atoms, and preferable groups are also the same as described above.

The compound represented by the formula (200) is also preferably a compound represented by one of formulae (207) to (212) below, more preferably a compound represented by one of the formulae (208) and (211).

[Formula 47]

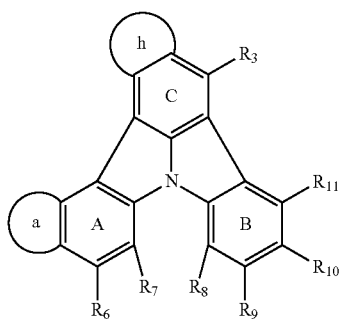
(207)

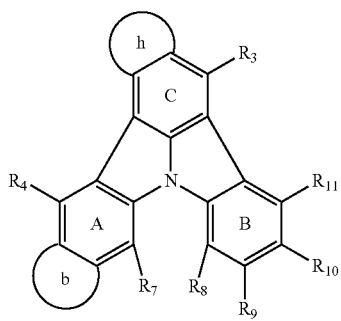
(208)

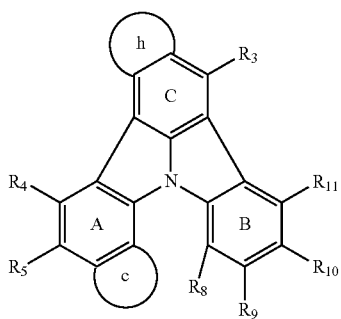
(209)

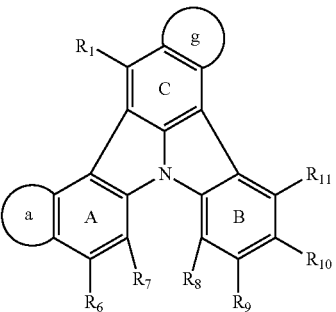
(210)

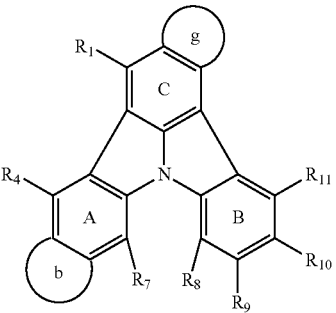
(211)

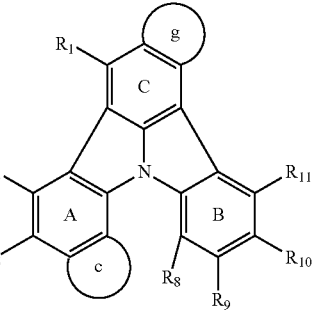
(212)

In the formulae (207) to (212), $R_1$ and $R_3$ to $R_{11}$ represent the same as described above. Specific examples, preferable number of carbon atoms, number of atoms, and preferable groups are also the same as described above. The rings a to c and g to h are each independently a three-or-more-atom cyclic structure formed of atoms selected from a carbon atom, oxygen atom, sulfur atom, and nitrogen atom. The ring(s) may include an additional substituent(s), the substituents being optionally mutually bonded to form a cyclic structure. The additional substituent is the same as the substituent represented by $R_1$ to $R_{11}$. It should be noted that the number of the atoms of the three-or-more-atom cyclic structure does not include the number of atoms of the additional substituent.

In the formulae (207) to (212), the three-or-more-atom cyclic structure formed of atoms selected from a carbon atom, oxygen atom, sulfur atom, and nitrogen atom in combination with two ring-forming carbon atoms, which is represented by the rings a to c and g to h, is, though not specifically limited, preferably a ring having 3 to 7 atoms, more preferably 5 or 6 atoms. Further, the three-or-more-atom cyclic structure is also preferably any one of rings selected from the formulae (2a) to (2g) and groups selected from the formulae (2h) to (2j).

In the formulae (207) to (212), specific examples of the additional substituent are the same as the groups described in $R_1$ to $R_{11}$. Specific examples, preferable number of carbon atoms, number of atoms, and preferable groups are also the same as described above.

The compound represented by the formula (200) is also preferably a compound represented by one of formulae (213) to (221) below, more preferably a compound represented by the formula (213).

[Formula 48]

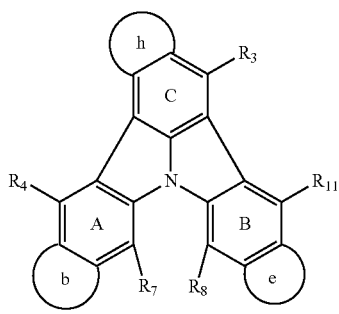

(213)

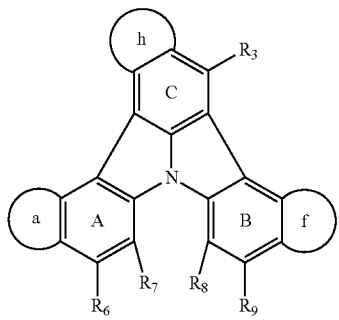

(214)

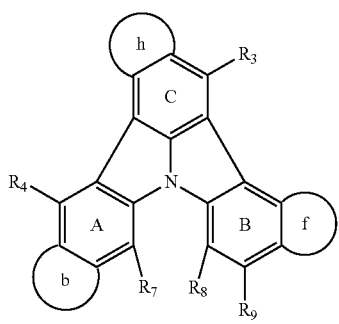

(215)

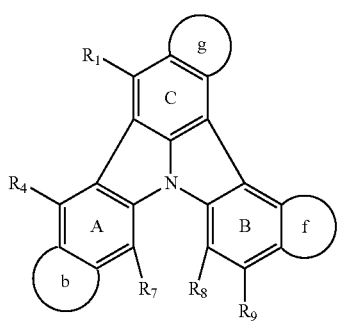

(216)

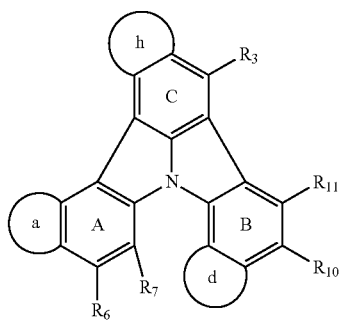

(217)

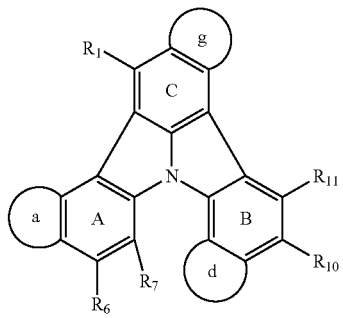

(218)

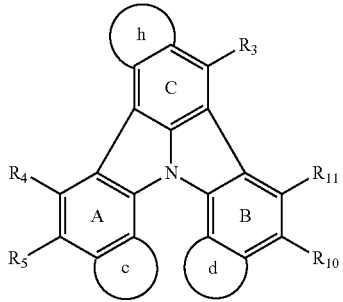

(219)

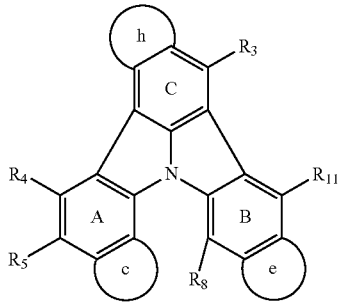

(220)

(221)

In the formulae (213) to (221), $R_1$ and $R_3$ to $R_{11}$ represent the same as described above. Specific examples, preferable number of carbon atoms, number of atoms, and preferable groups are also the same as described above. The rings a to h are each independently a three-or-more-atom cyclic structure formed of atoms selected from a carbon atom, oxygen atom, sulfur atom, and nitrogen atom. The ring(s) may further include a substituent(s), the substituents being optionally mutually bonded to form a cyclic structure. The additional substituent is the same as the substituent represented by $R_1$ to $R_{11}$. It should be noted that the number of the atoms of the three-or-more-atom cyclic structure does not include the number of atoms of the additional substituent.

In the formulae (213) to (221), the three-or-more-atom cyclic structure formed of atoms selected from a carbon atom, oxygen atom, sulfur atom, and nitrogen atom, which is represented by the rings a to h, is, though not specifically limited, preferably a ring having 3 to 7 atoms, more preferably 5 or 6 atoms. Further, the three-or-more-atom cyclic structure is also preferably any one of rings selected from the formulae (2a) to (2g) and (2h) to (2j).

In the formulae (213) to (221), the three-or-more-atom cyclic structure formed of atoms selected from a carbon atom, oxygen atom, sulfur atom, and nitrogen atom, which is represented by the rings a to h, is a three-or-more-atom cyclic structure formed of atoms selected from a carbon atom, oxygen atom, and sulfur atom, for instance. Further, when the ring g or h has a substituent, the hetero atom included in the heteroaryl group of the substituent is, for instance, a sulfur atom and/or an oxygen atom.

In the formulae (213) to (221), specific examples of the additional substituent are the same as the groups described in $R_1$ to $R_{11}$. Specific examples, preferable number of carbon atoms, number of atoms, and preferable groups are also the same as described above.

In the formulae (201) to (206), (207) to (212) and (213) to (221), it is preferable that the additional substituent Ry included in the rings a to h or $R_1$ to $R_{11}$ not forming the rings a to h are each independently selected from the group consisting of a hydrogen atom, a substituted or unsubstituted alkyl group having 1 to 20 carbon atoms, a group represented by —N($R_{104}$)($R_{105}$), a substituted or unsubstituted aryl group having 6 to 50 ring carbon atoms, substituted or unsubstituted heteroaryl group having 5 to 50 ring atoms, a group represented by a formula (s-1) below, a group represented by a formula (s-2) below, a group represented by a formula (s-3) below, and a group represented by a formula (s-4) below.

[Formula 49]

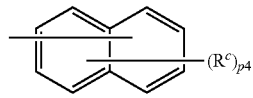
(s-1)

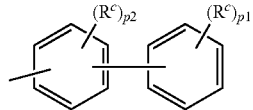
(s-2)

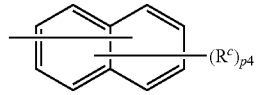
(s-3)

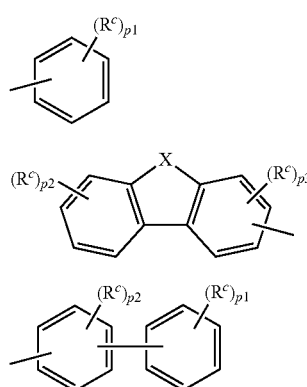
(s-4)

In the formulae: $R_C$ represents the same as the above-described $R_1$ to $R_{11}$. X represents the same as the above-described X;

p1 is 5, p2 is 4, p3 is 3, p4 is 7; and

Examples, specific example and preferable examples of $R_{23}$ to $R_{25}$ and $R^c$ included in X are the same as those of $R_1$ to $R_{11}$ in the formula (200).

When the ring g or h has an additional substituent, examples of the substituent include a substituted or unsubstituted alkyl group having 1 to 20 carbon atoms, a substituted or unsubstituted aryl group having 6 to 50 ring carbon atoms, the group represented by the formula (s-1) below, the group represented by the formula (s-3) below, and the group represented by the formula (s-4) below.

[Formula 50]

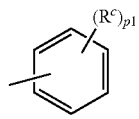
(s-1)

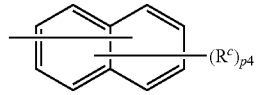
(s-3)

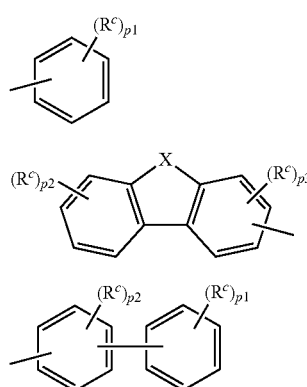
(s-4)

In the formulae: $R_C$ each independently represents the same as the above-described $R_1$ to $R_{11}$; p1 is 5; p2 is 4; and p4 is 7.

The compound represented by the formula (200) is preferably represented by one of formulae (201-1), (202-1), (203-1), and (204-1).

[Formula 51]

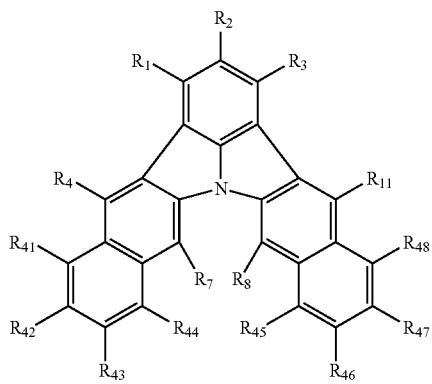
(201-1)

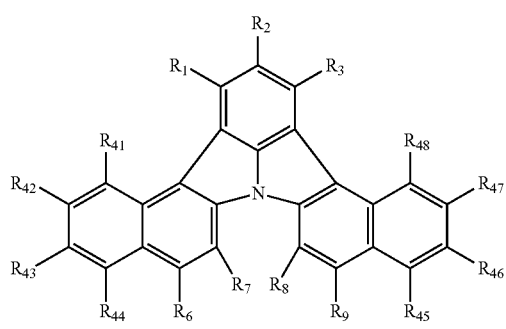

(202-1)

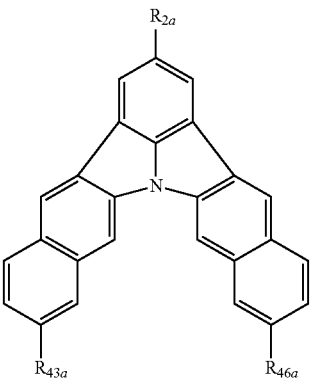

(210)

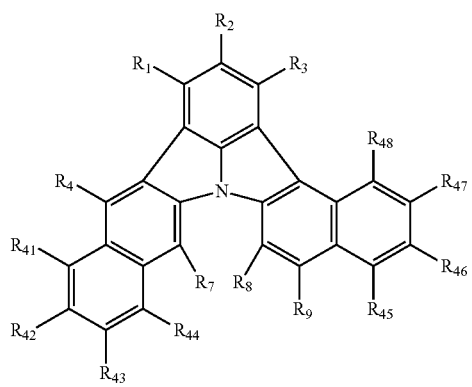

(203-1)

In the formulae (210): $R_{2a}$ is a substituted or unsubstituted aryl group having 6 to 30 ring carbon atoms; and $R_{43a}$ and $R_{46a}$ each independently selected from the group consisting of a substituted or unsubstituted aryl group having 6 to 30 ring carbon atoms, and a substituted amino group.

$R_{2a}$ is preferably a substituted or unsubstituted phenyl group, the substituent for the phenyl group preferably being an alkyl group having 1 to 5 carbon atoms.

$R_{43a}$ and $R_{46a}$ are each preferably an unsubstituted phenyl group.

$R_{43a}$ and $R_{46a}$ are also each preferably an arylamino group, the arylamino group preferably being a diphenylamino group.

The compound represented by the formula (200) is also preferably represented by a formula (5-1) below.

[Formula 54]

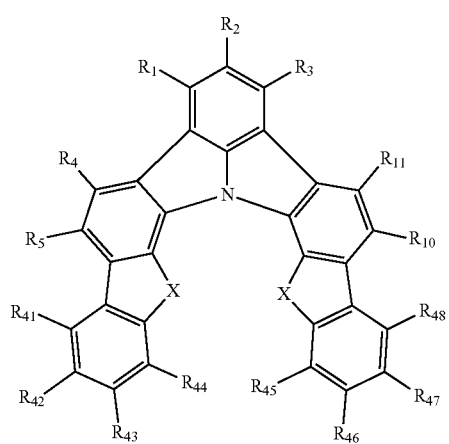

(204-1)

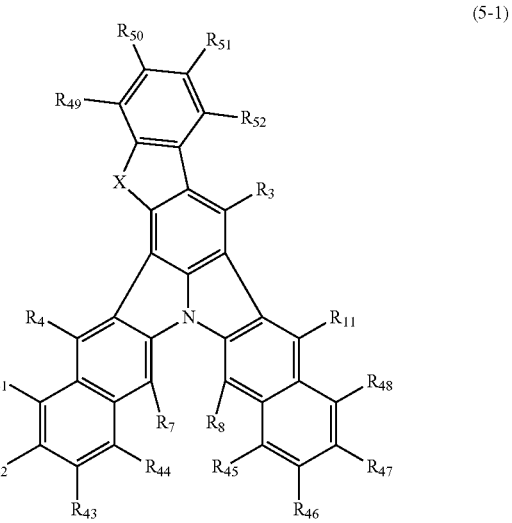

(5-1)

In the formulae (201-1), (202-1), (203-1), and (204-1), X is selected from the group consisting of $C(R_{23})(R_{24})$, $NR_{25}$, O (oxygen atom), and S (sulfur atom). $R_1$ to $R_{11}$, $R_{41}$ to $R_{48}$, and $R_{23}$ to $R_{25}$ are each independently the same as the above-described $R_1$ to $R_{11}$.

Examples, specific example and preferable examples of $R_1$ to $R_{11}$, $R_{41}$ to $R_{48}$ and $R_{23}$ to $R_{25}$ are the same as those of $R_1$ to $R_{11}$ in the formula (200).

The compound represented by the formula (200) is also preferably a compound represented by a formula (210) below.

In the formula (5-1), X is selected from the group consisting of $C(R_{23})(R_{24})$, $NR_{25}$, an oxygen atom, and a sulfur atom. $R_3$, $R_4$, $R_7$, $R_8$, $R_{11}$, $R_{41}$ to $R_{52}$, and $R_{23}$ to $R_{25}$ are each independently the same as the above-described $R_1$ to $R_{11}$.

Examples, specific example and preferable examples of $R_3$, $R_4$, $R_7$, $R_8$, $R_{11}$, $R_{41}$ to $R_{52}$, and $R_{23}$ to $R_{25}$ are the same as those of $R_1$ to $R_{11}$ in the formula (200). For instance, $R_{25}$ is preferably a substituted or unsubstituted aryl group having 6 to 50 ring carbon atoms.

Preparing Method of Second Compound

The second compound of the organic EL device according to the first exemplary embodiment can be prepared, for instance, in accordance with the method described later in Examples. Further, the second compound of the organic EL device according to the first exemplary embodiment can be prepared, for instance, by application of known substitution reactions and/or materials depending on a target compound according to reactions described later in Examples.

Specific examples of the second compound of the organic EL device according to the first exemplary embodiment are shown below. It should be noted that the second compound according to the invention is not limited to these specific examples.

In the specific examples below, Ph denotes a phenyl group, and D denotes a deuterium atom.

[Formula 55]

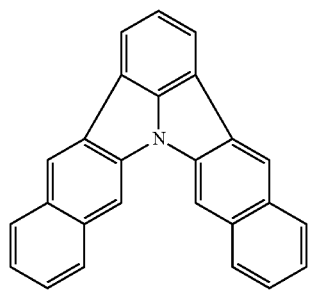

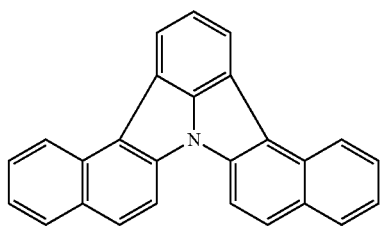

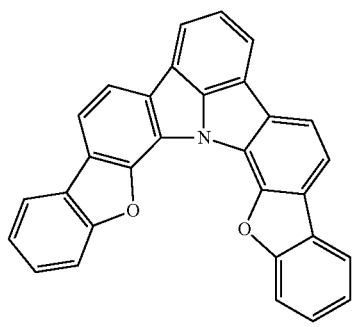

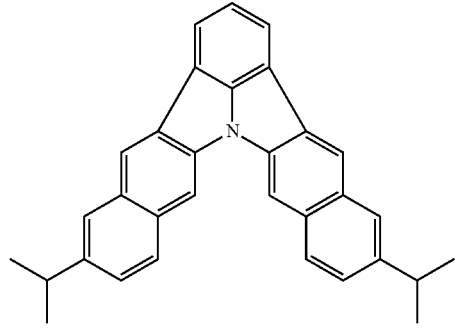

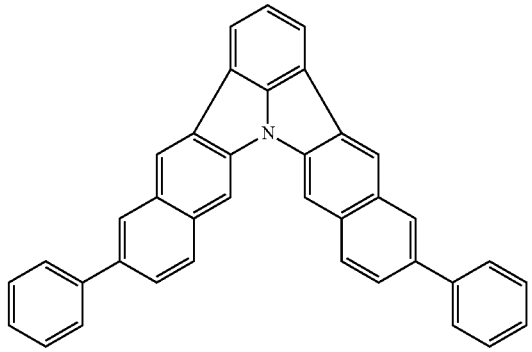

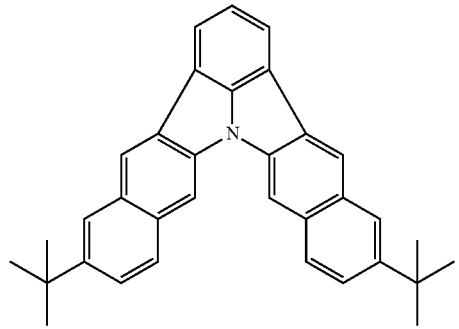

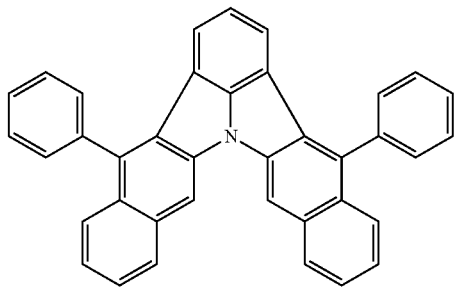

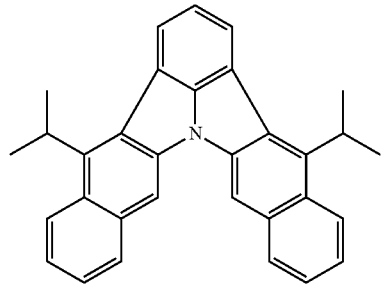

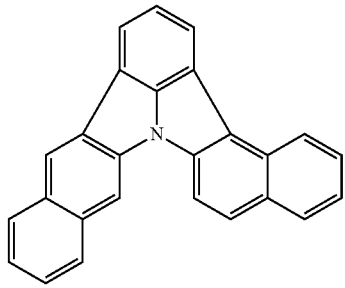

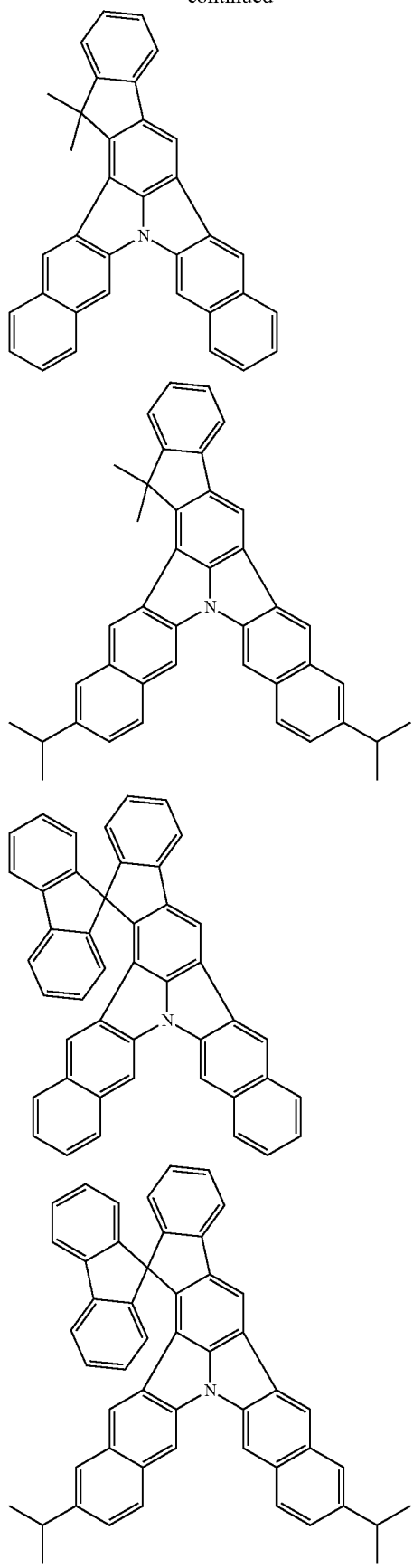
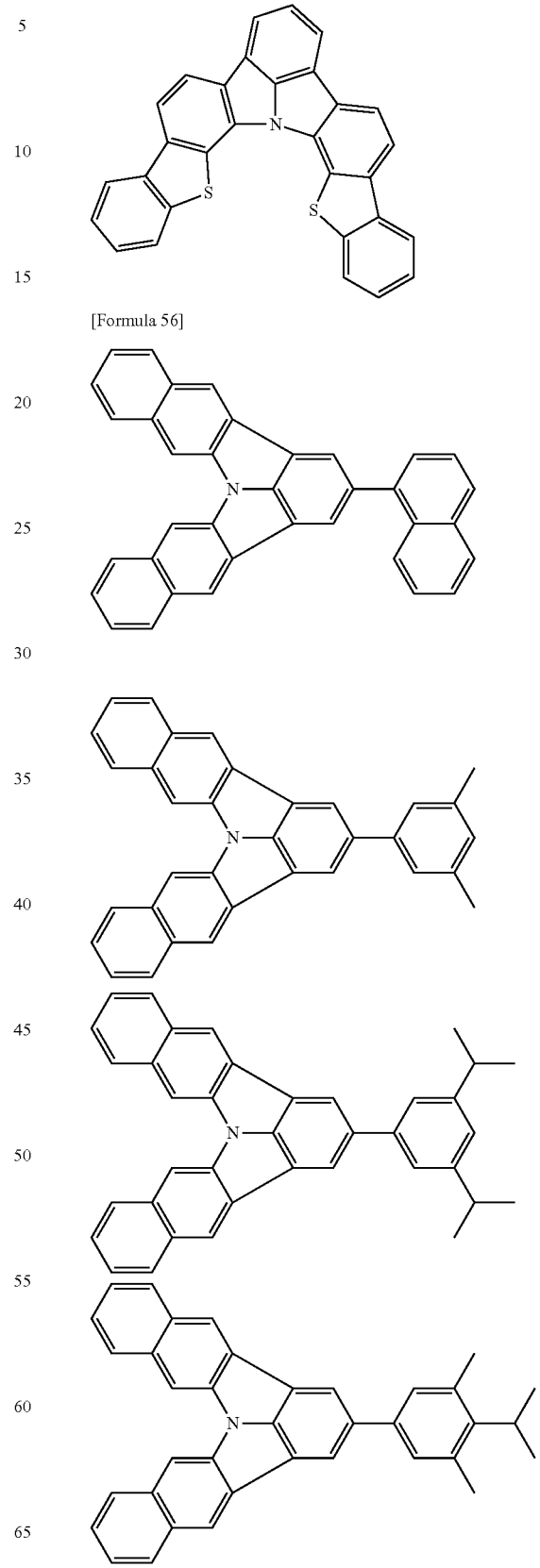

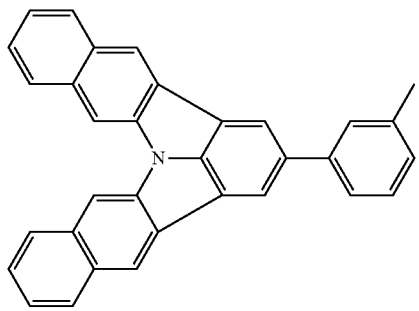
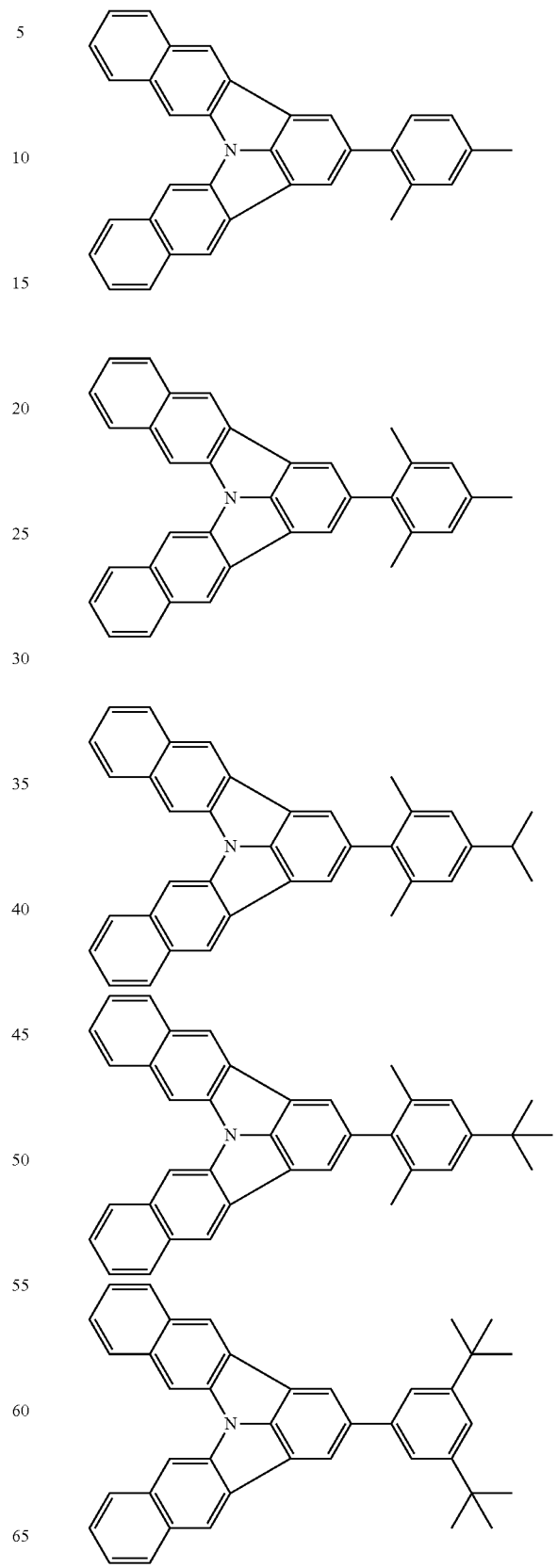

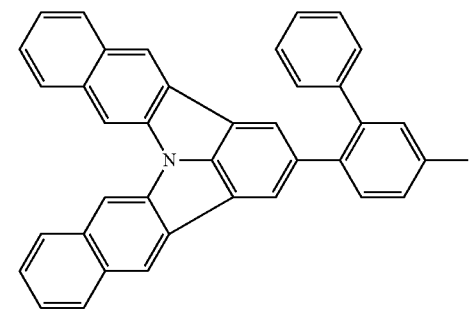
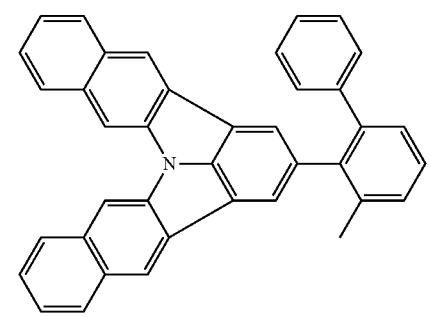
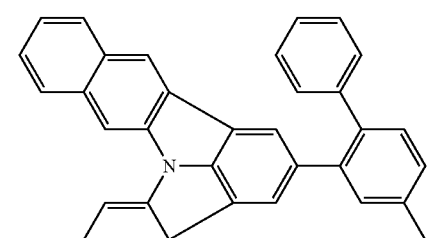
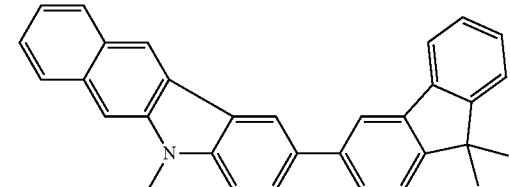
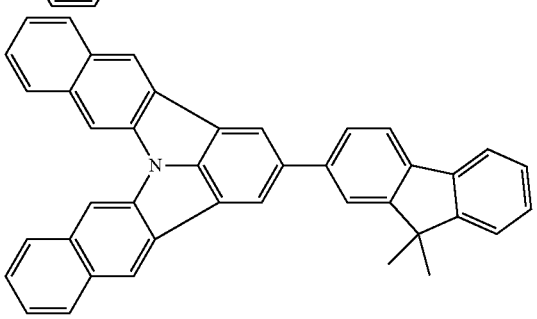
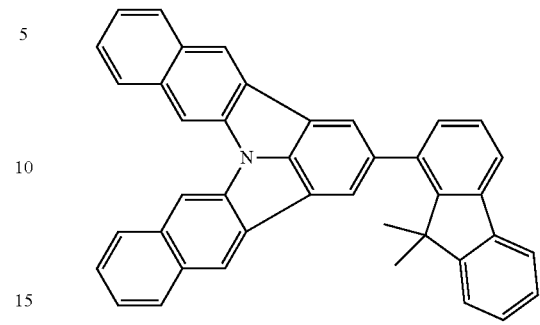
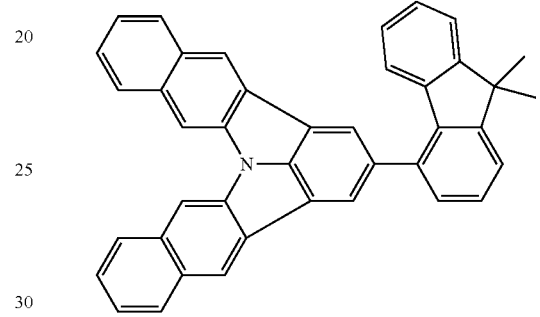
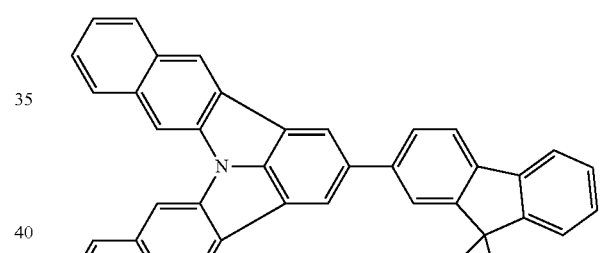
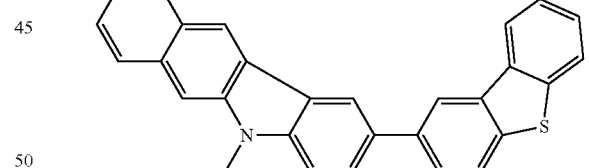
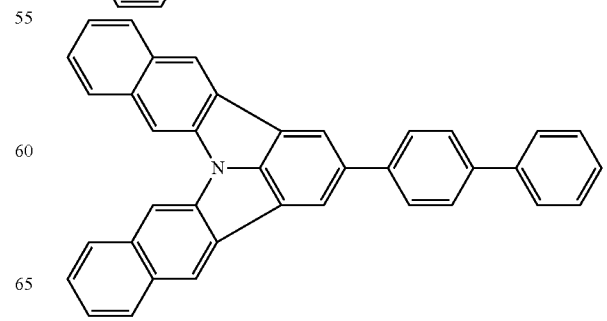

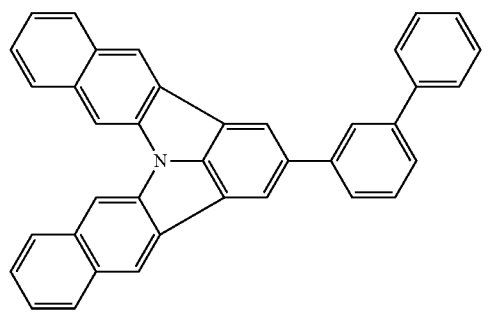
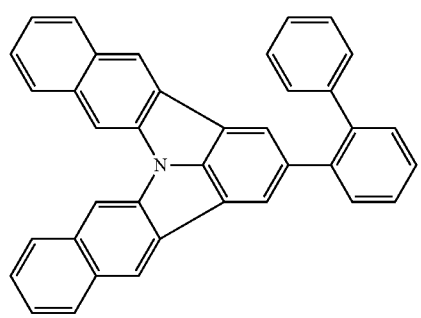
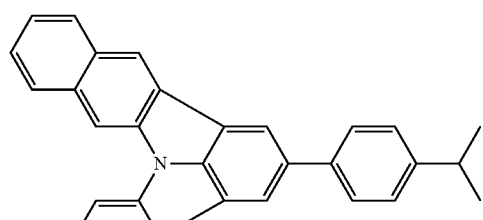
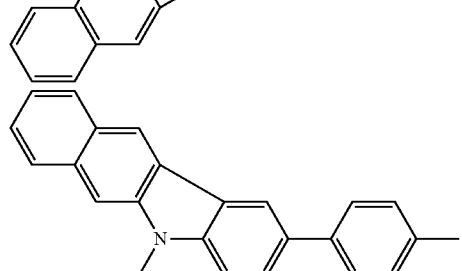
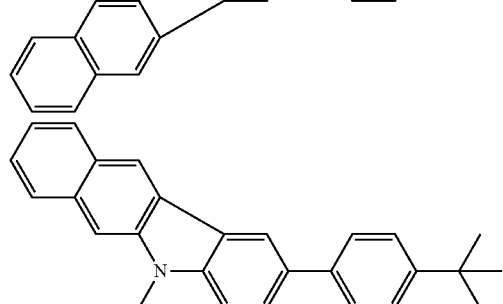
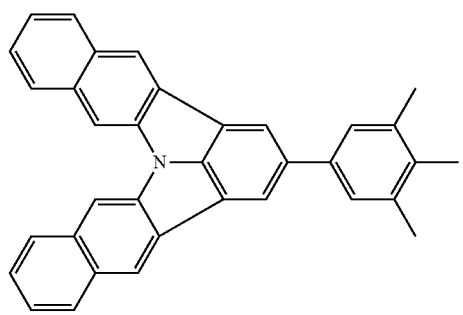
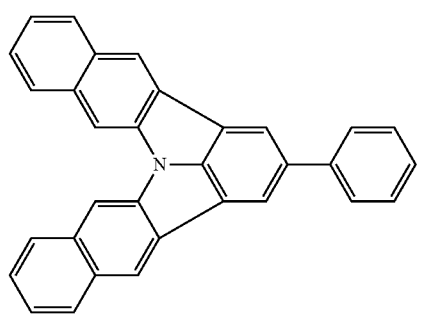
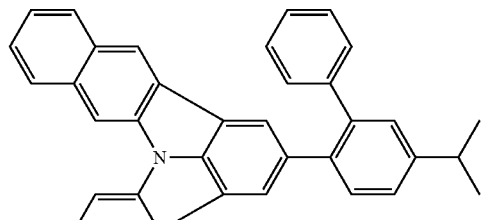
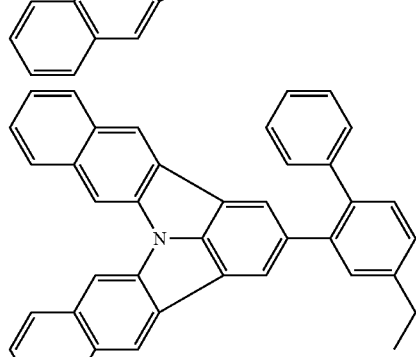
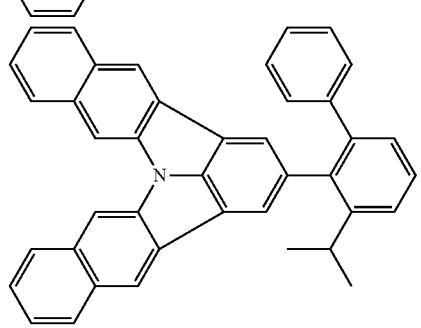

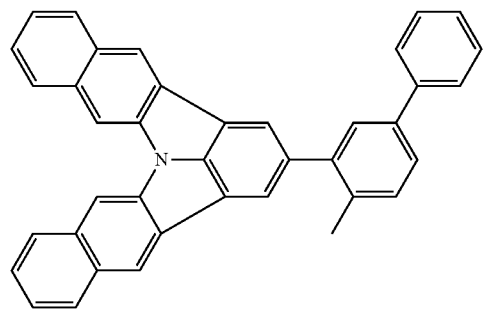
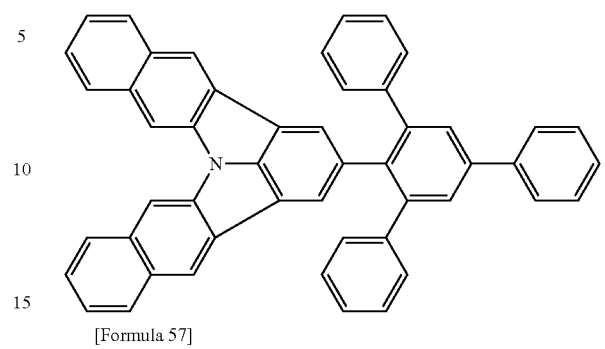
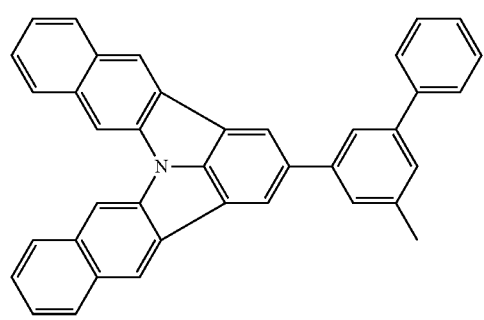
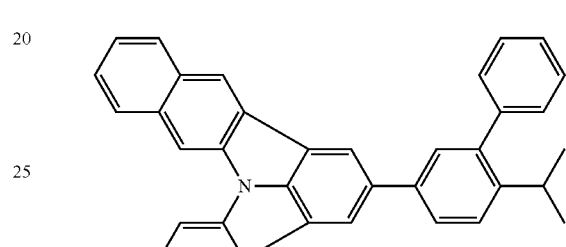
[Formula 57]
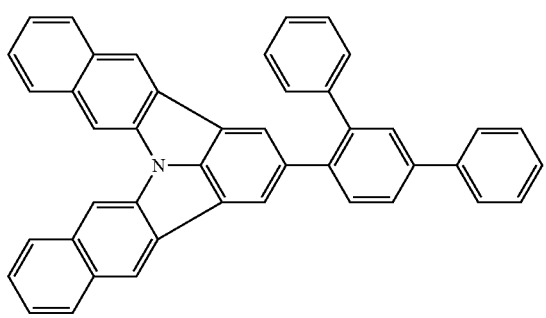
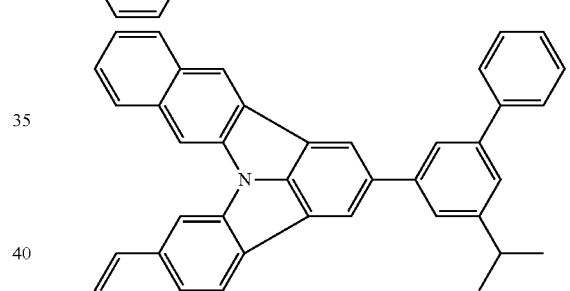
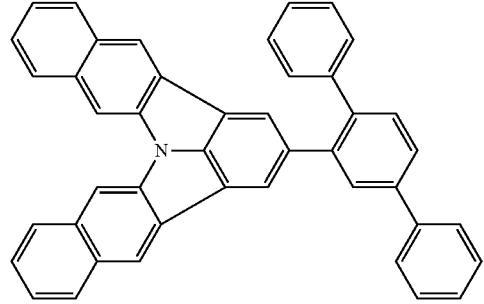
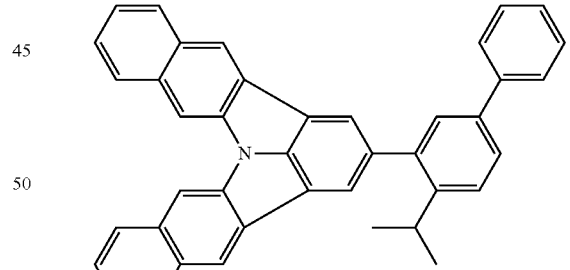
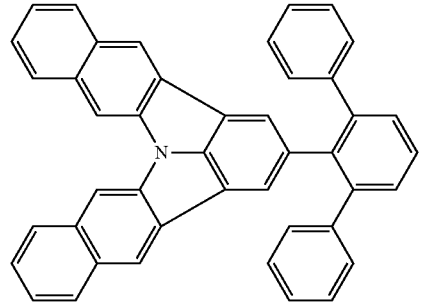
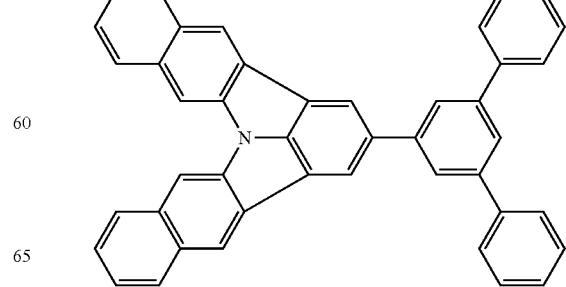

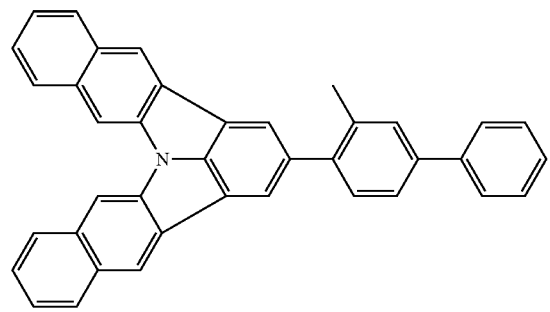
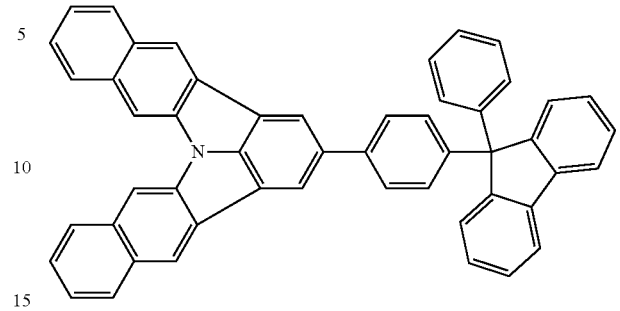
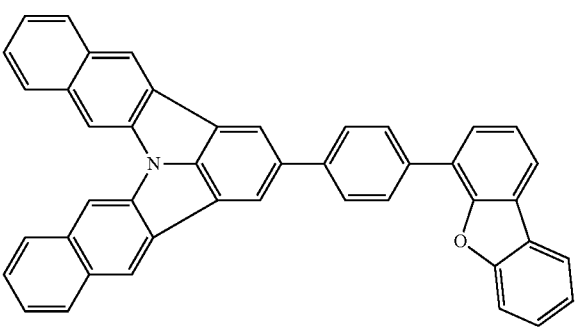
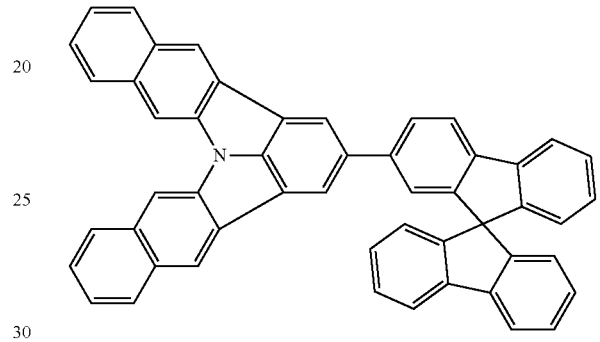
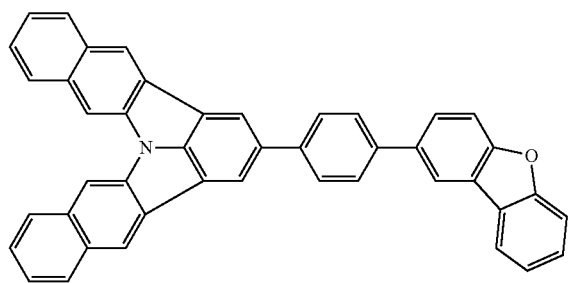
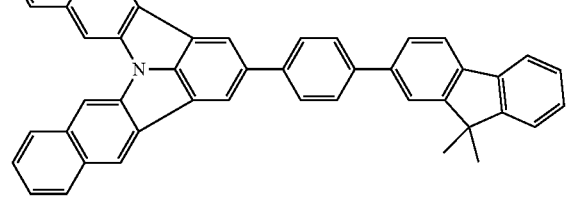

-continued
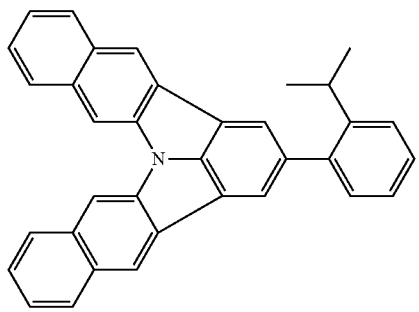
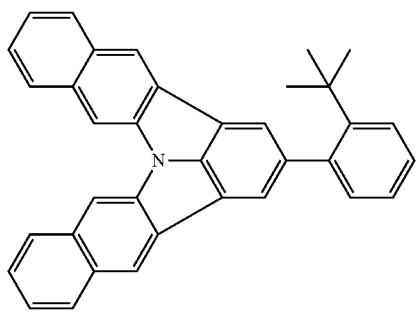
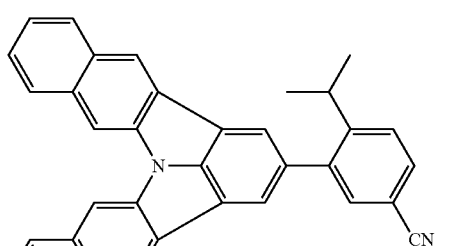
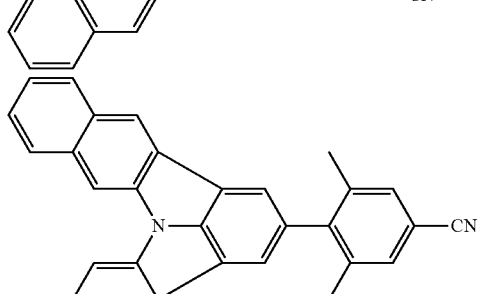
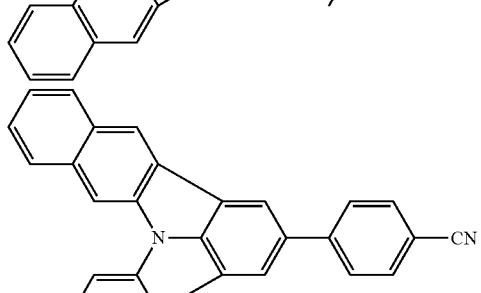
-continued
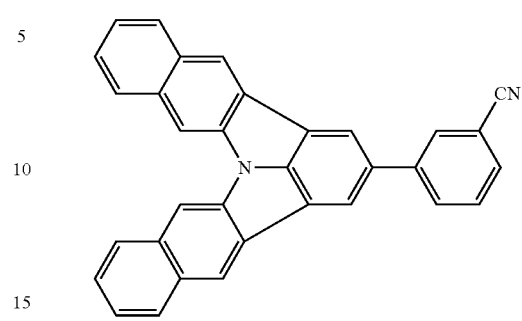
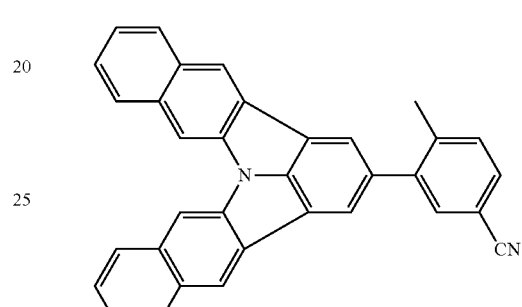
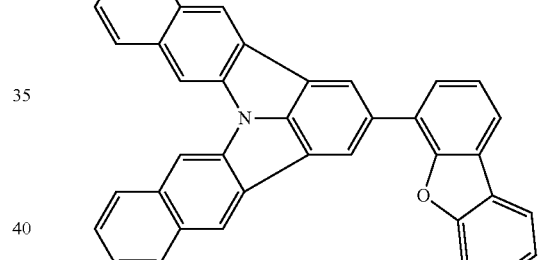
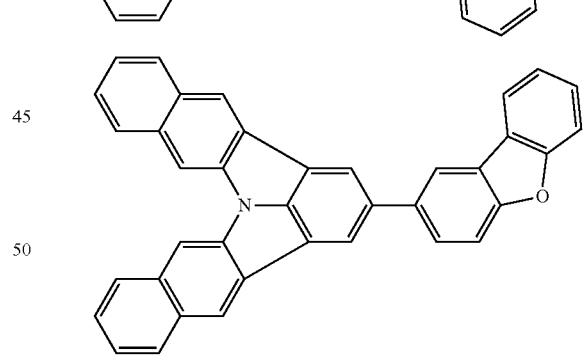
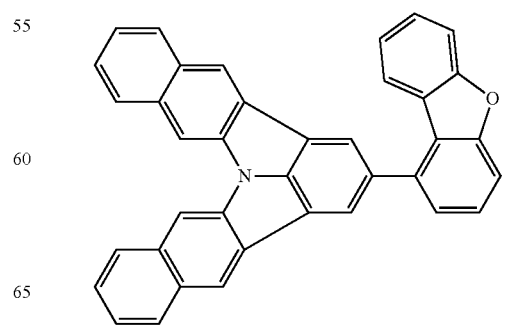

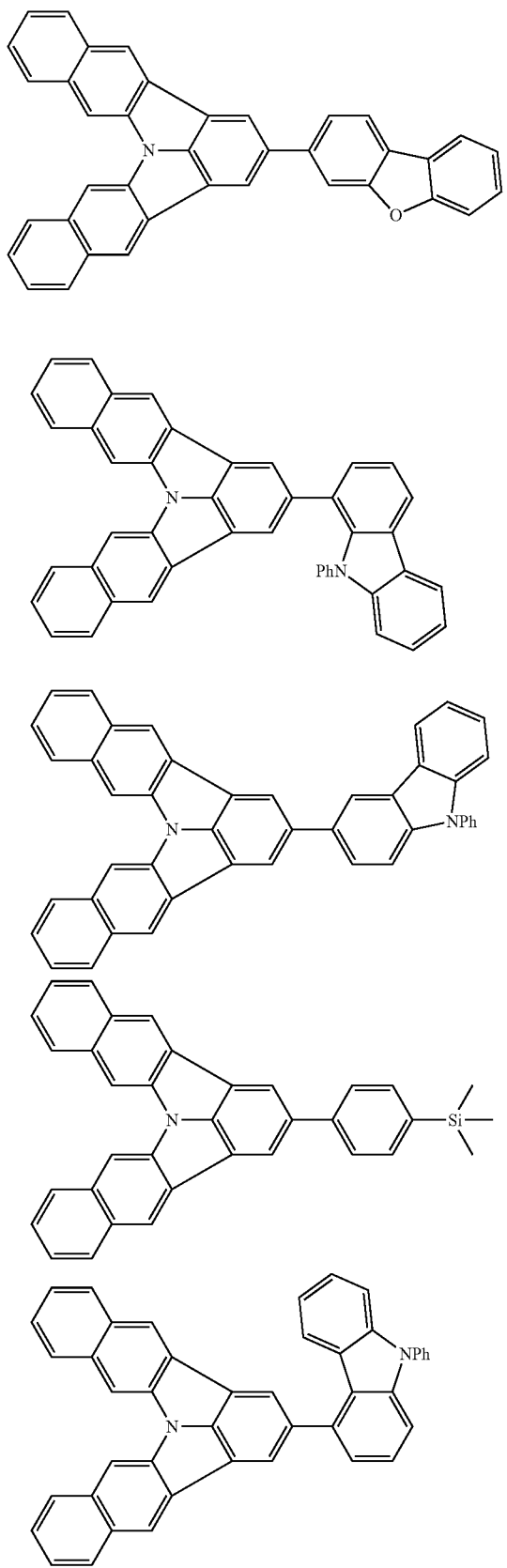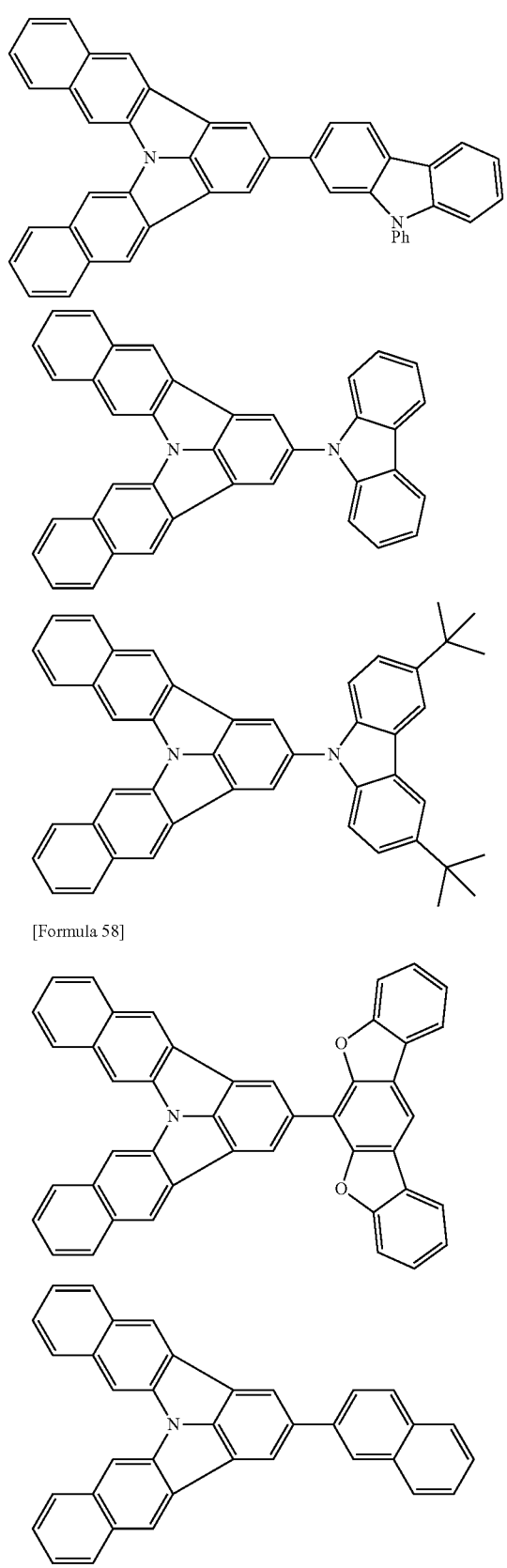
[Formula 58]

71
-continued
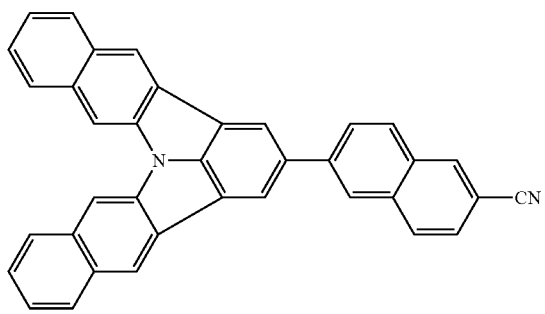
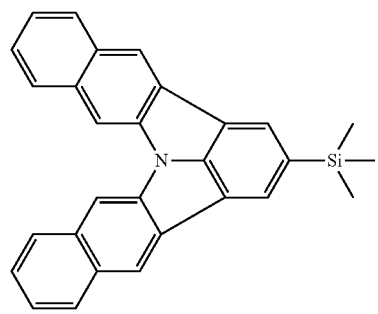
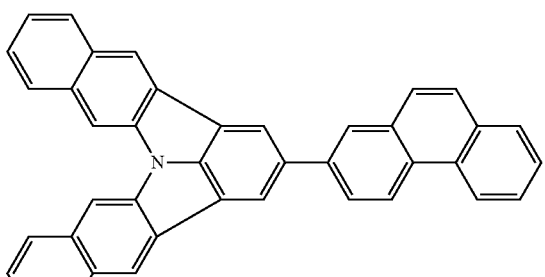
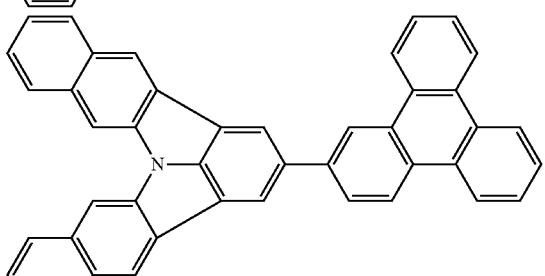
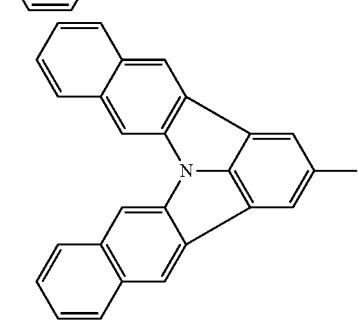
72
-continued
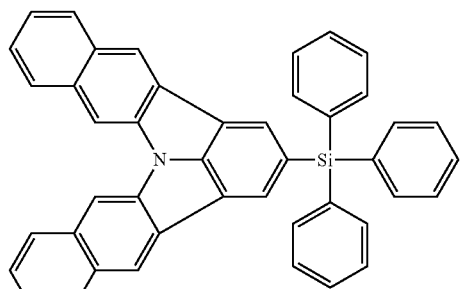
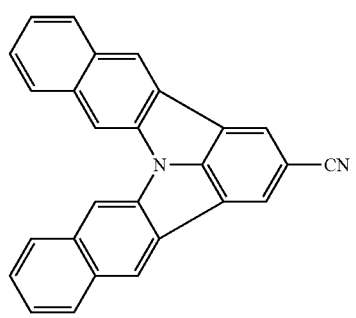
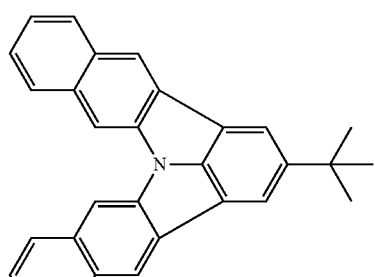
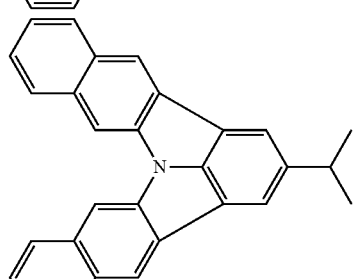
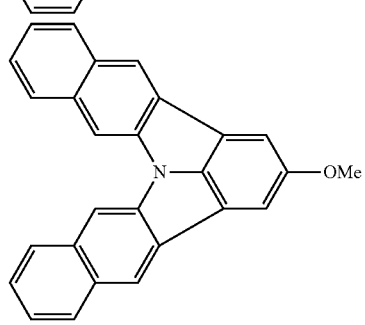

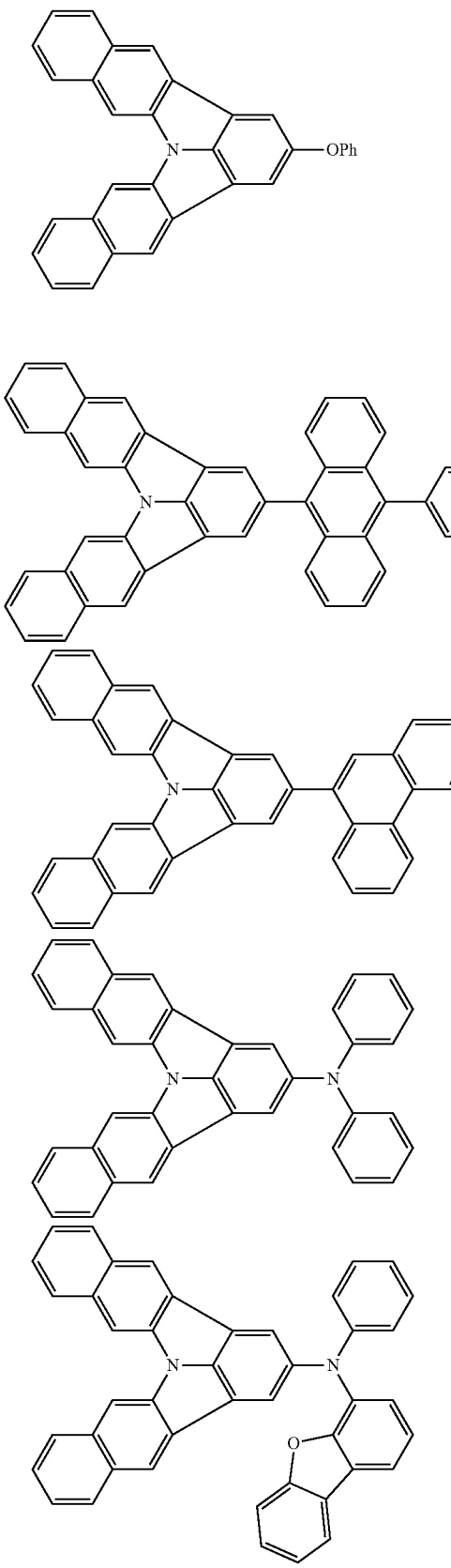
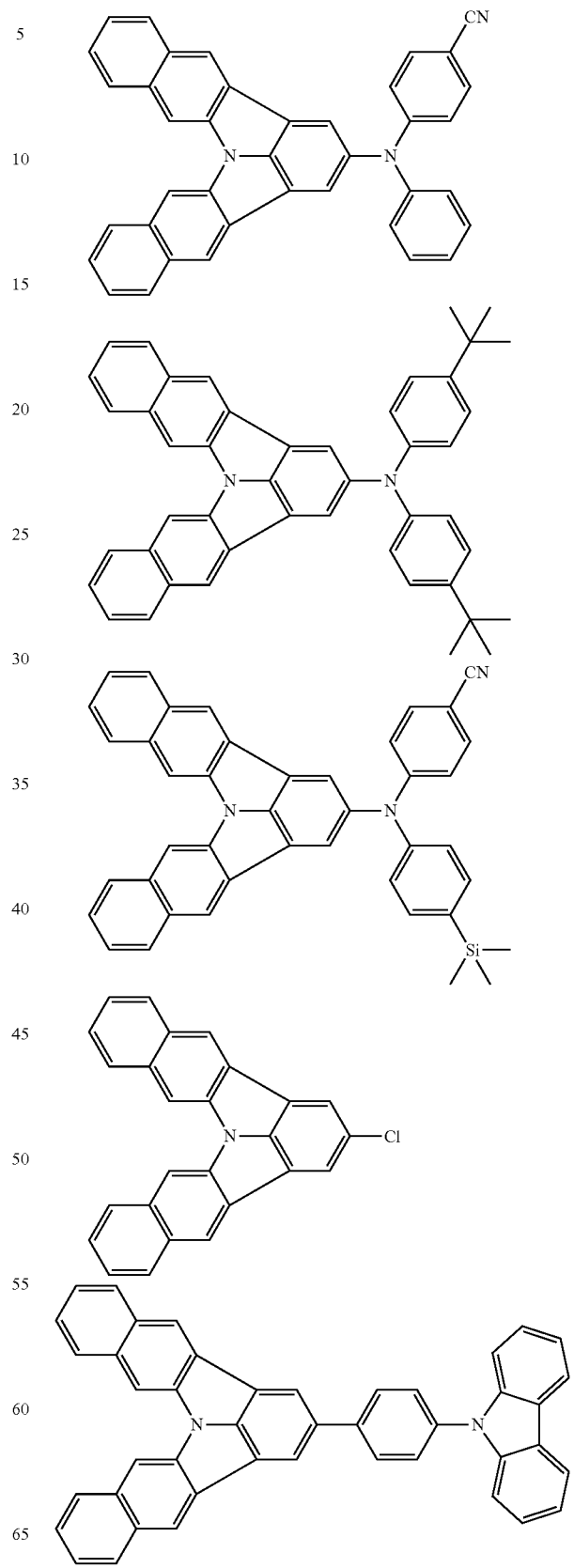

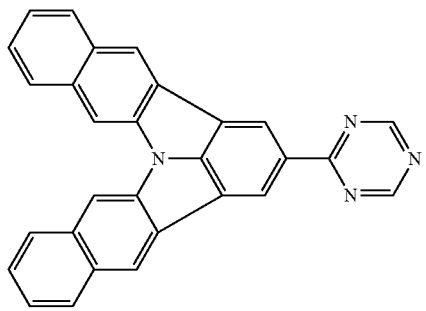
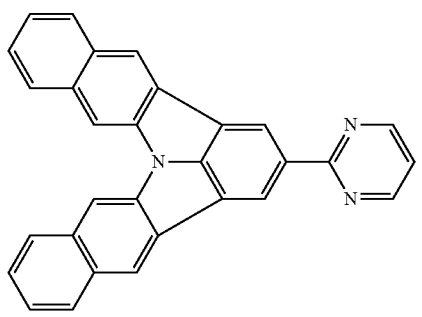
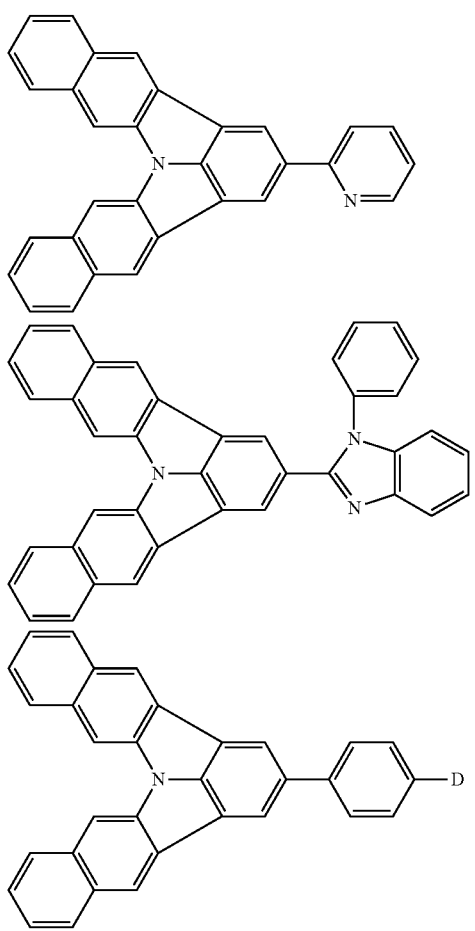
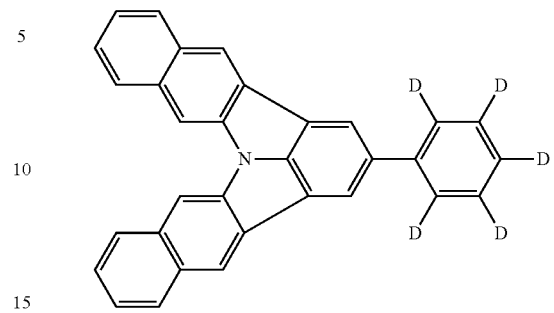
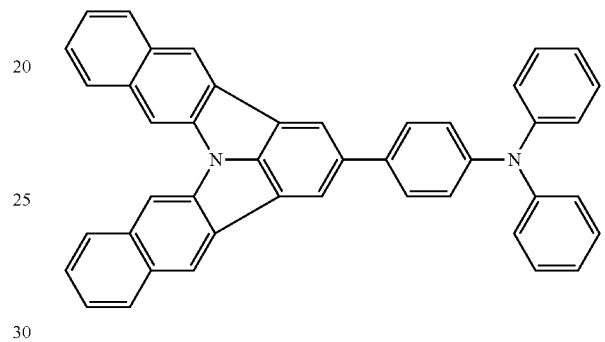
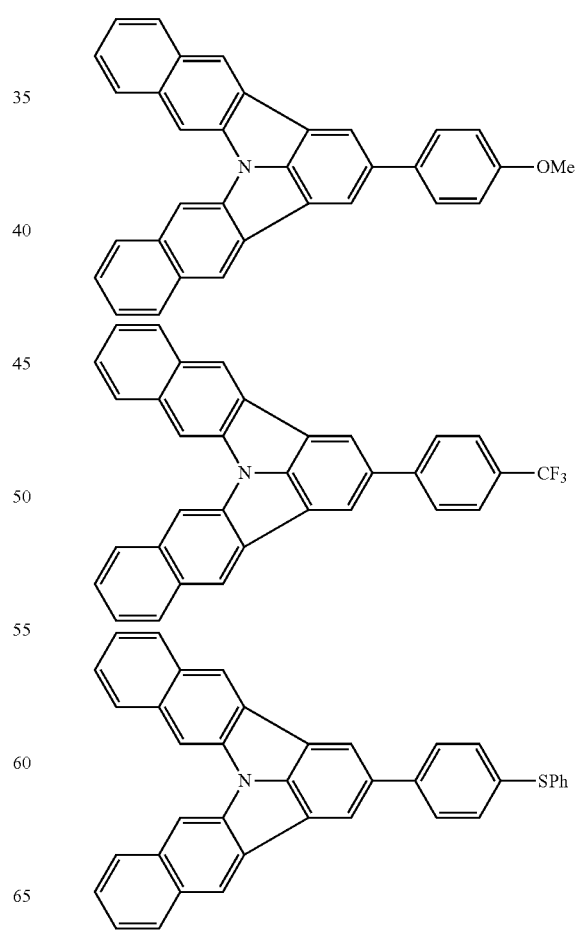

[Formula 59]
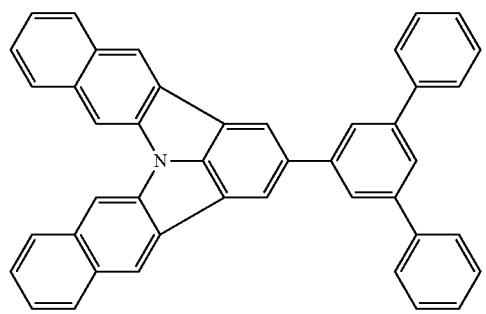
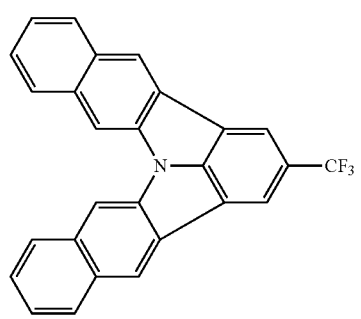
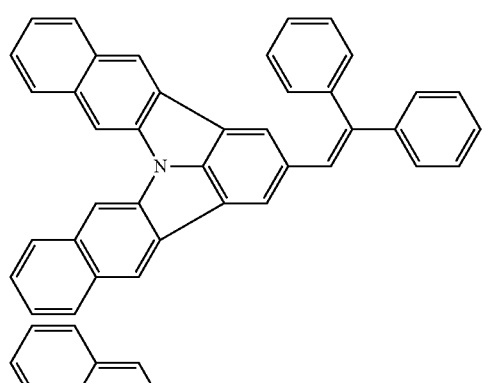
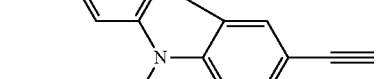
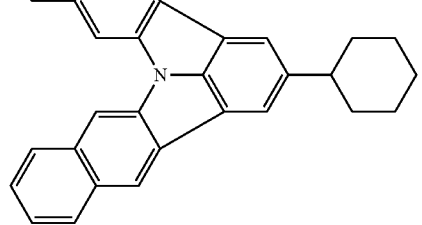
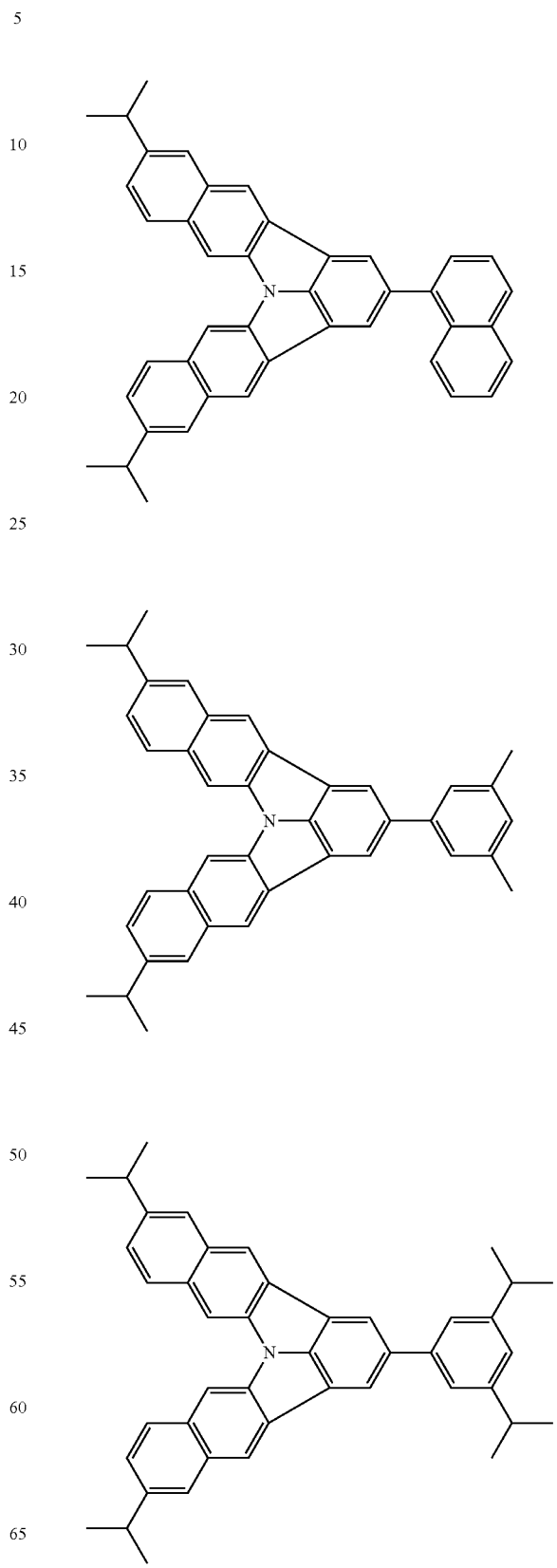

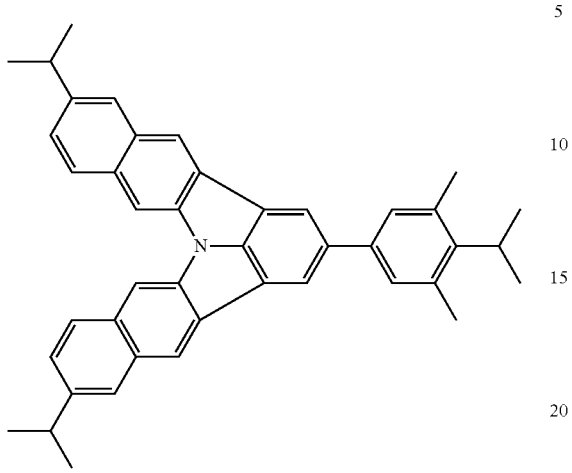
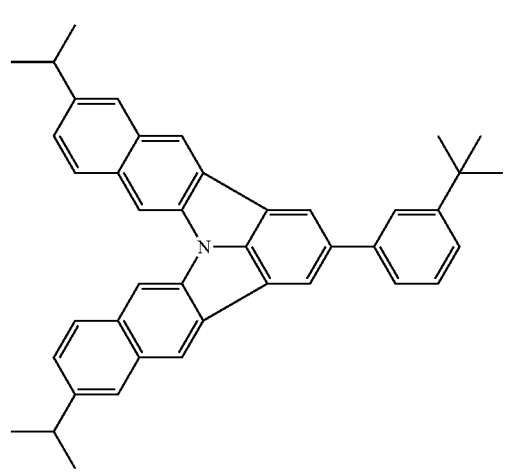
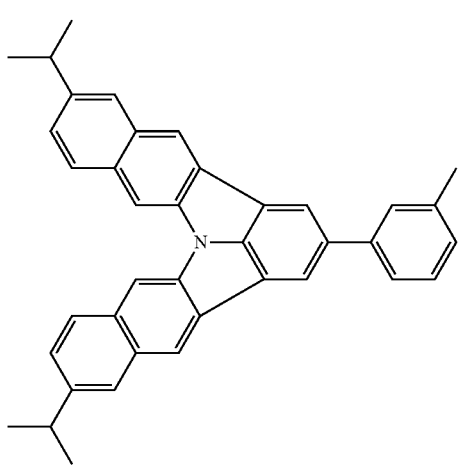
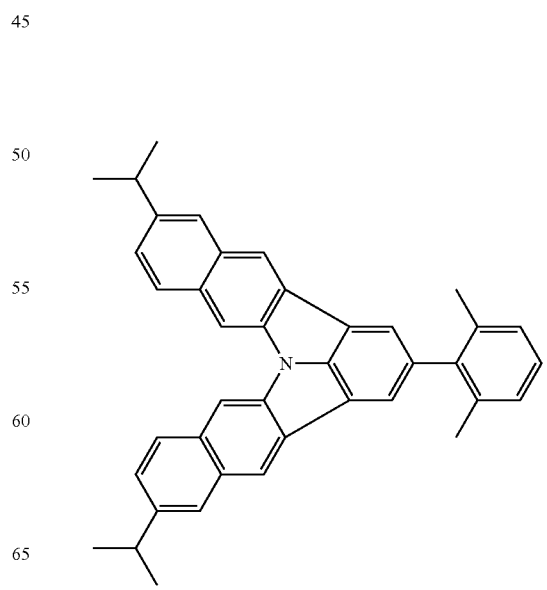

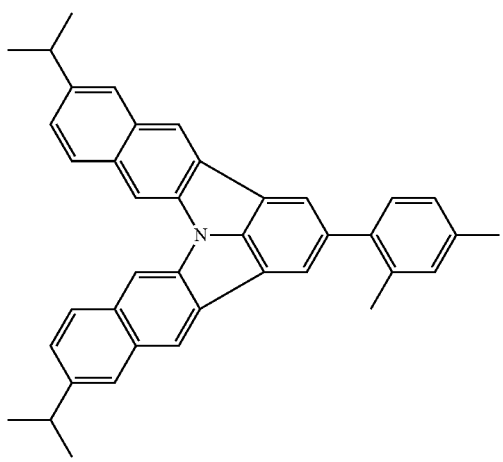
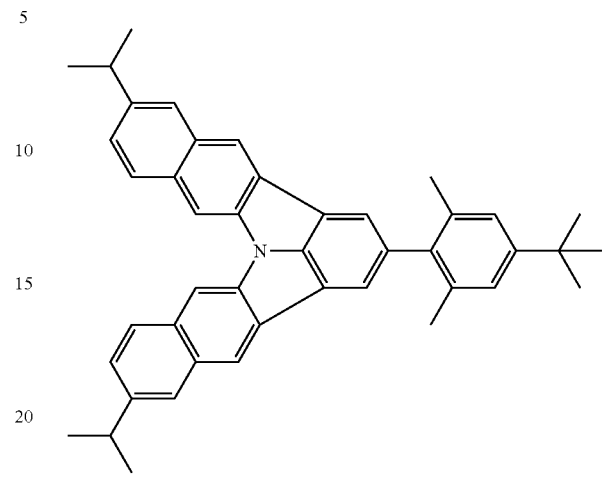
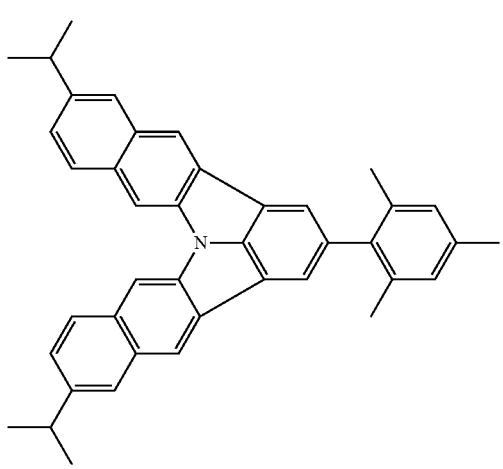
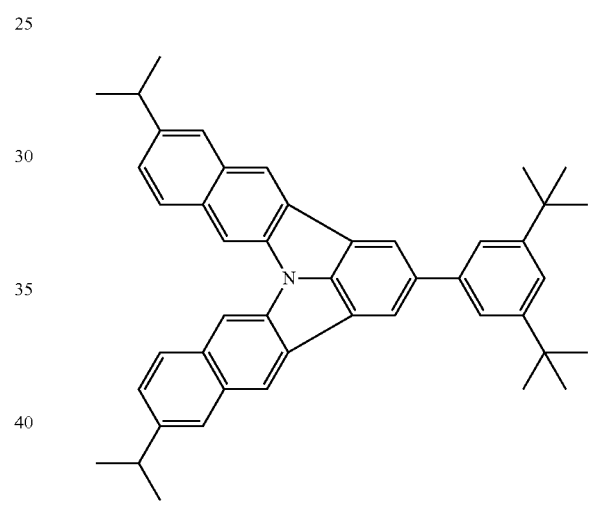
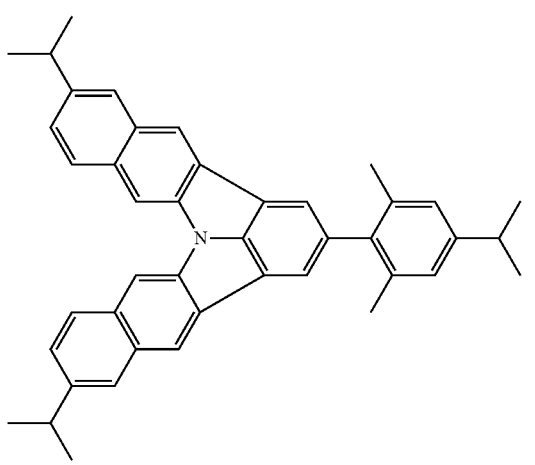
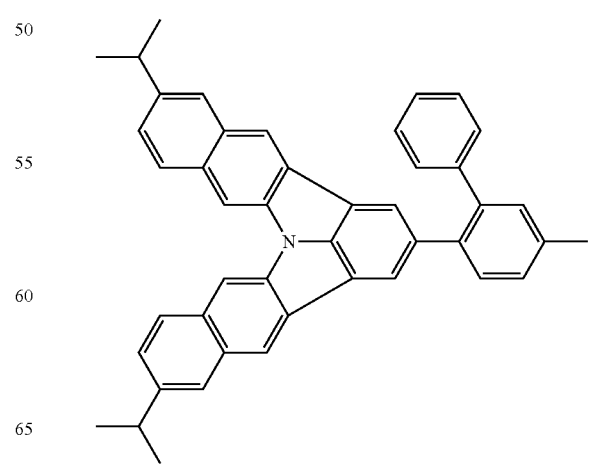

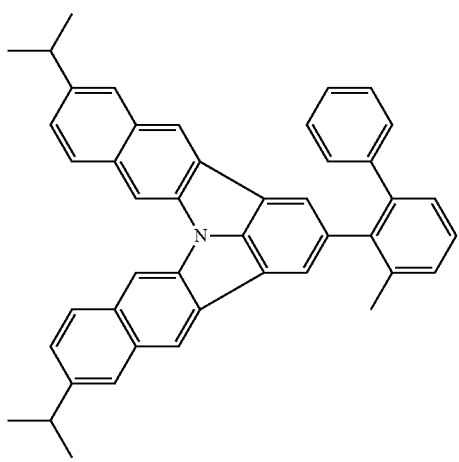
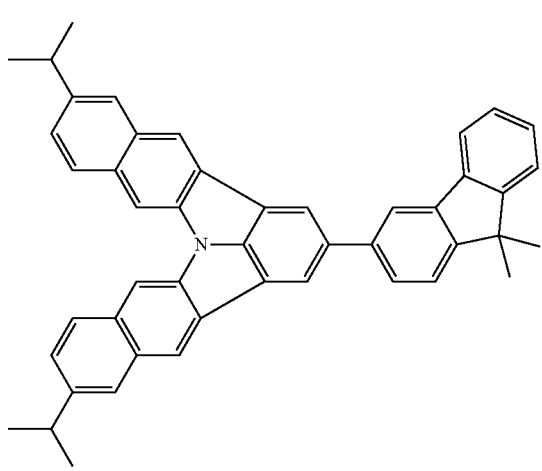
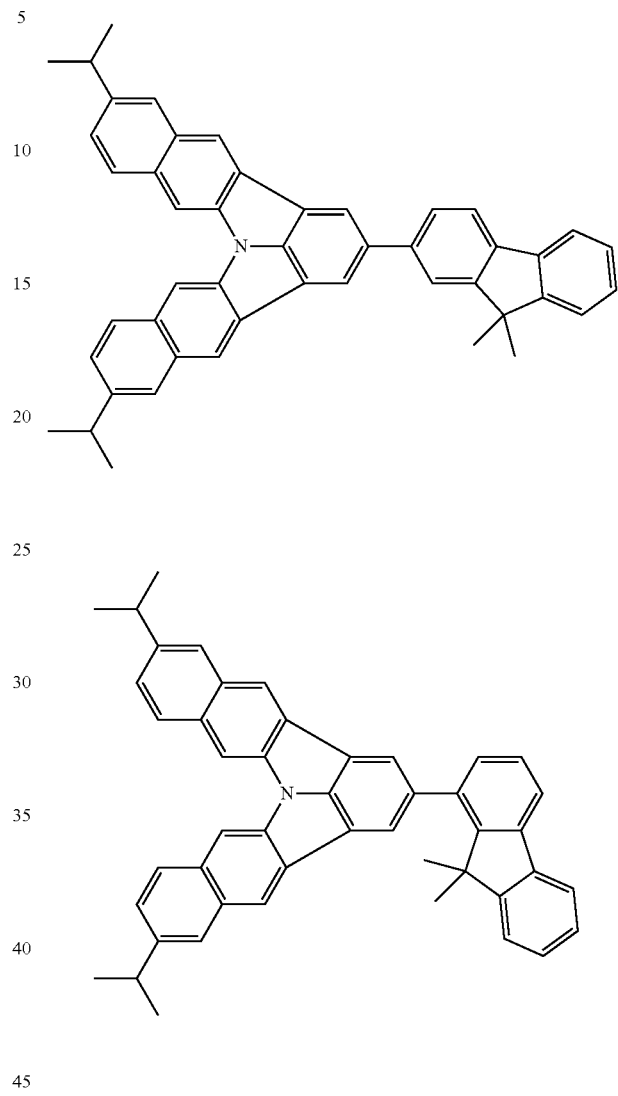

[Formula 60]
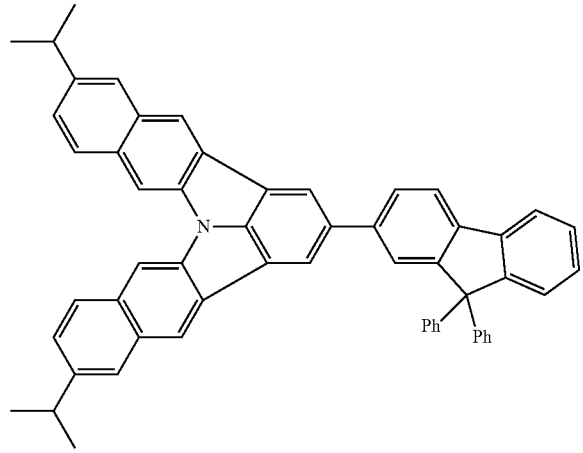
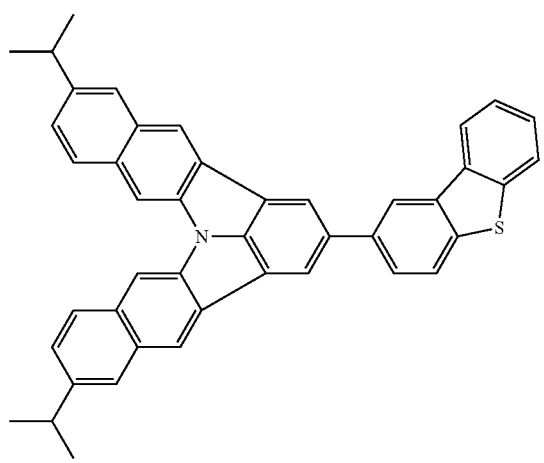
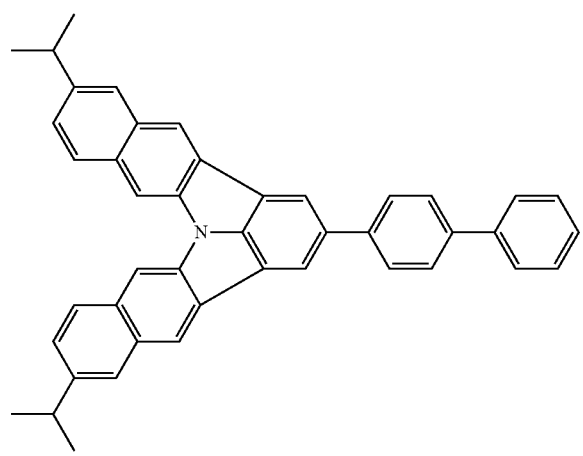
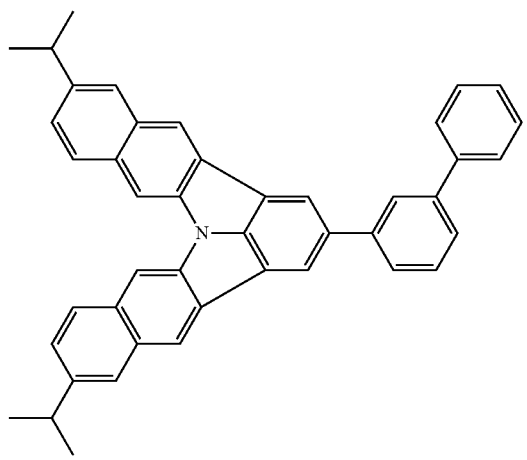
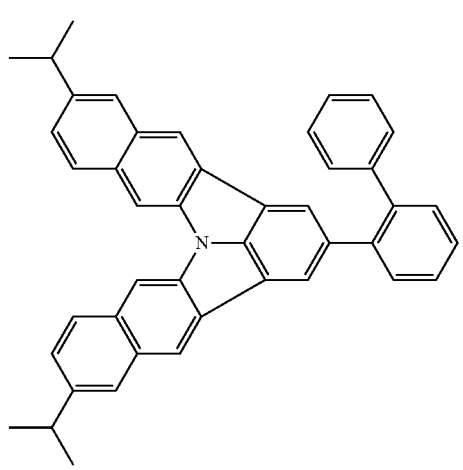
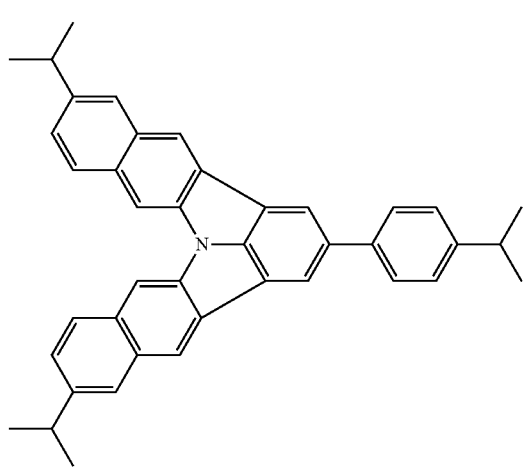

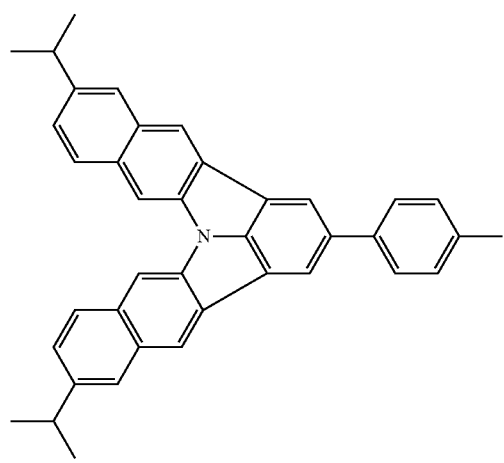
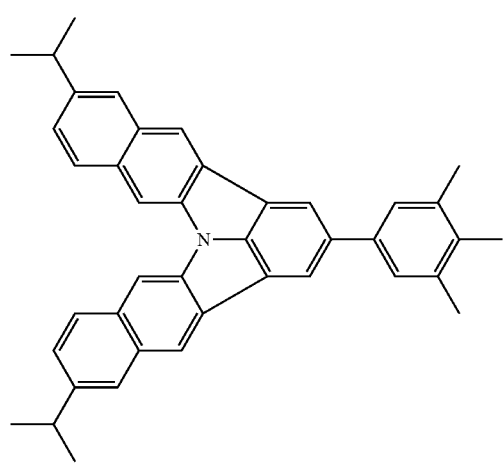
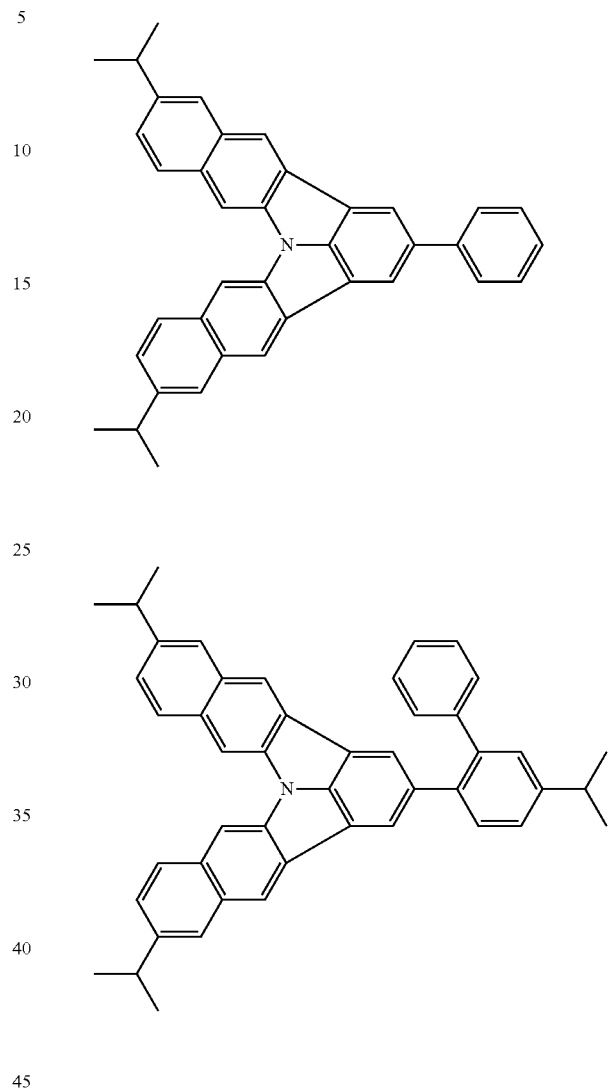
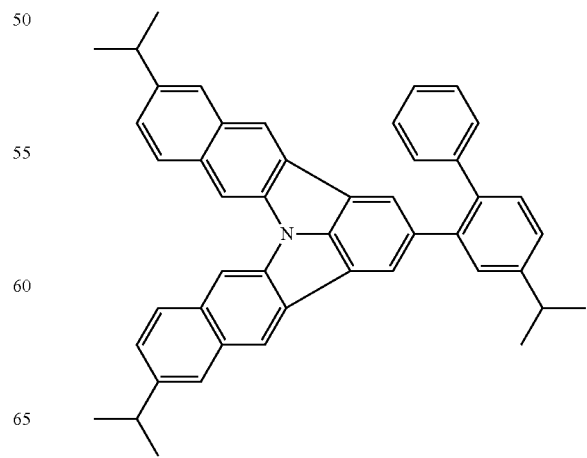

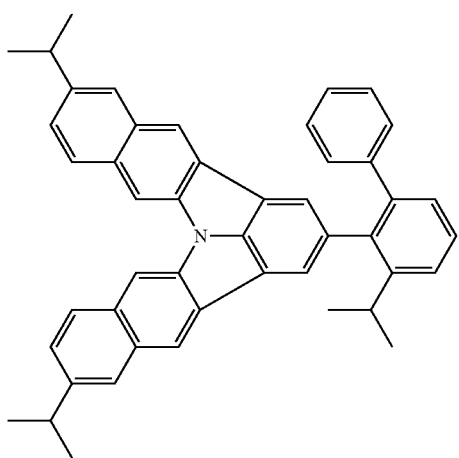
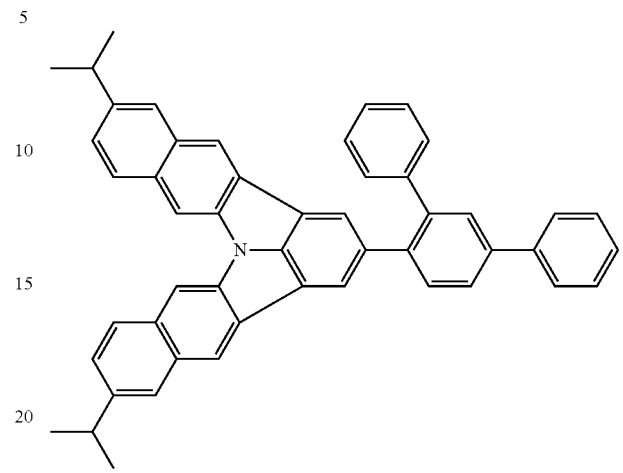
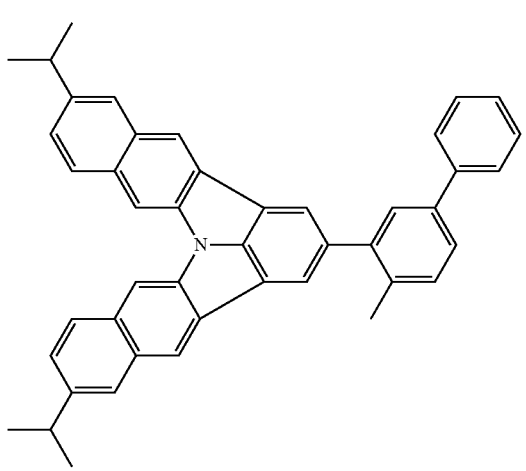
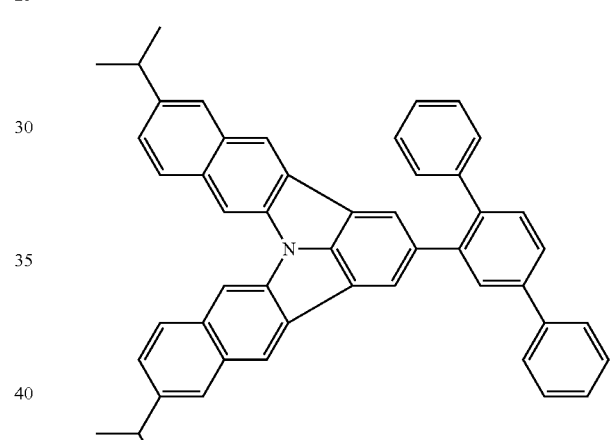
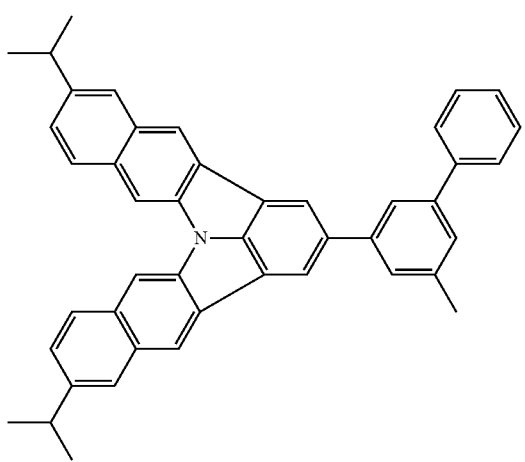
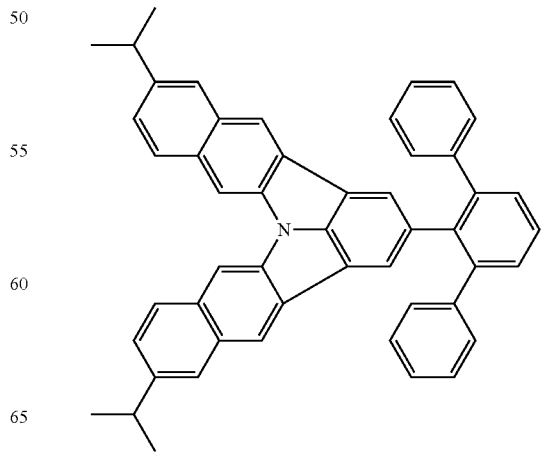

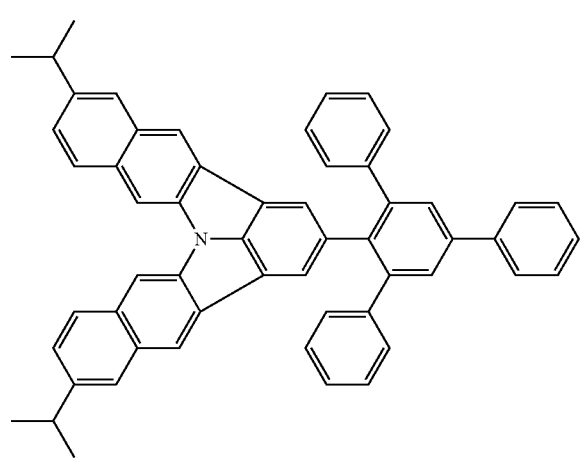
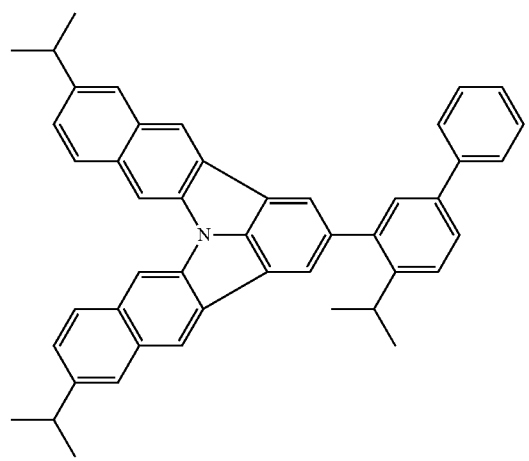
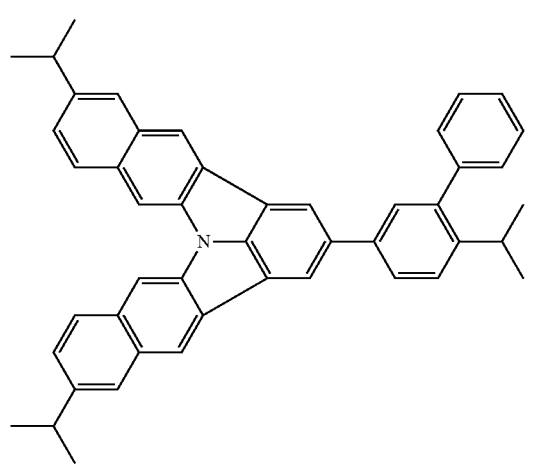
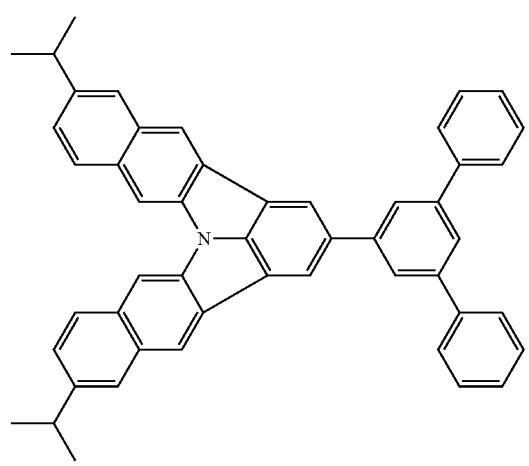
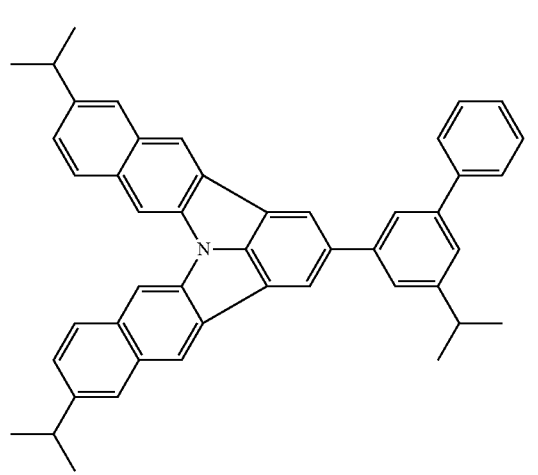
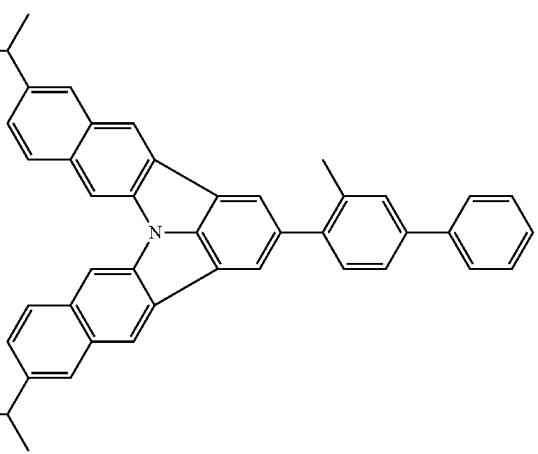

[Formula 61]
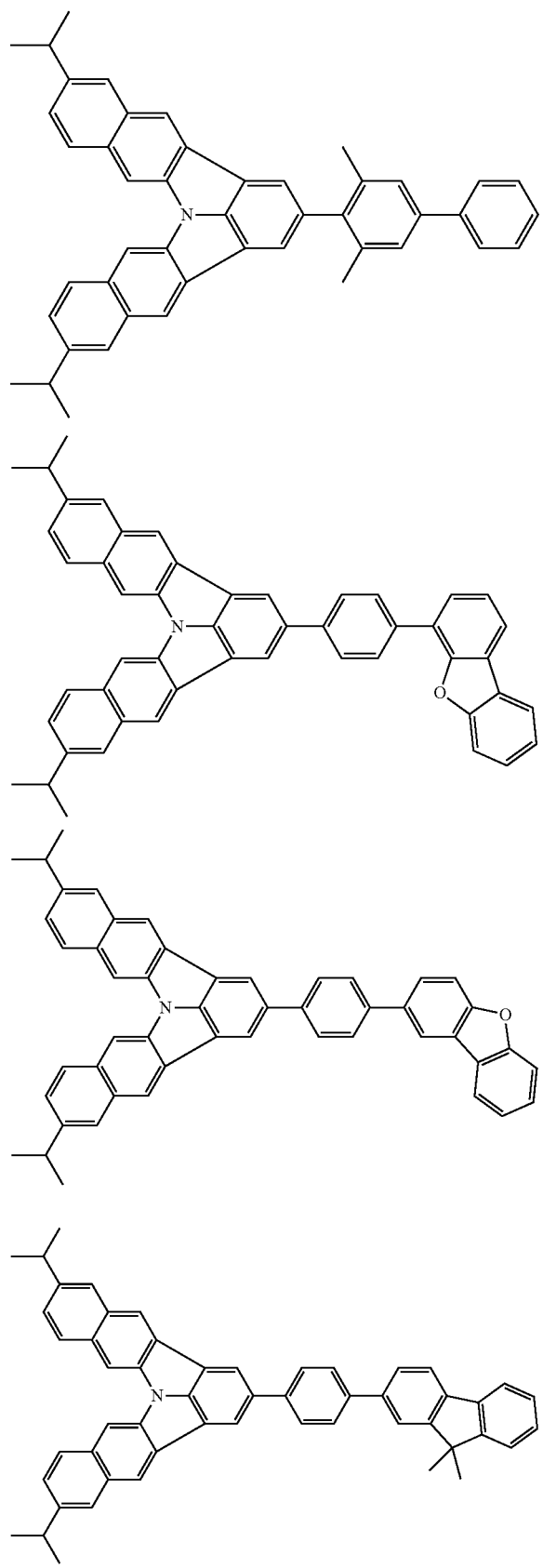
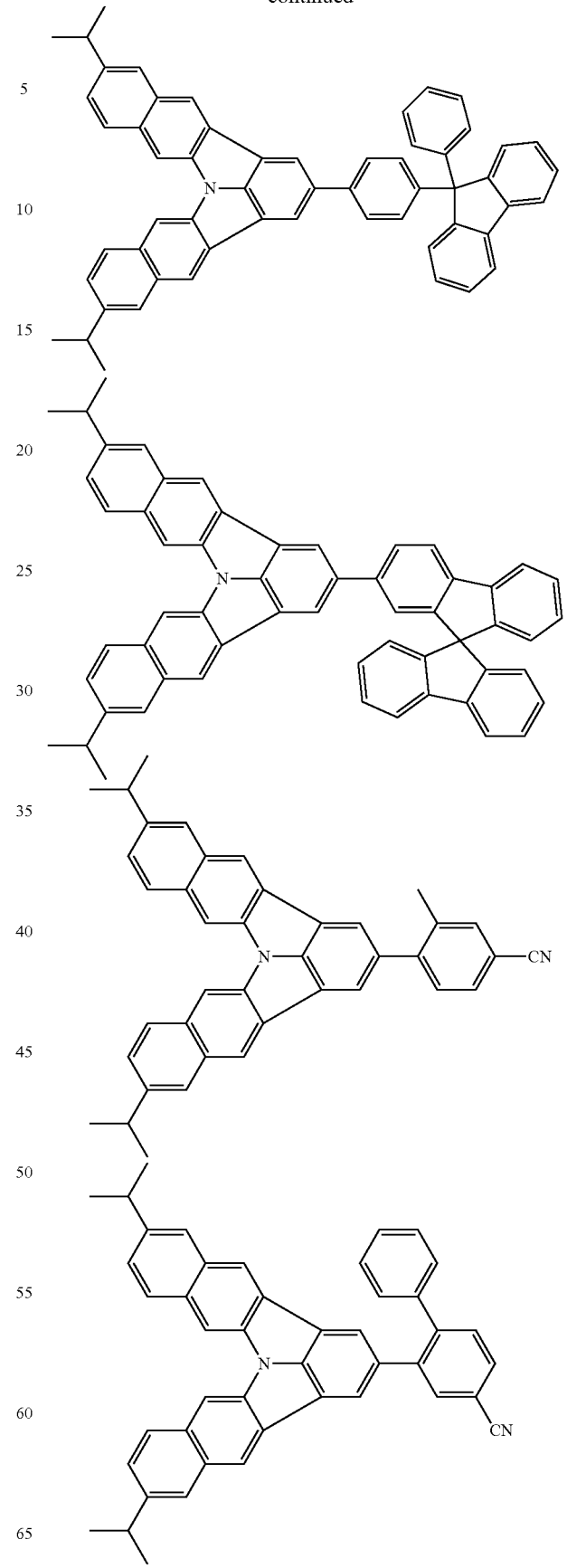

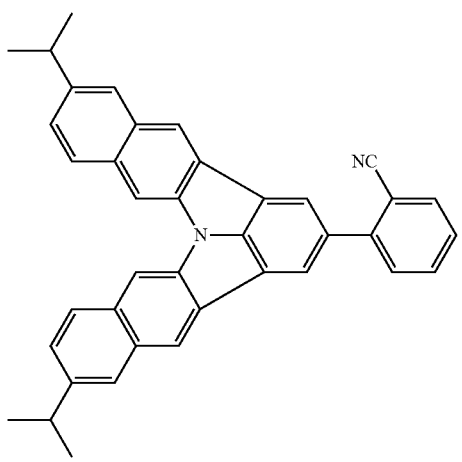
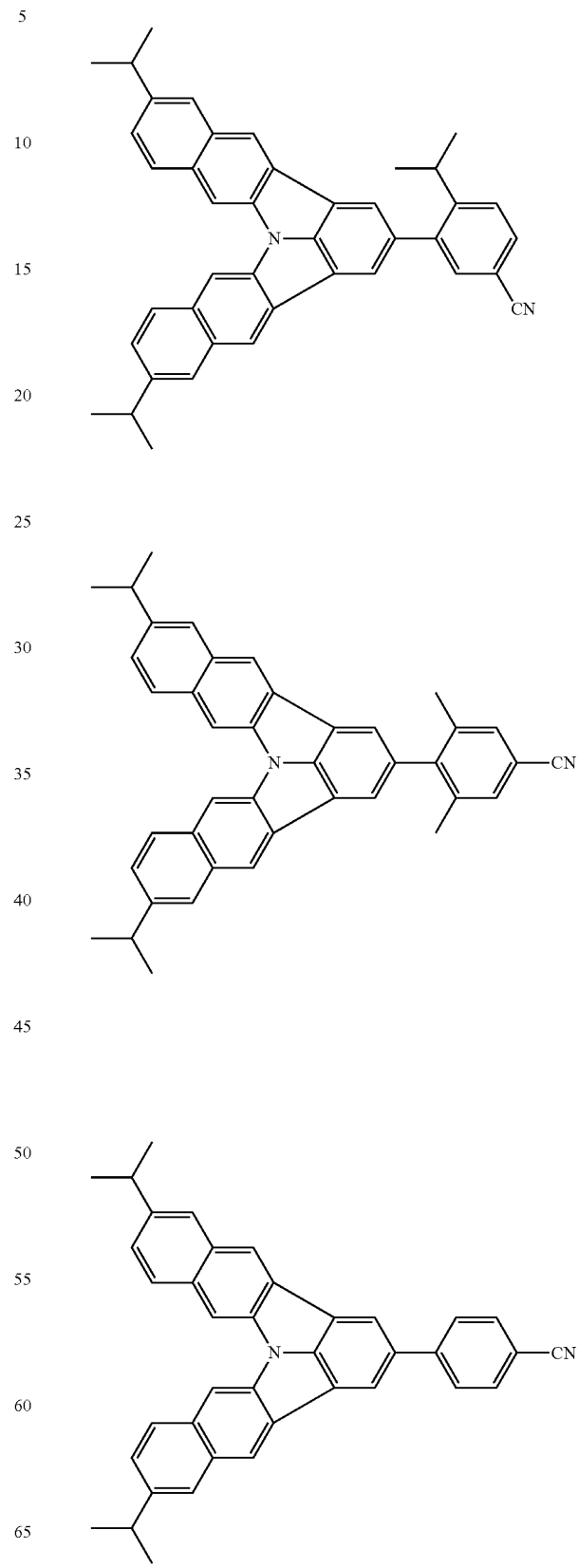

97
-continued
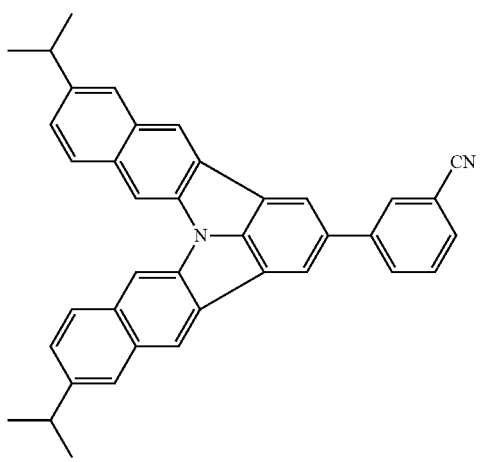
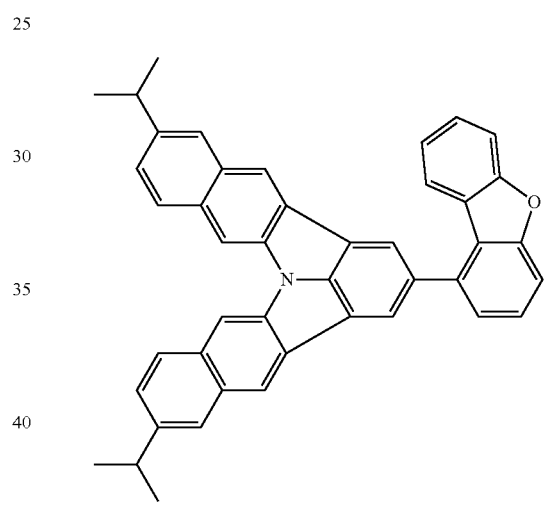
98
-continued
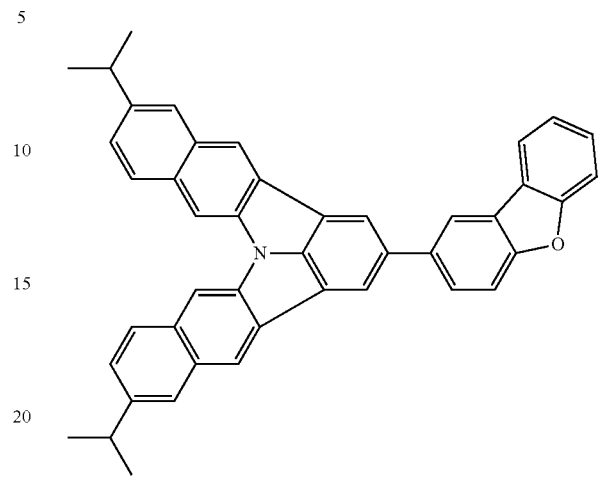
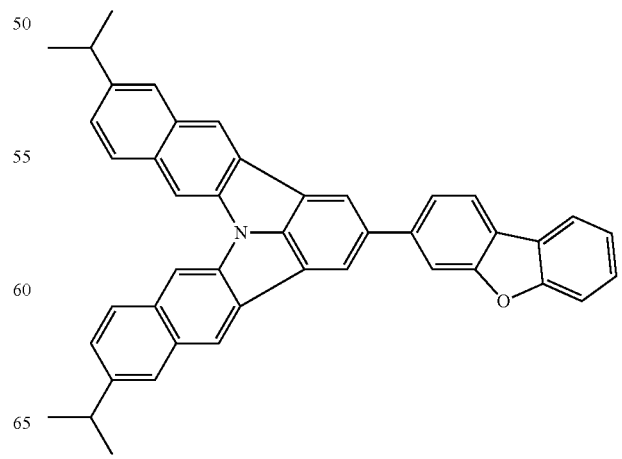

-continued
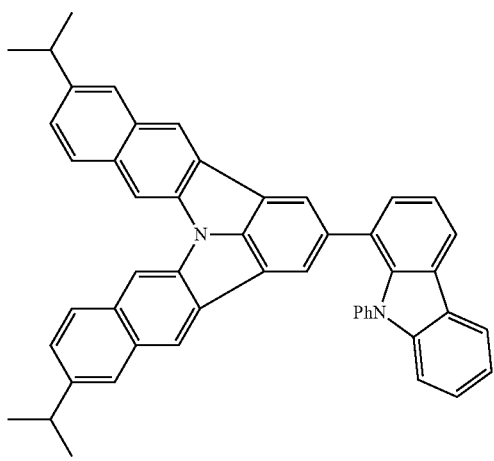
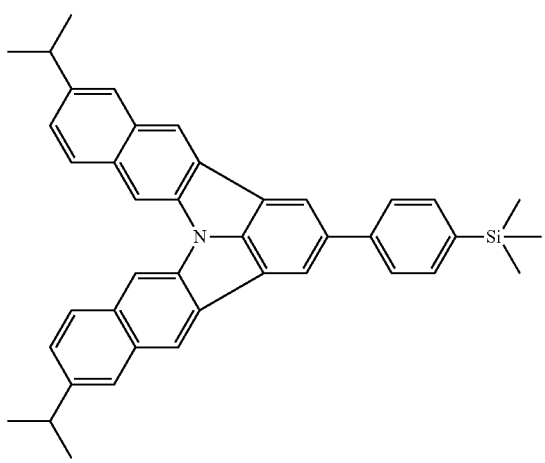
-continued
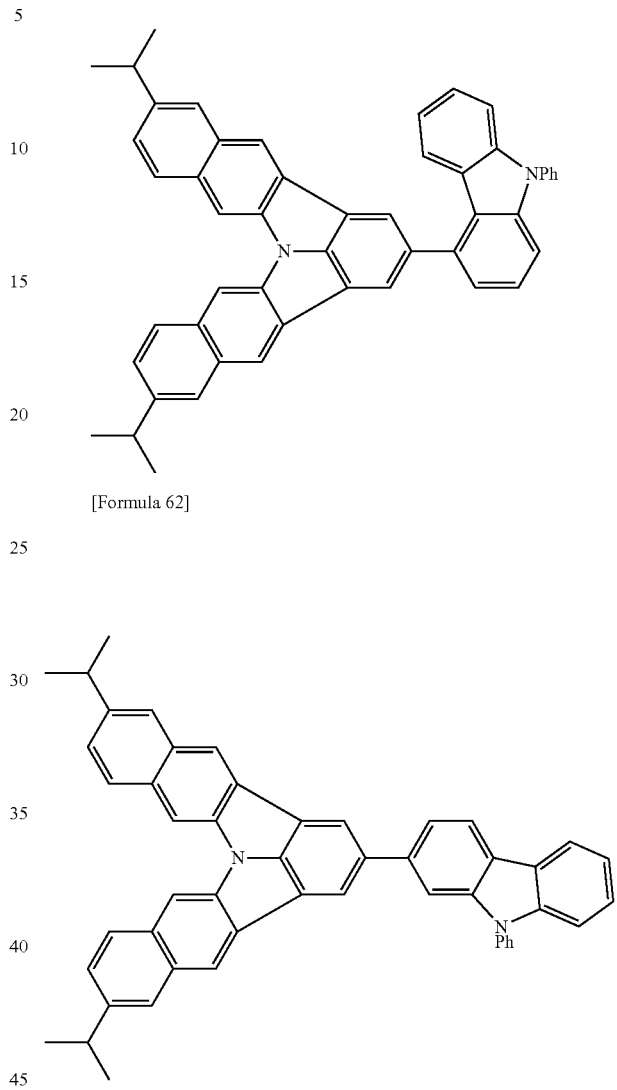
[Formula 62]

101
-continued
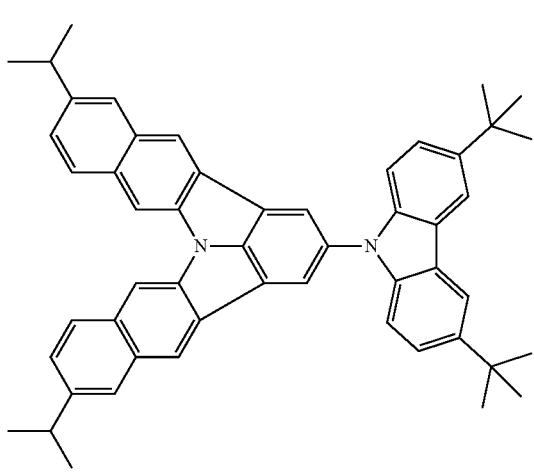
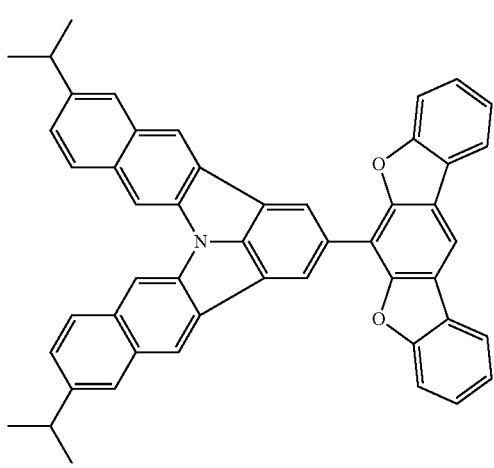
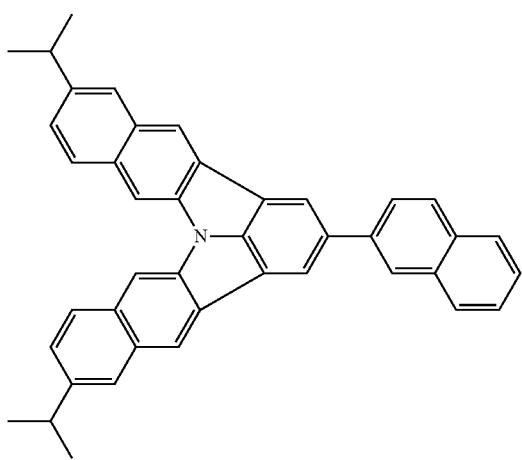
102
-continued
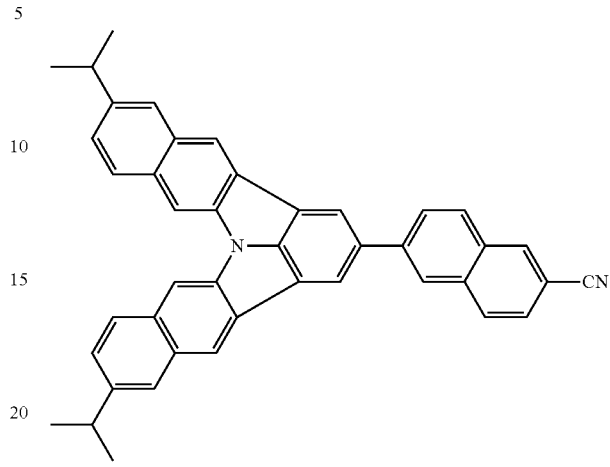
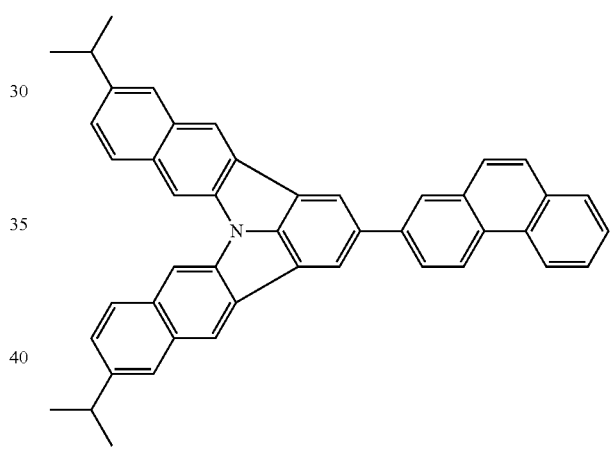
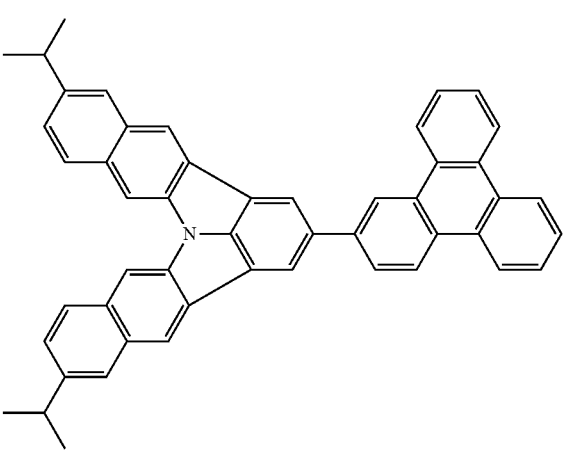

103
-continued
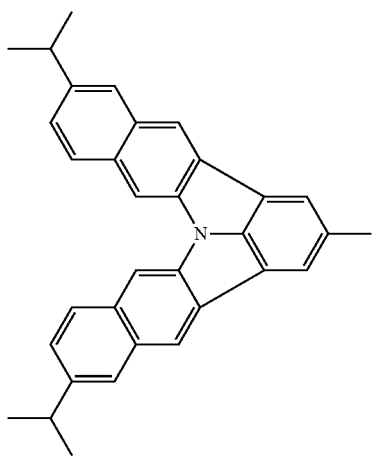
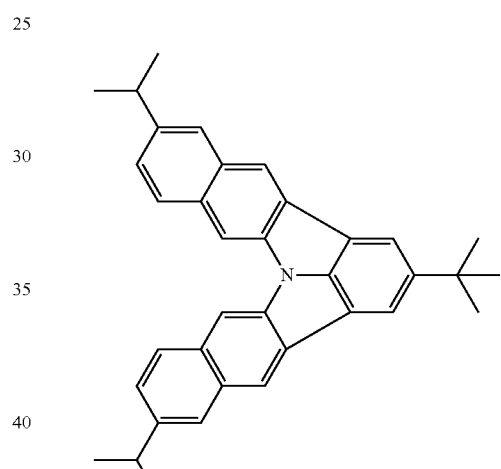
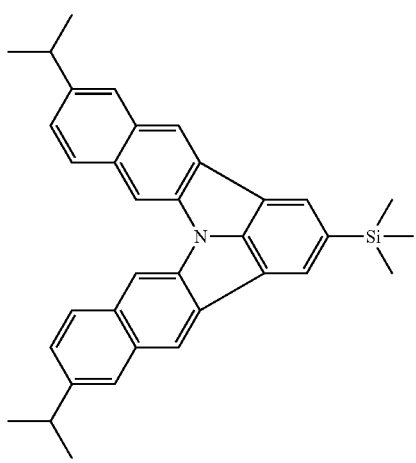
104
-continued
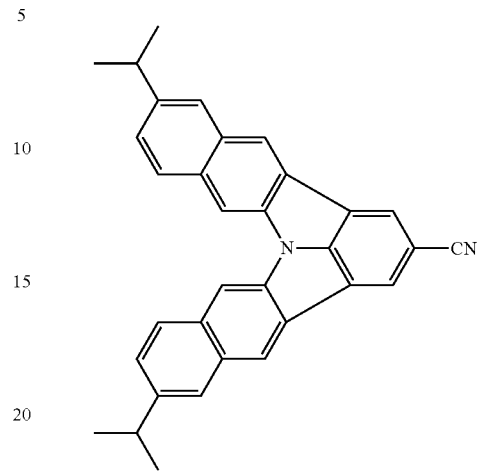
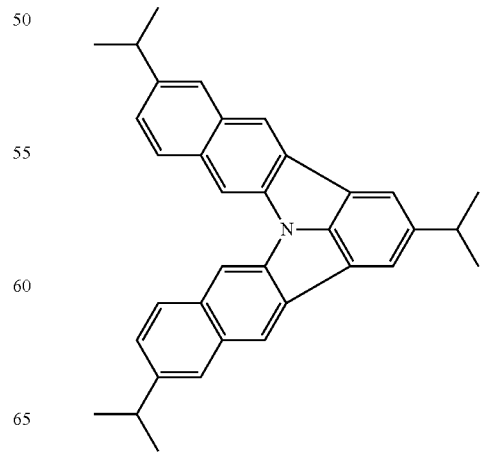

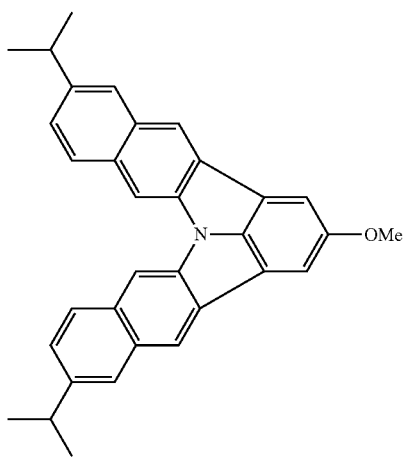
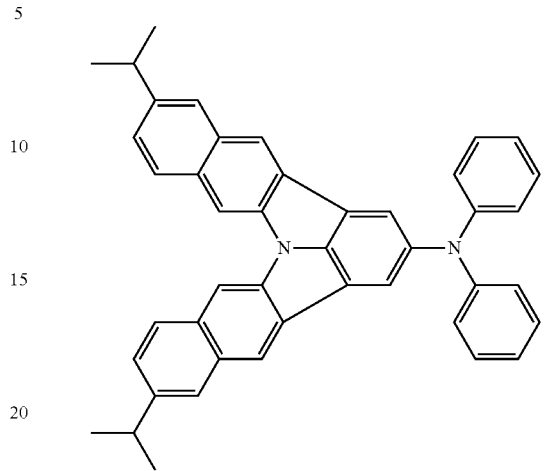
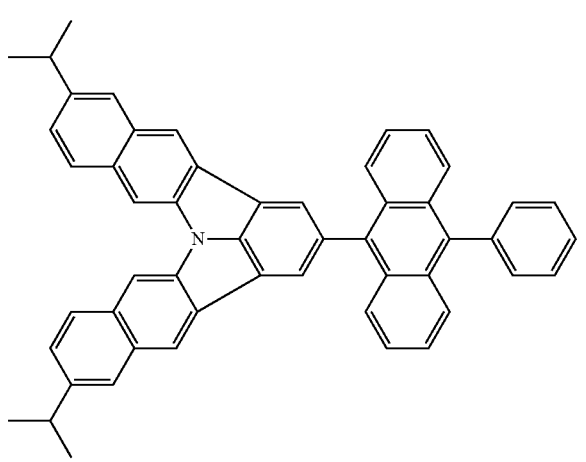
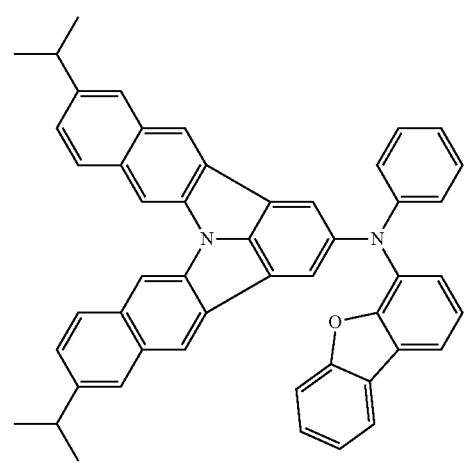
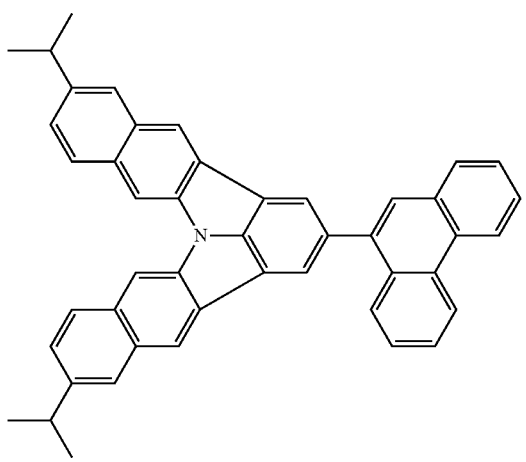
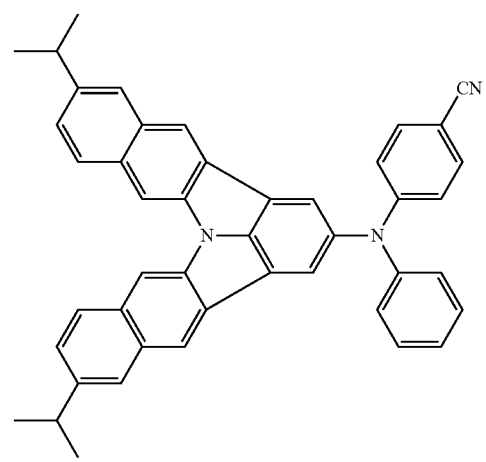

107
-continued
108
-continued
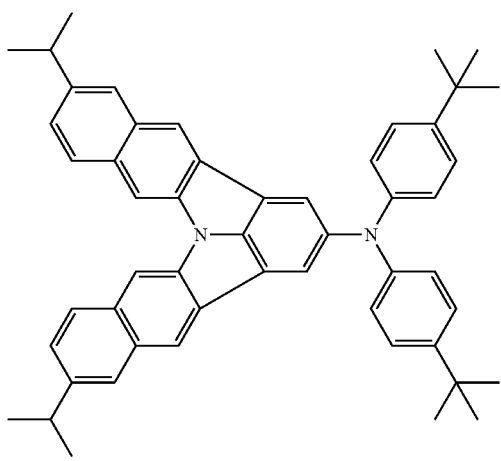
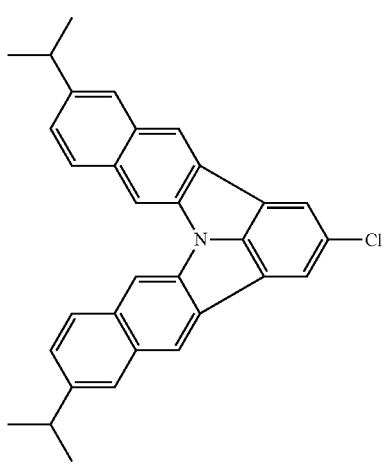
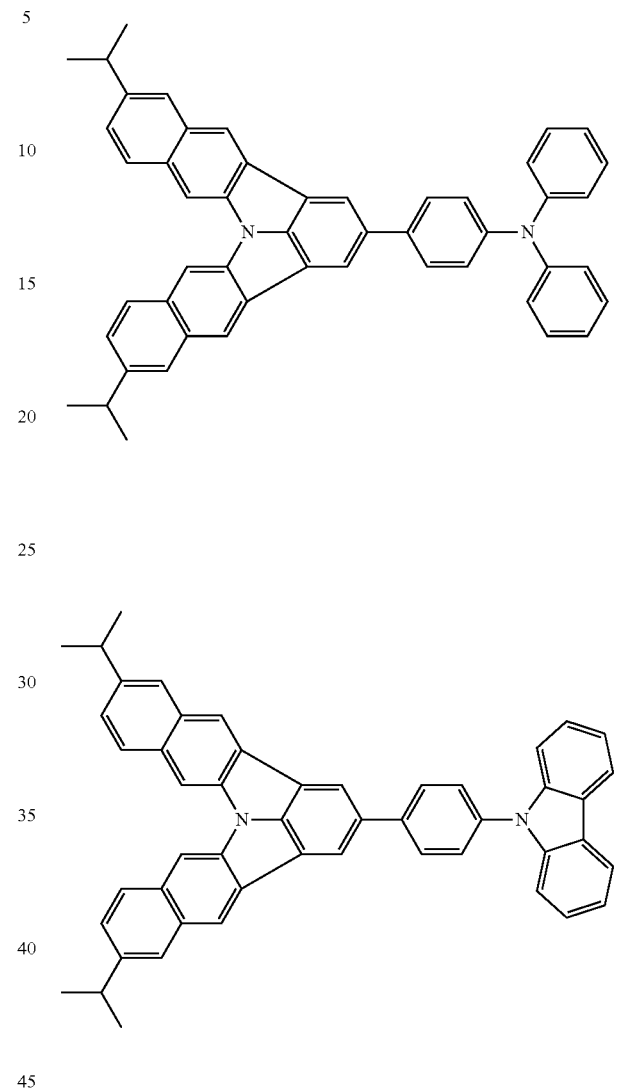

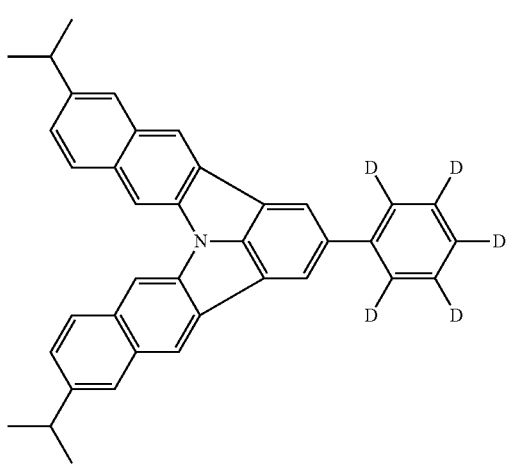
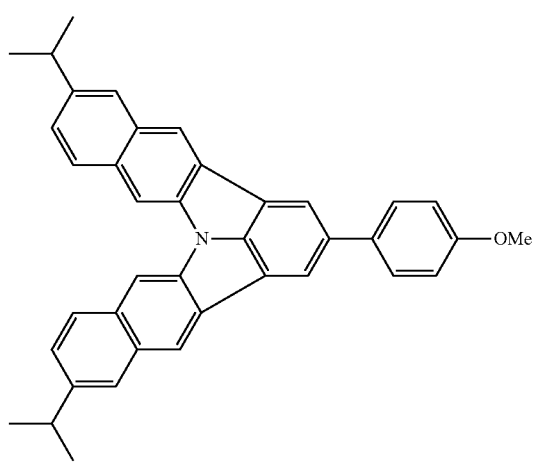
[Formula 63]
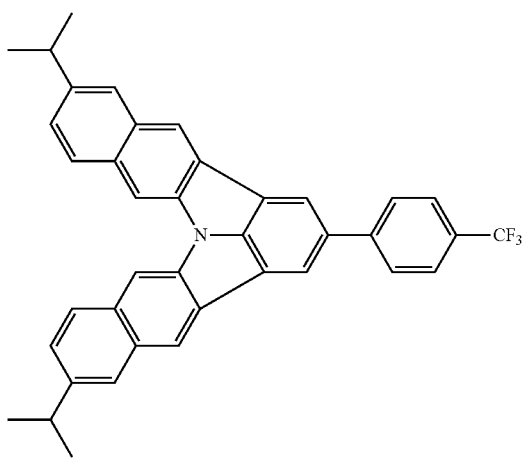
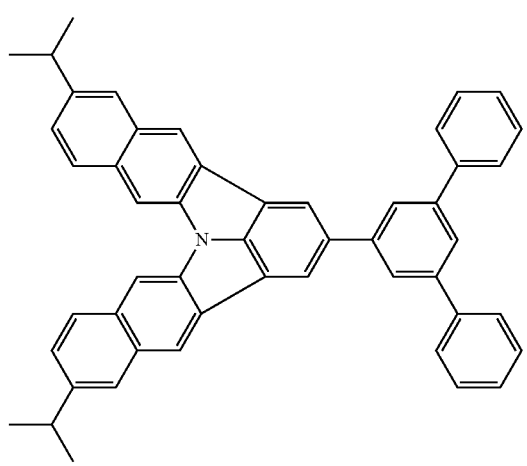
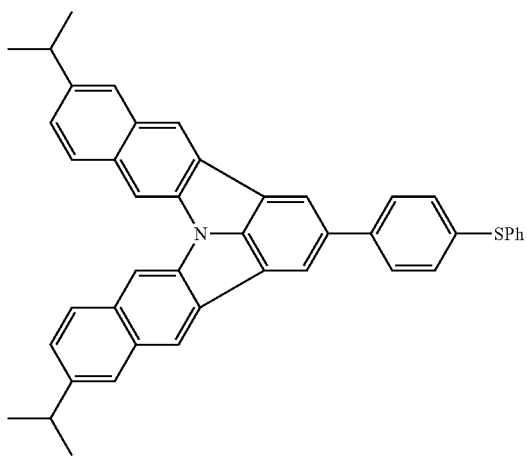
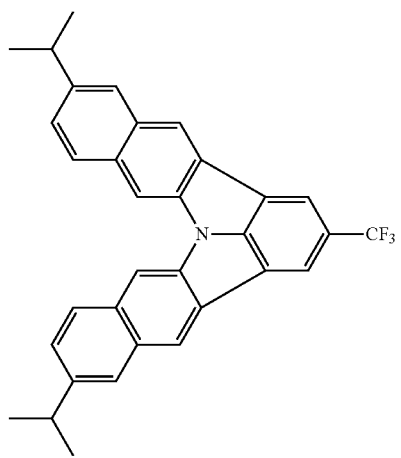

111
-continued
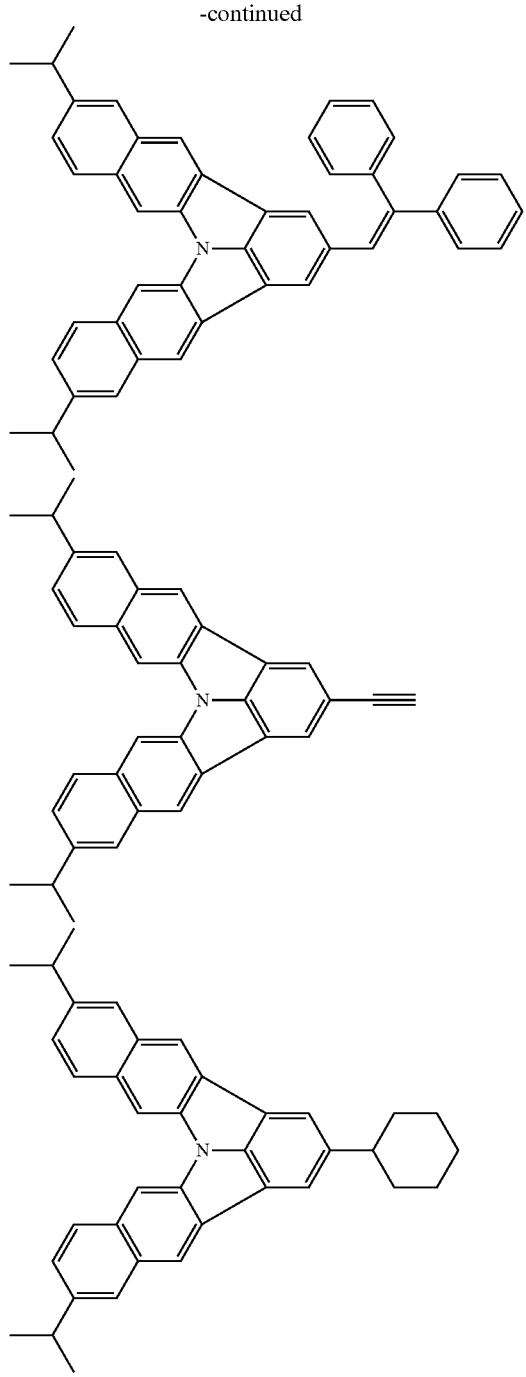
[Formula 64]
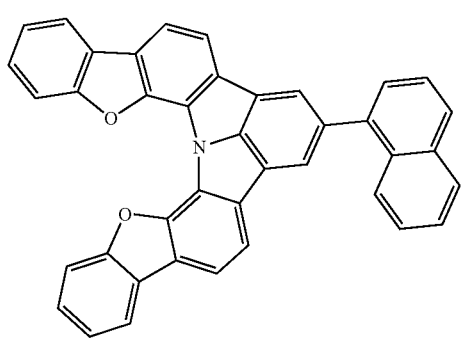
112
-continued
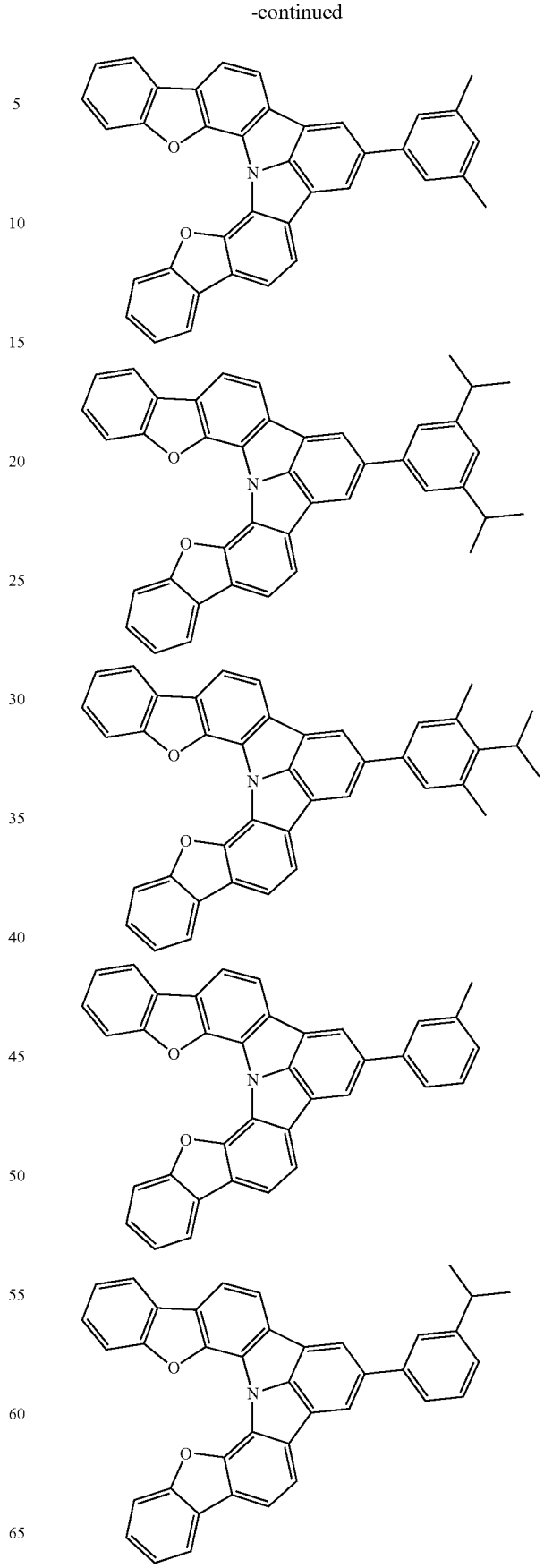

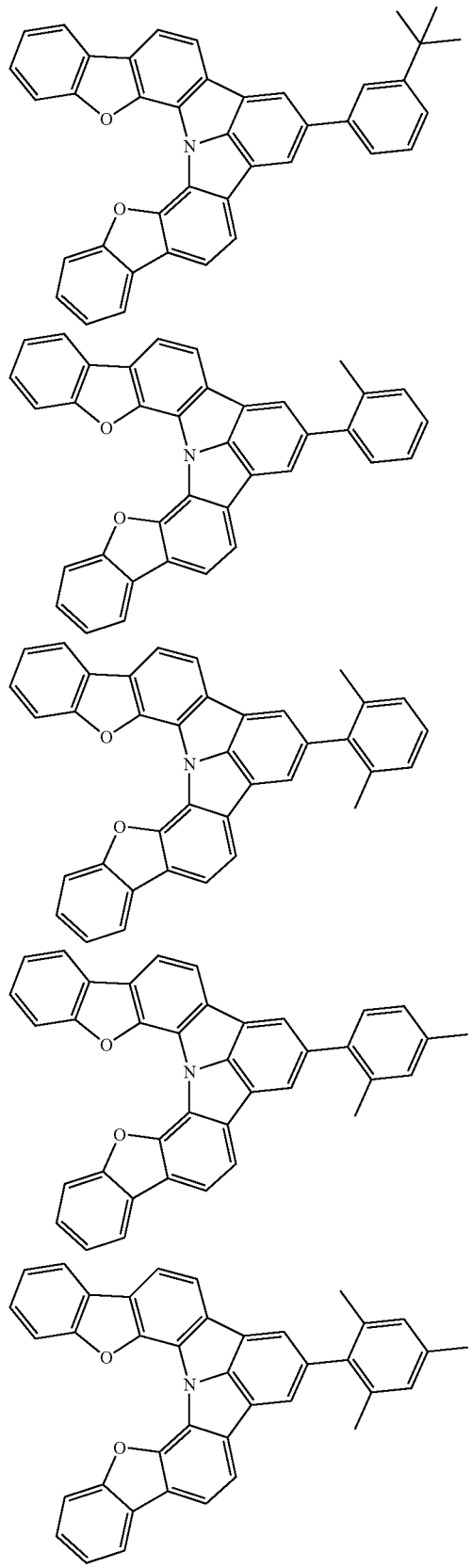
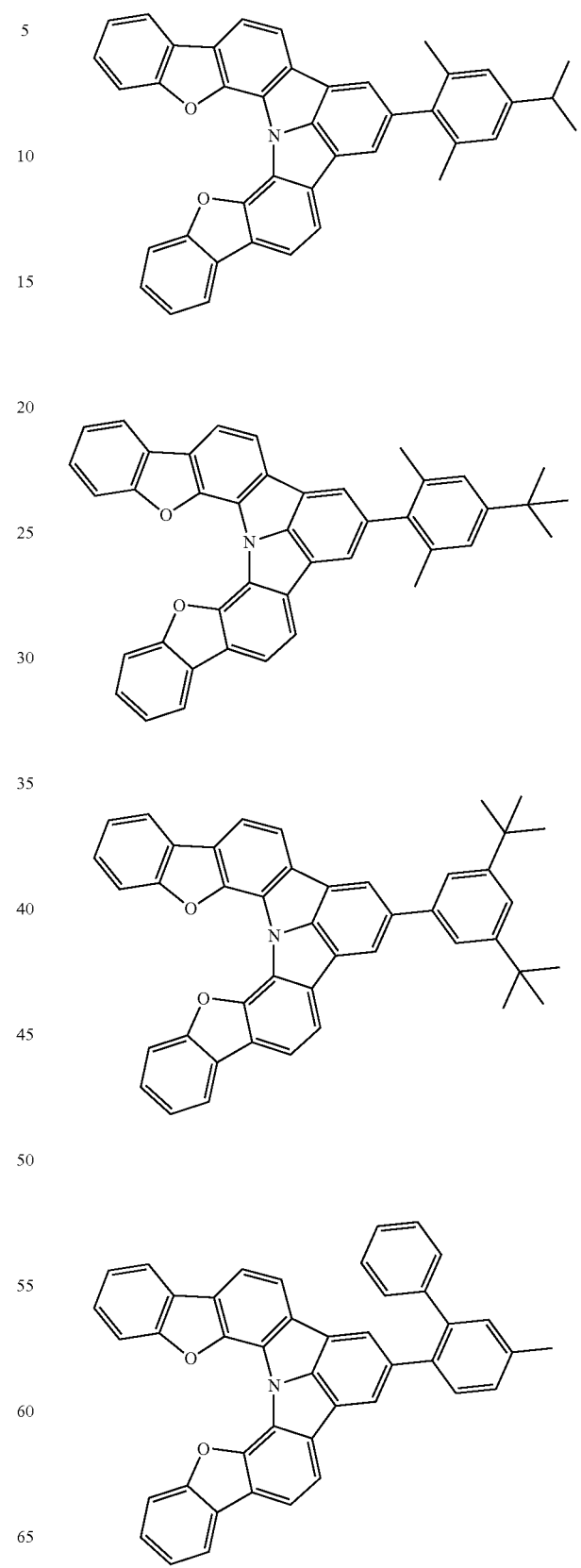

115
-continued
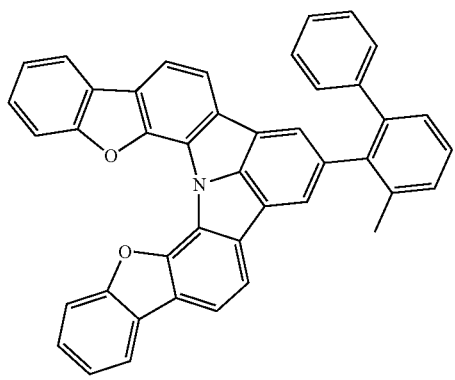
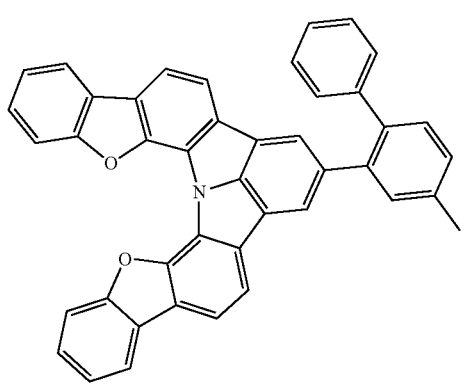
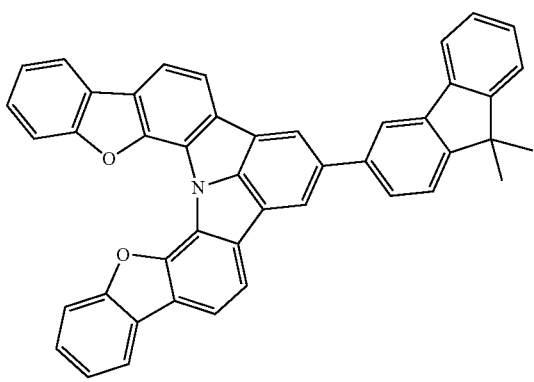
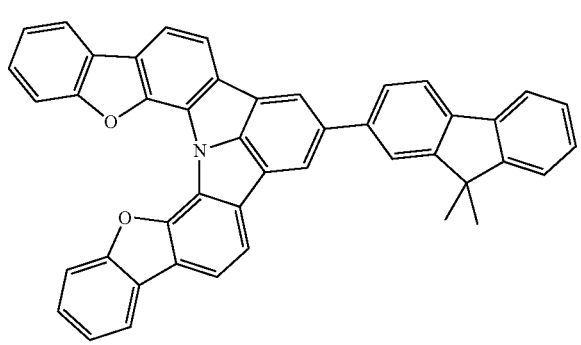
116
-continued
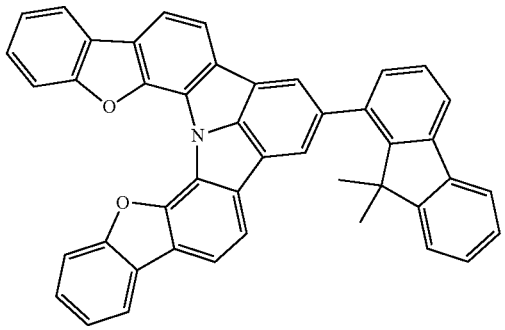
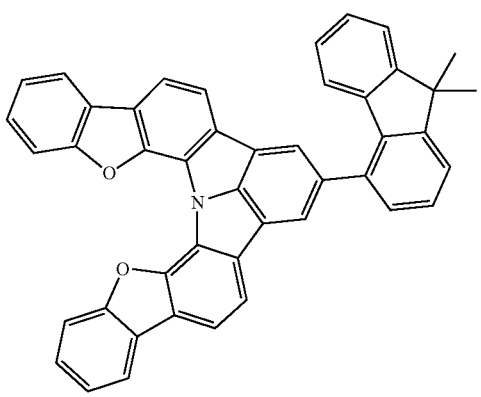
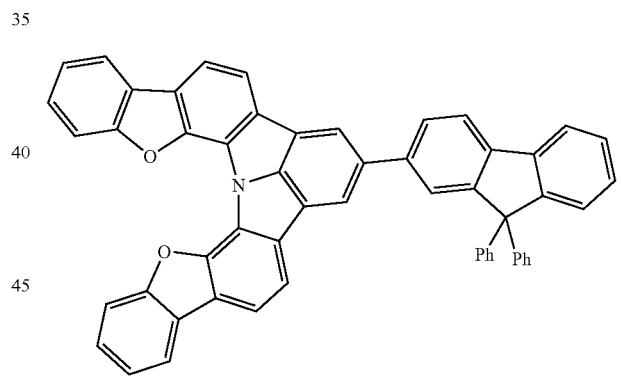
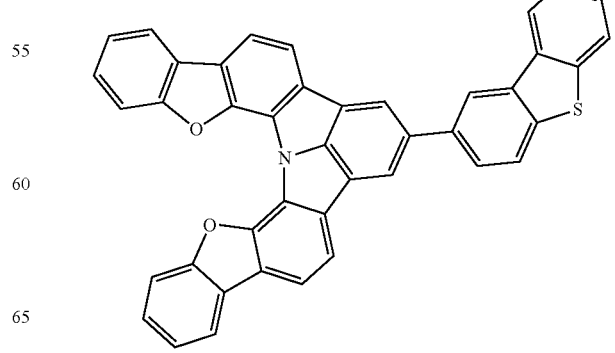

117
-continued
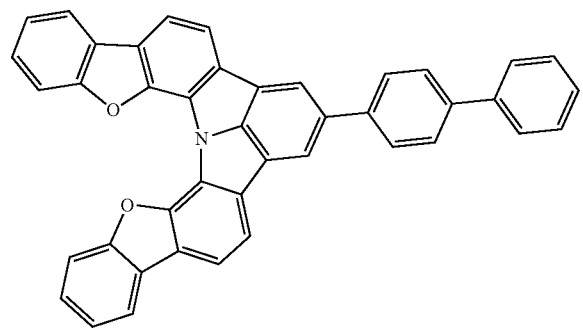
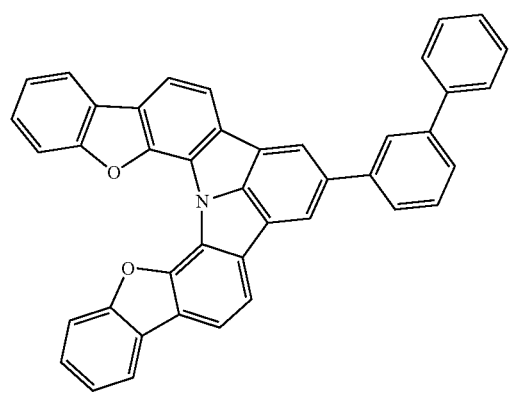
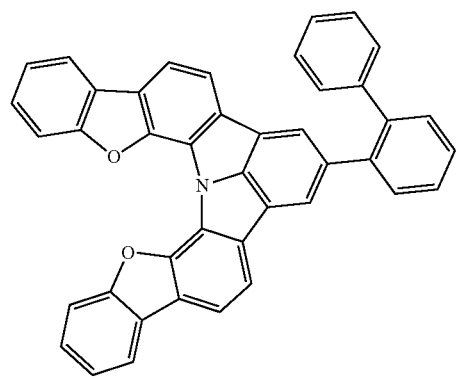
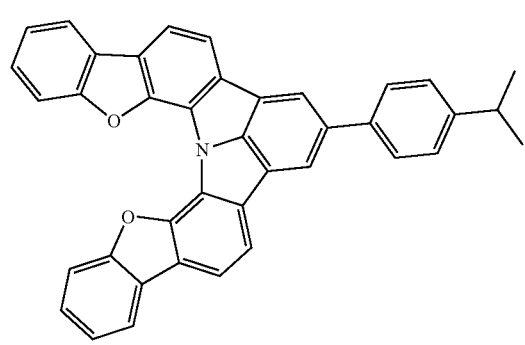
118
-continued
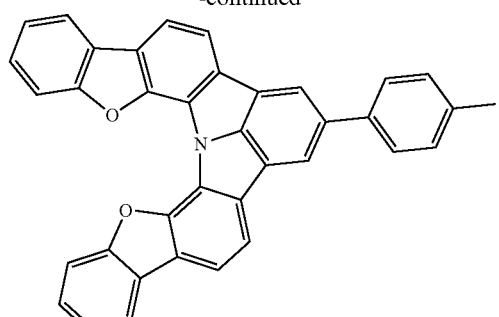
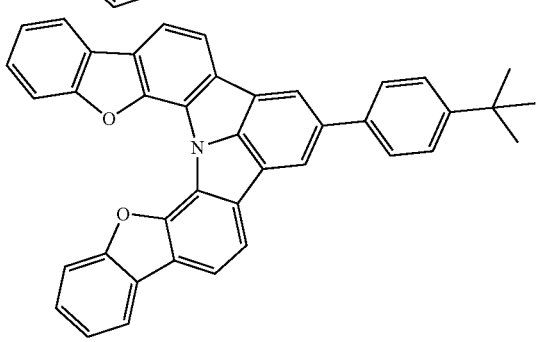
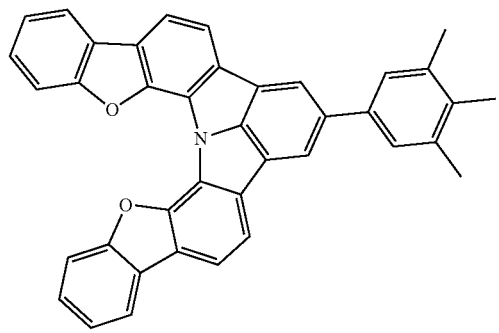
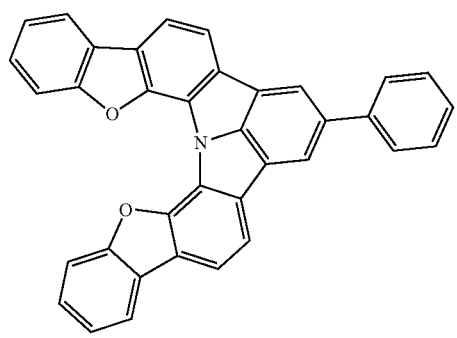
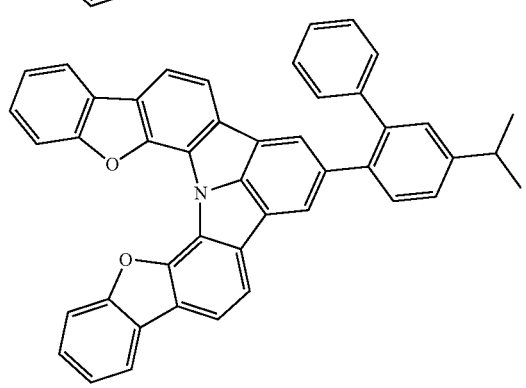

[Formula 65]
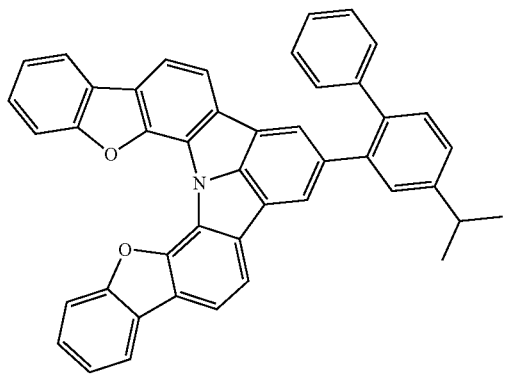
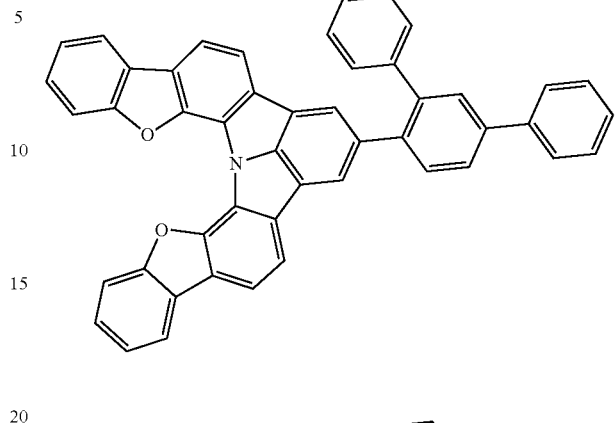
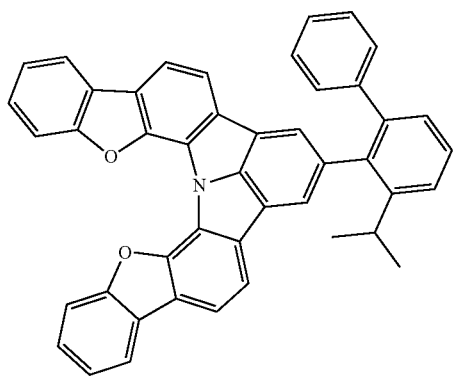
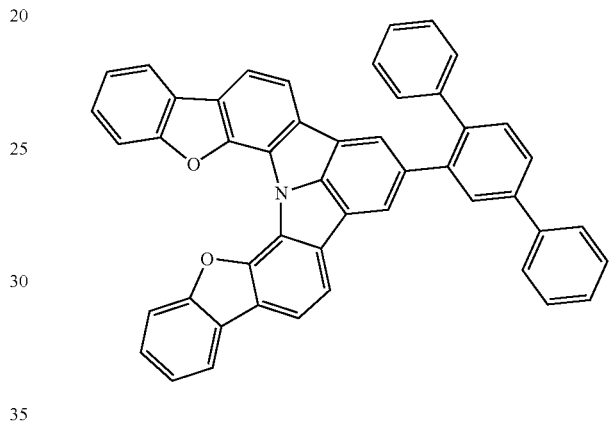
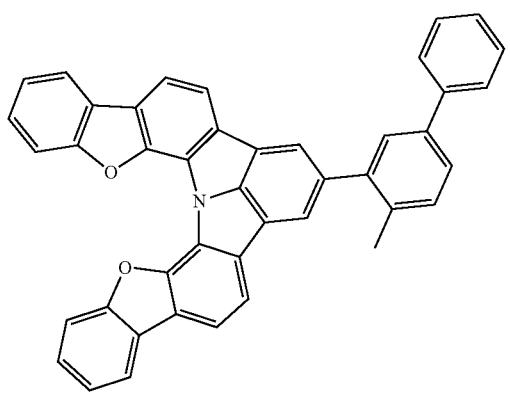
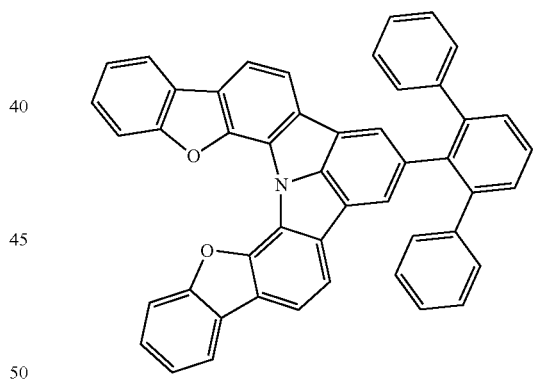
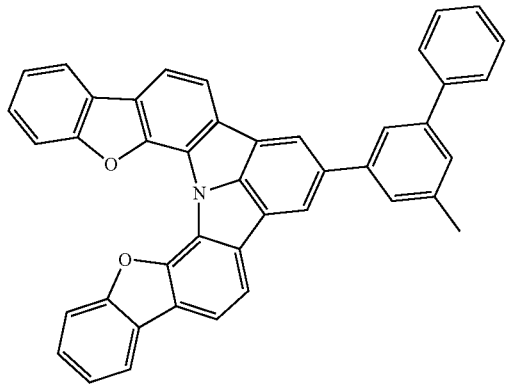
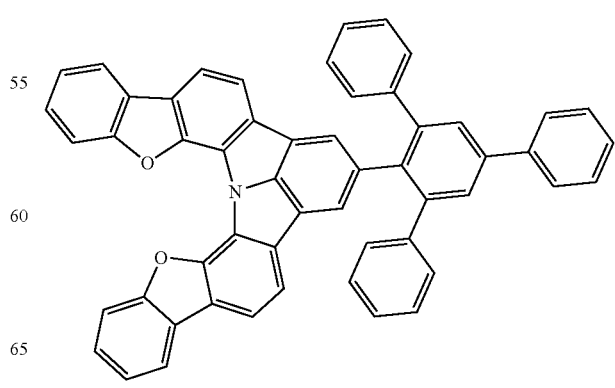

121
-continued
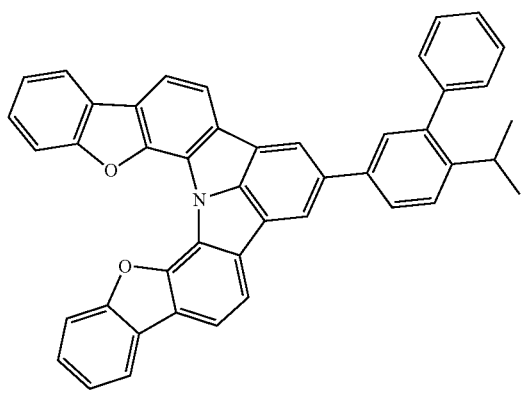
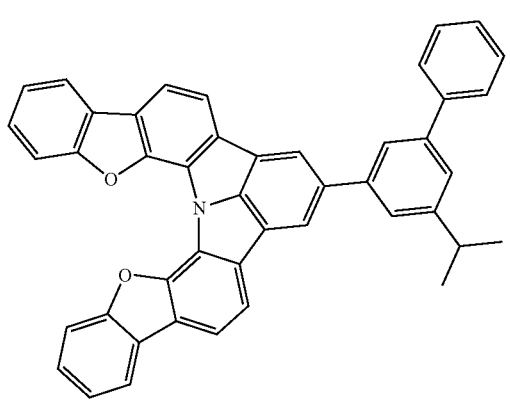
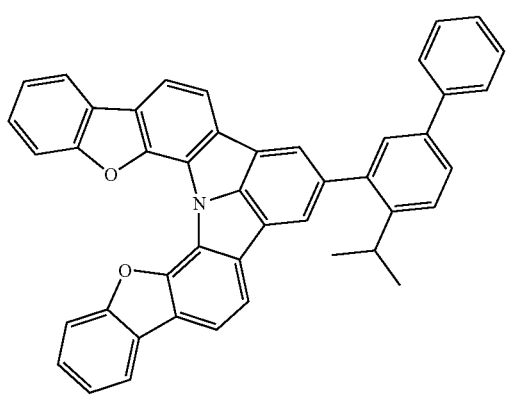
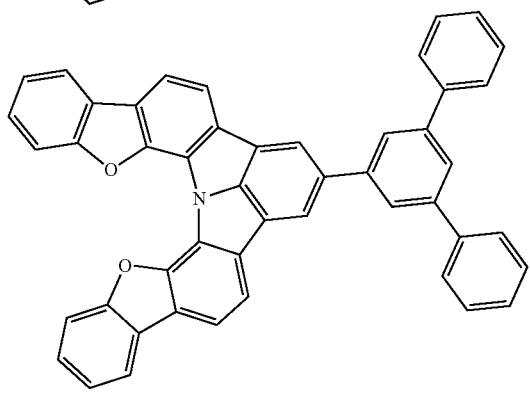
122
-continued
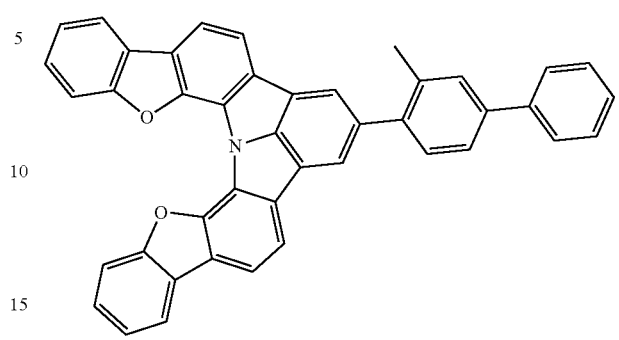
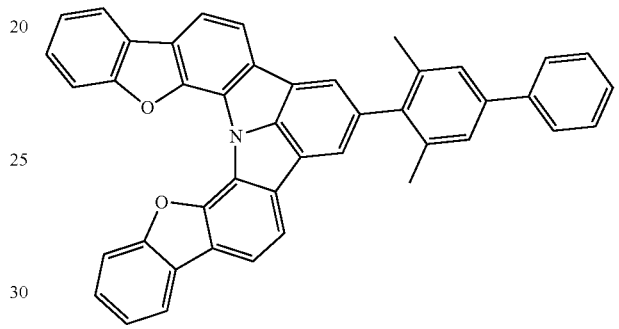
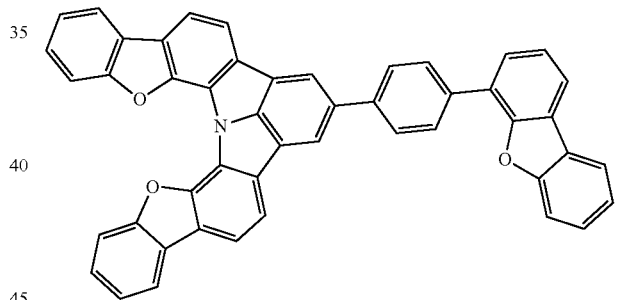
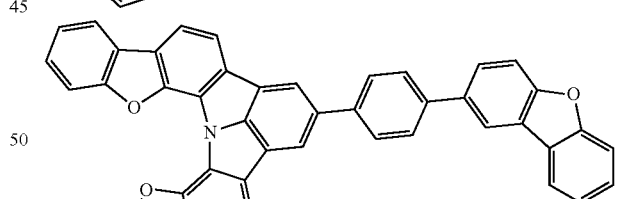
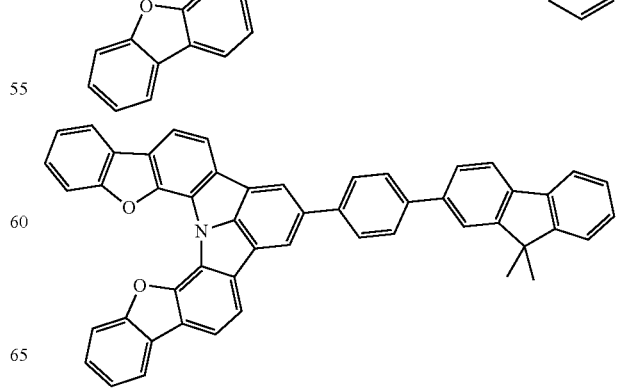

123
-continued
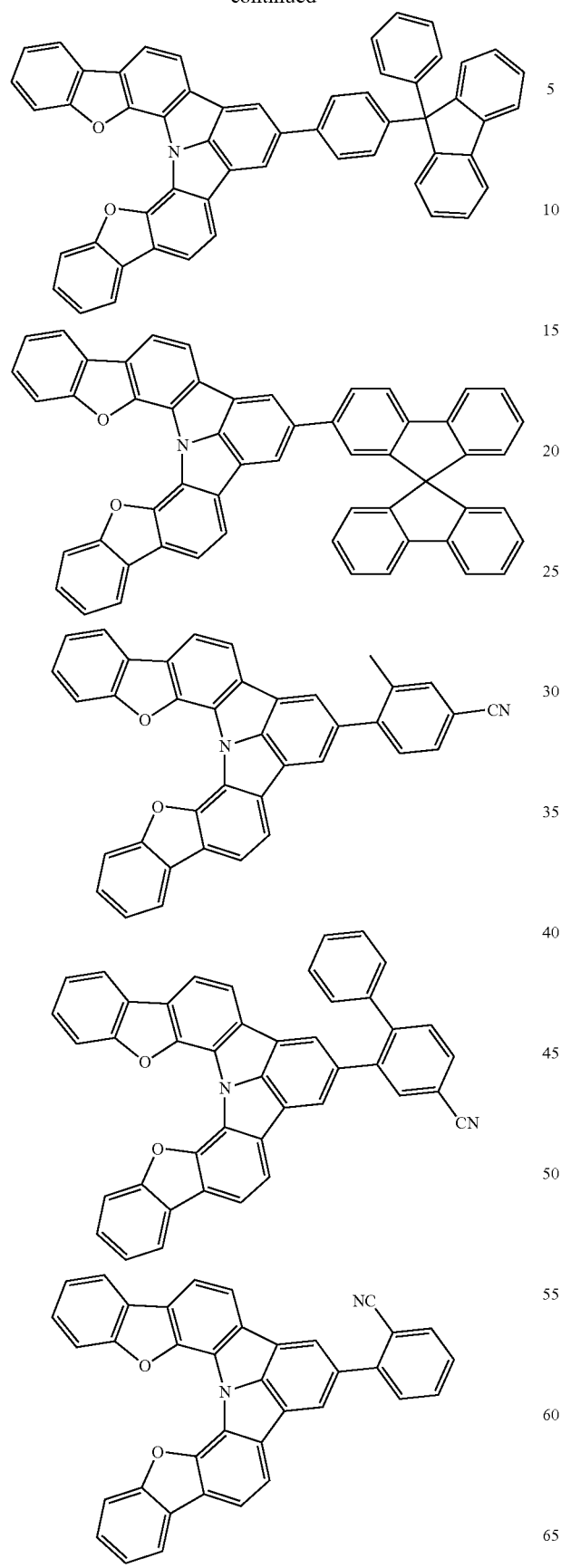
124
-continued
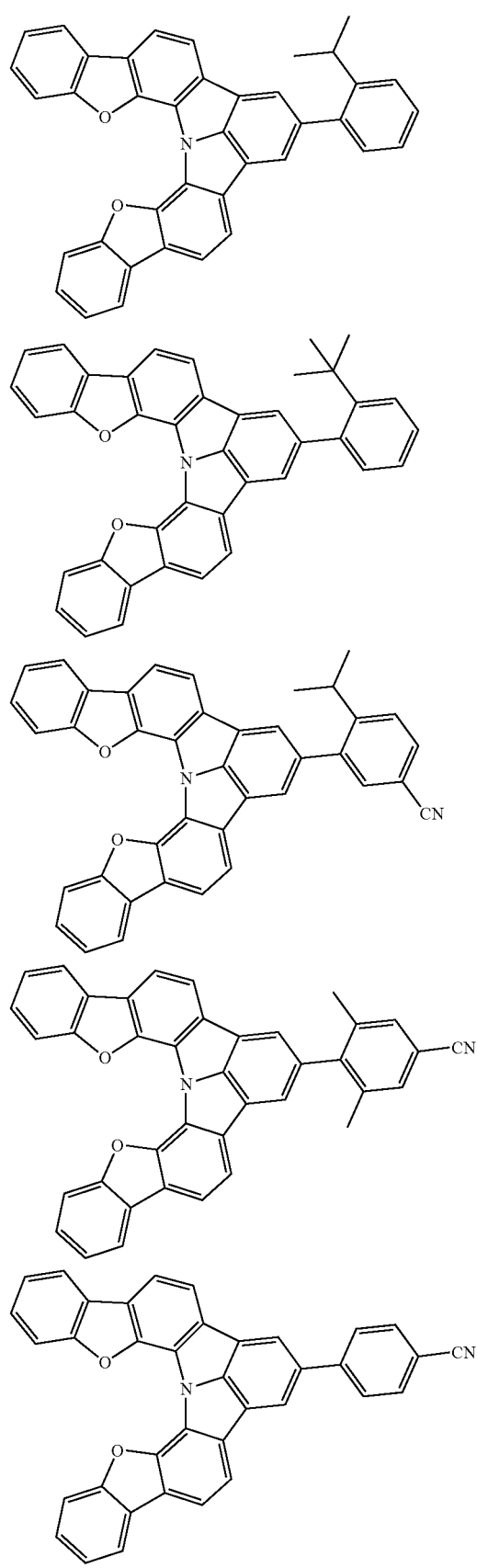

-continued
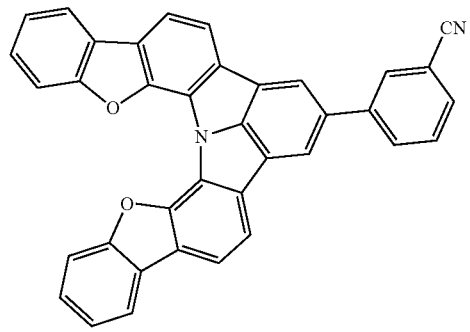
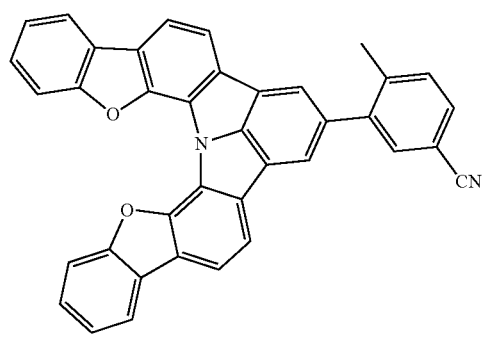
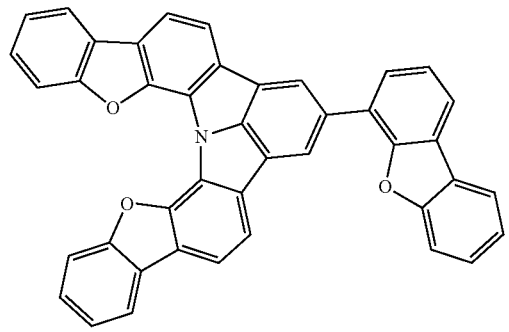
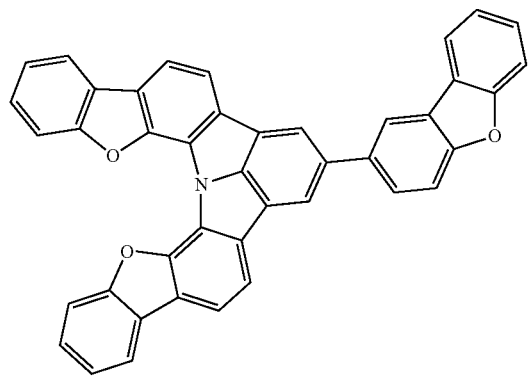
[Formula 66]
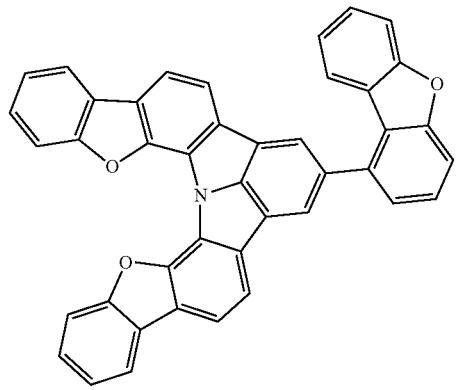
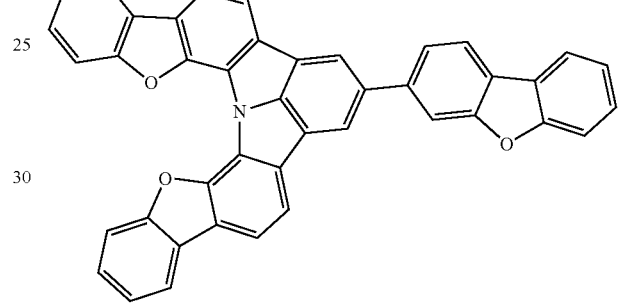
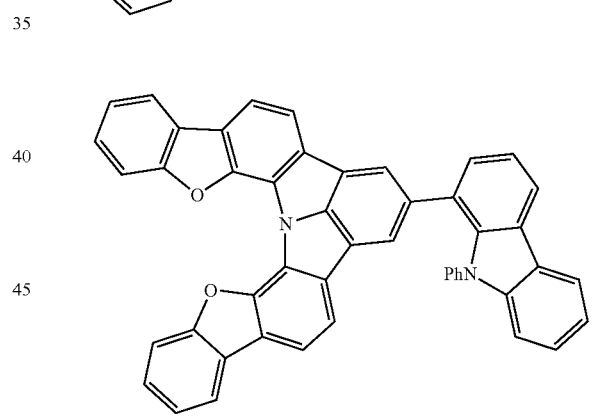
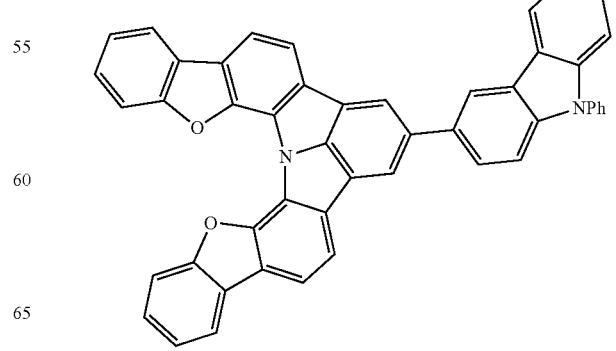

127
-continued
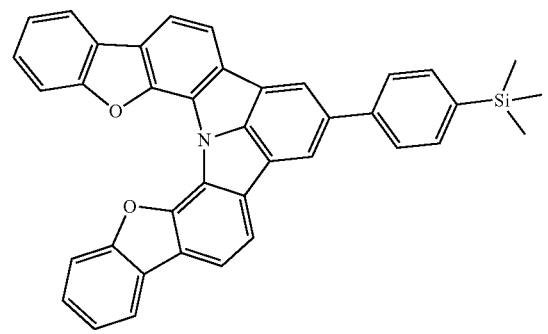
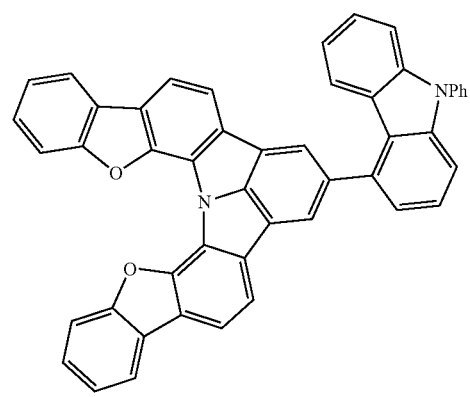
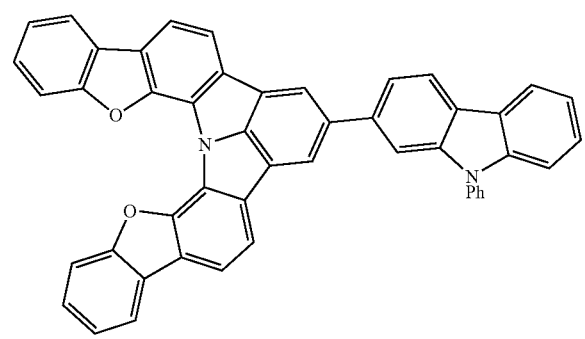
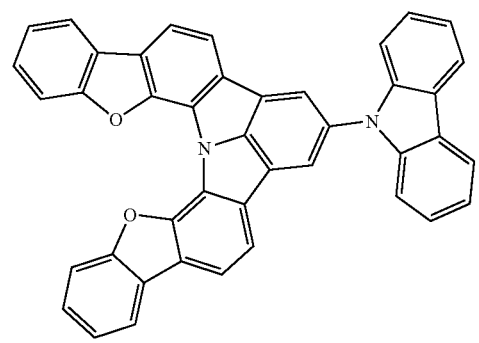
128
-continued
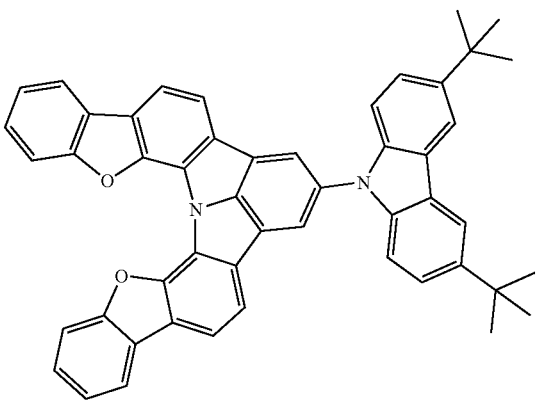
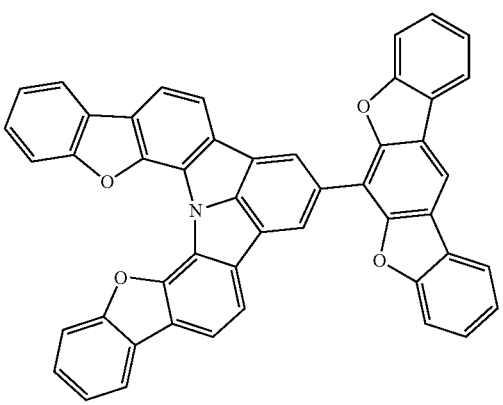
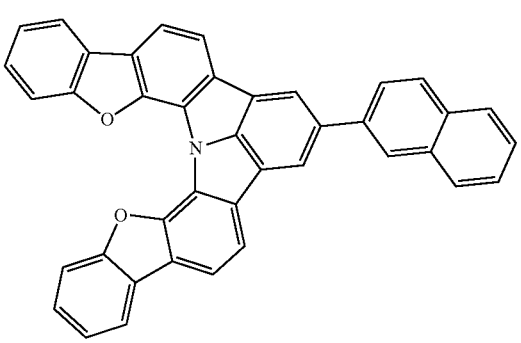
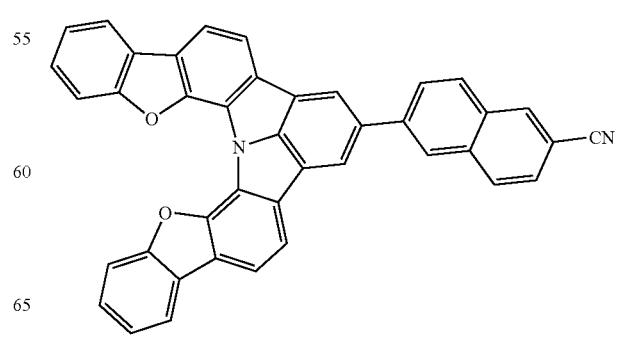

129
-continued
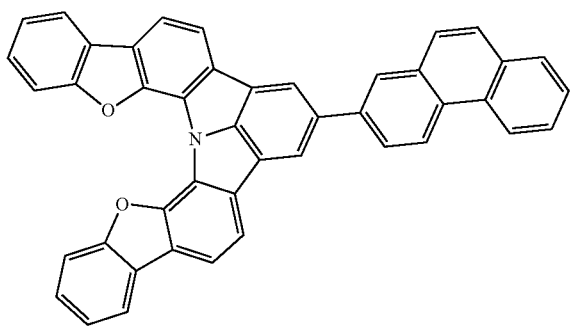
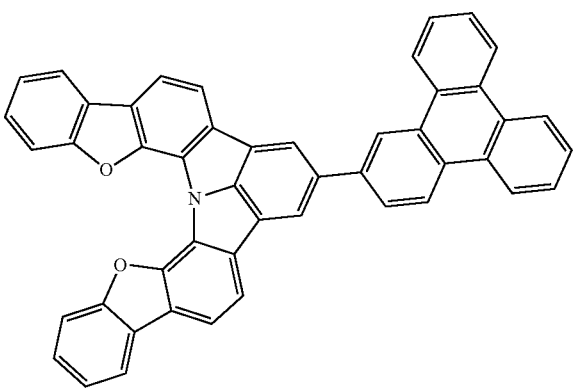
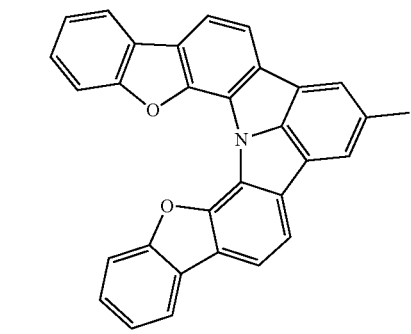
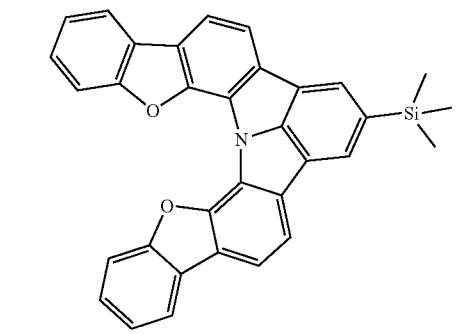
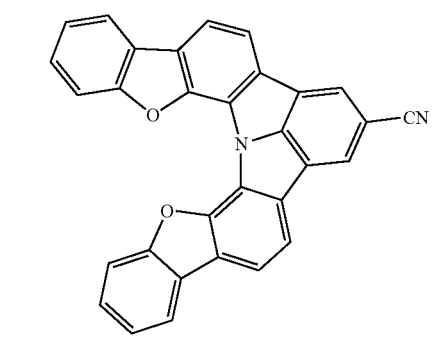
130
-continued
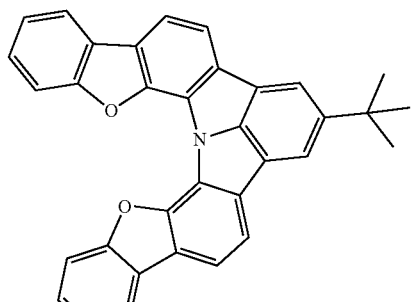
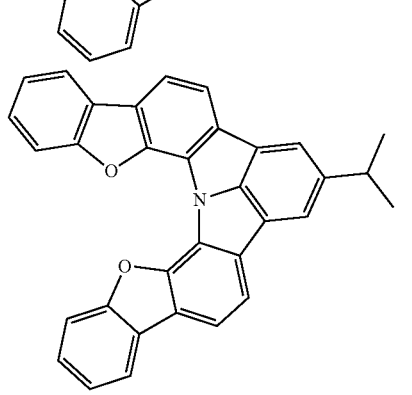
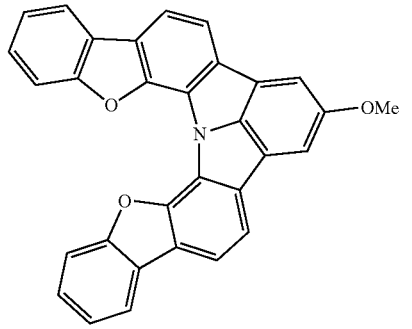
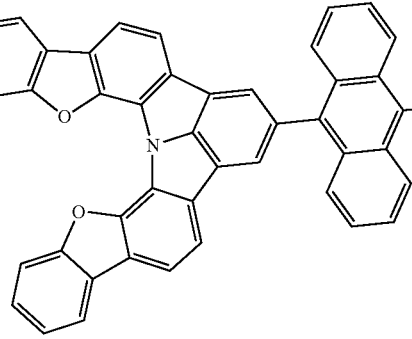
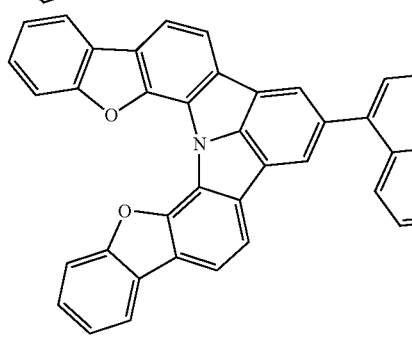

131
-continued
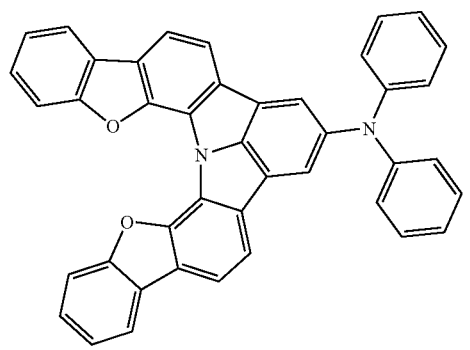
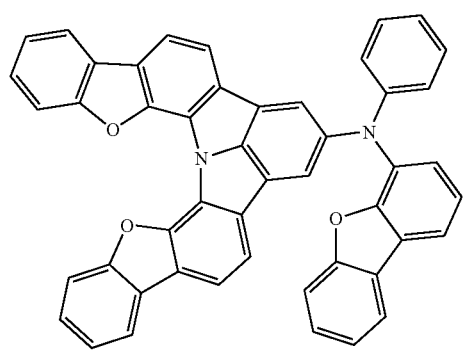
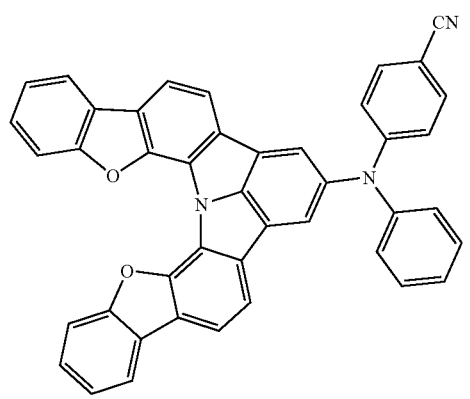
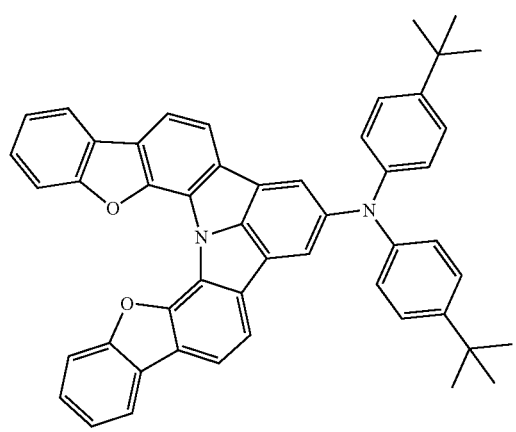
132
-continued
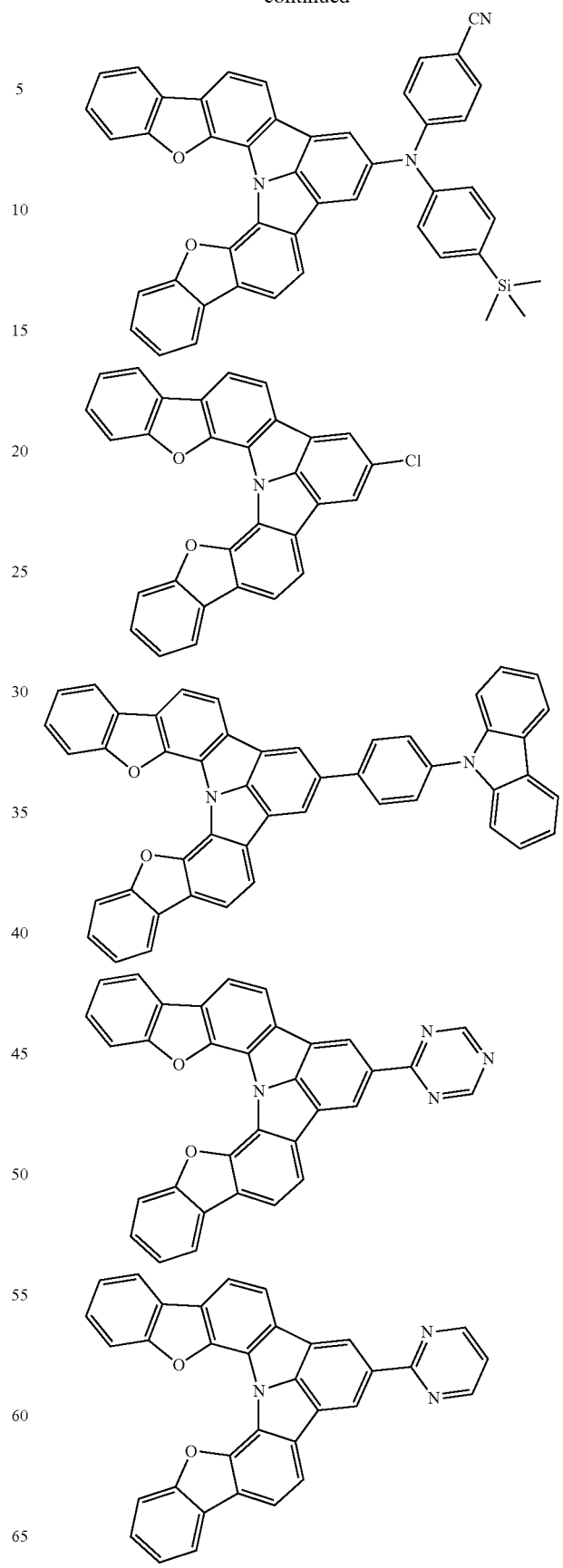

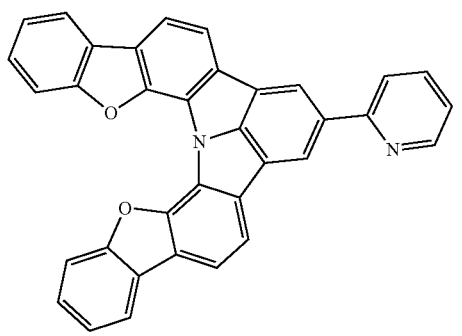
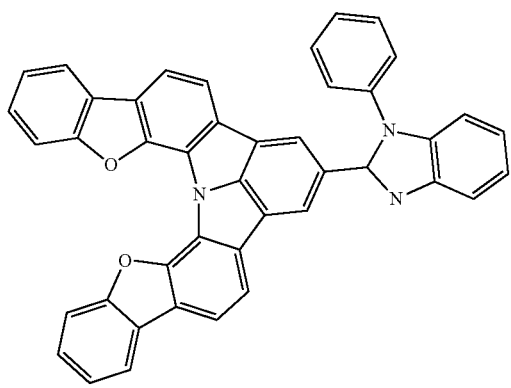
[Formula 67]
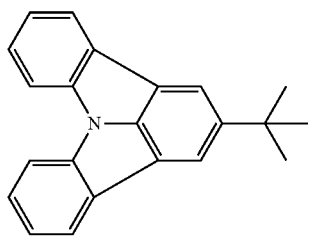
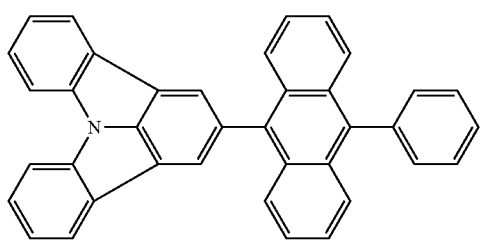
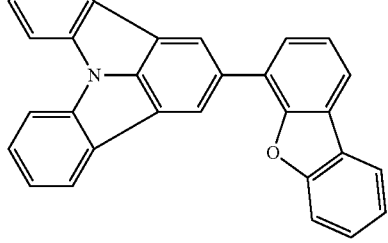
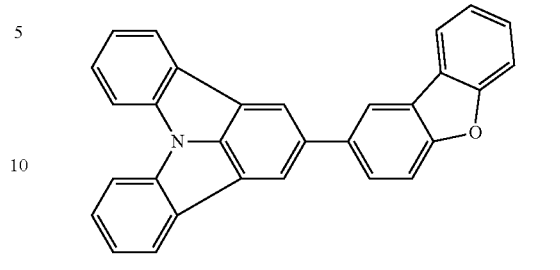
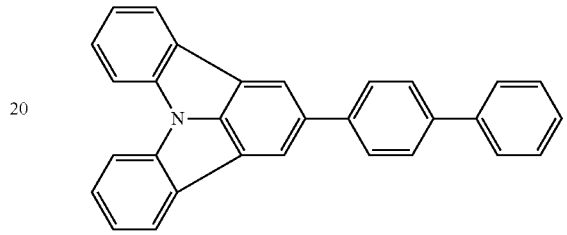
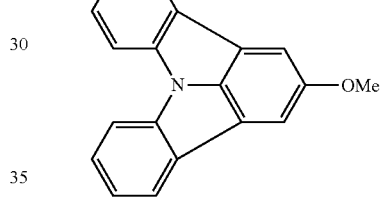
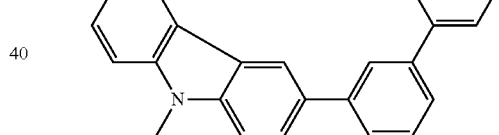
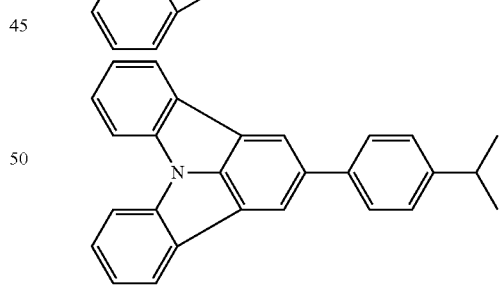
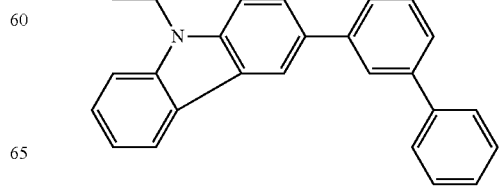

135
-continued
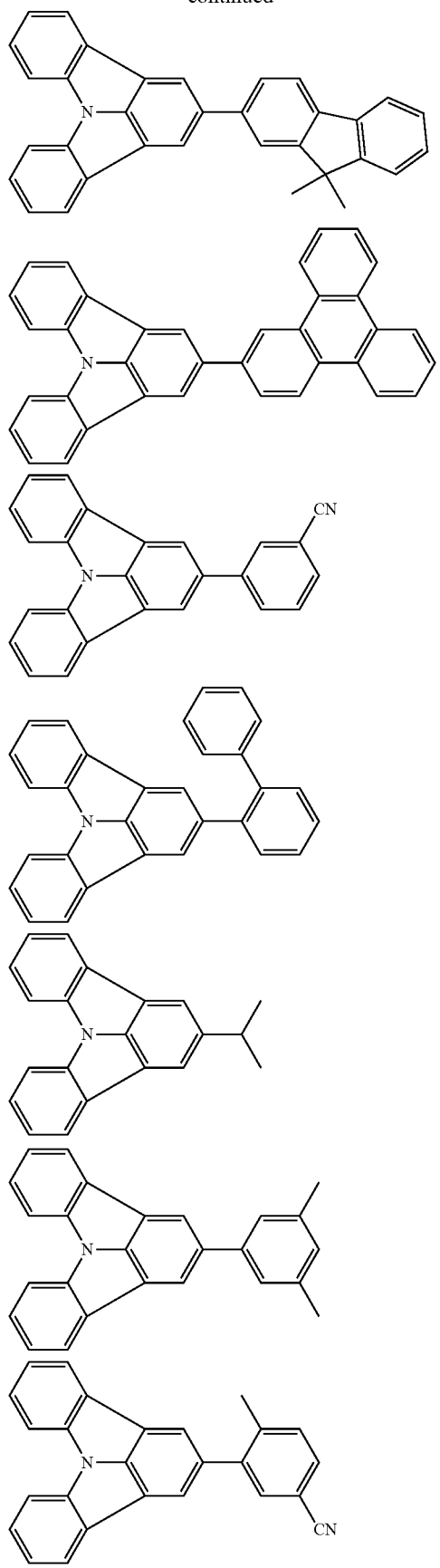
136
-continued
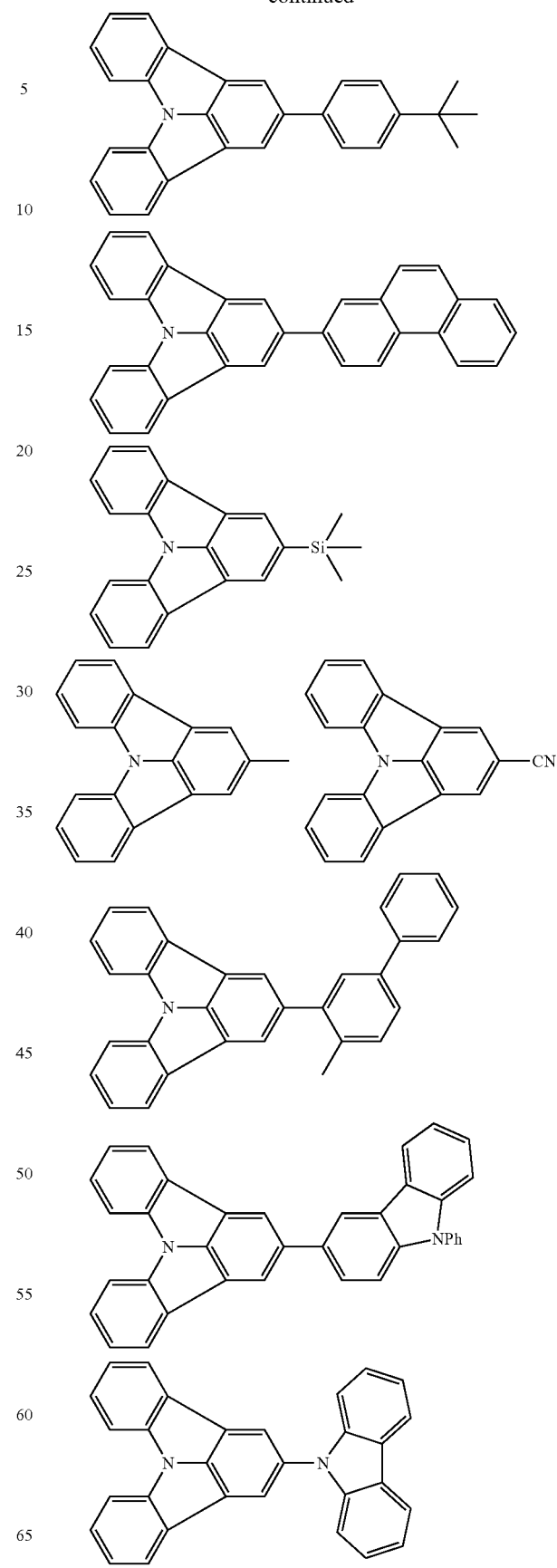

137
-continued
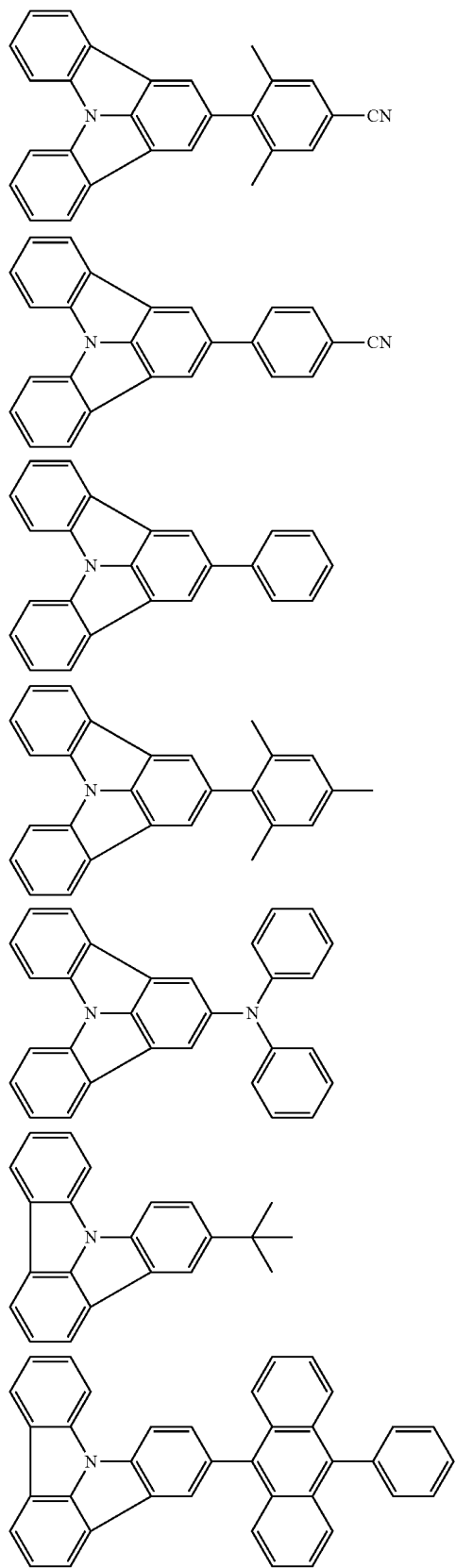
138
-continued
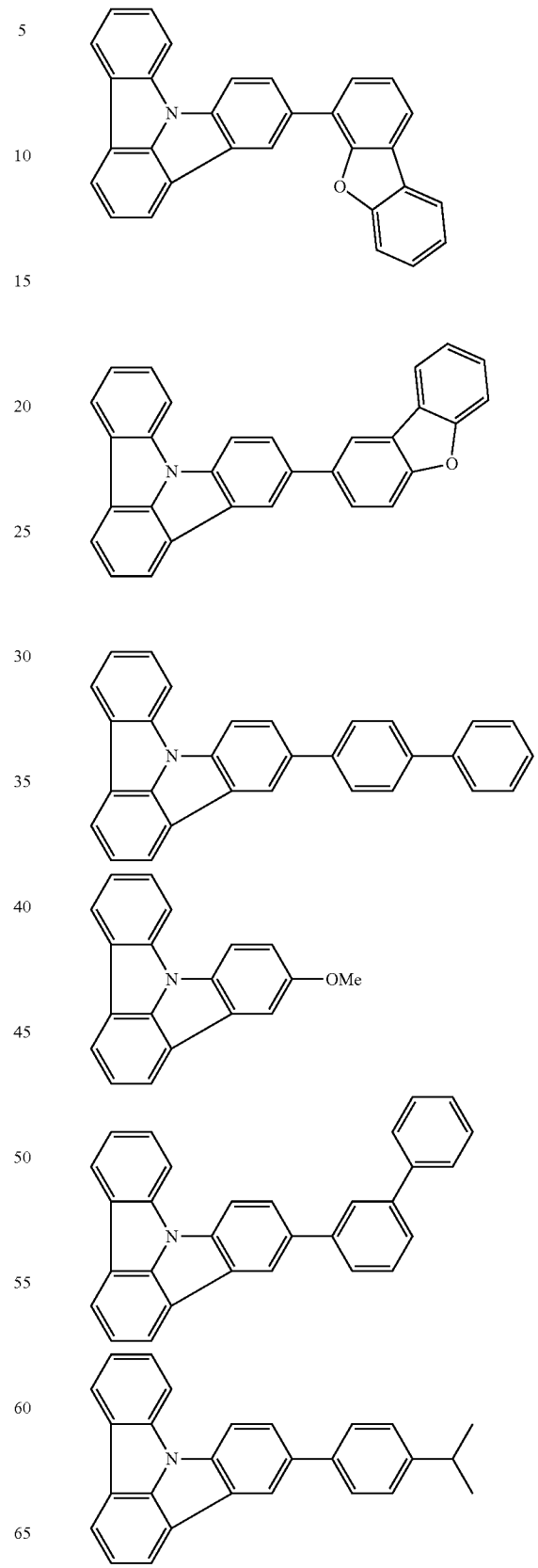

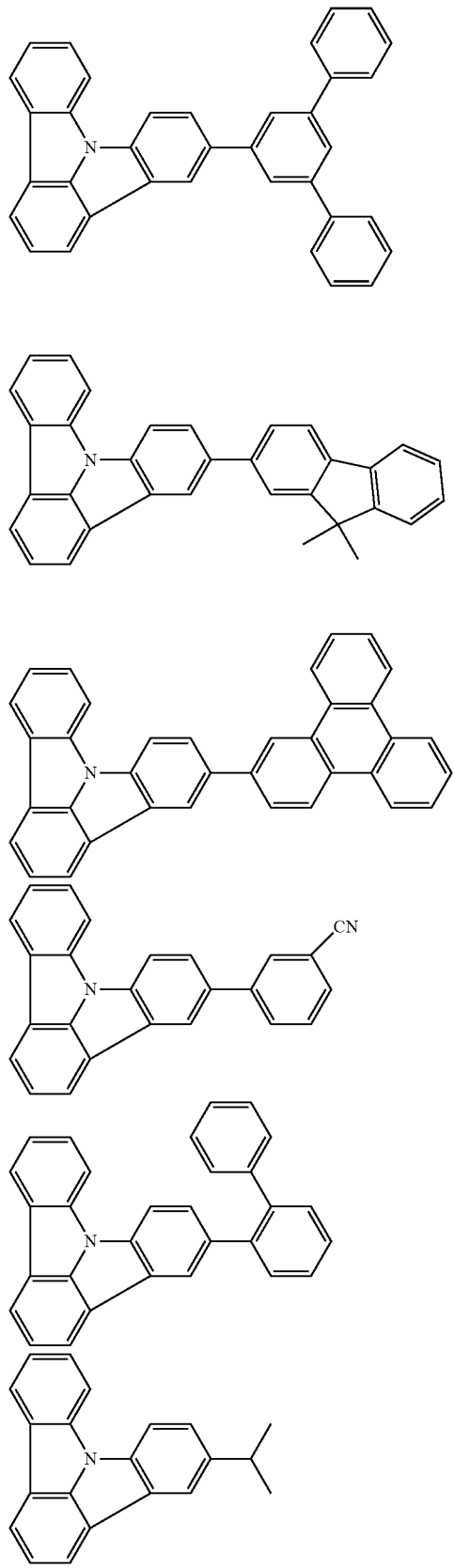
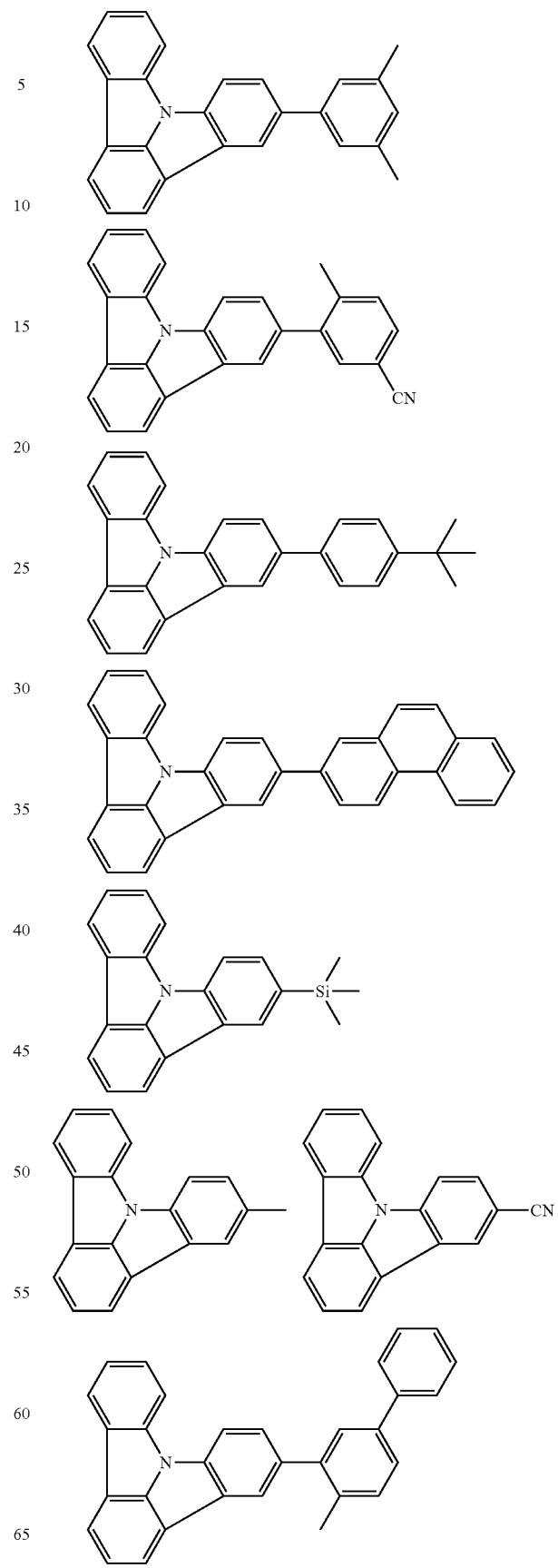

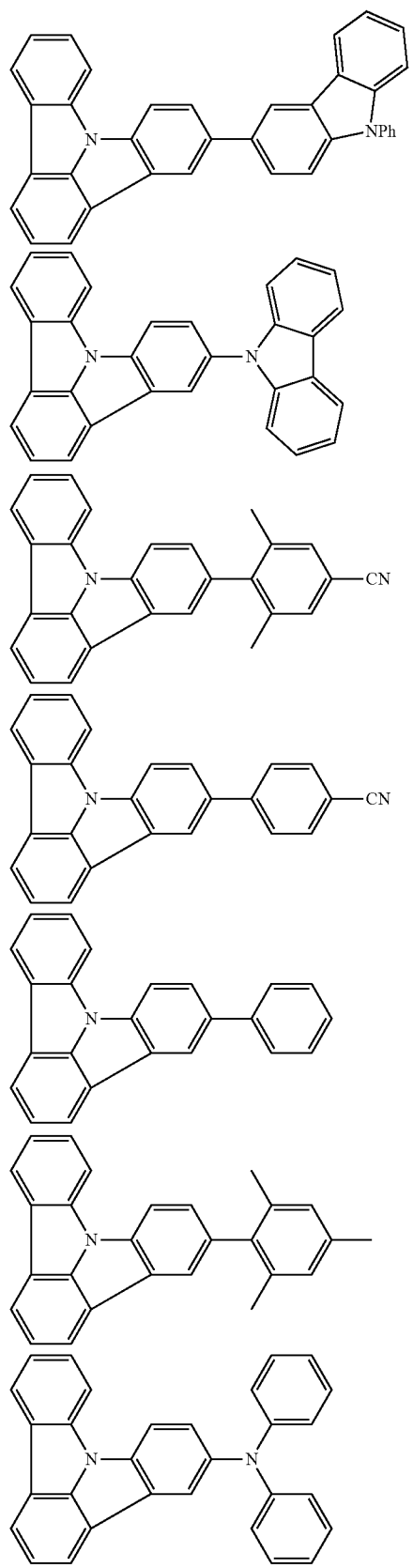
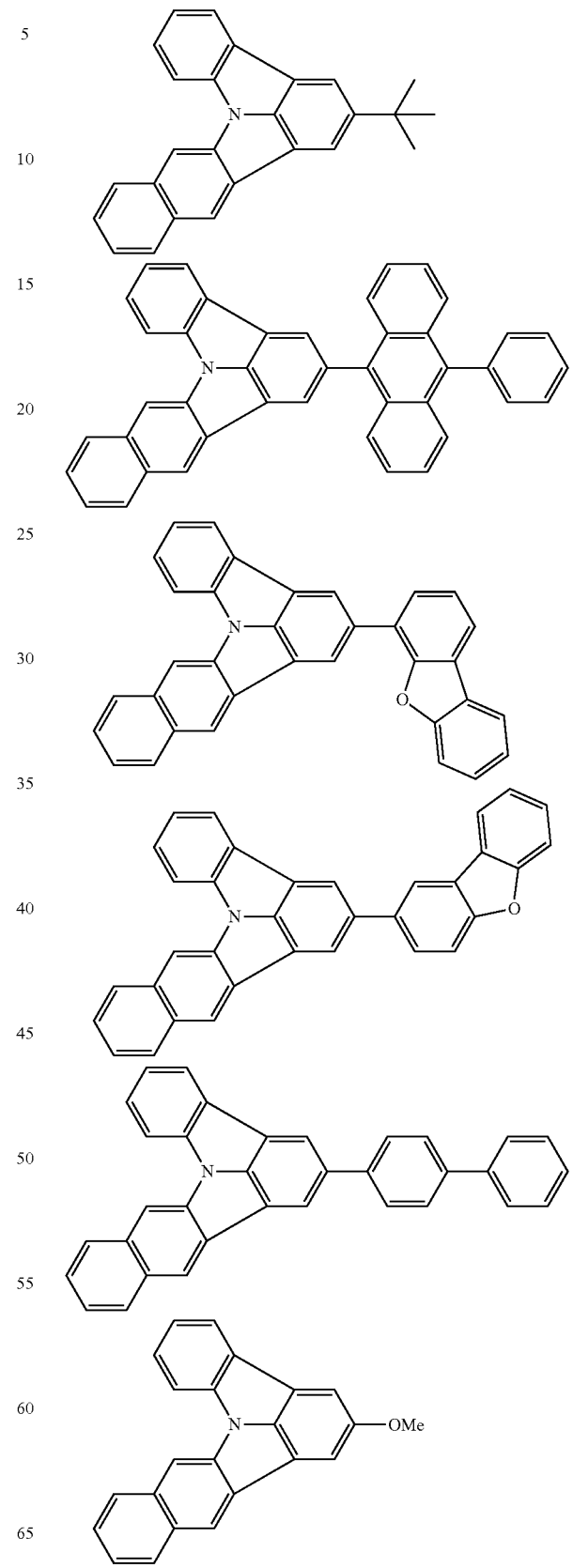

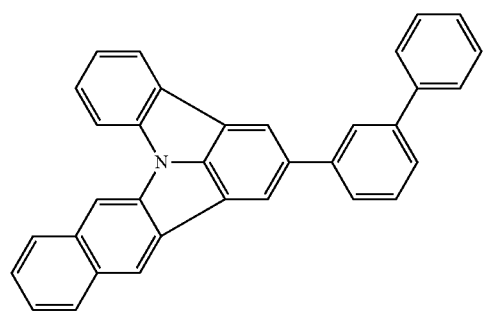
[Formula 68]
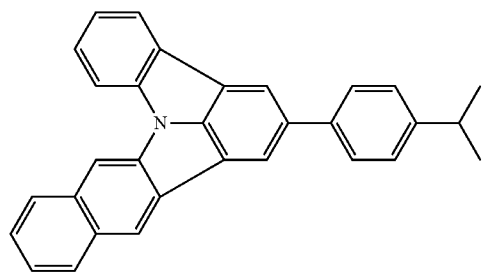
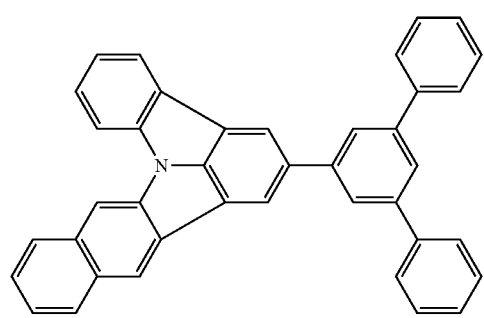
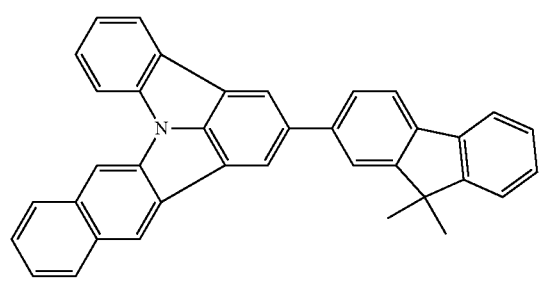
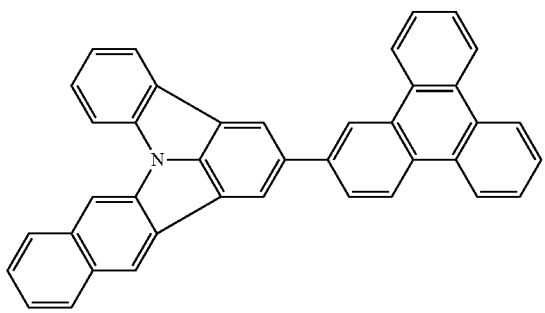
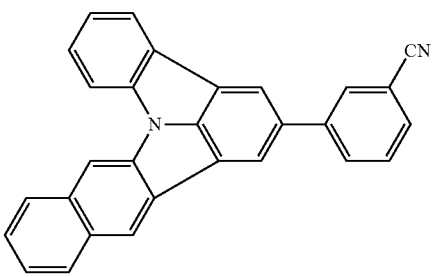
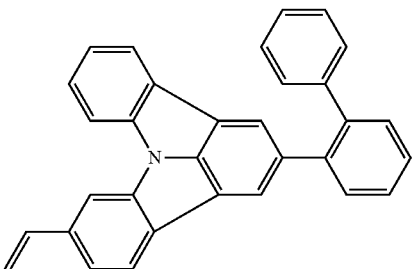
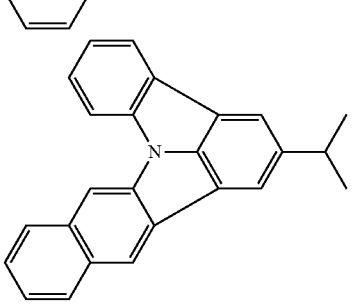
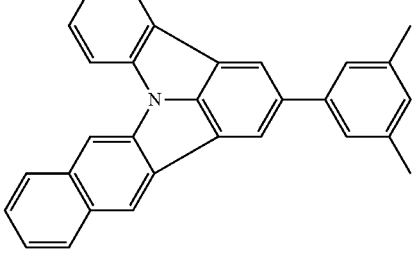
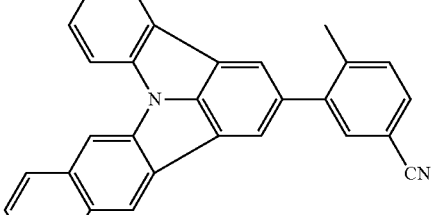
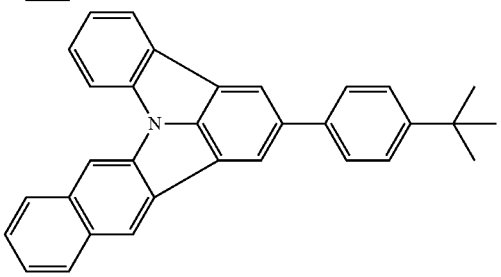

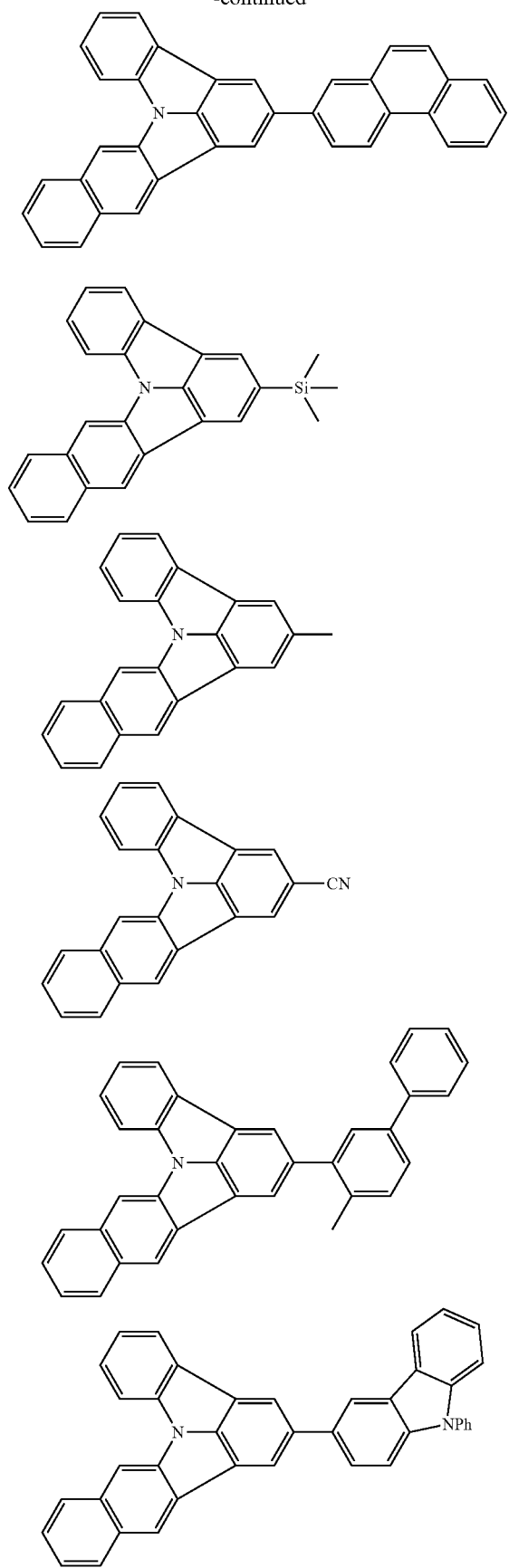
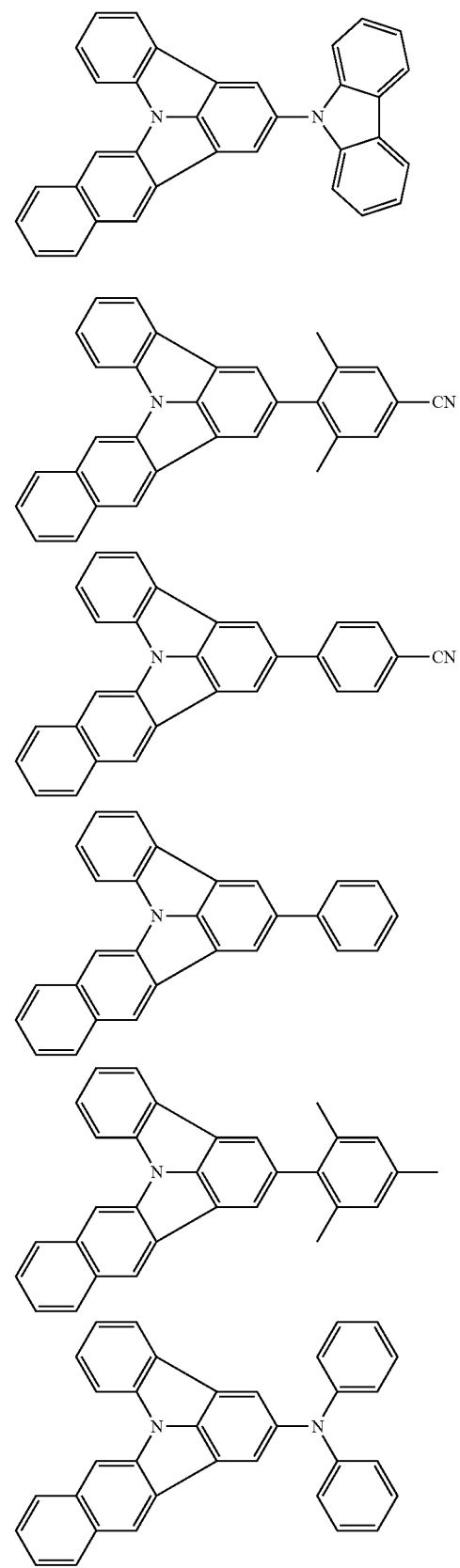

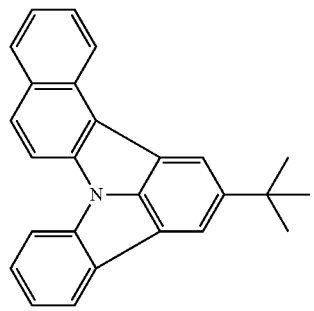
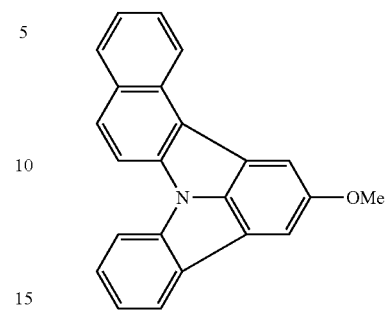
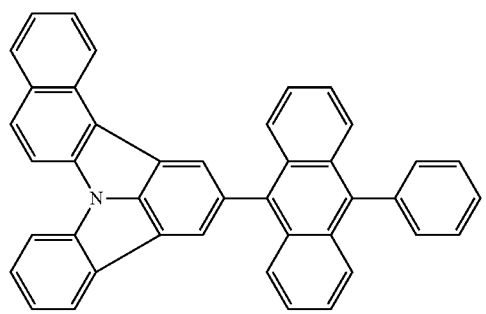
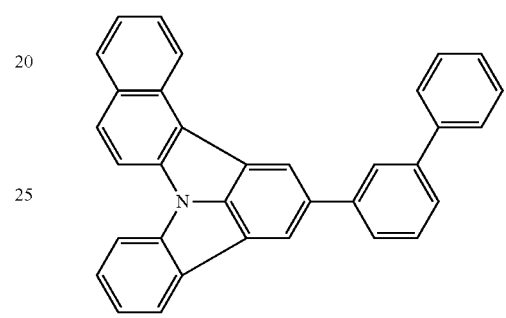
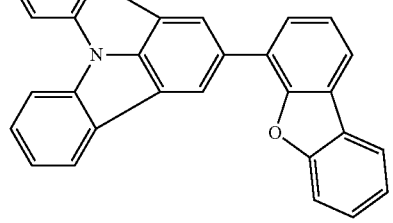
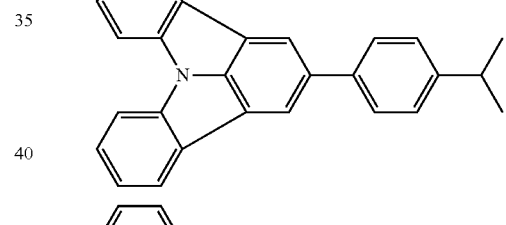
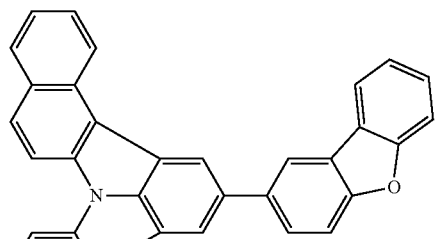
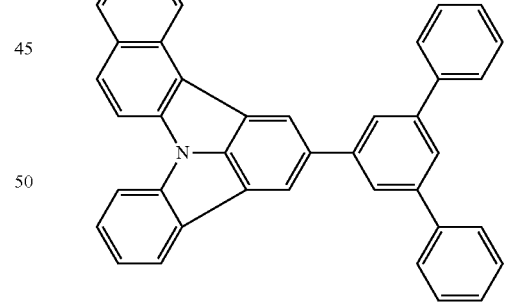
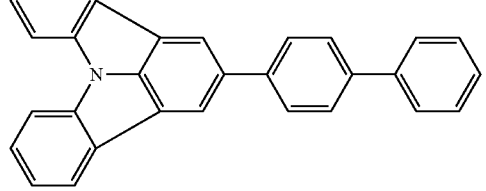
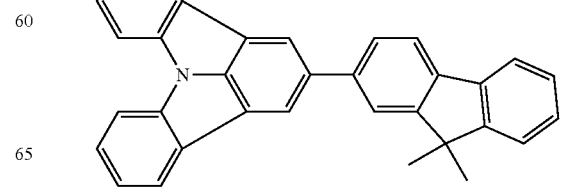

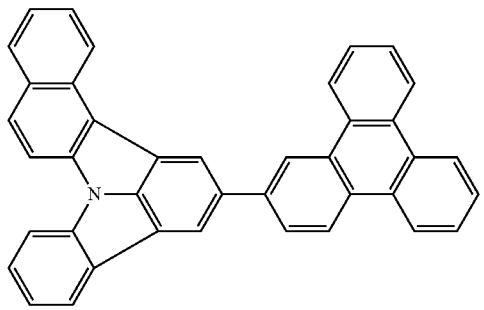
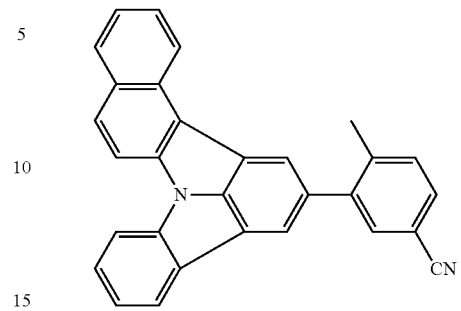
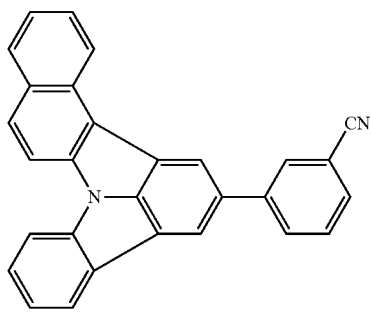
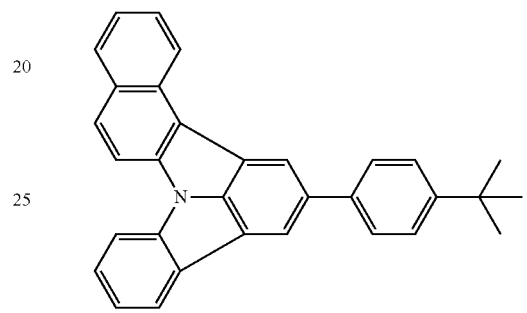
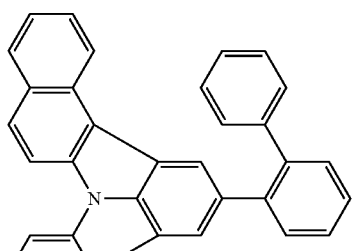
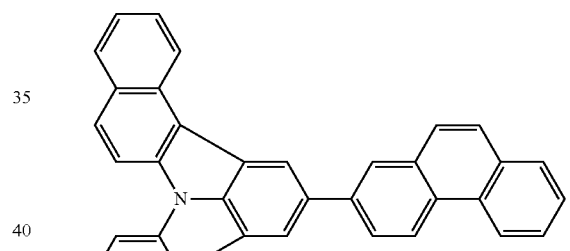
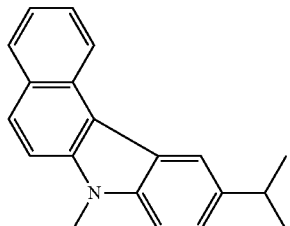
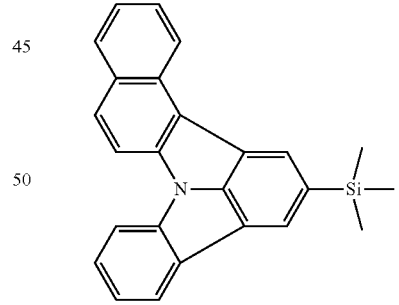
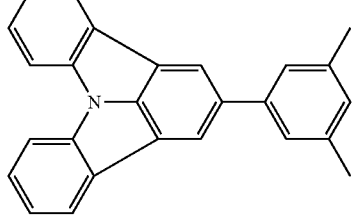
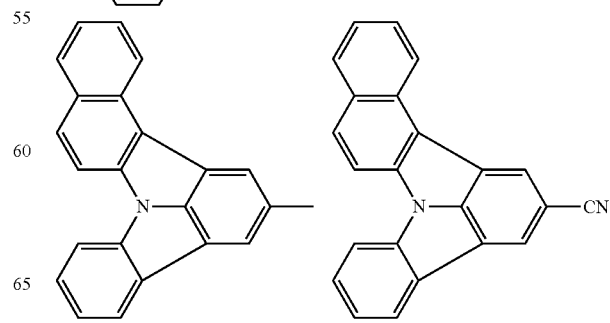

-continued
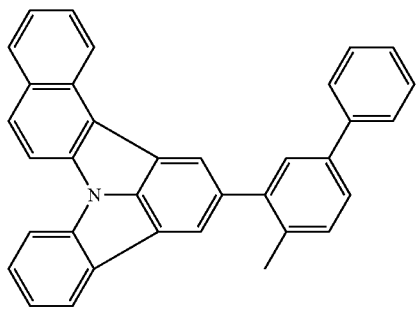
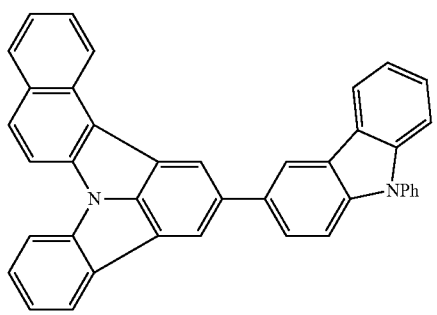
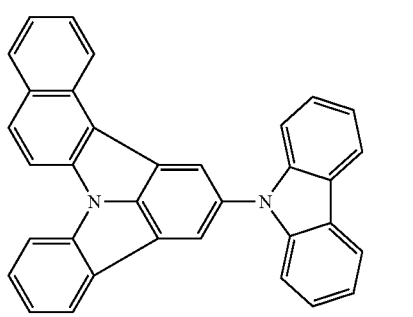
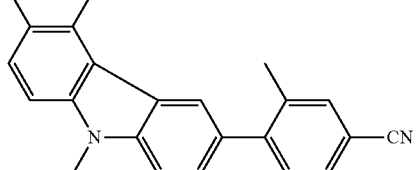

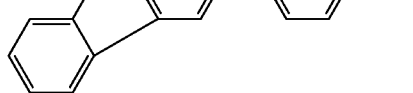
-continued
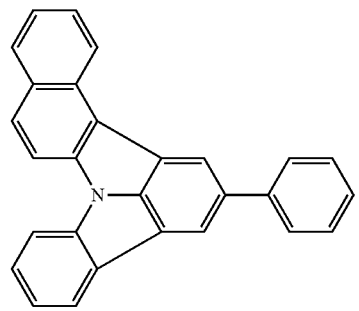
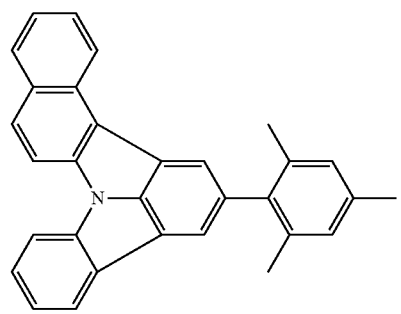
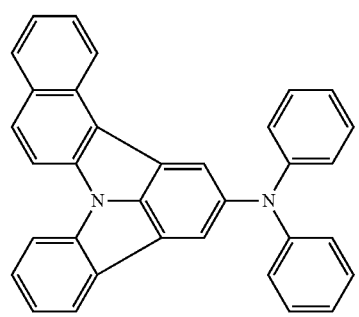
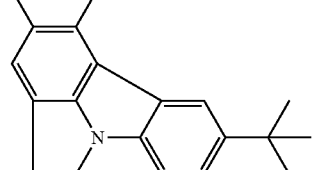
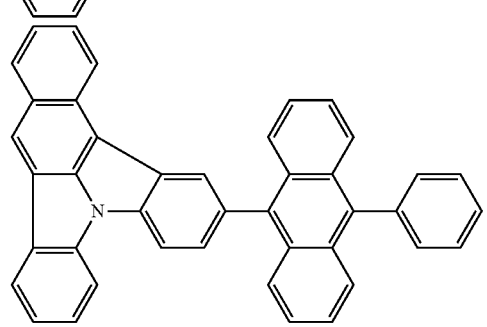

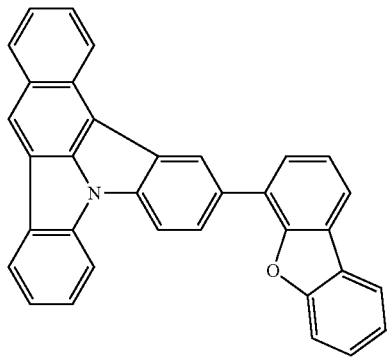
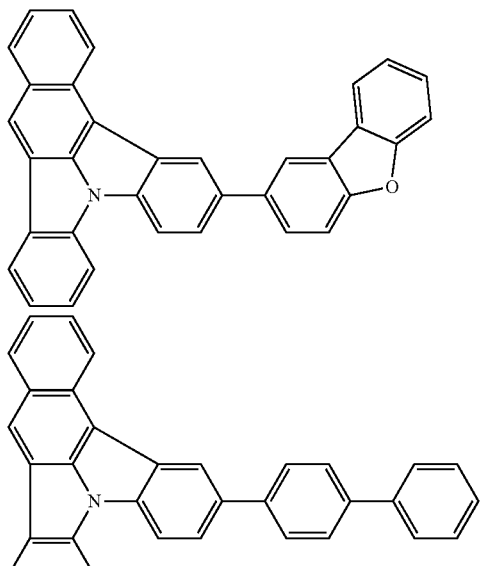
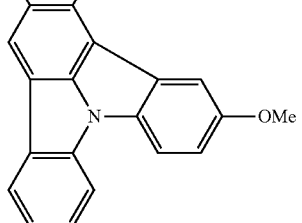
[Formula 69]
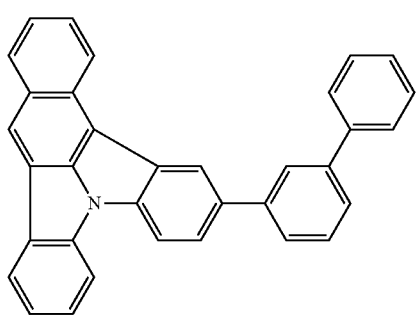
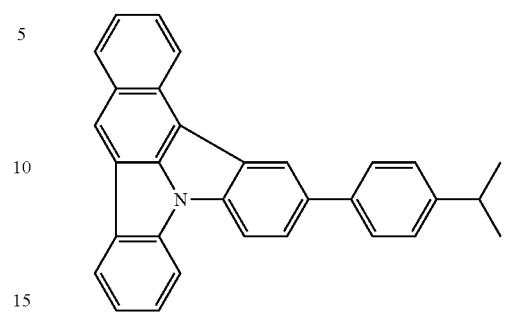
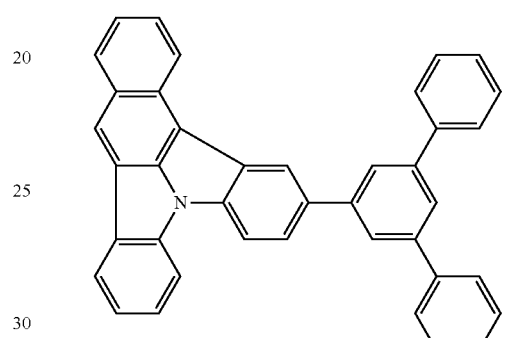
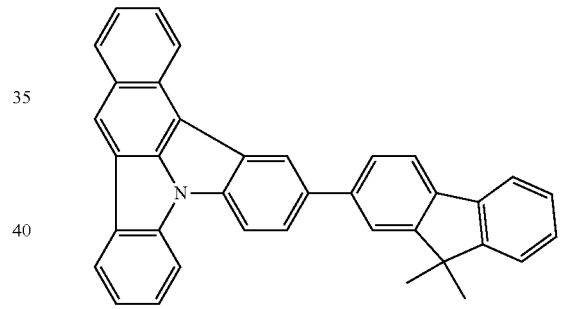
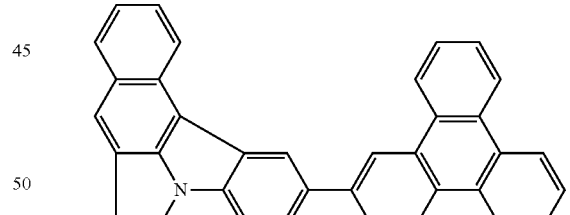
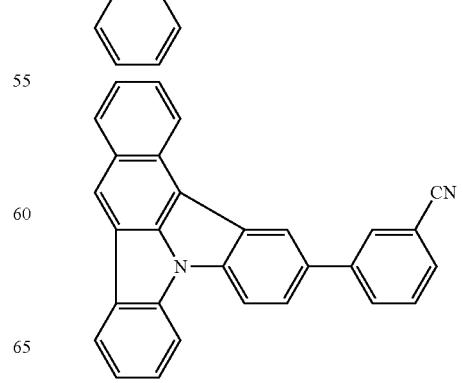

155
-continued
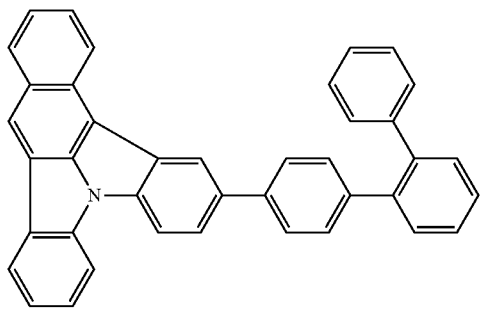
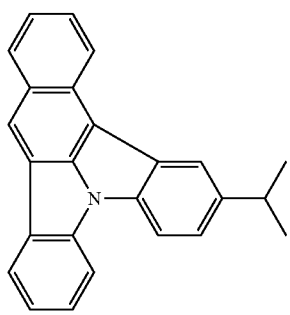
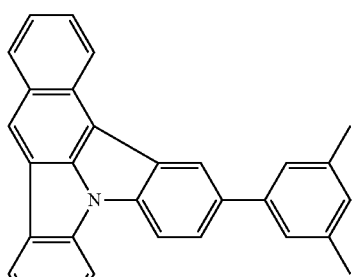
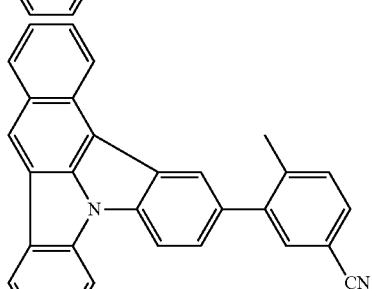
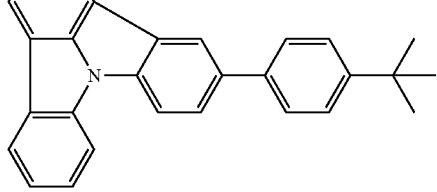
156
-continued
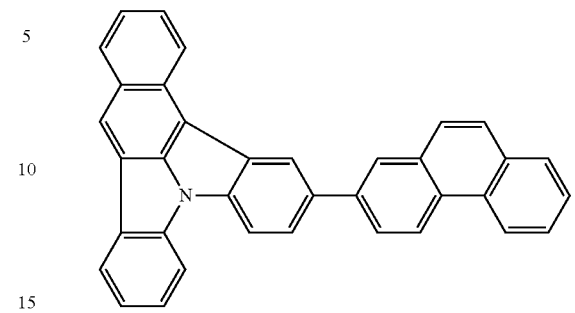
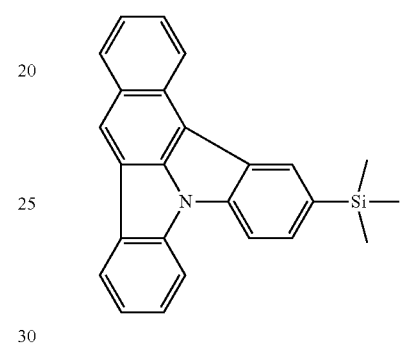
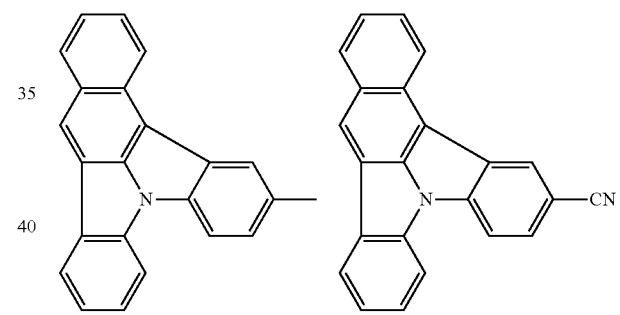
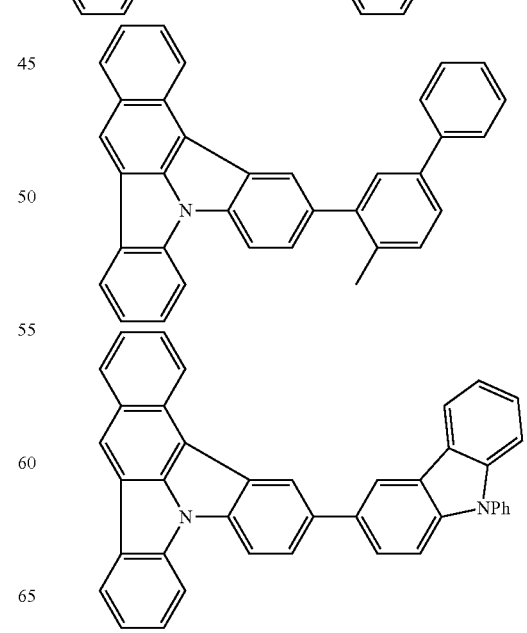

157
-continued
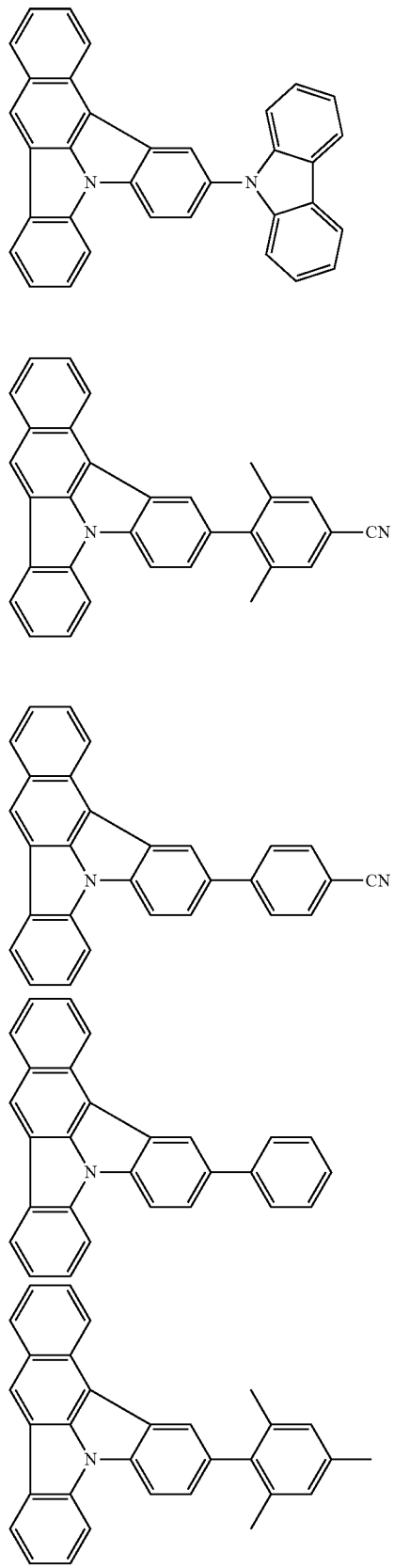
158
-continued
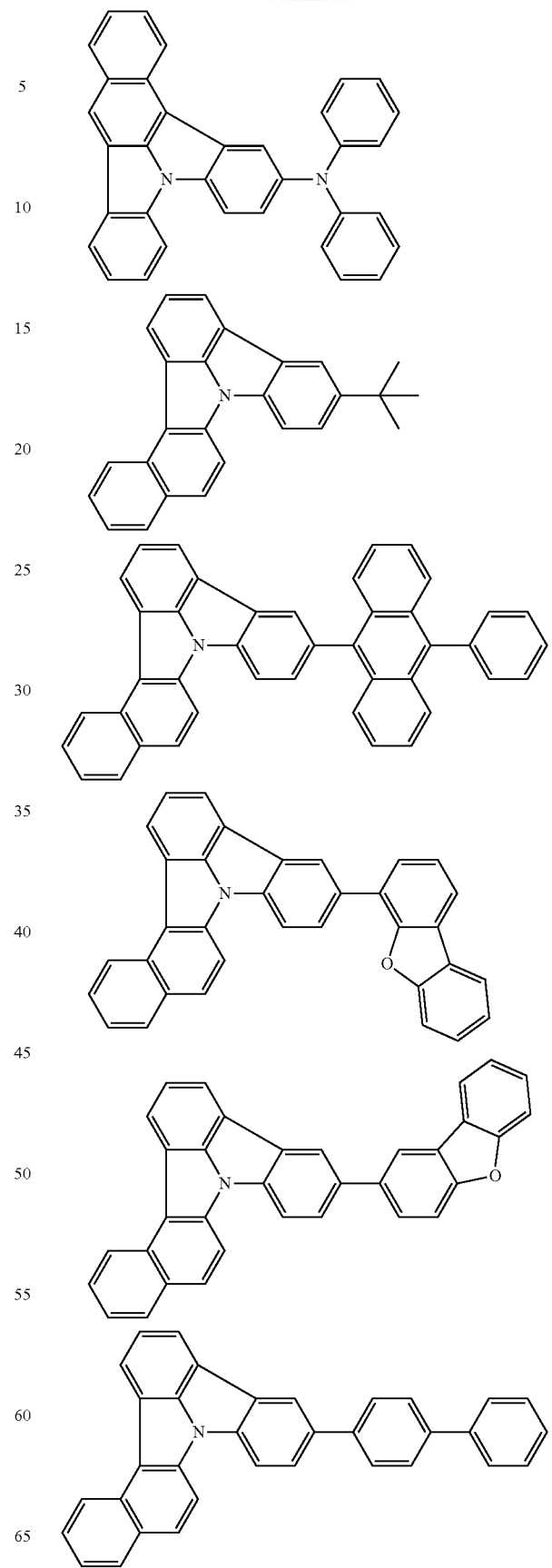

159
-continued
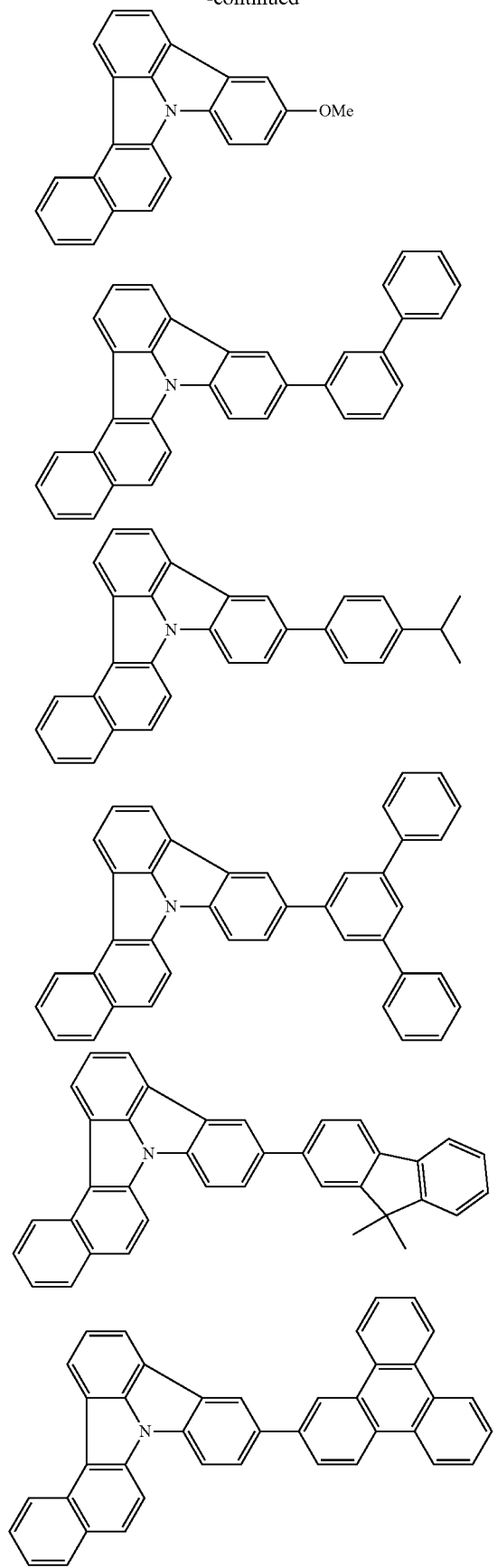
160
-continued
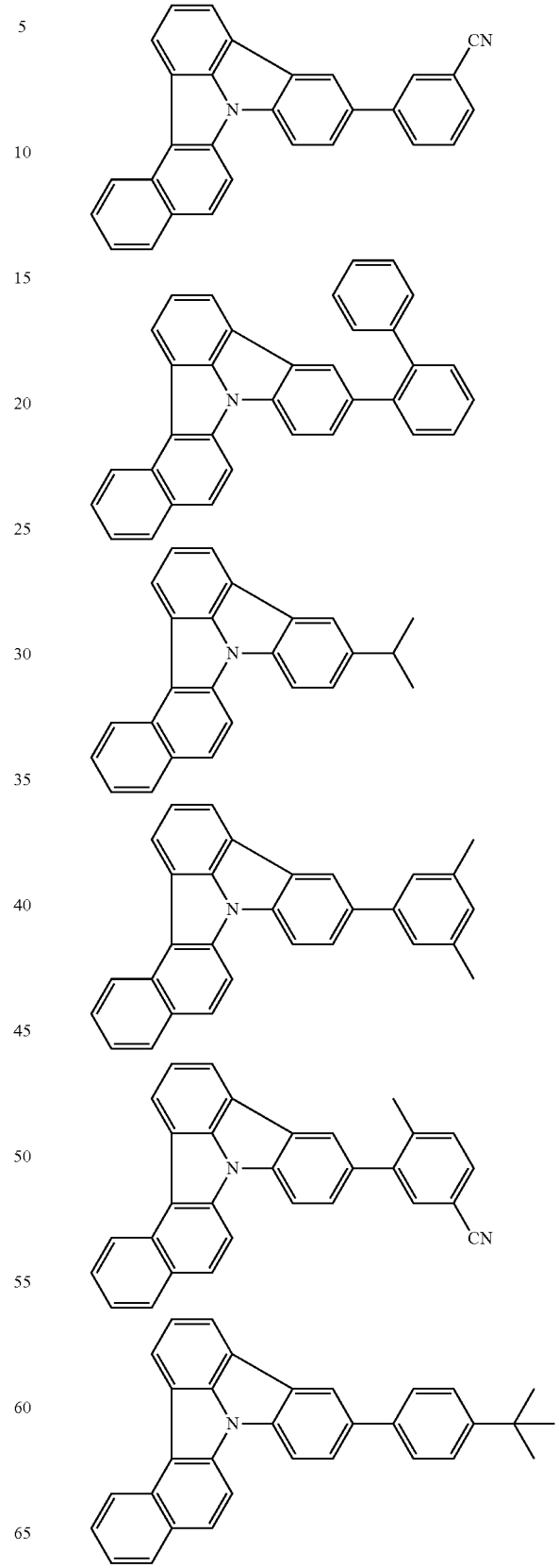

161
-continued
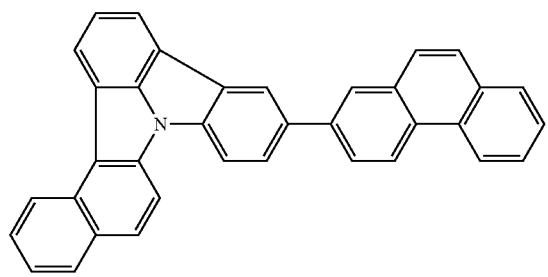
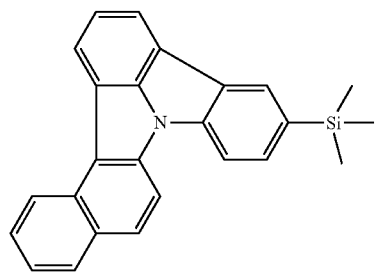
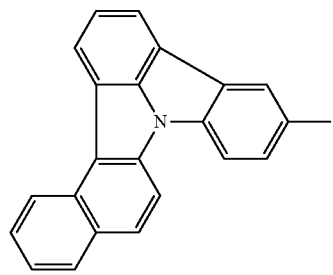
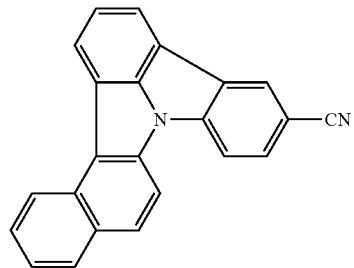
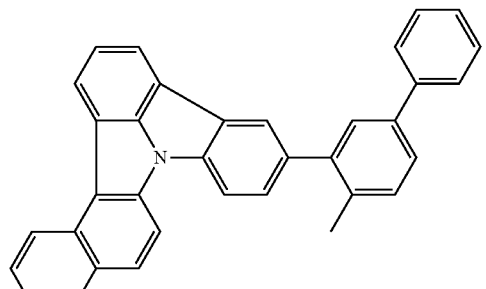
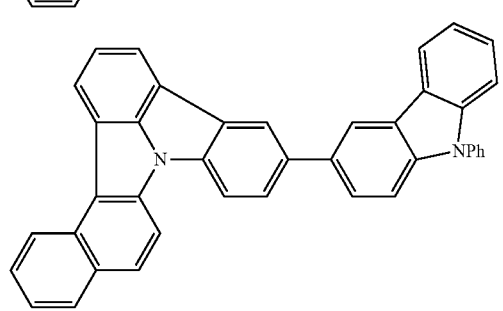
162
-continued
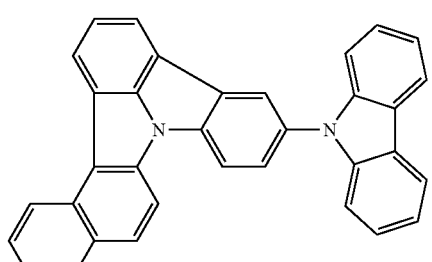
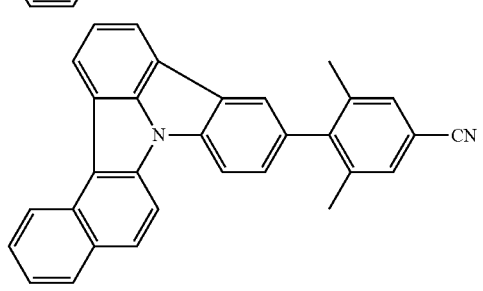
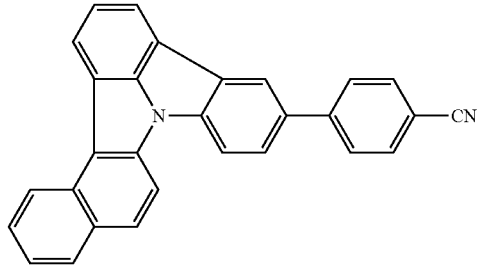
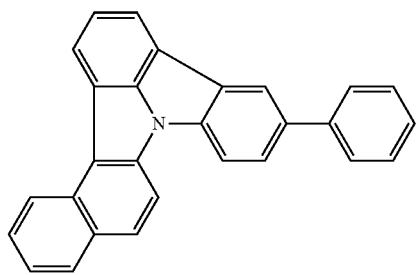
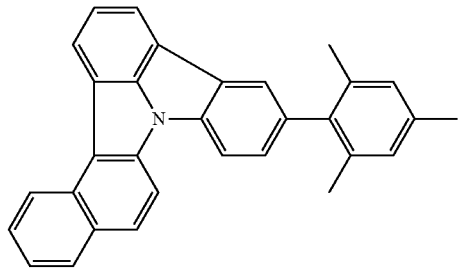
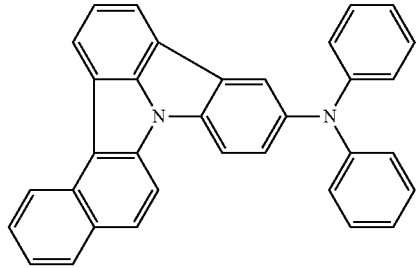

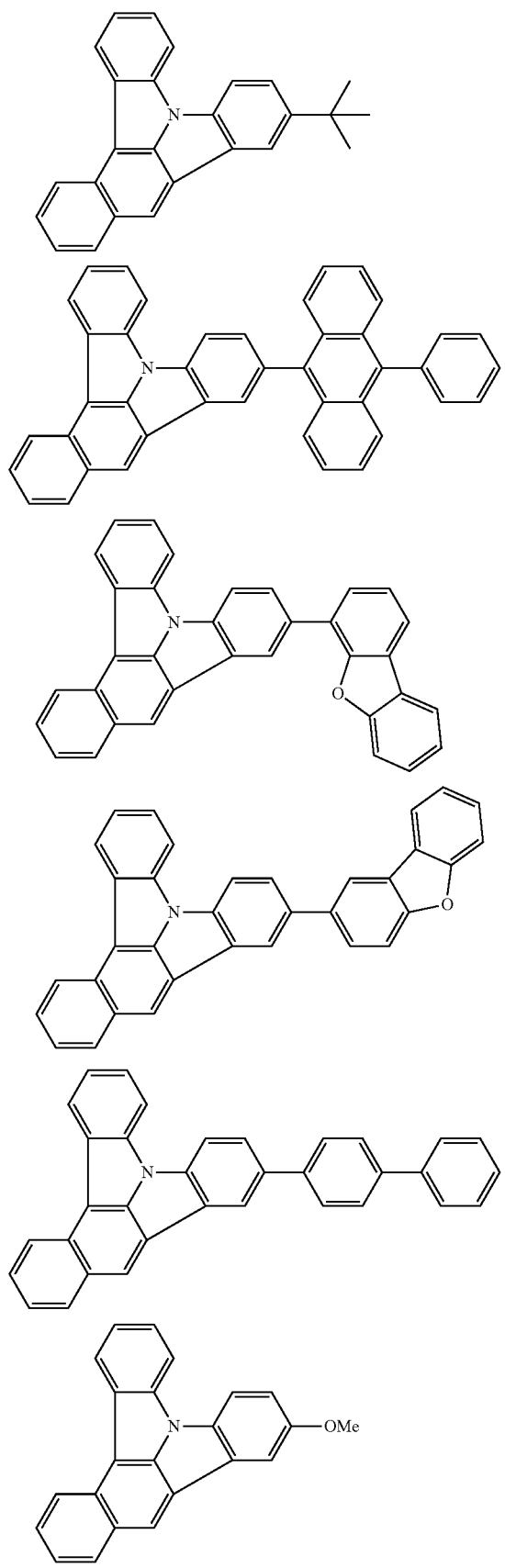
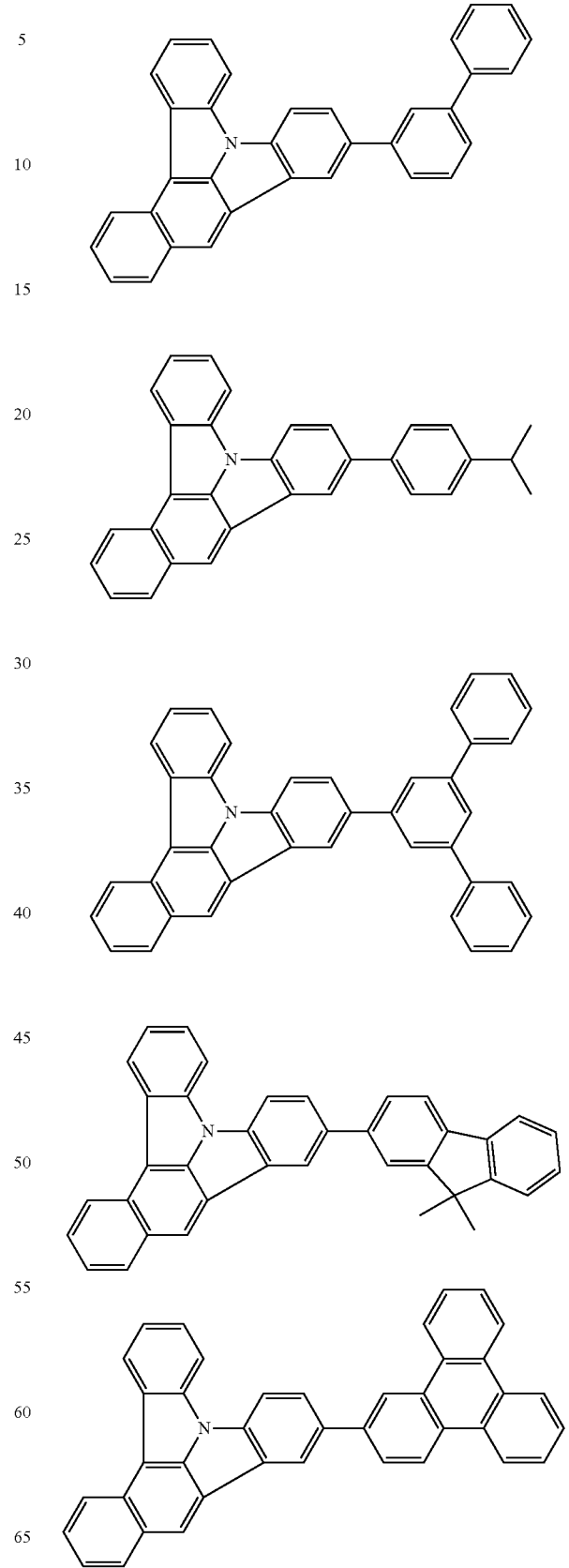
[Formula 70]

165
-continued
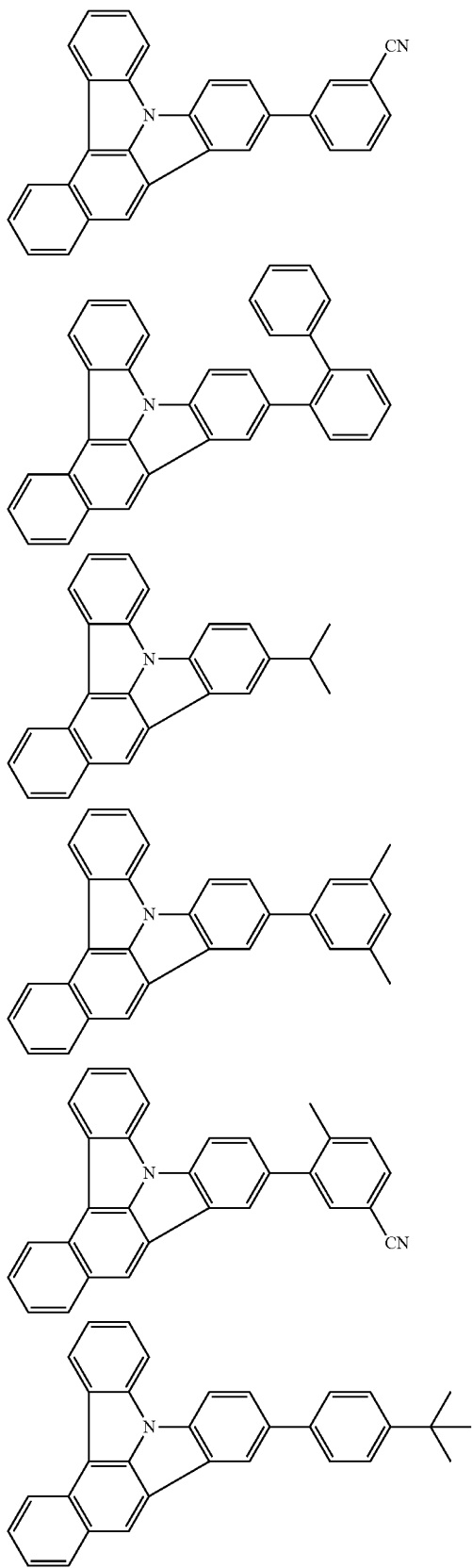
166
-continued
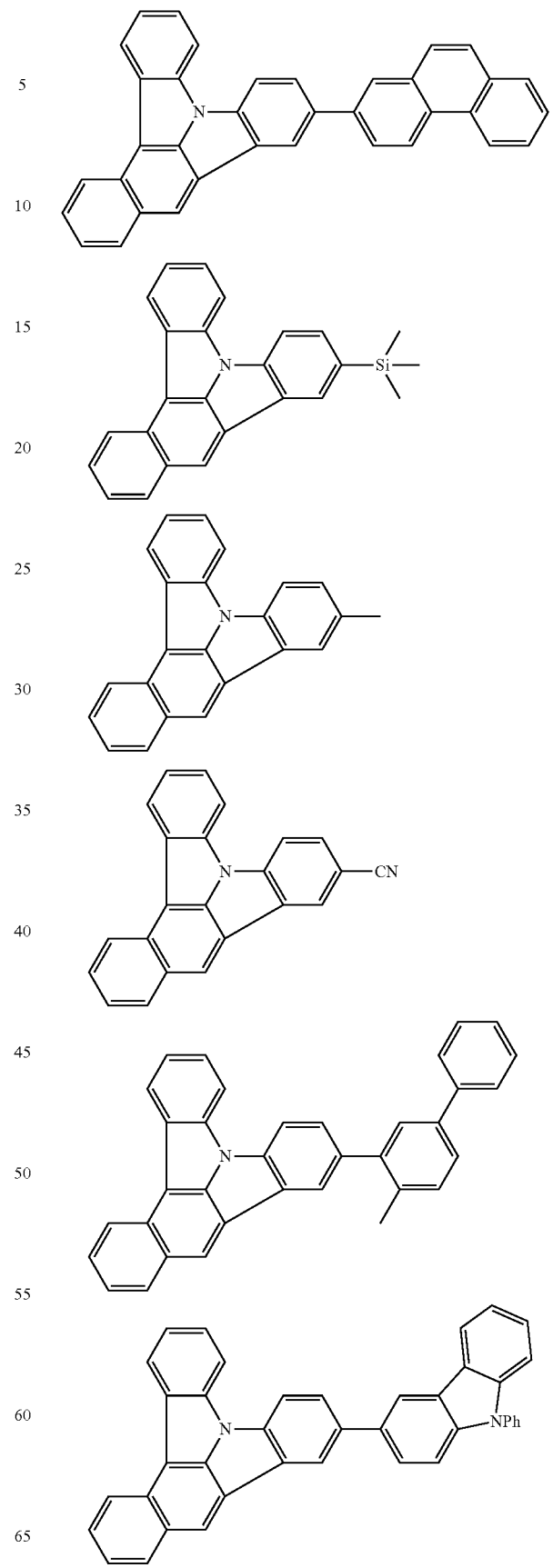

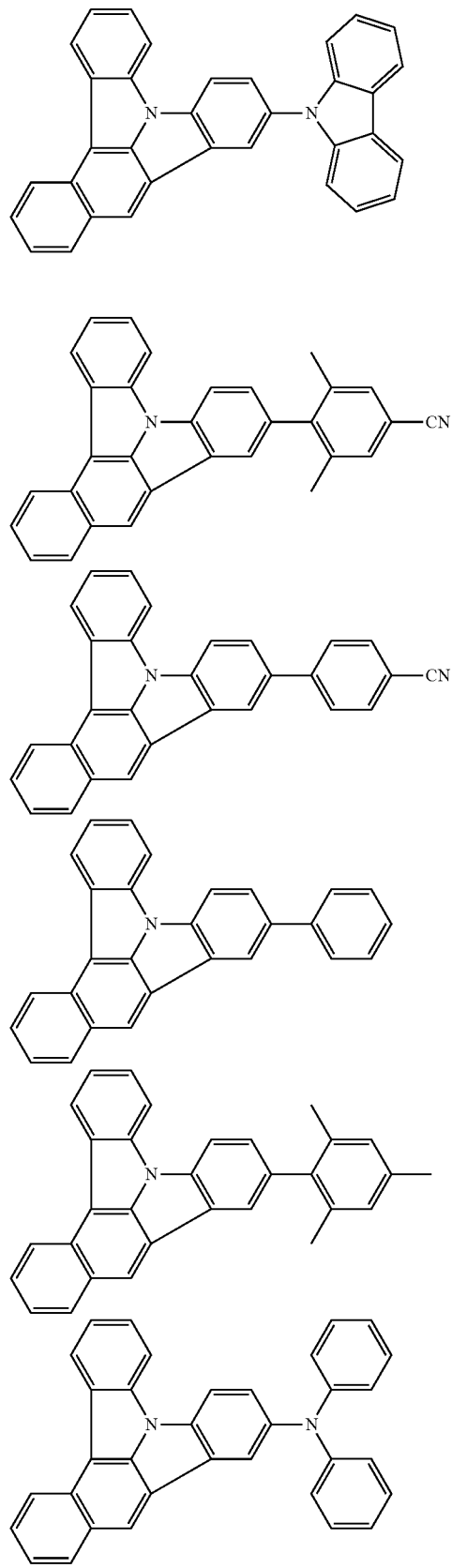
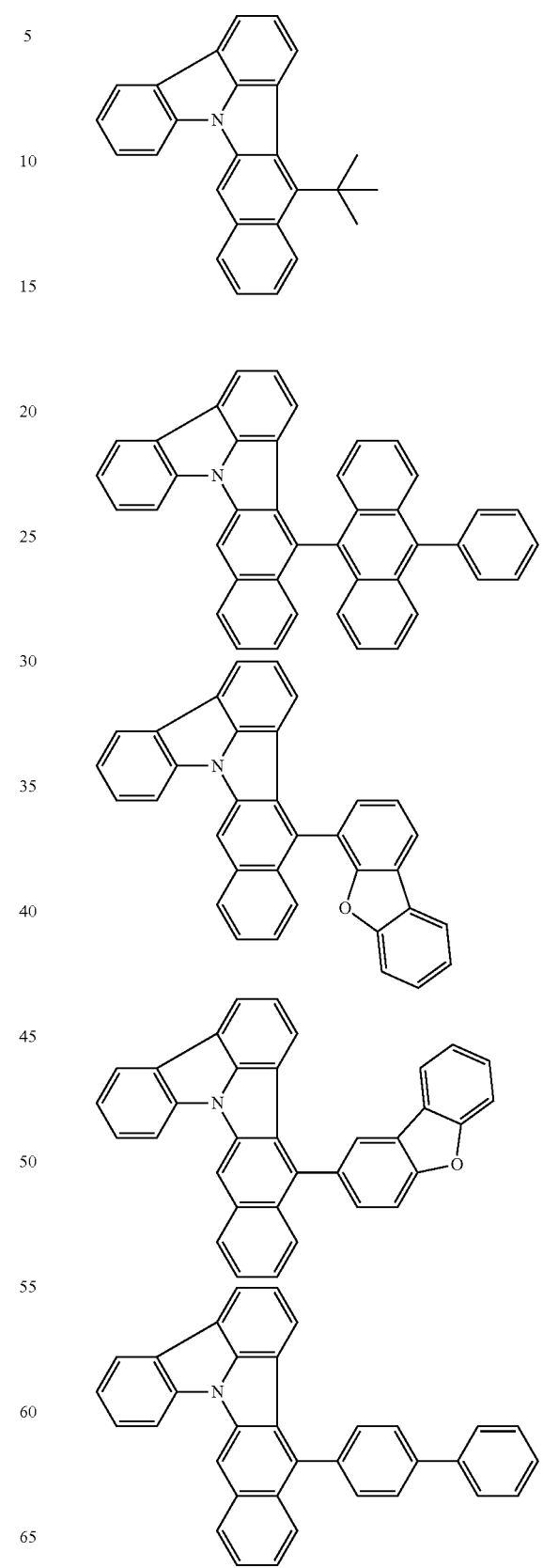

169
-continued
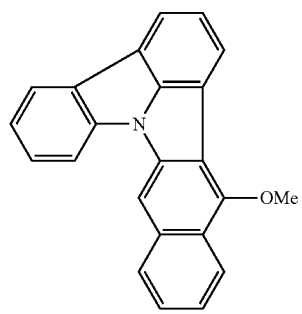
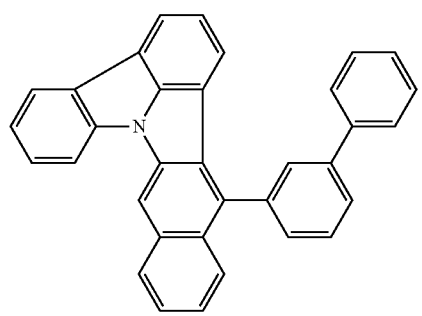
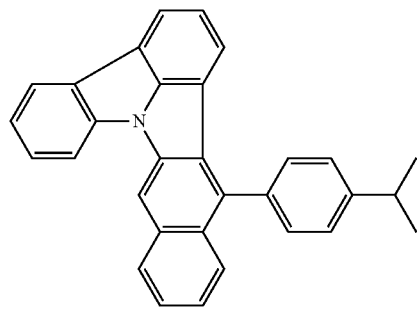
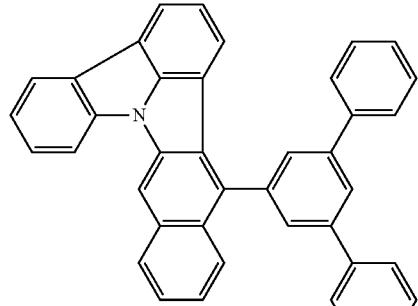
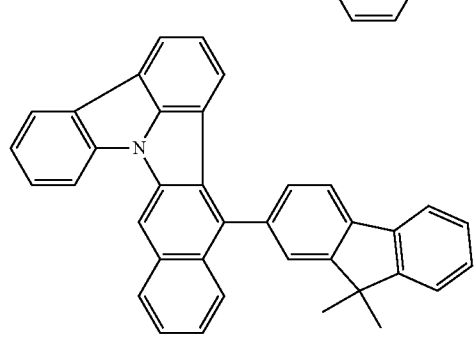
170
-continued
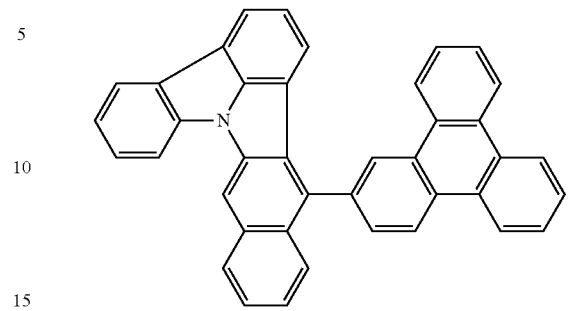
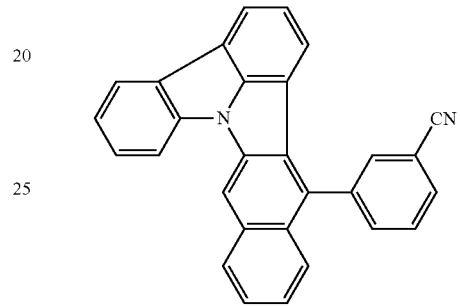
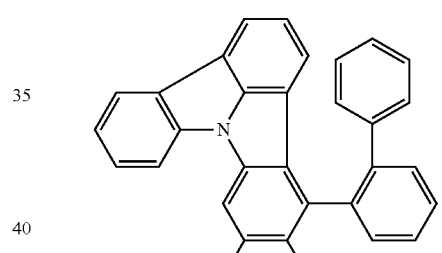
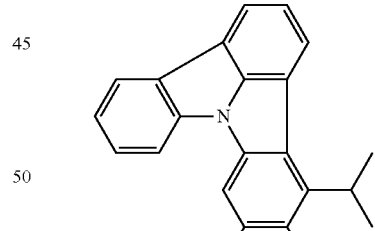
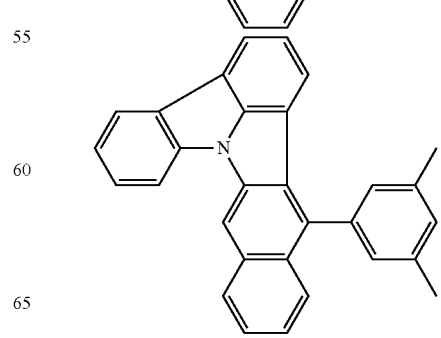

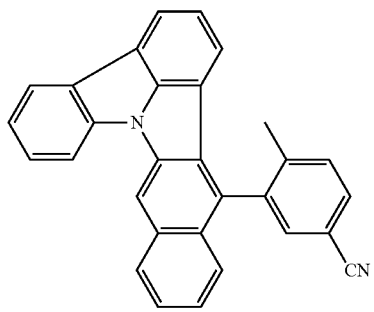
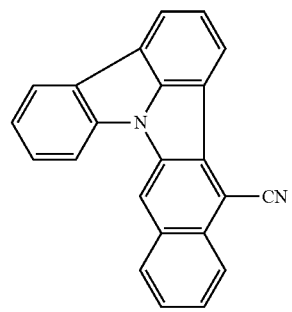
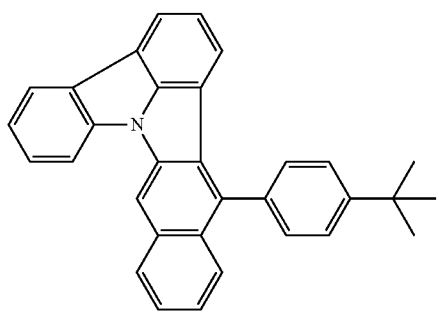
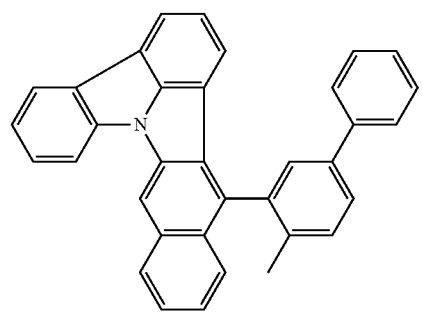
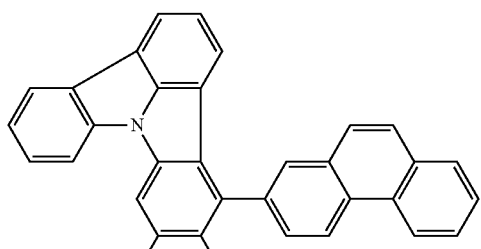
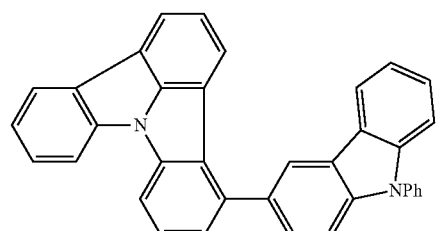
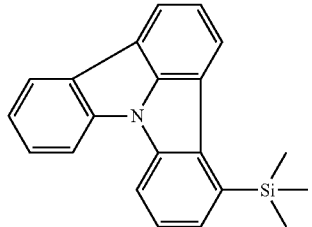
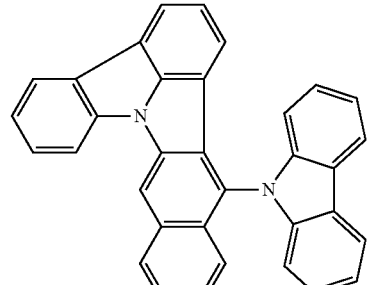
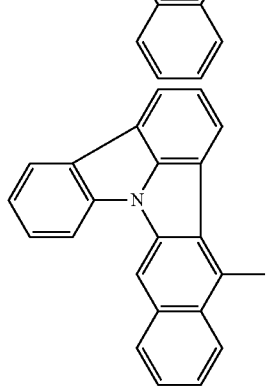
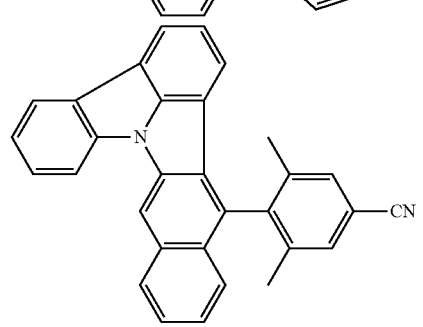

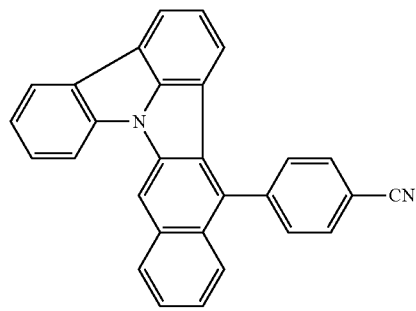
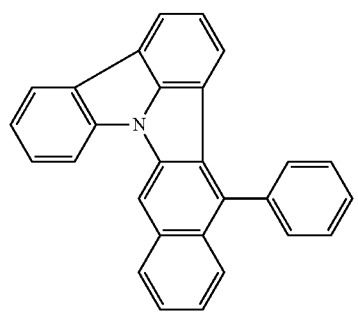
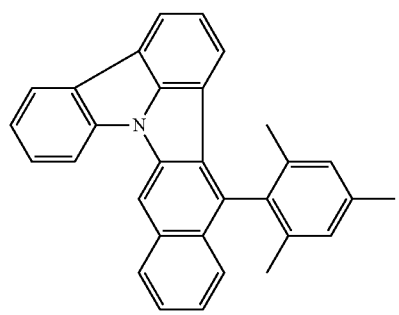
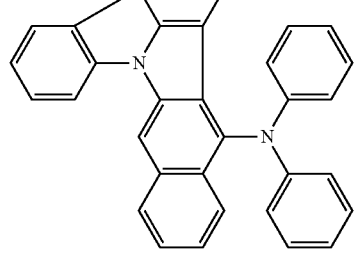
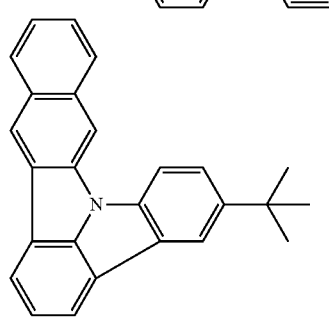
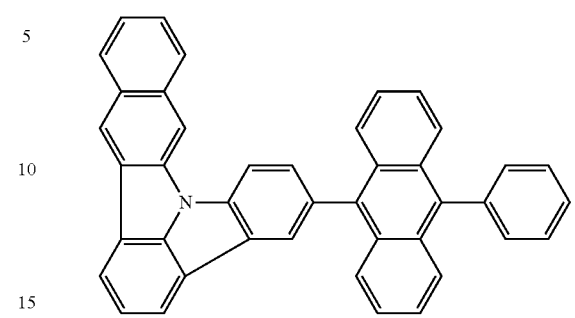
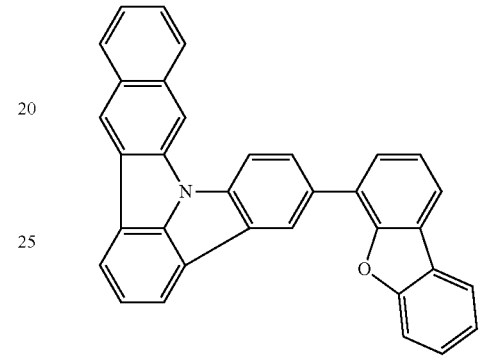
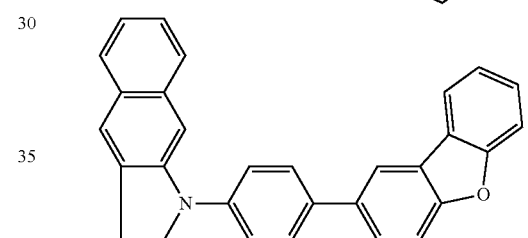
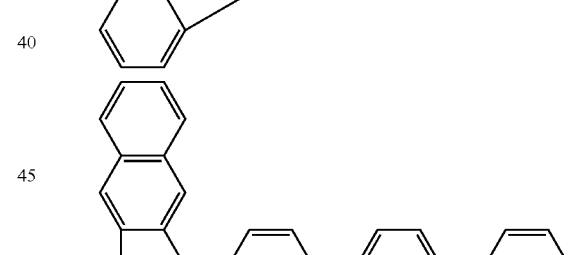
[Formula 71]
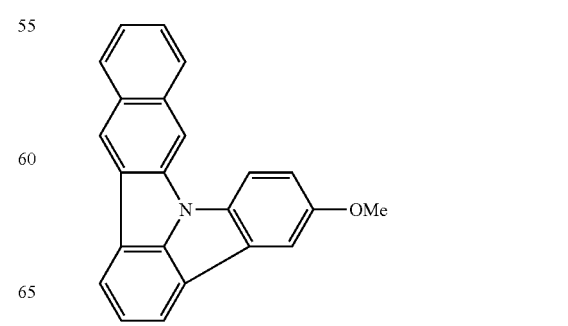

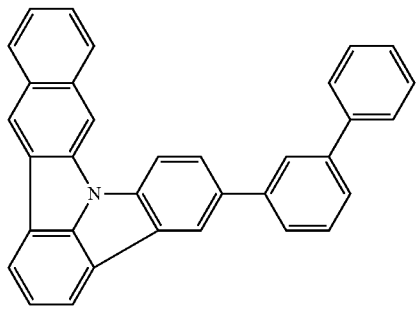
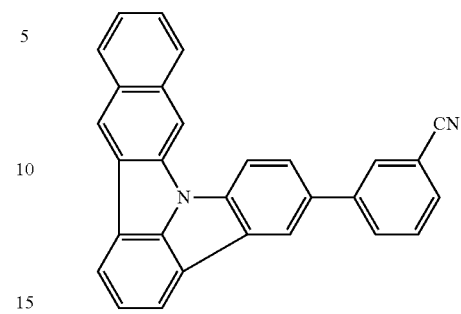
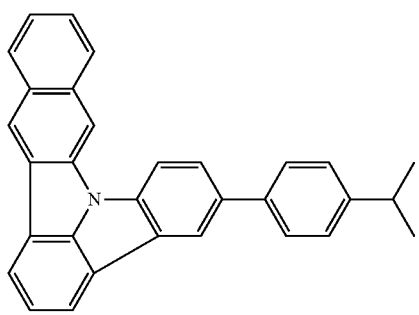
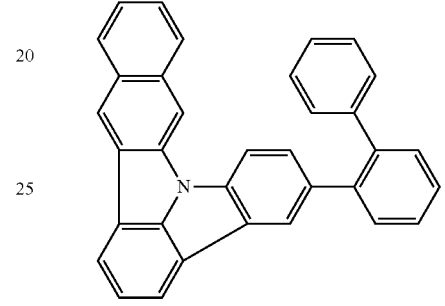
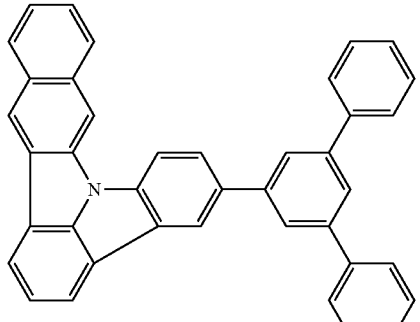
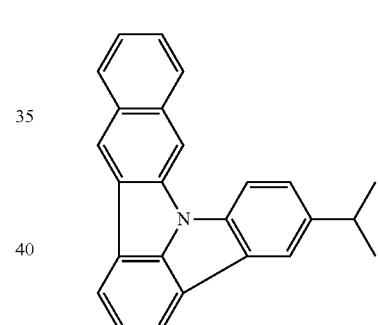
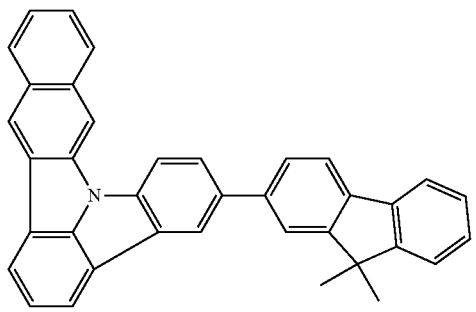
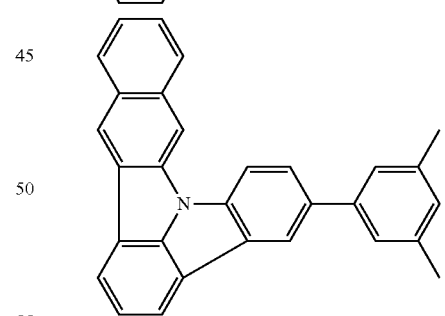
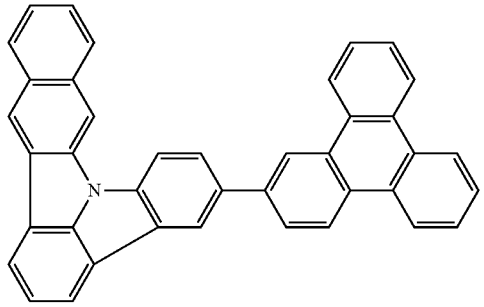
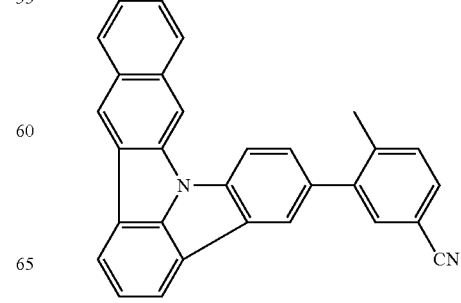

177
-continued
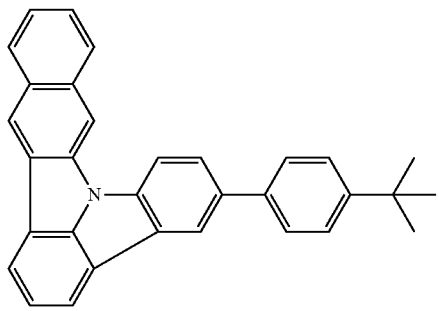
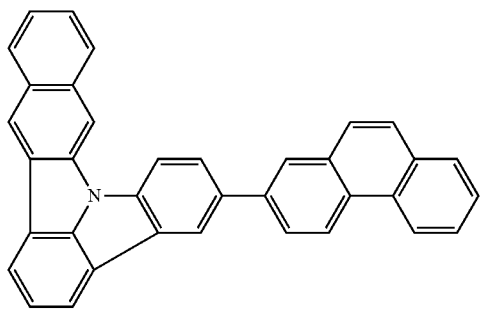
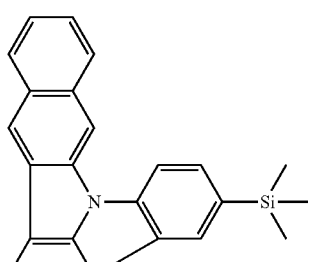
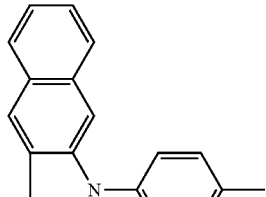
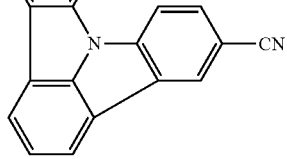
178
-continued
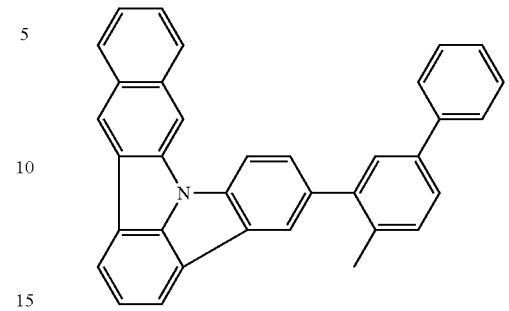
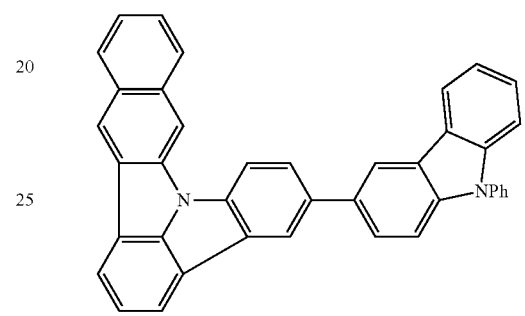
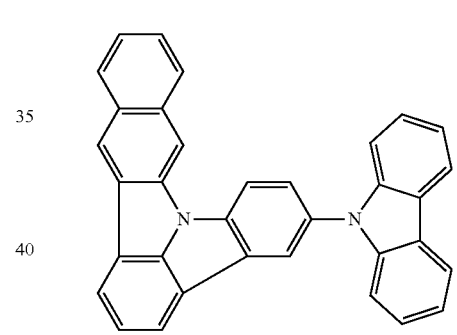
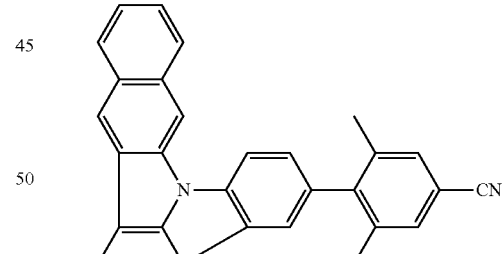
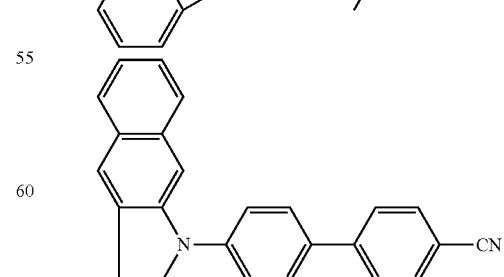

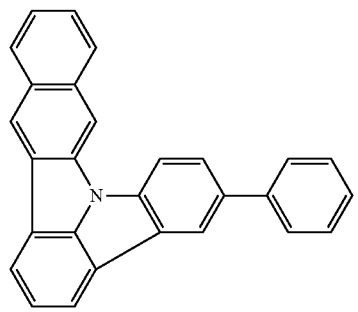
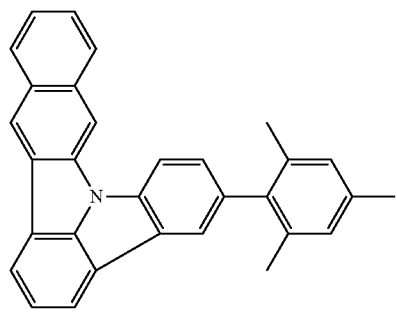
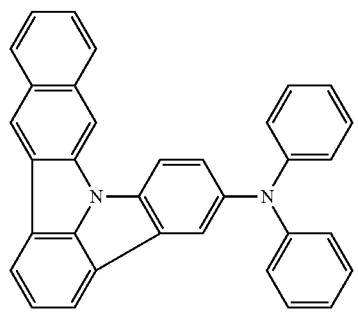
[Formula 72]
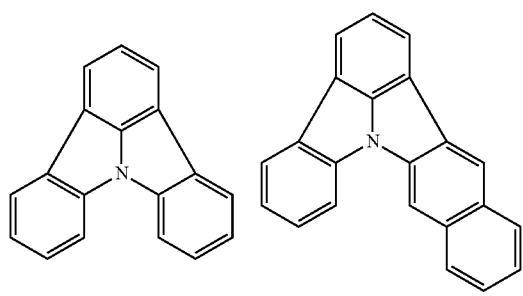
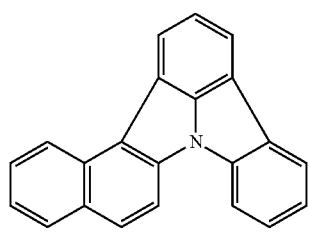
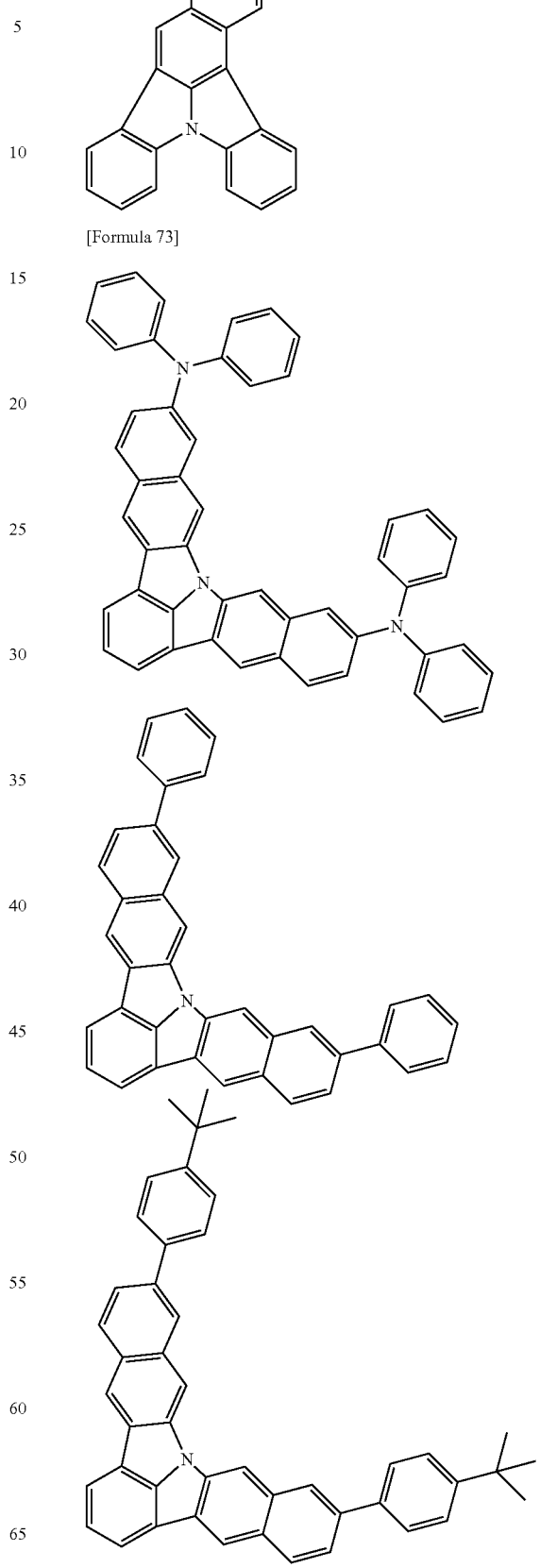
[Formula 73]

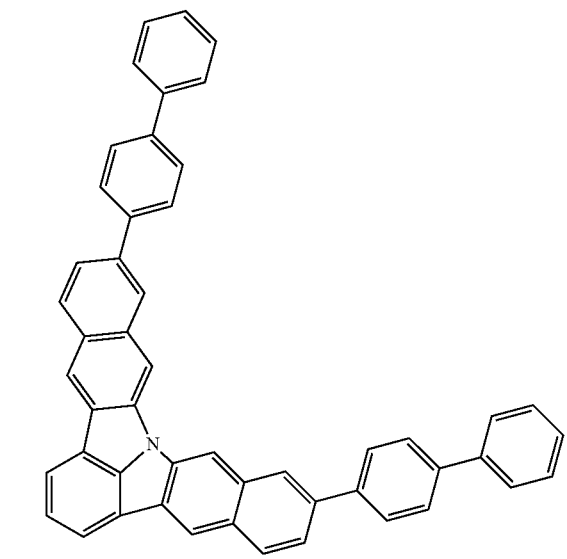
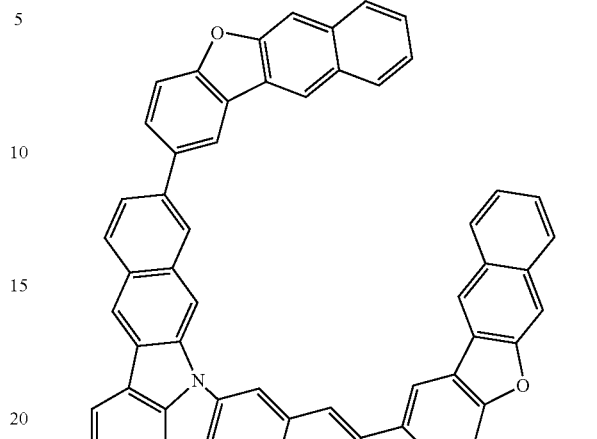
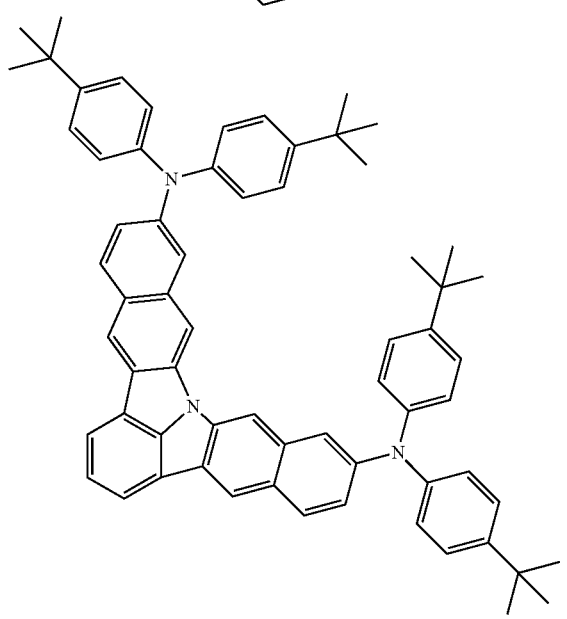
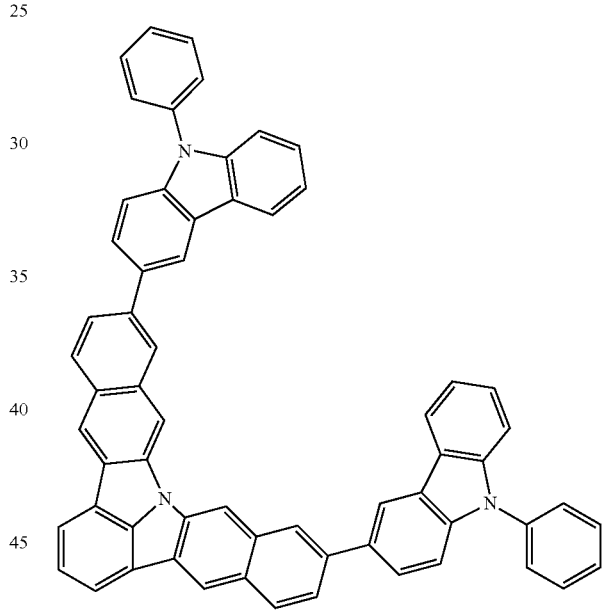
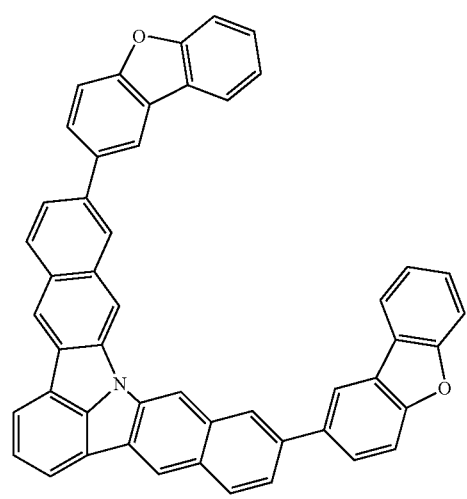
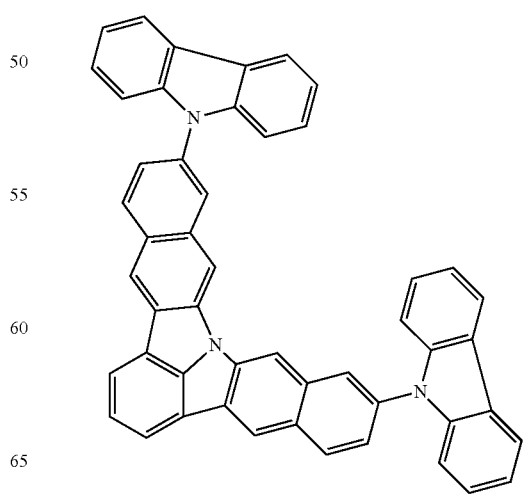

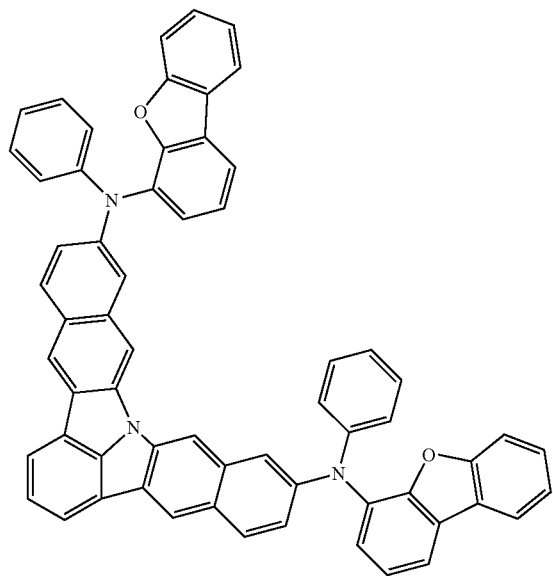
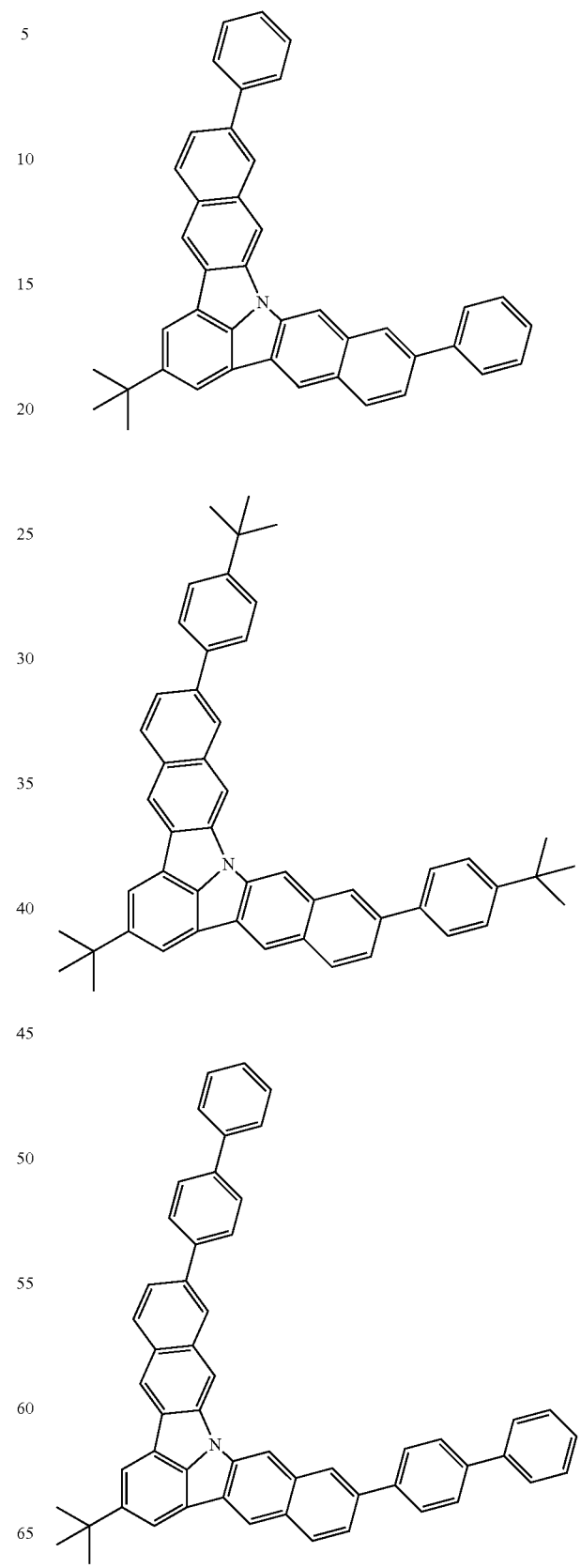

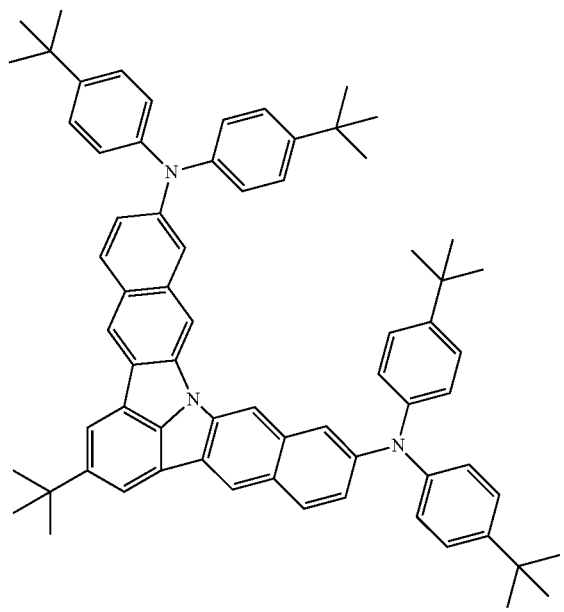
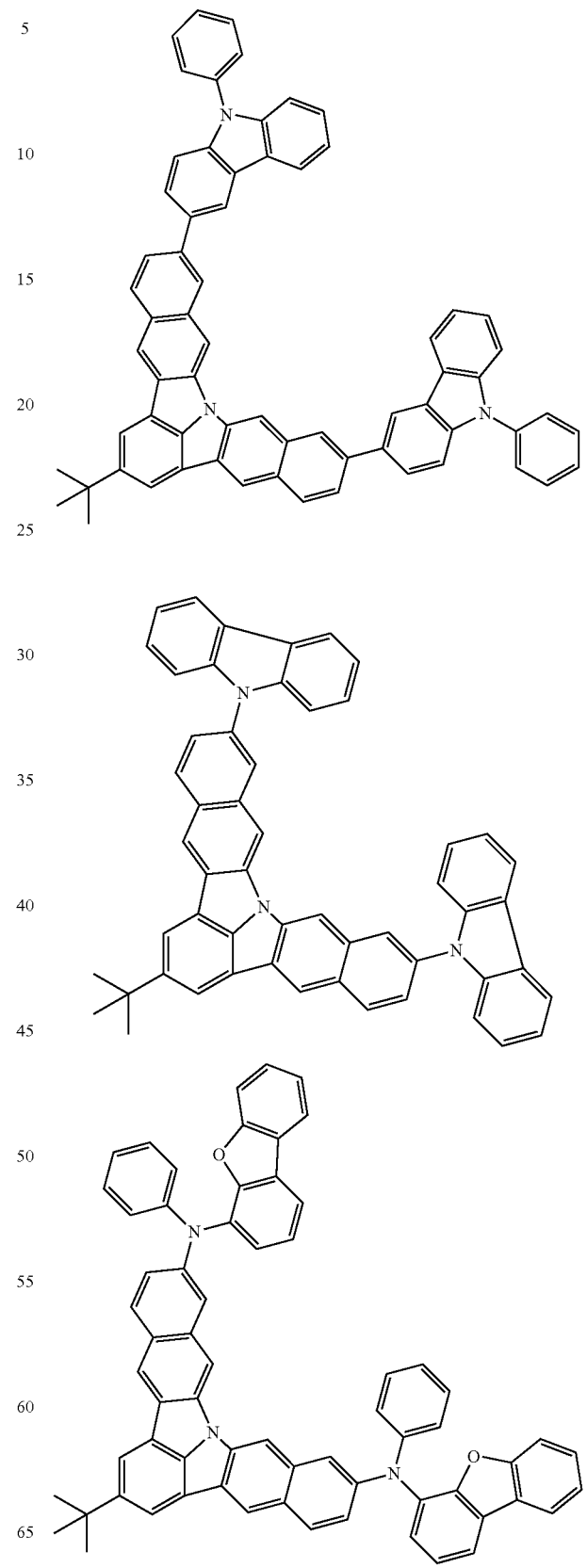

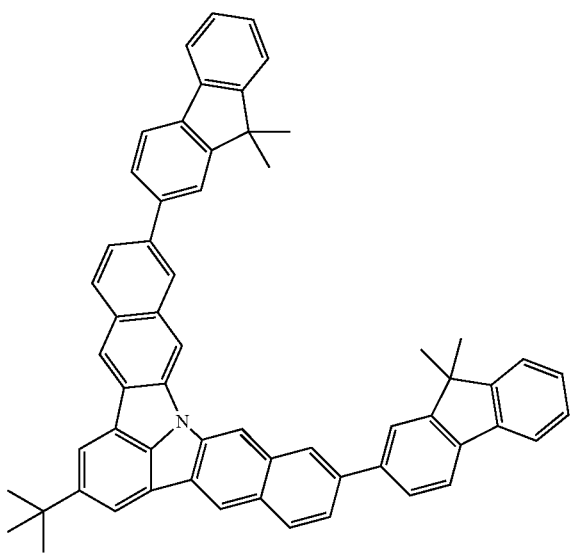
[Formula 74]
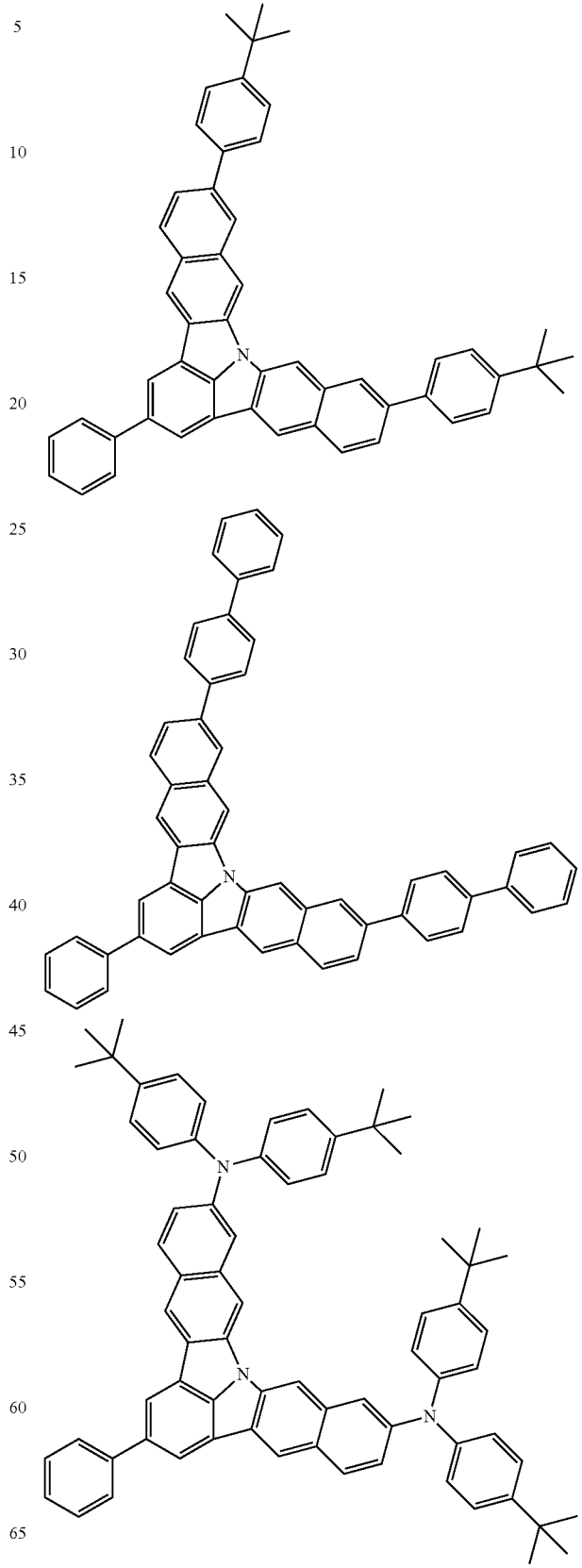

189
-continued
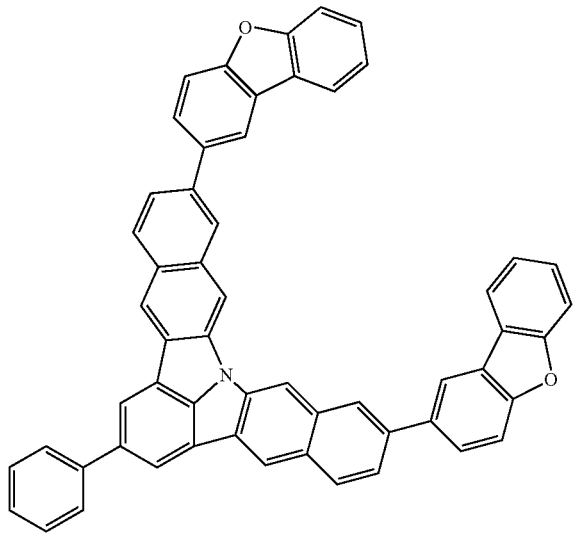
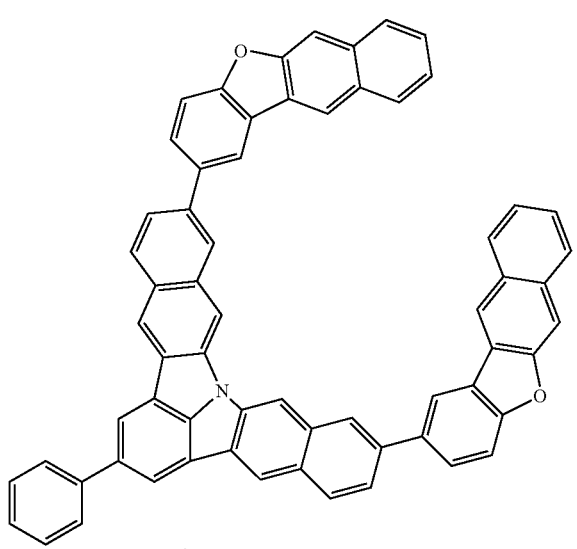
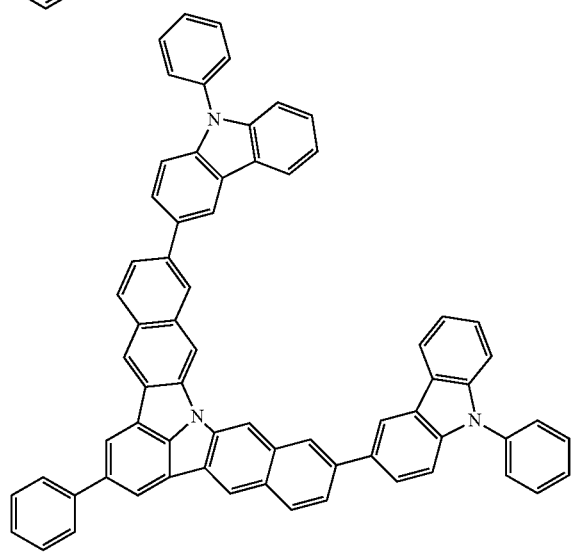
190
-continued
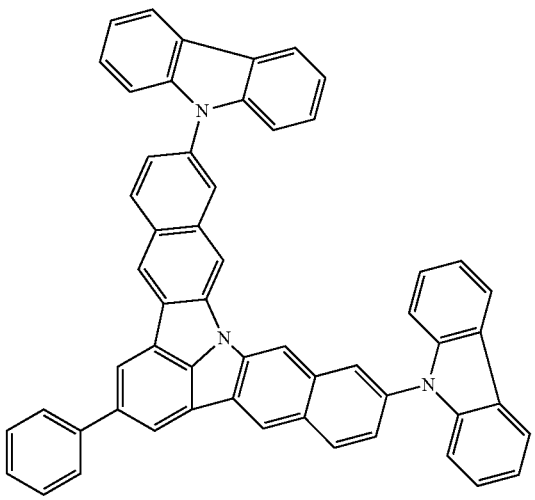
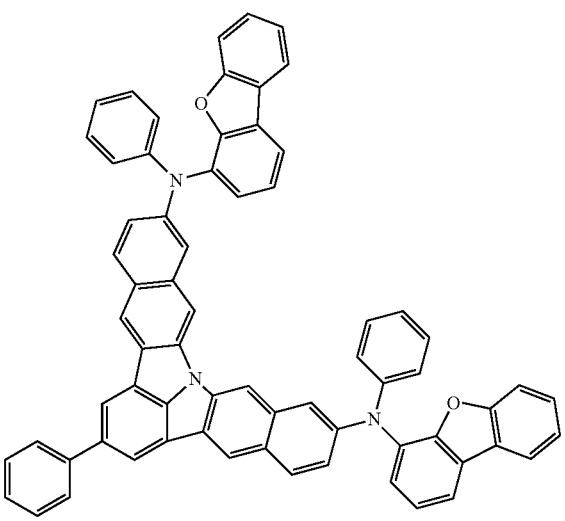
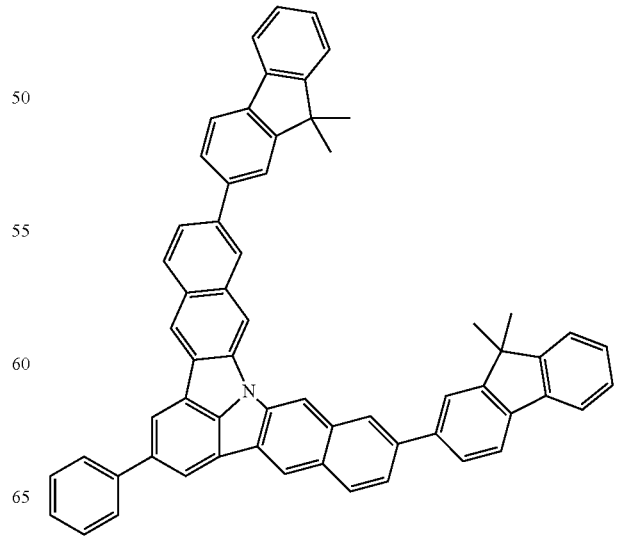

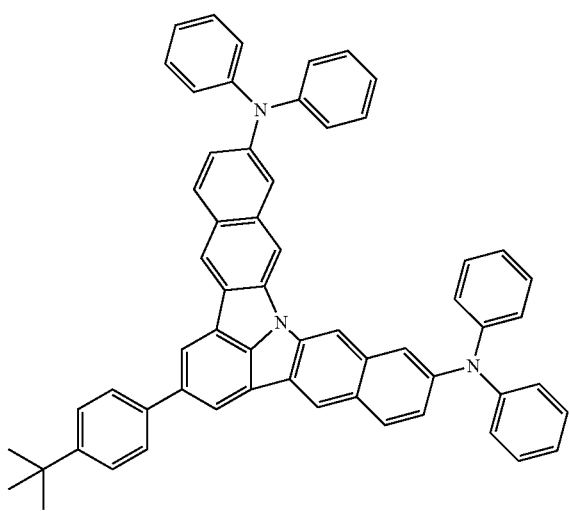
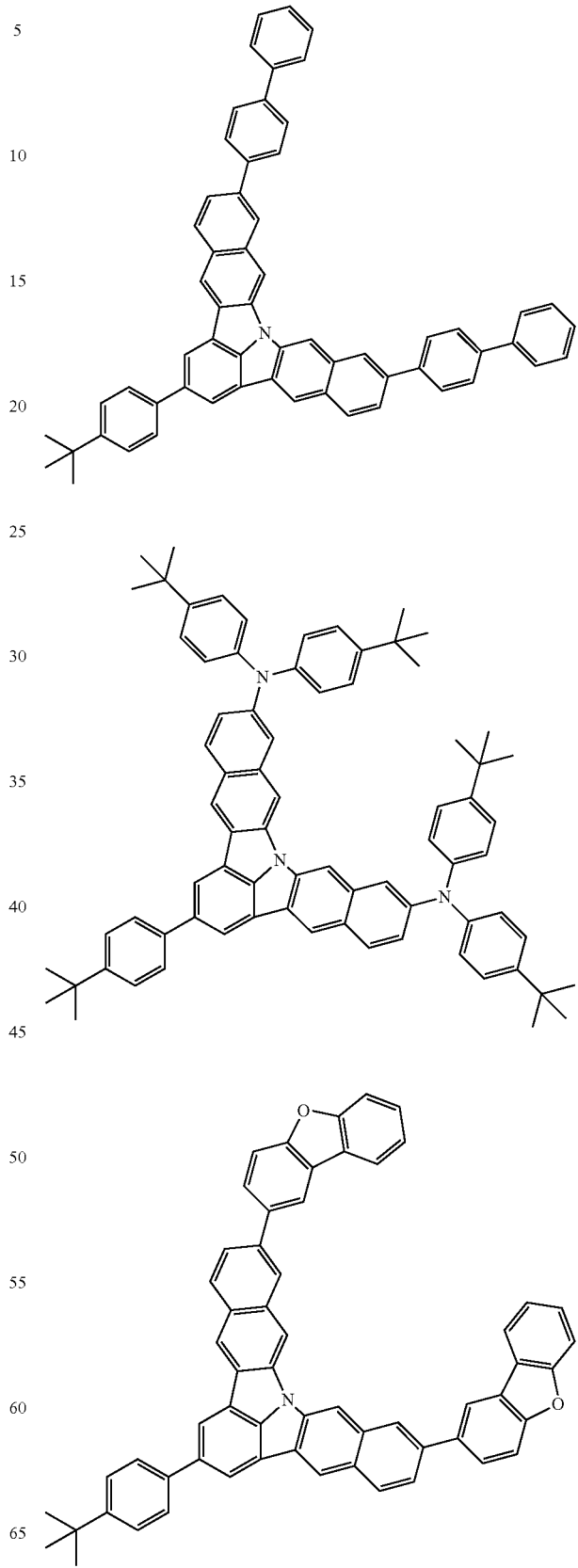

193
-continued
194
-continued
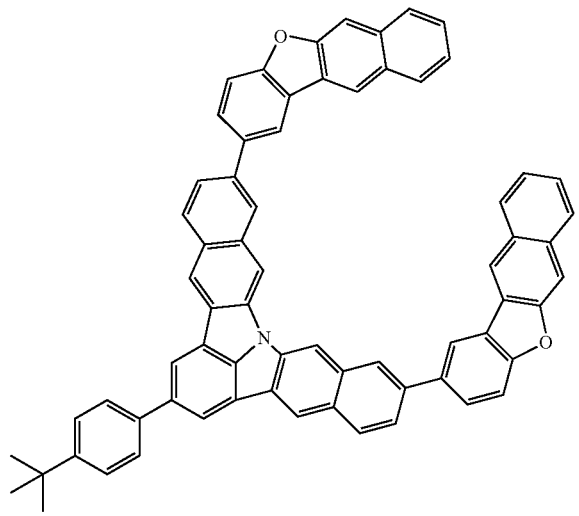
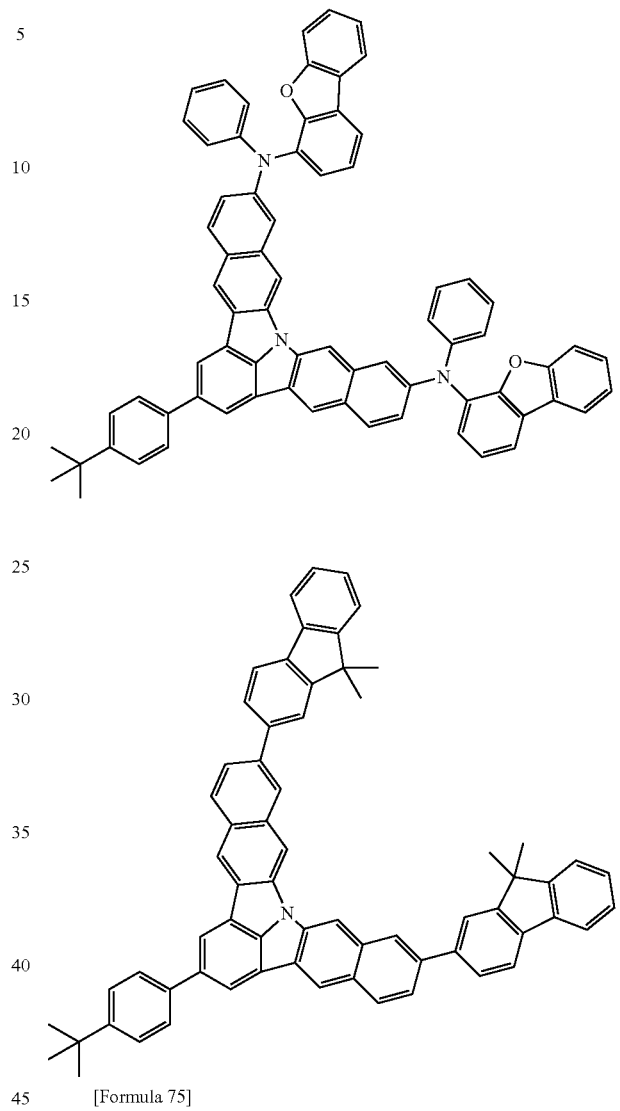
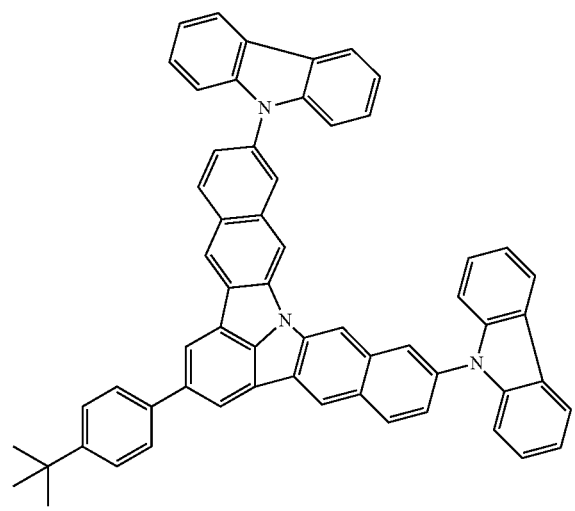
[Formula 75]
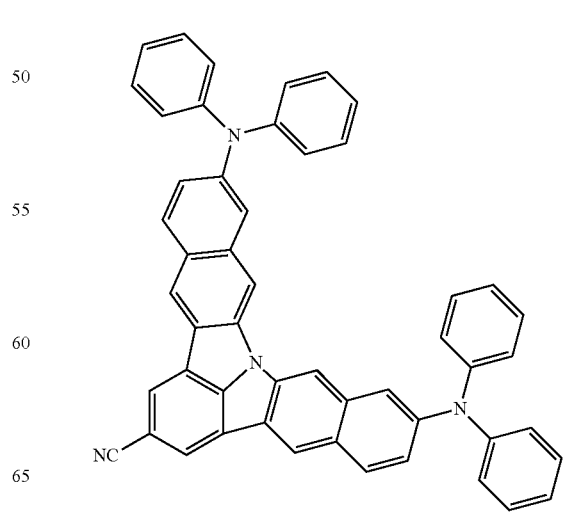

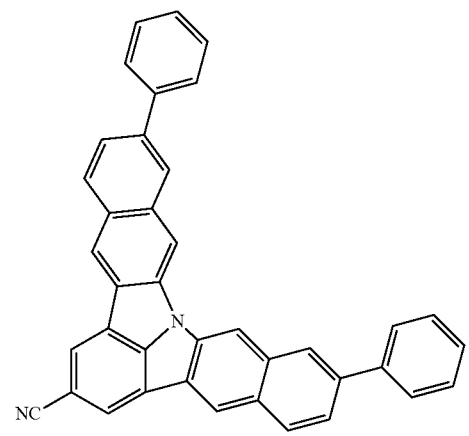
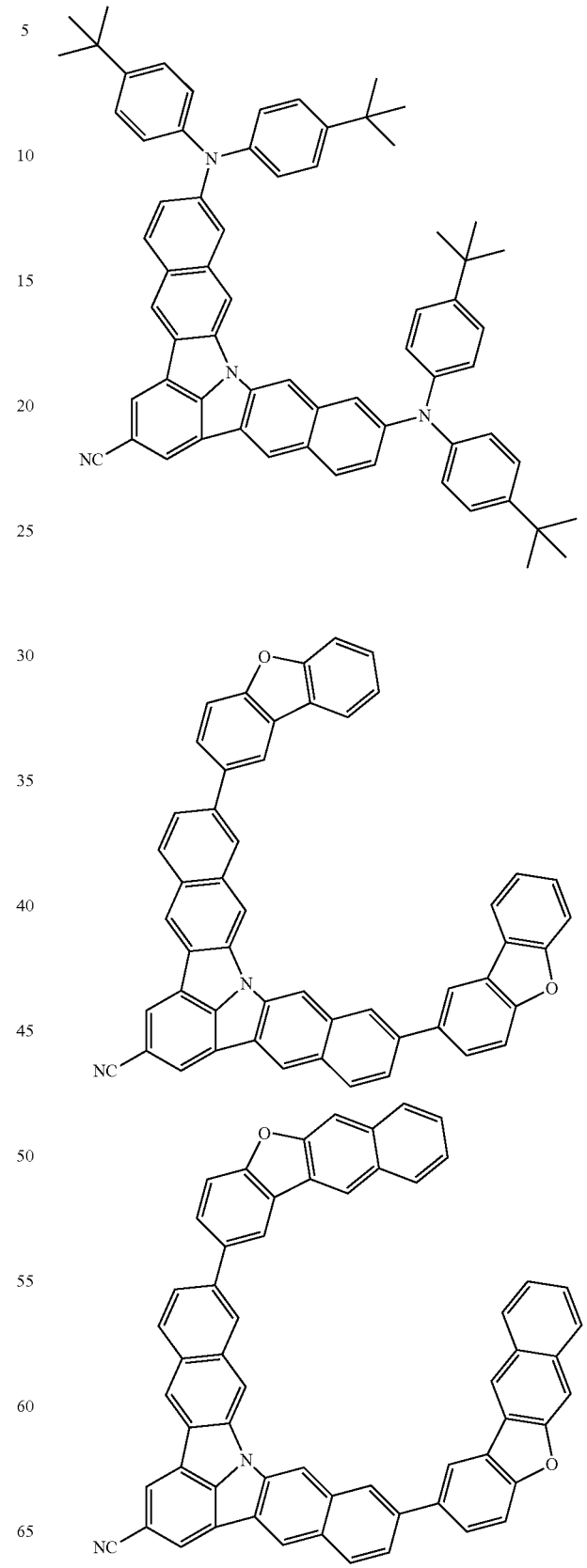

197
-continued
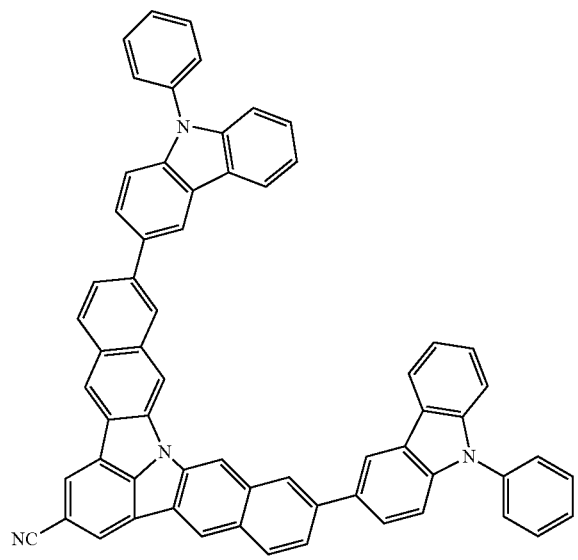
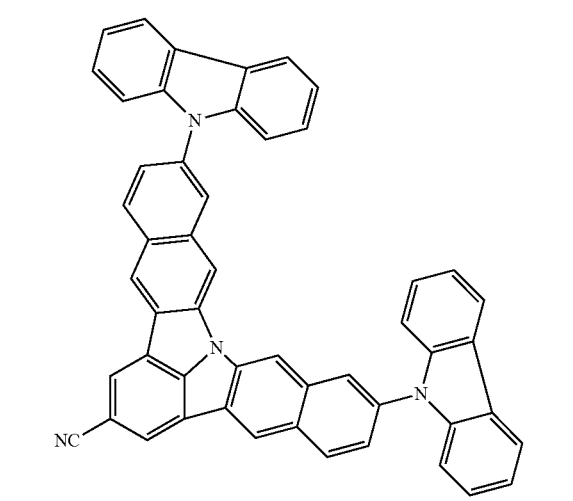
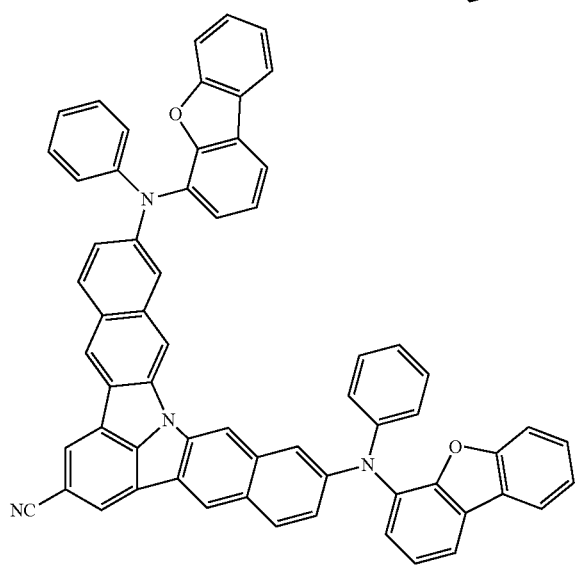
198
-continued
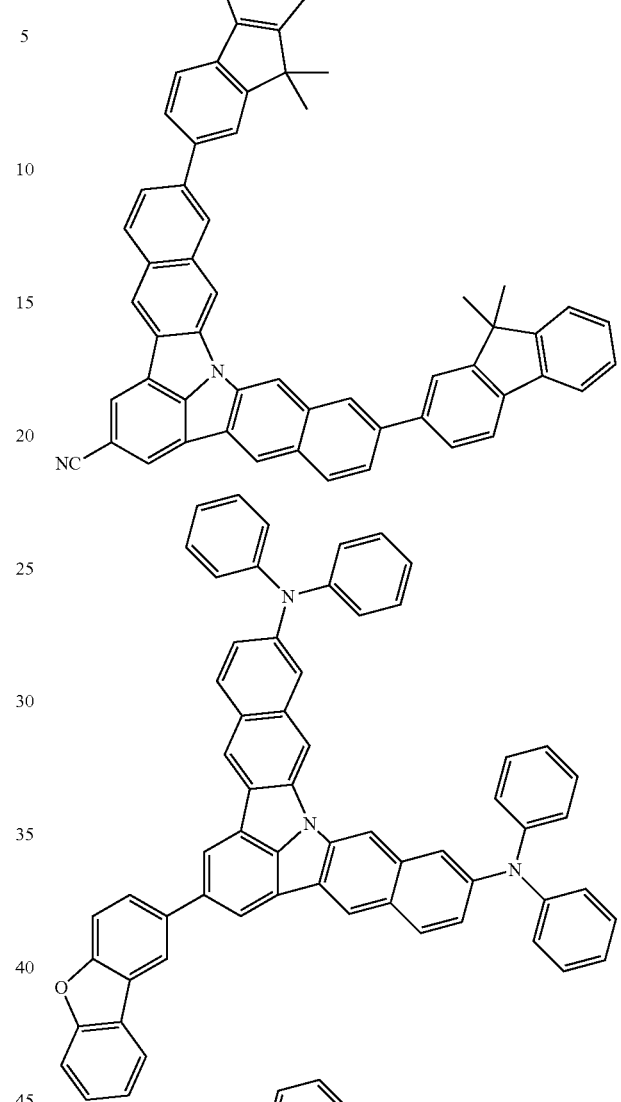
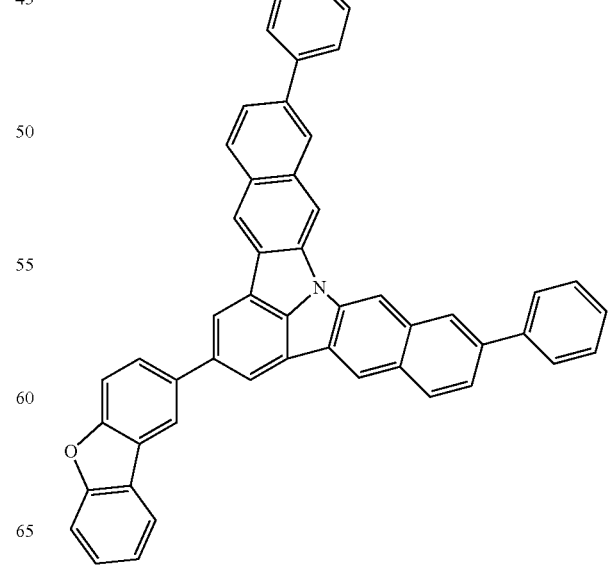

| 199 -continued | 200 -continued |
|---|---|
| 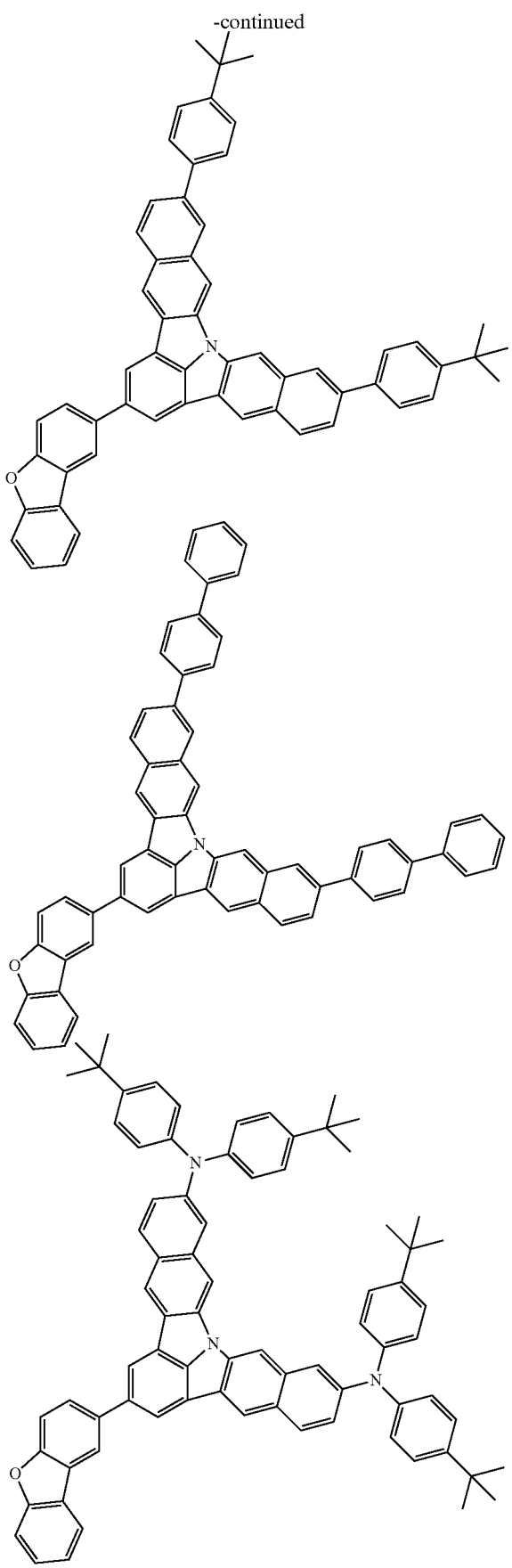 | 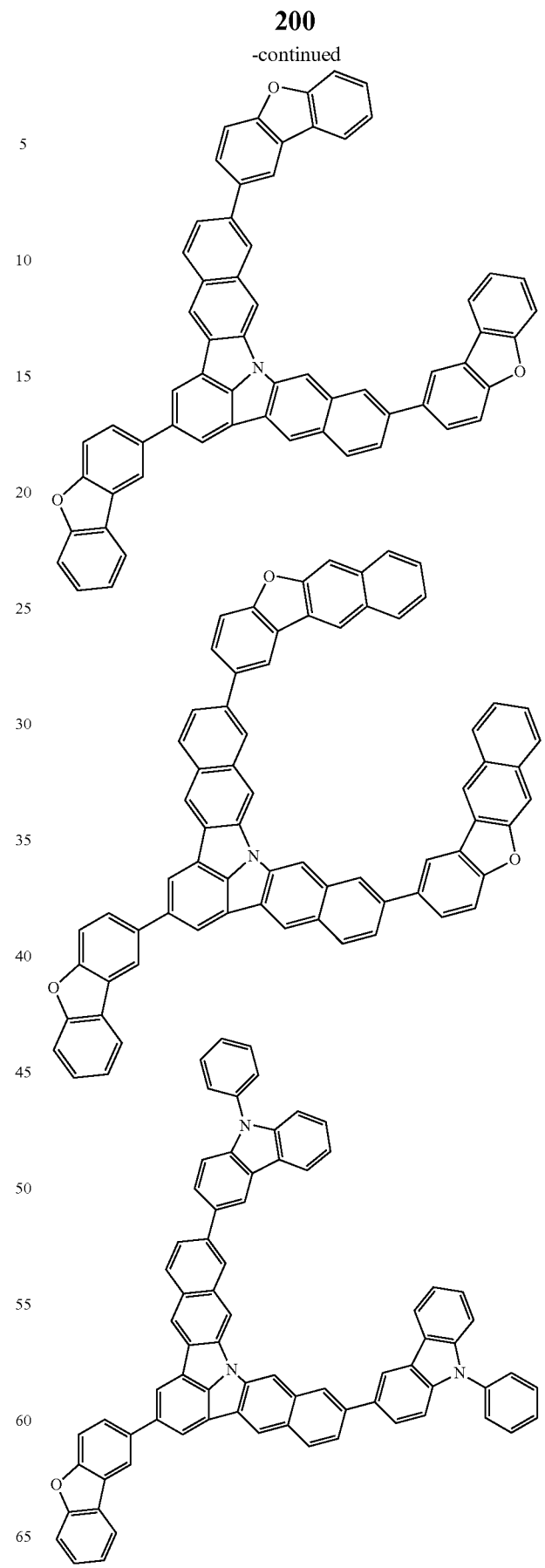 |

201
-continued
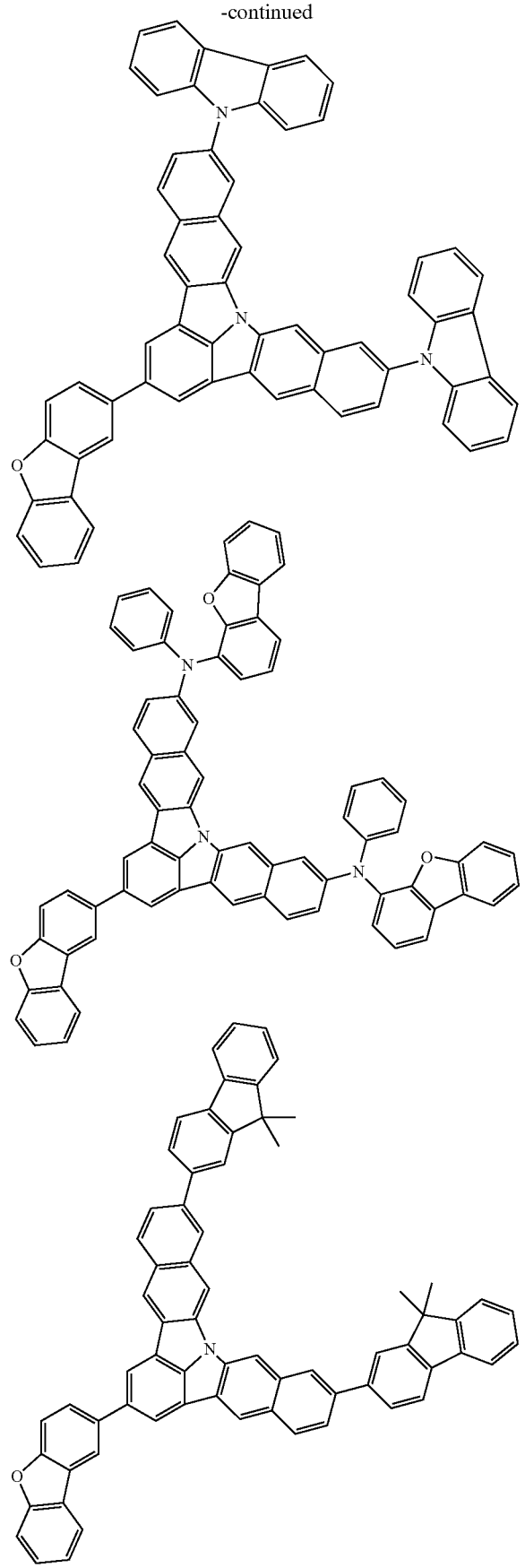
202
-continued
[Formula 76]
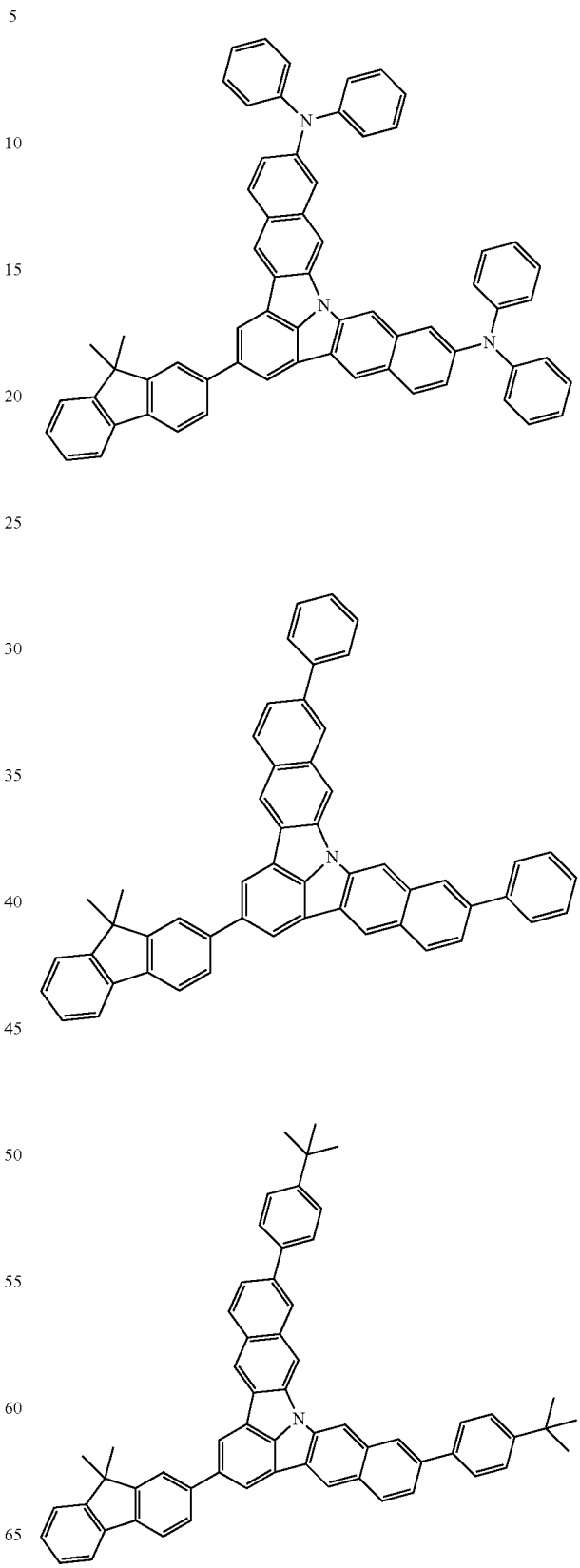

203
-continued
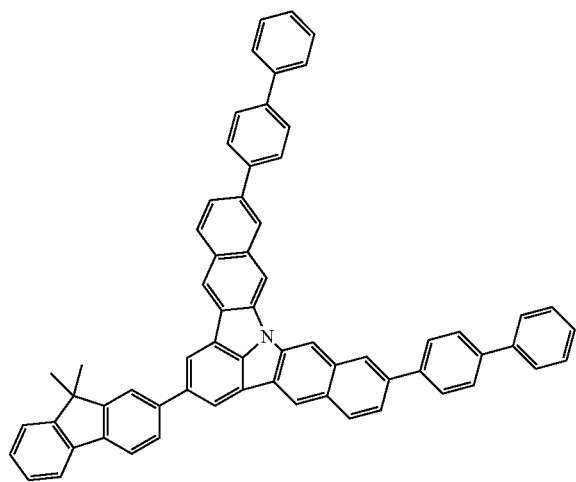
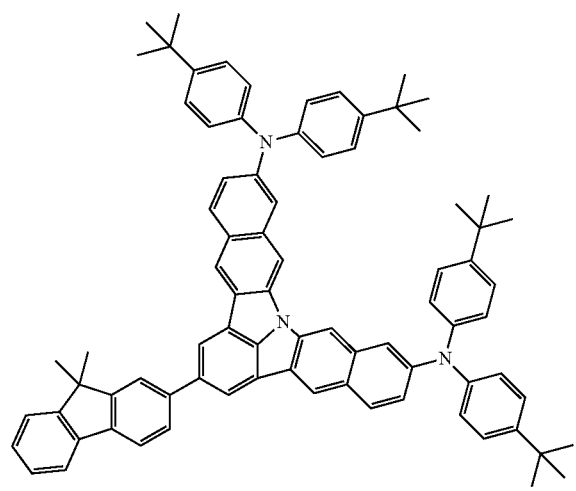
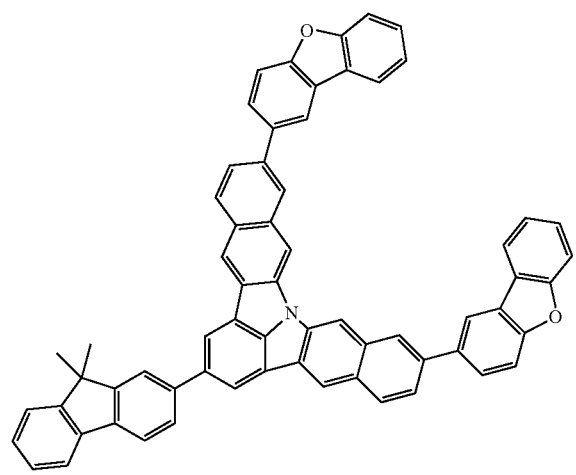
204
-continued
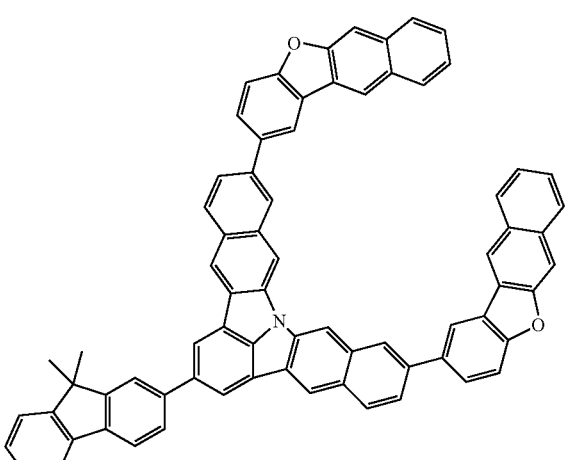
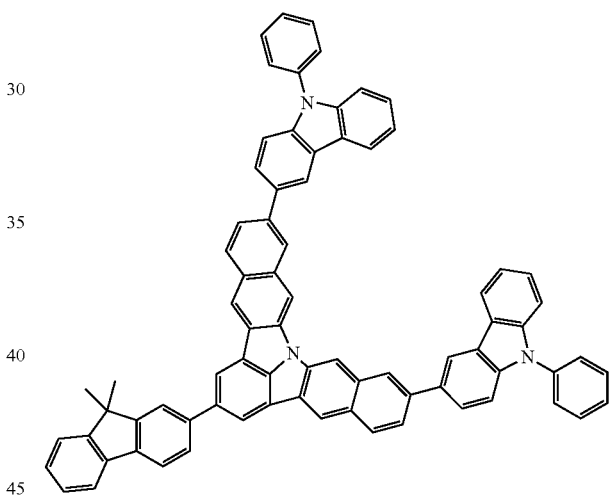
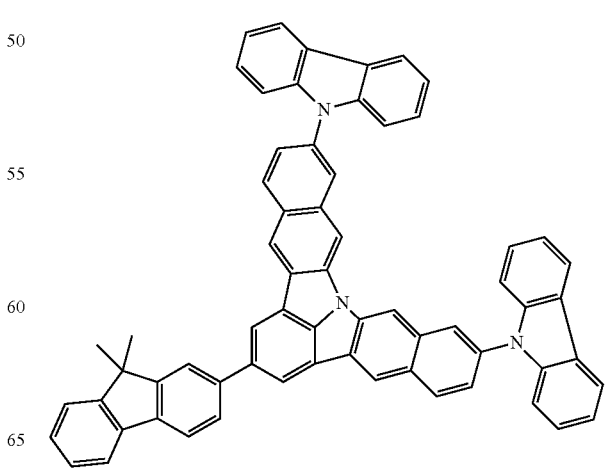

205
-continued
206
-continued
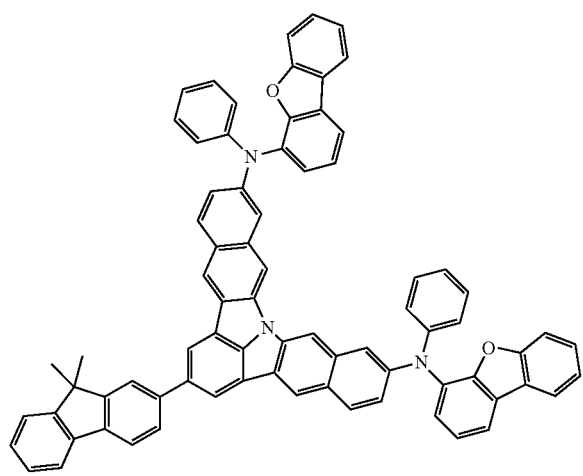
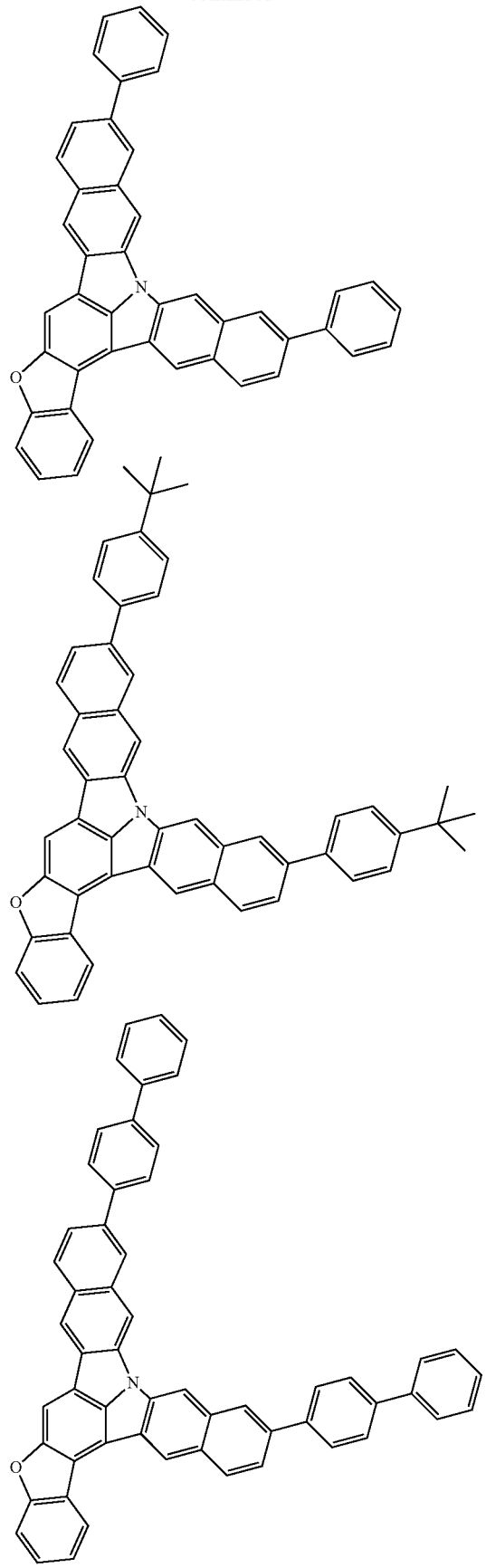

207
-continued
208
-continued
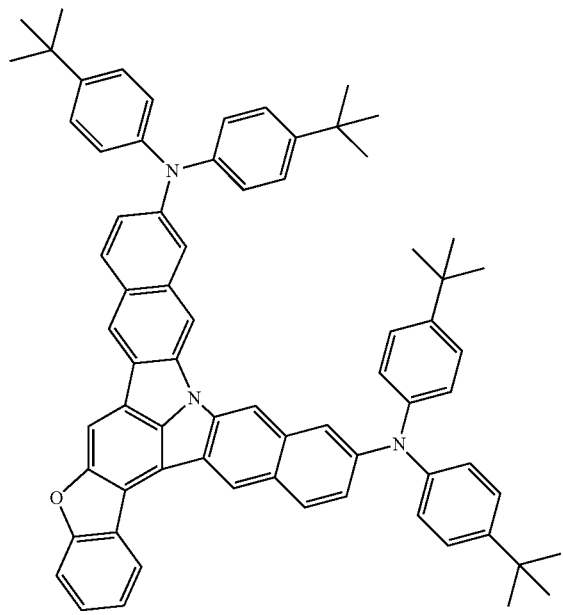
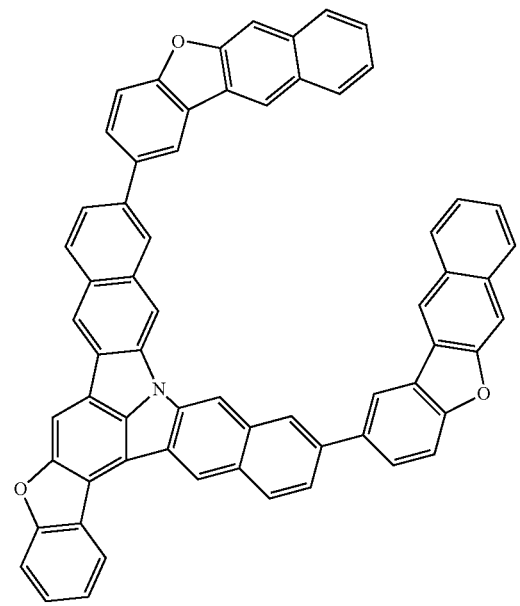
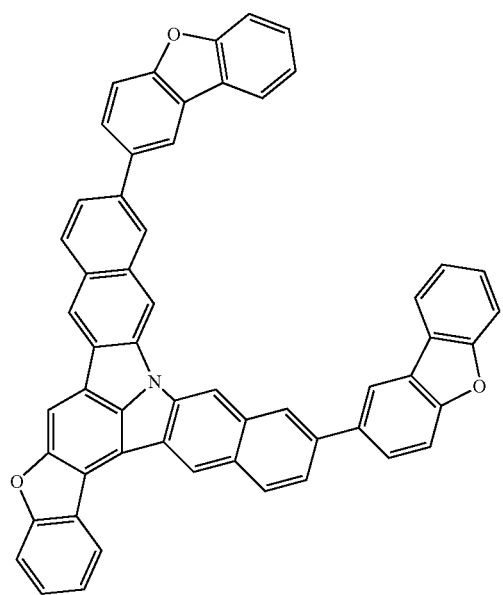
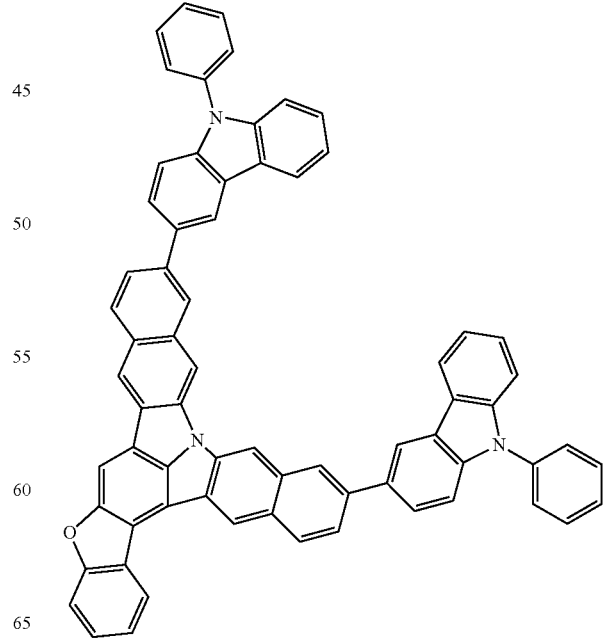

209
-continued
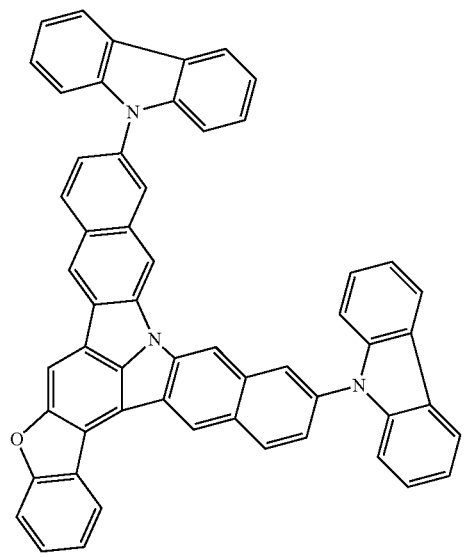
210
-continued
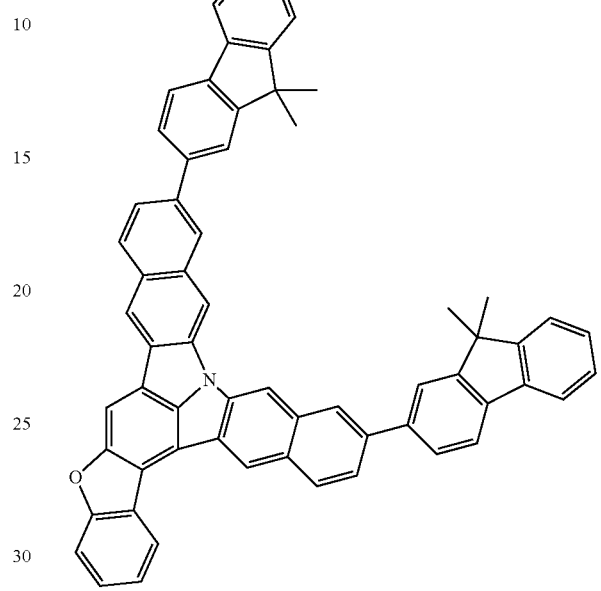
[Formula 77]
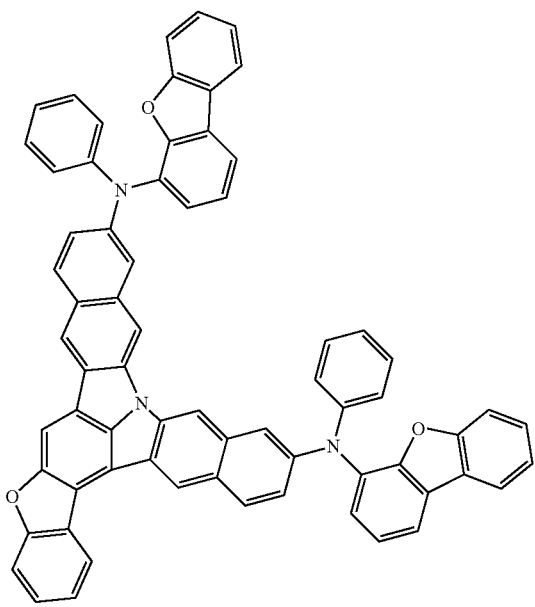
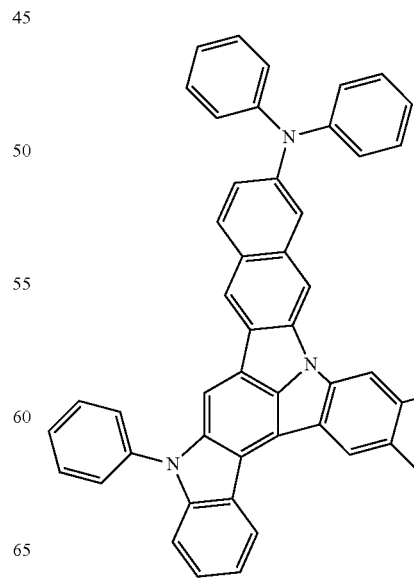

211
-continued
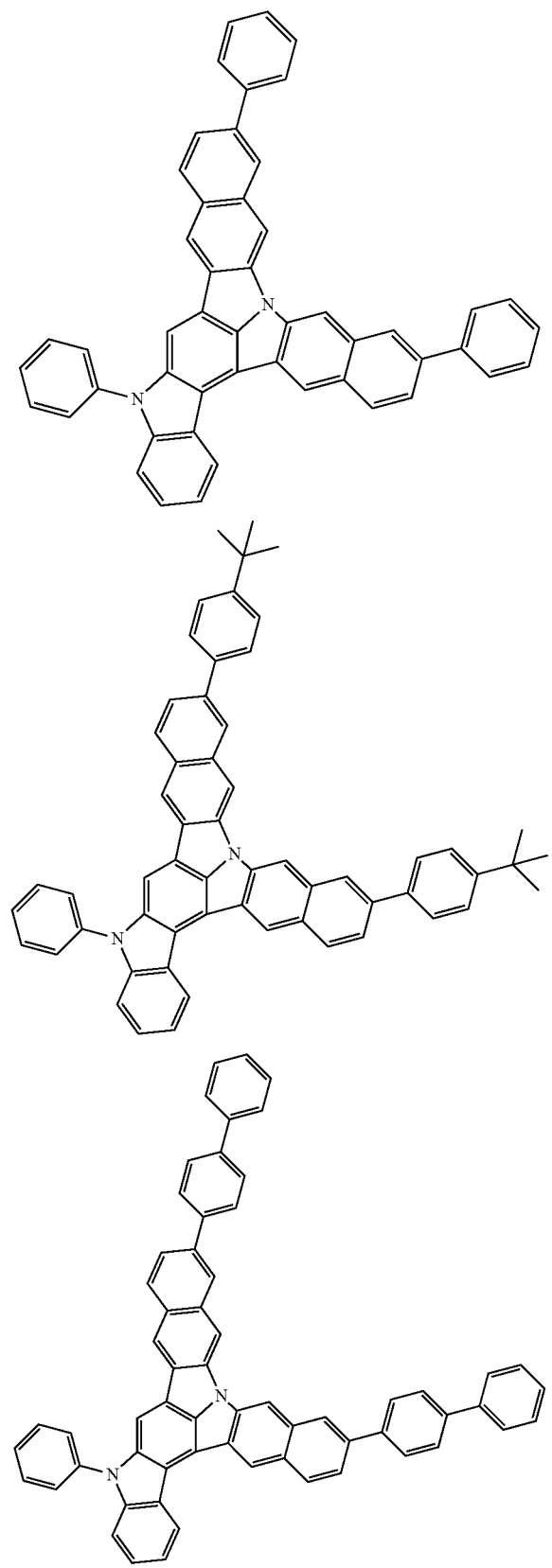
212
-continued
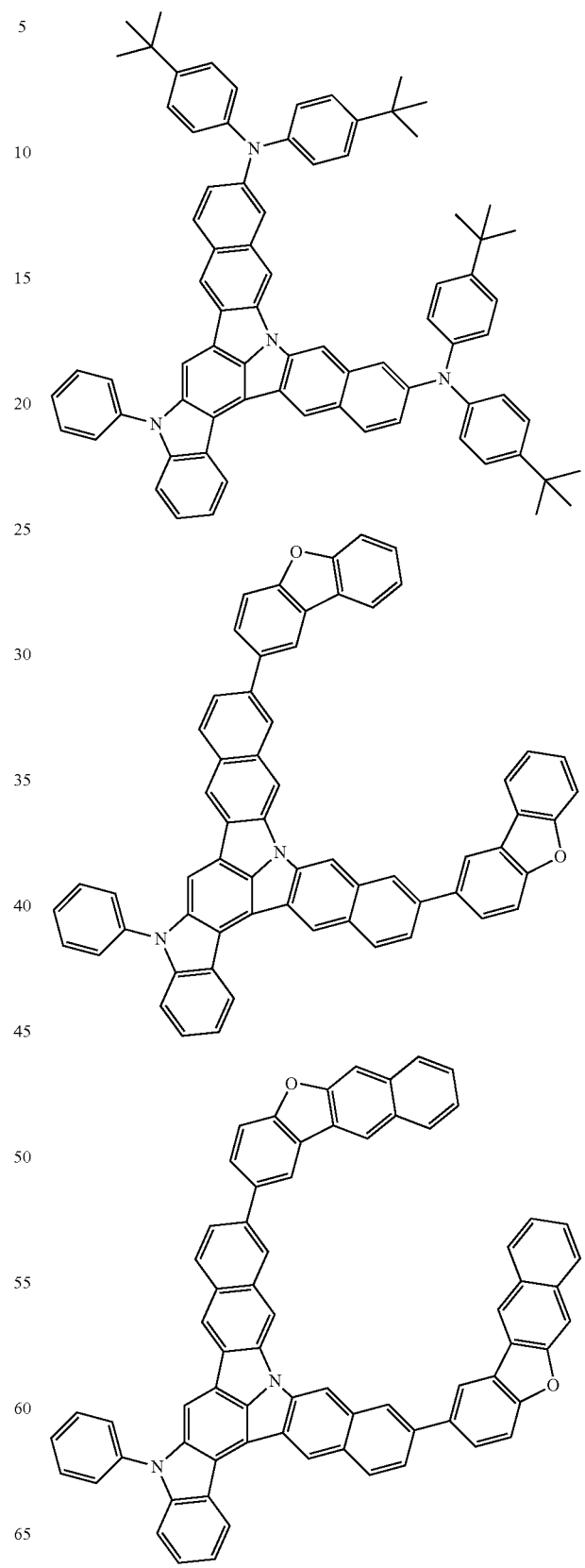

213
-continued
214
-continued
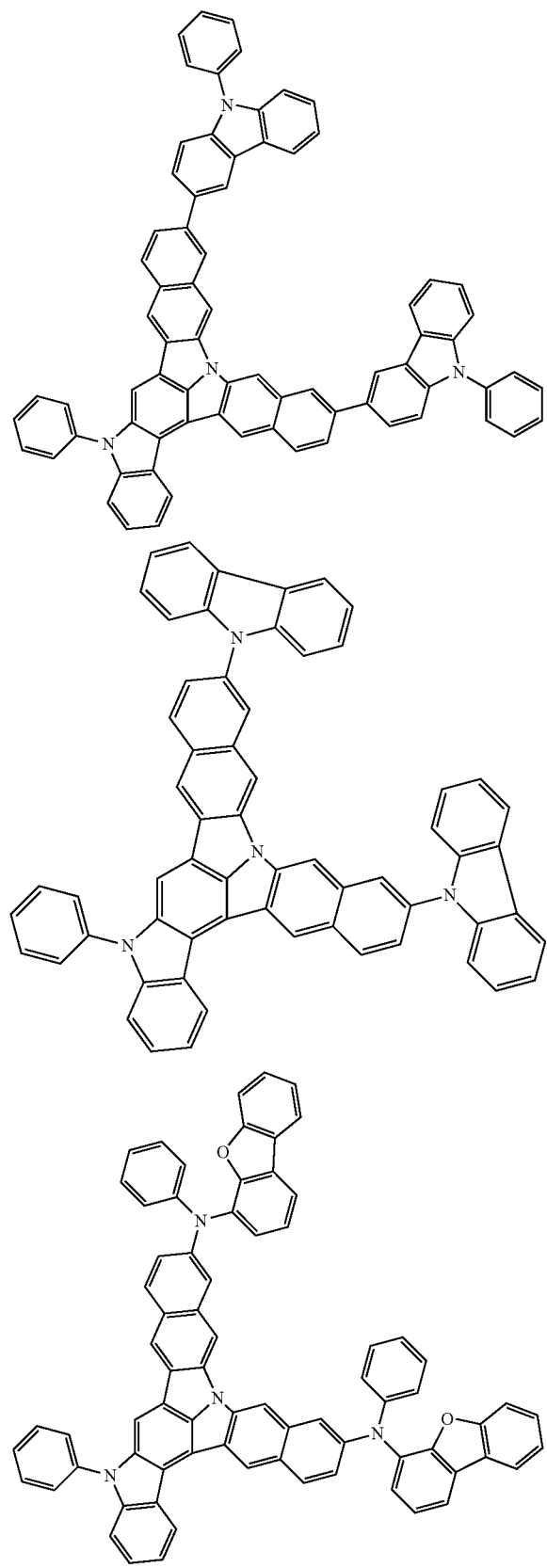
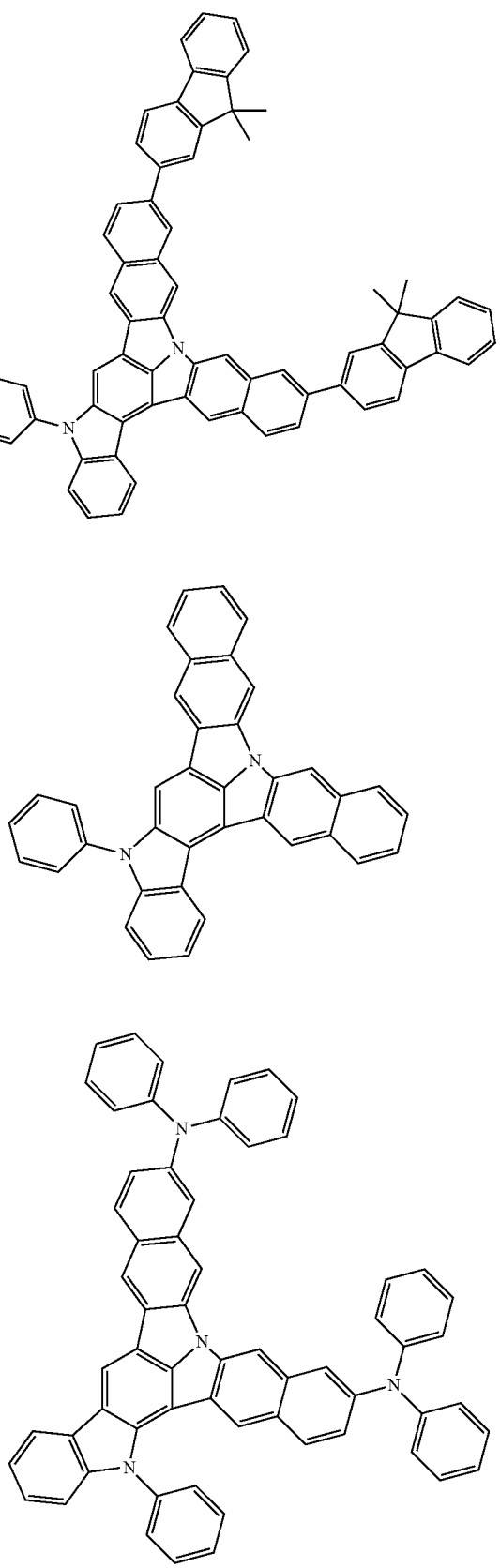

215
-continued
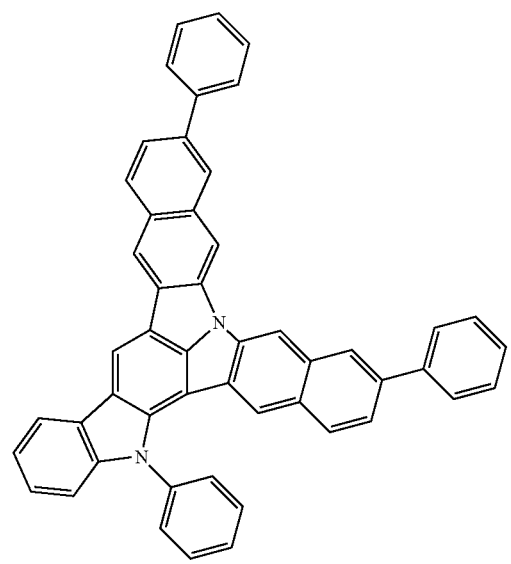
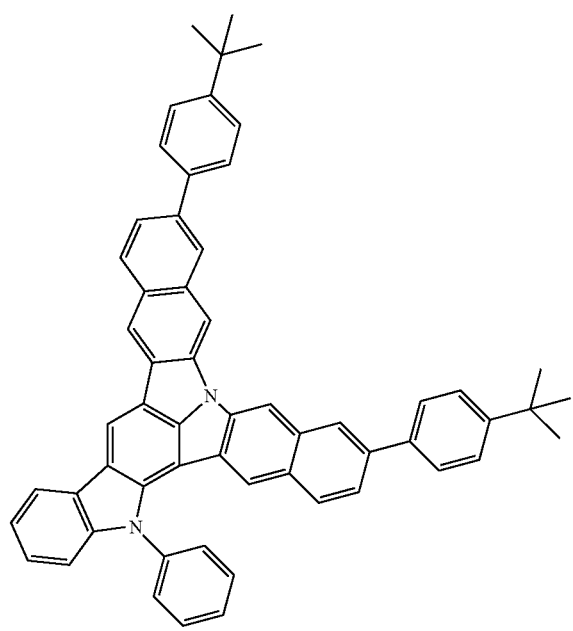
216
-continued
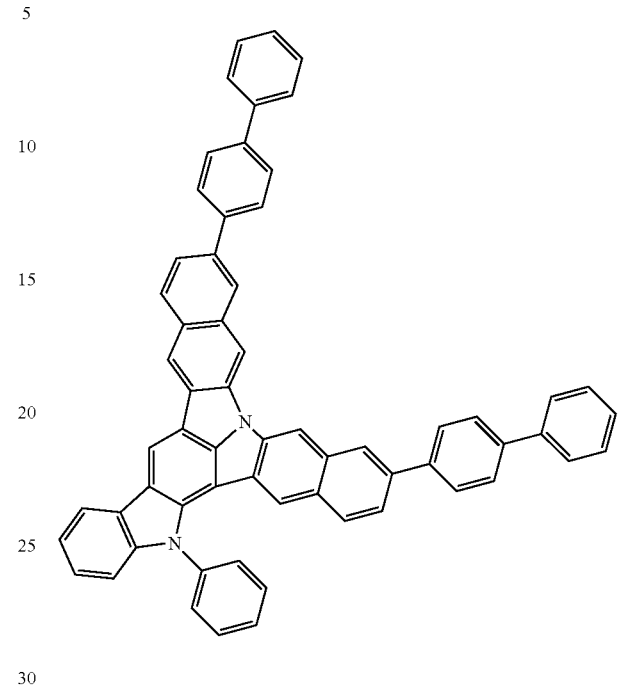
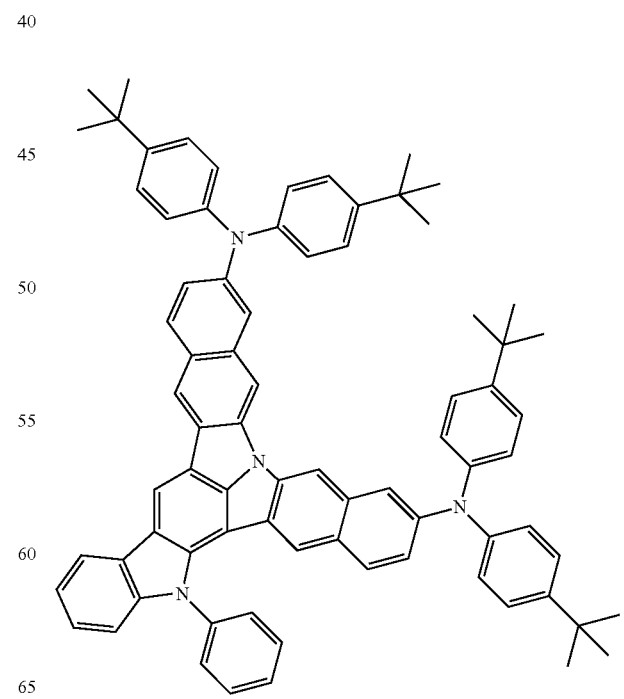

217
-continued
218
-continued
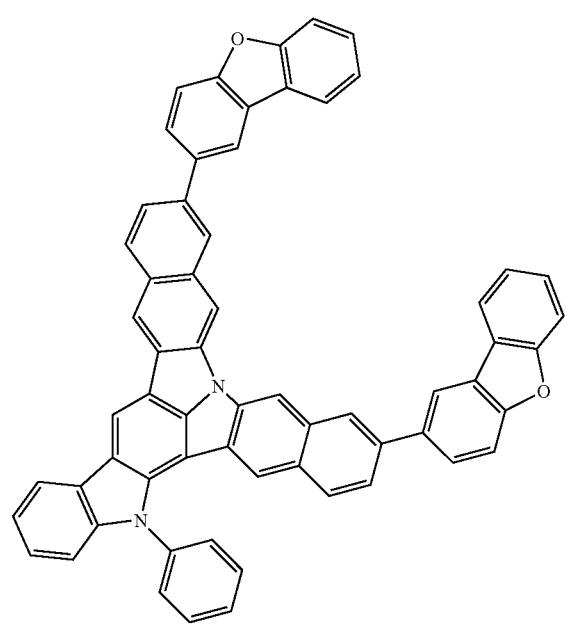
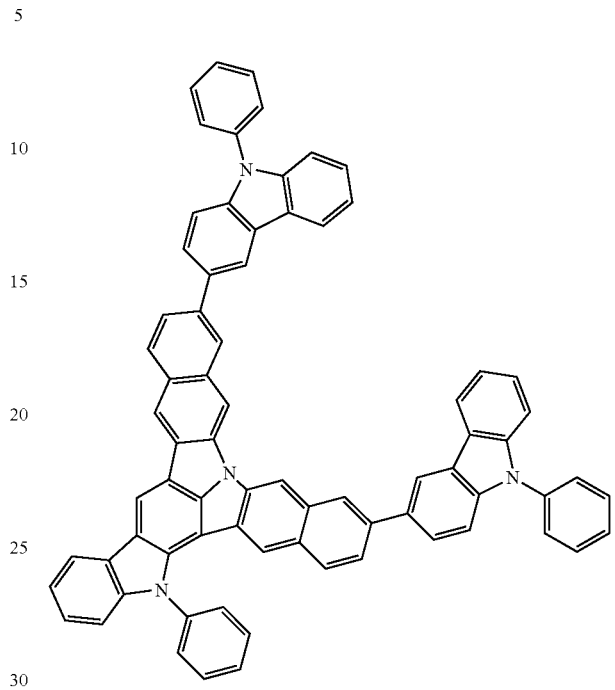
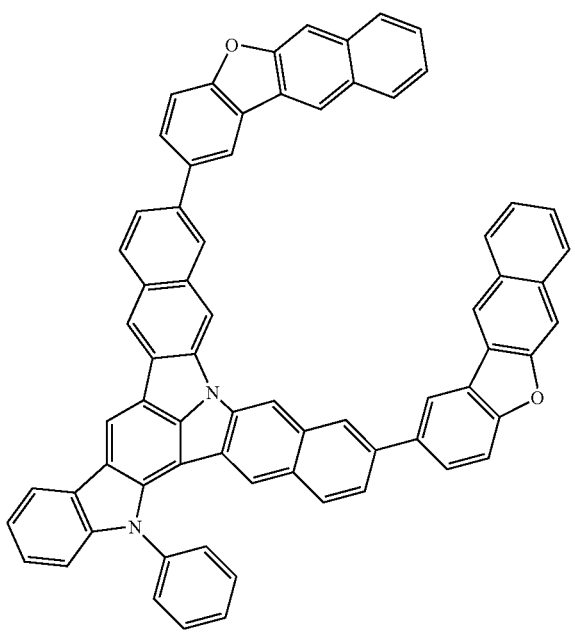
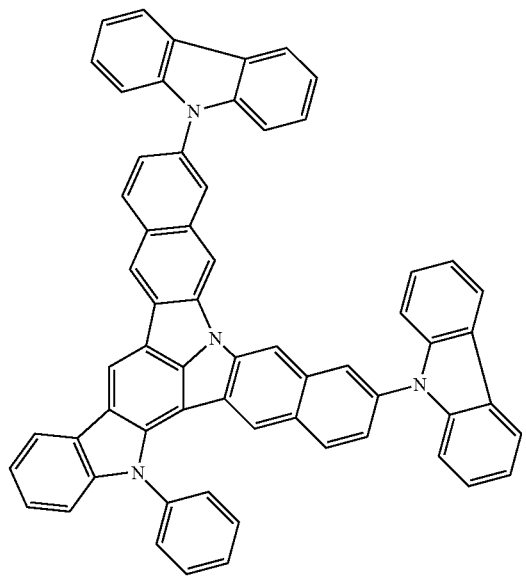

219
-continued
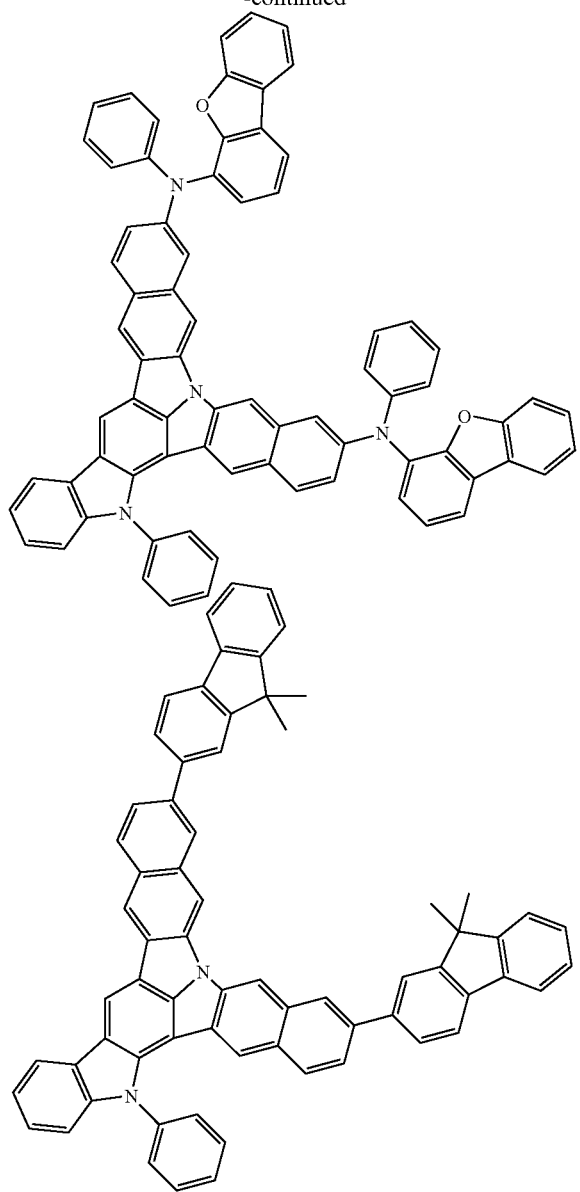
[Formula 78]
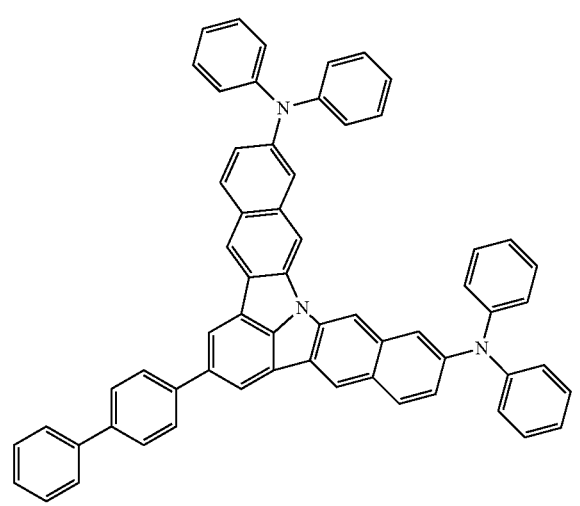
220
-continued
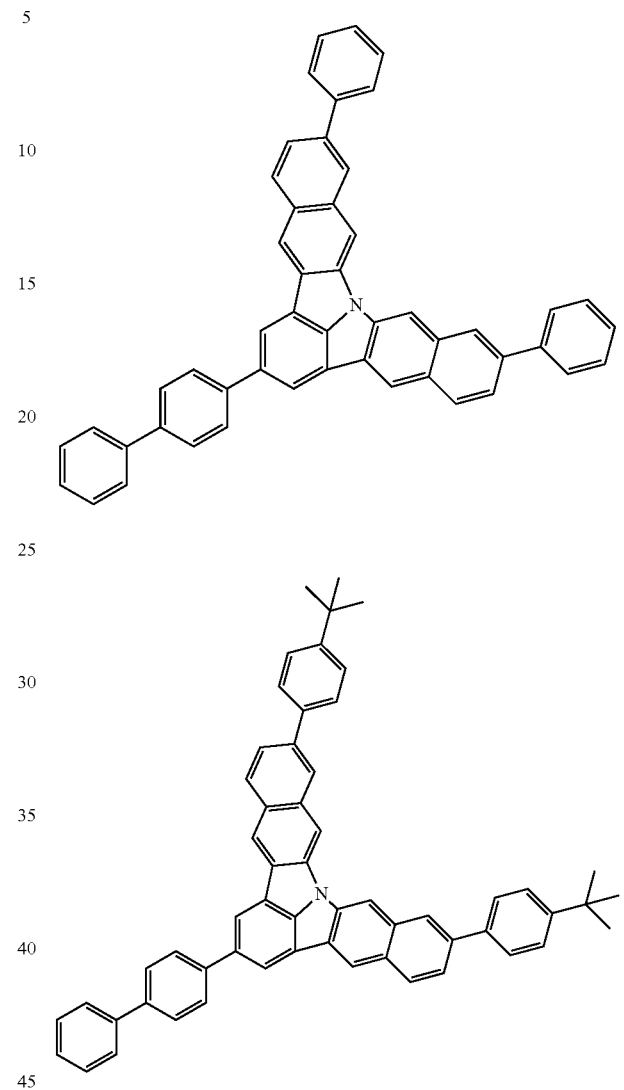
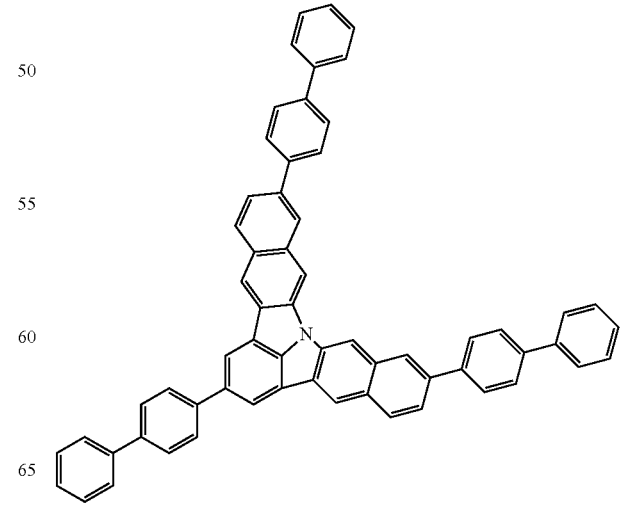

221
-continued
222
-continued
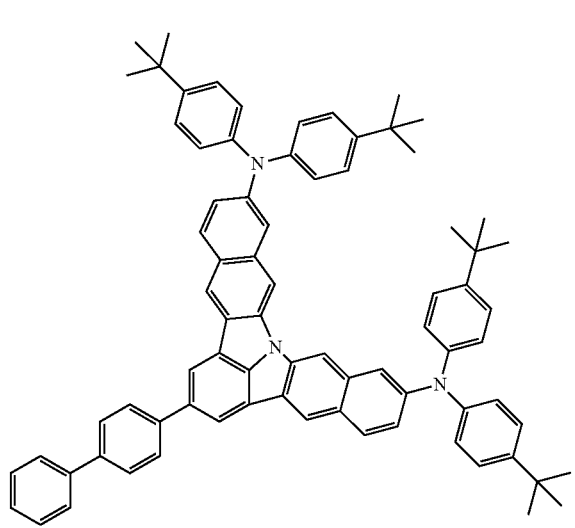
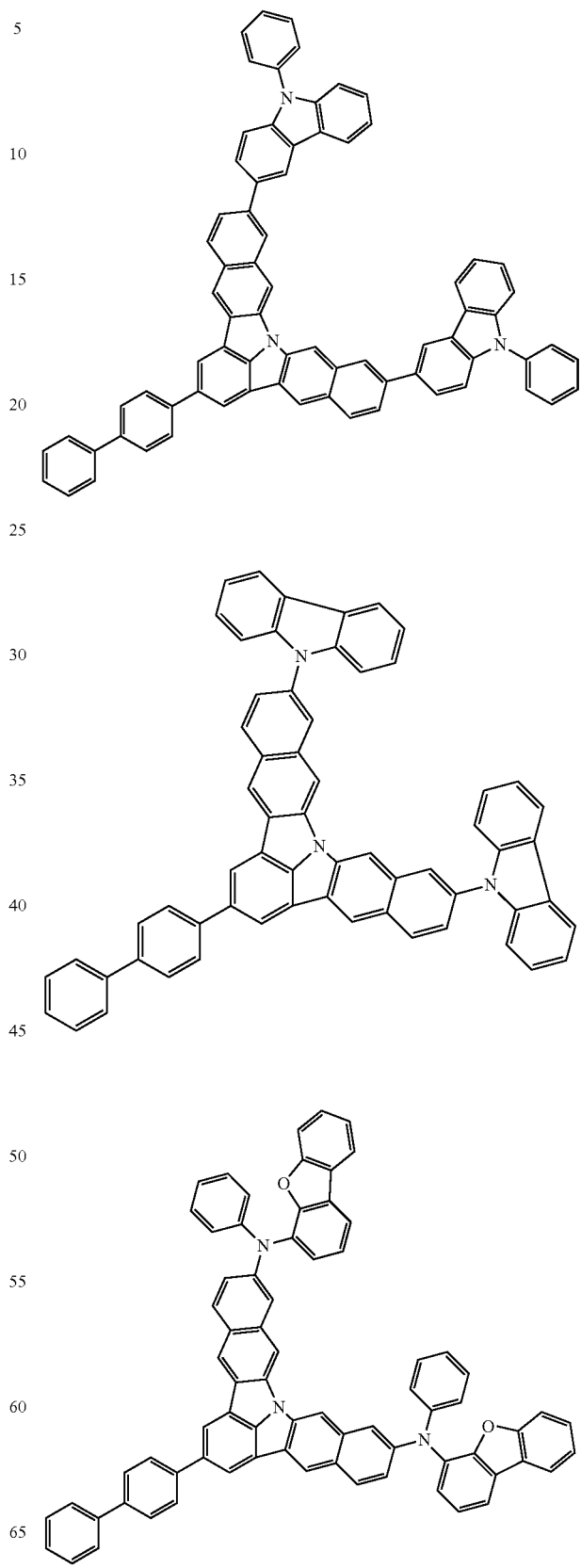

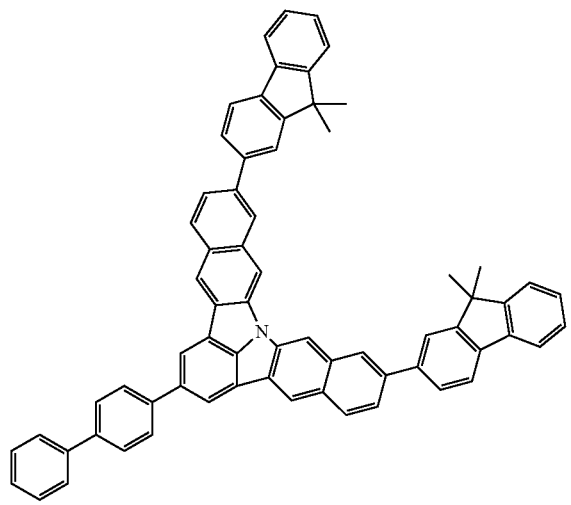
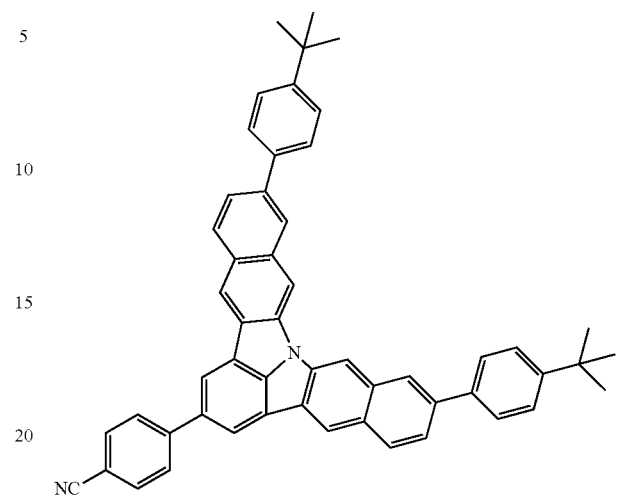
[Formula 79]
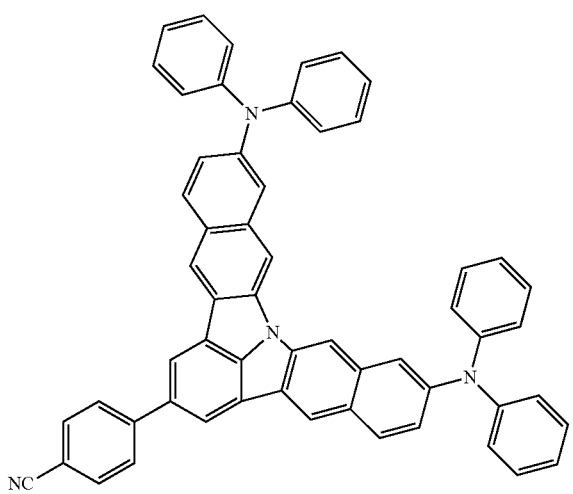
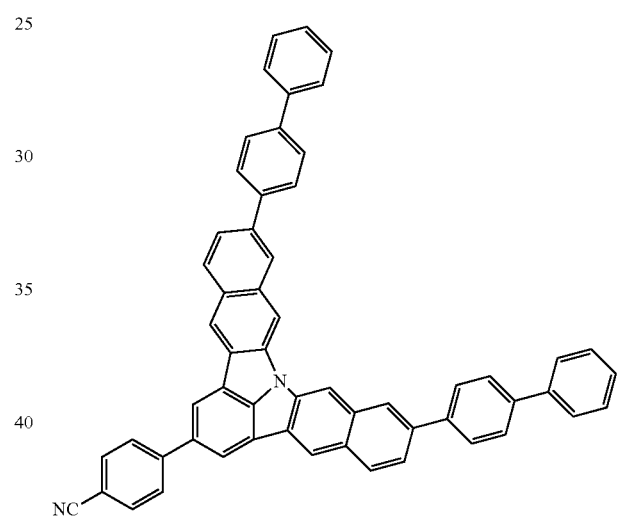
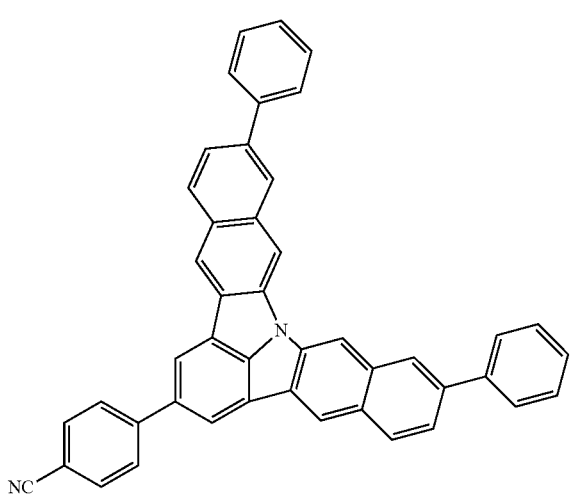
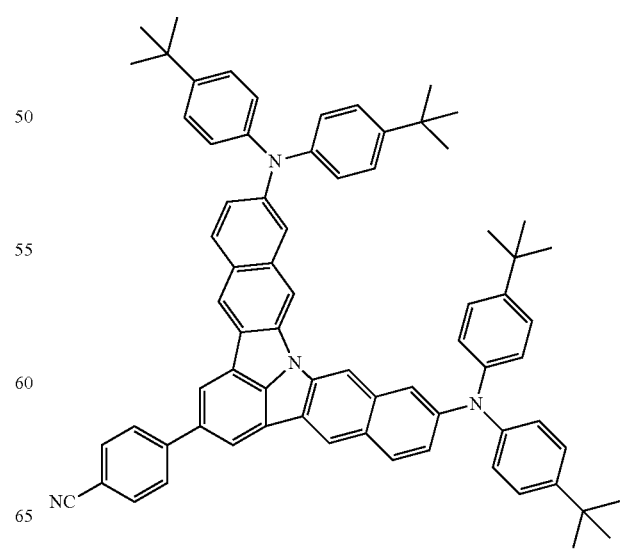

225
-continued
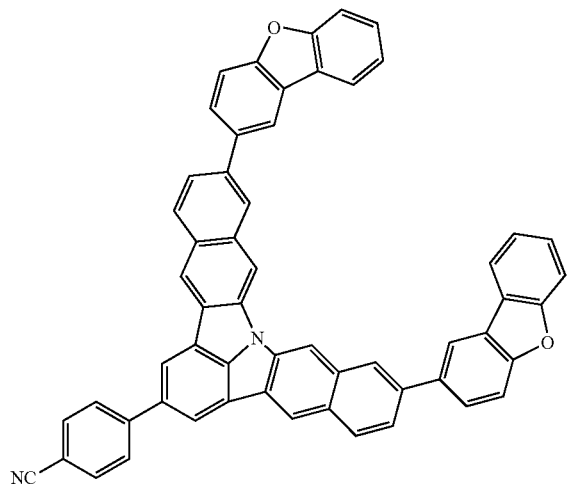
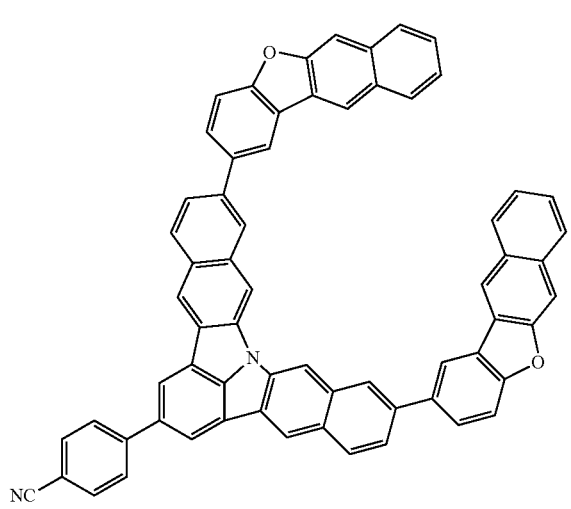
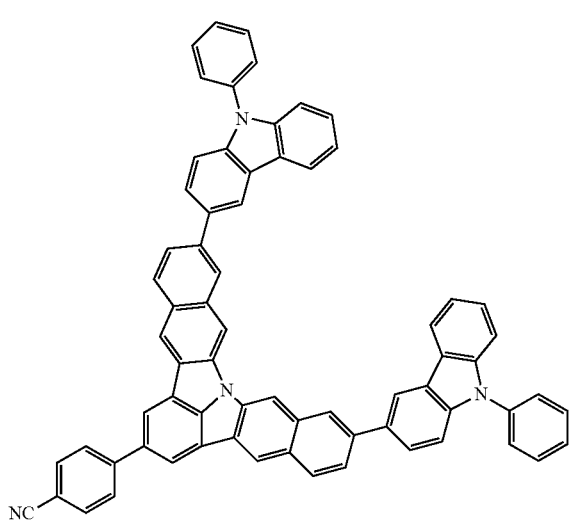
226
-continued
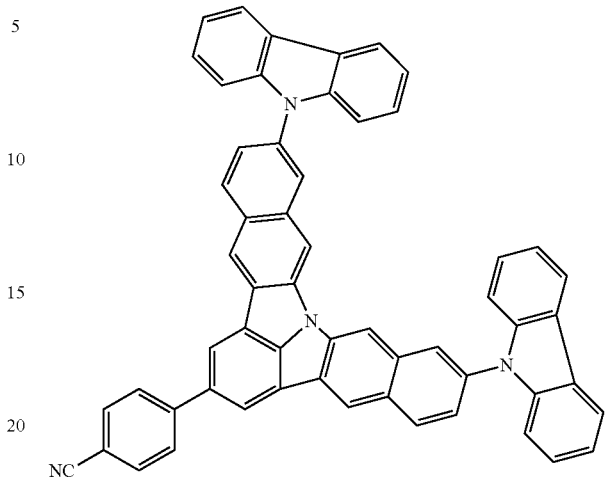
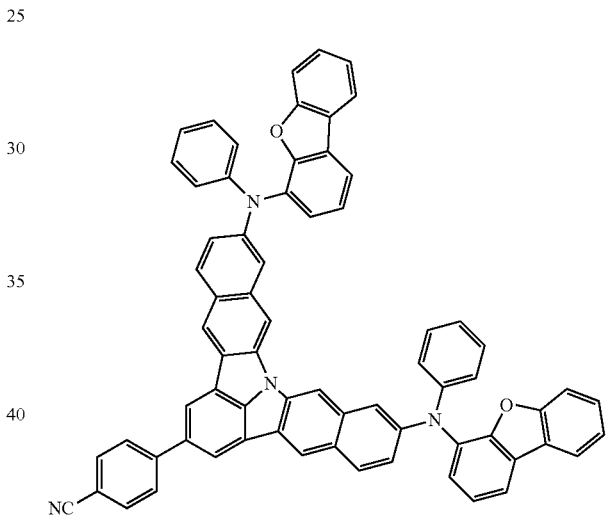
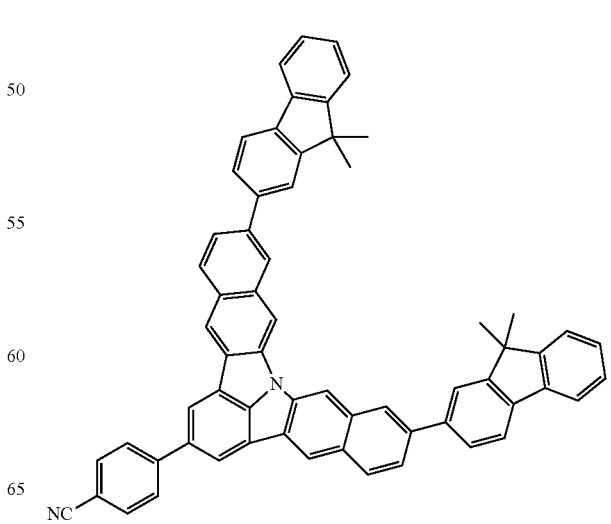

227
-continued
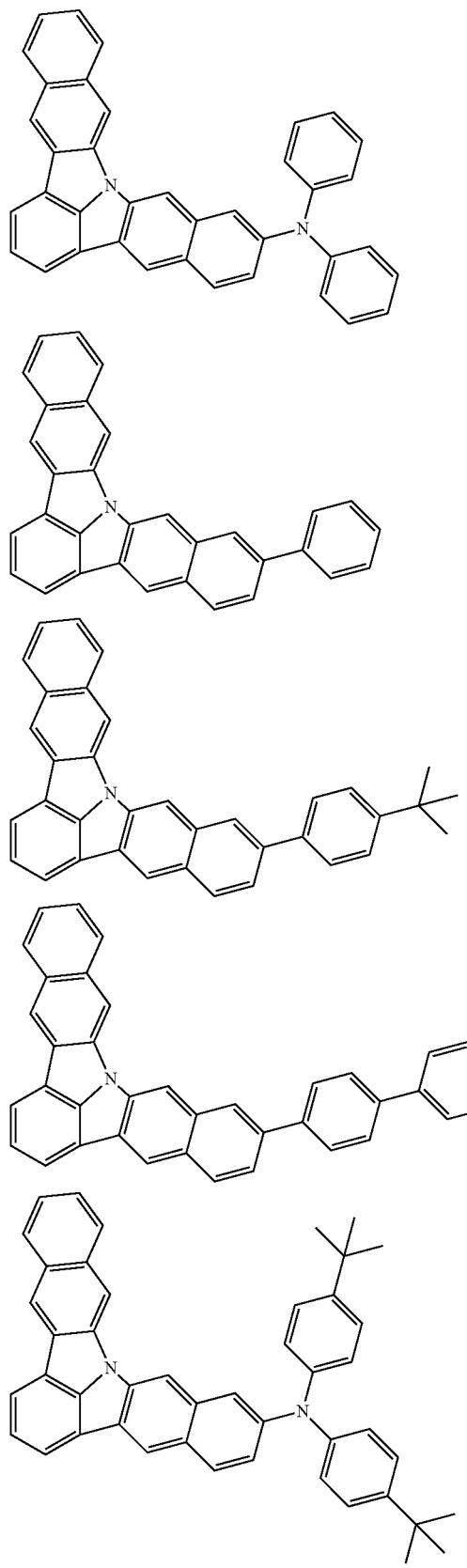
228
-continued
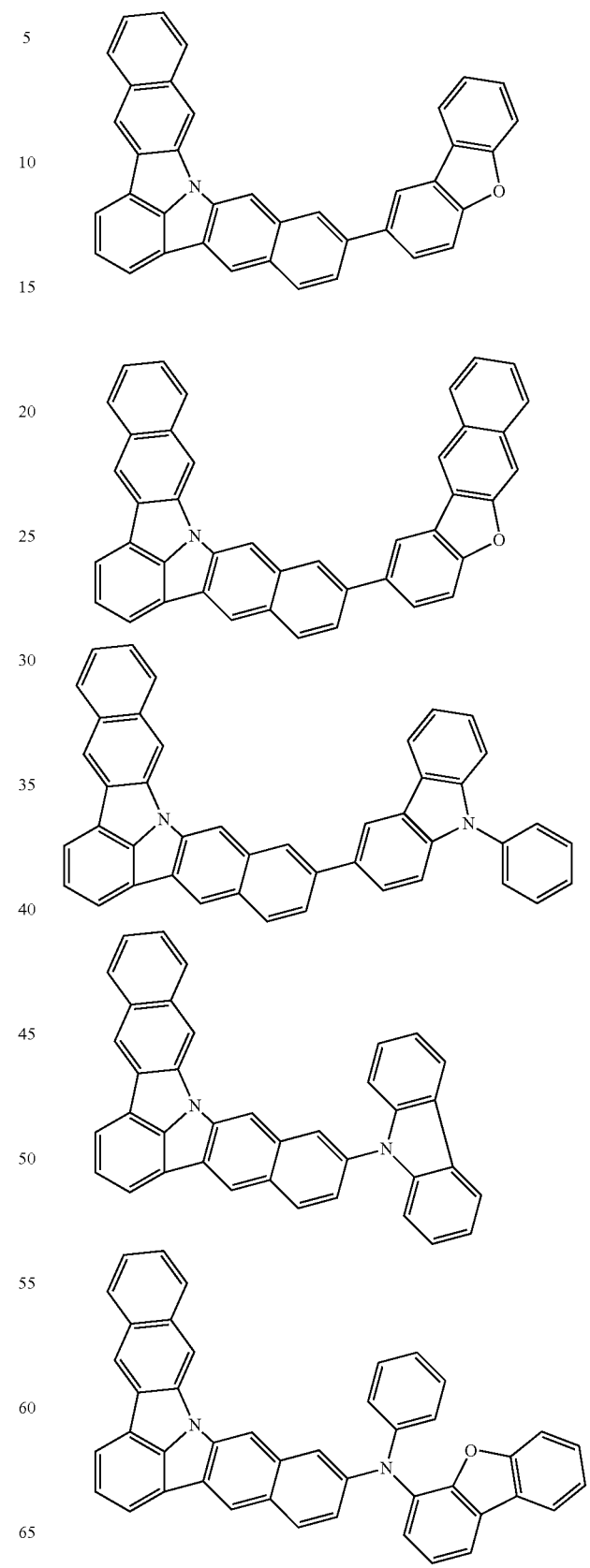

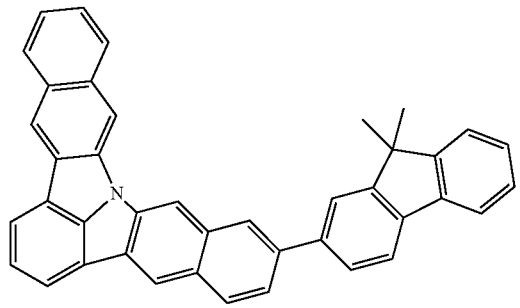
[Formula 80]
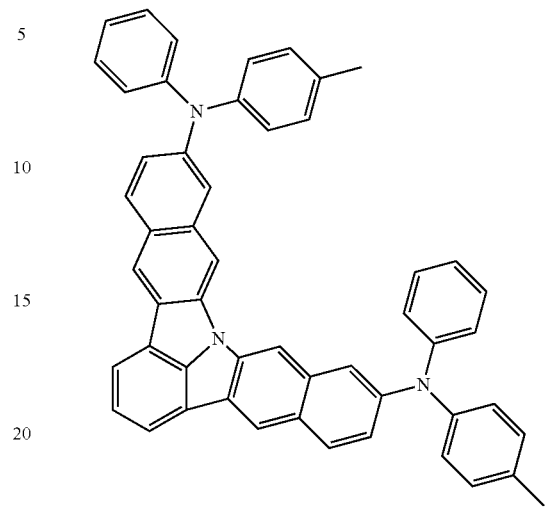
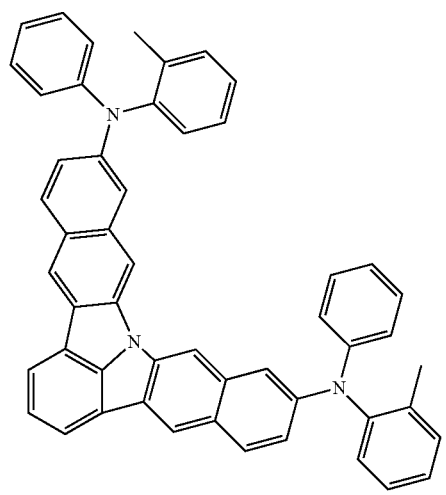
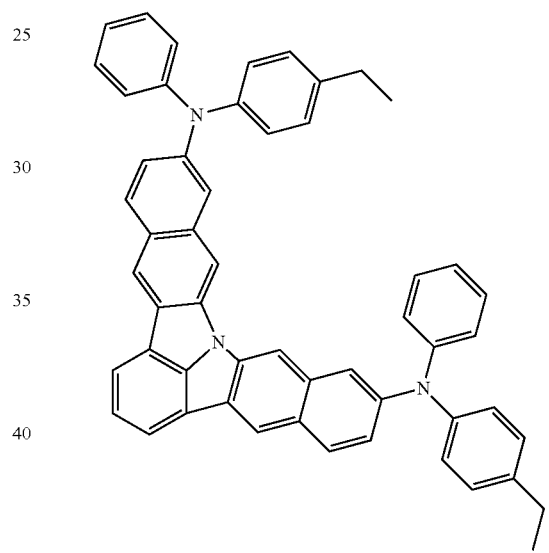
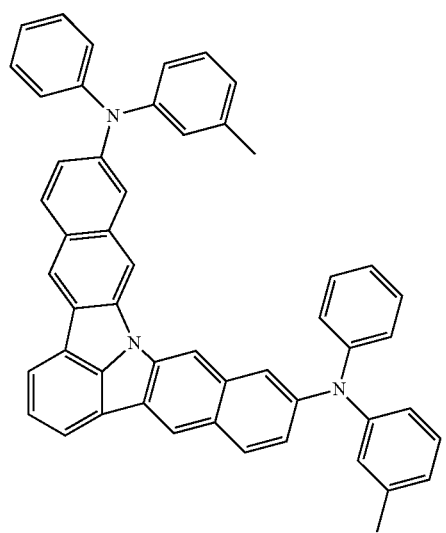
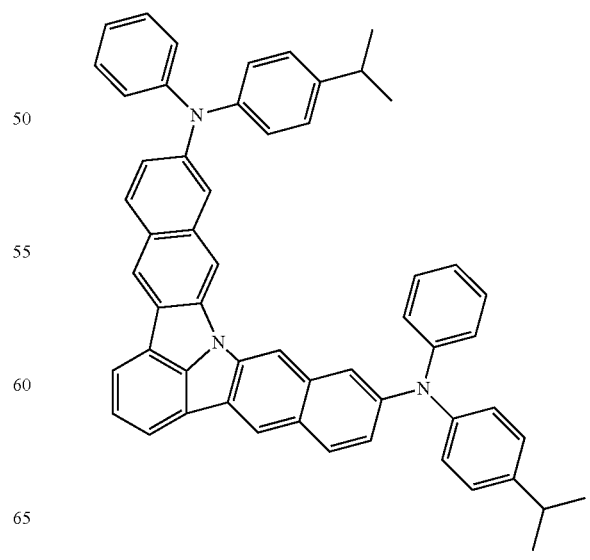

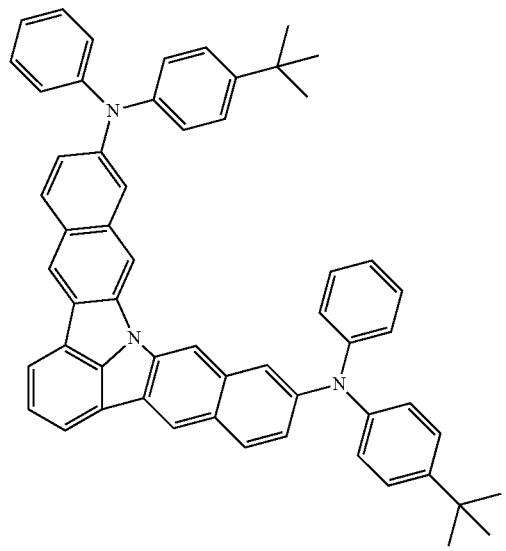
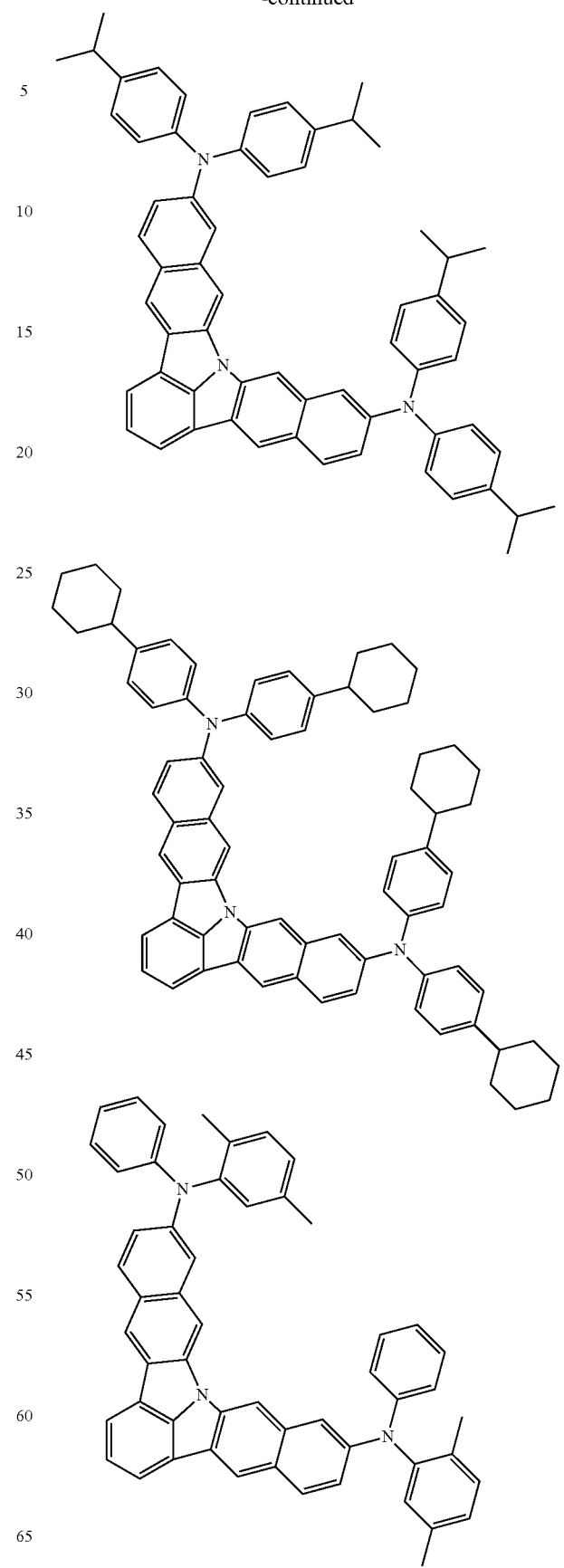

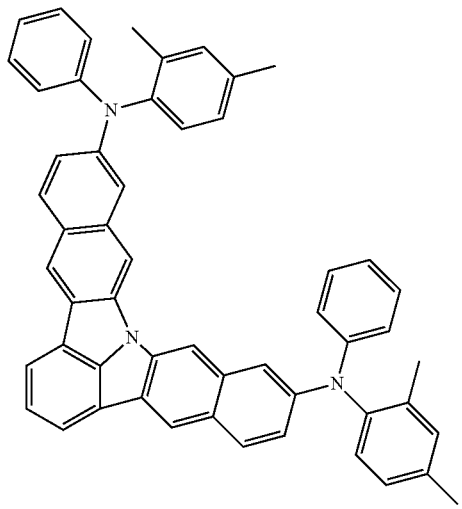
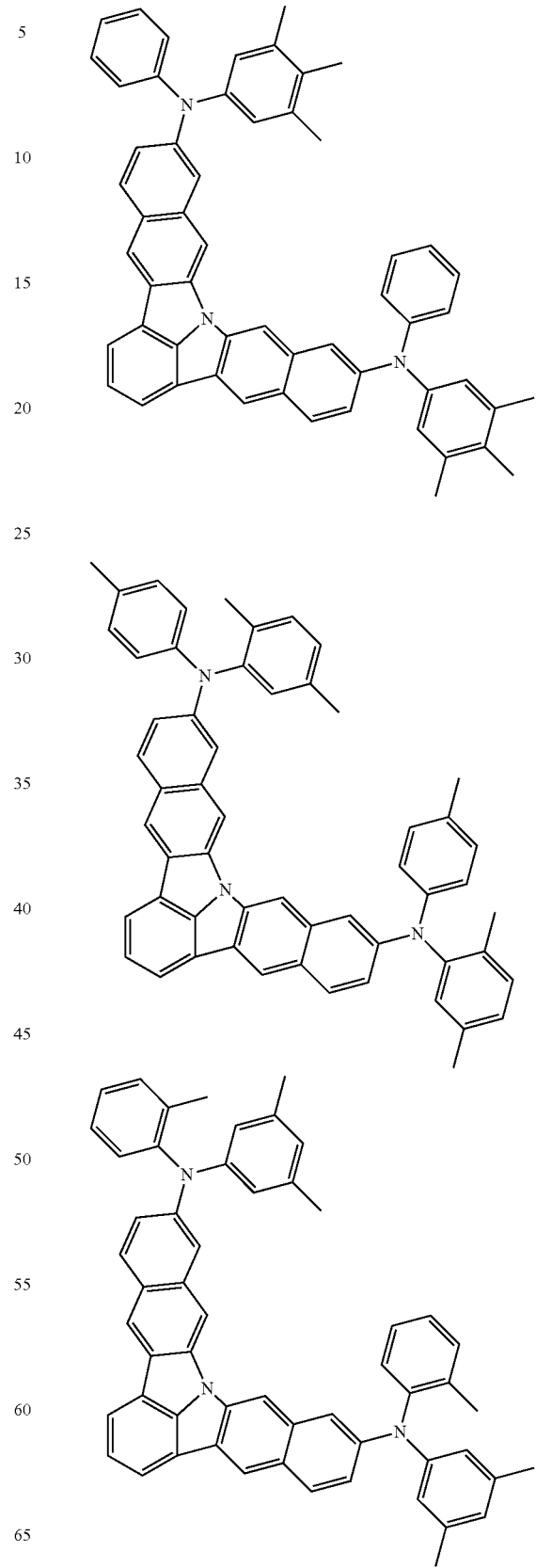

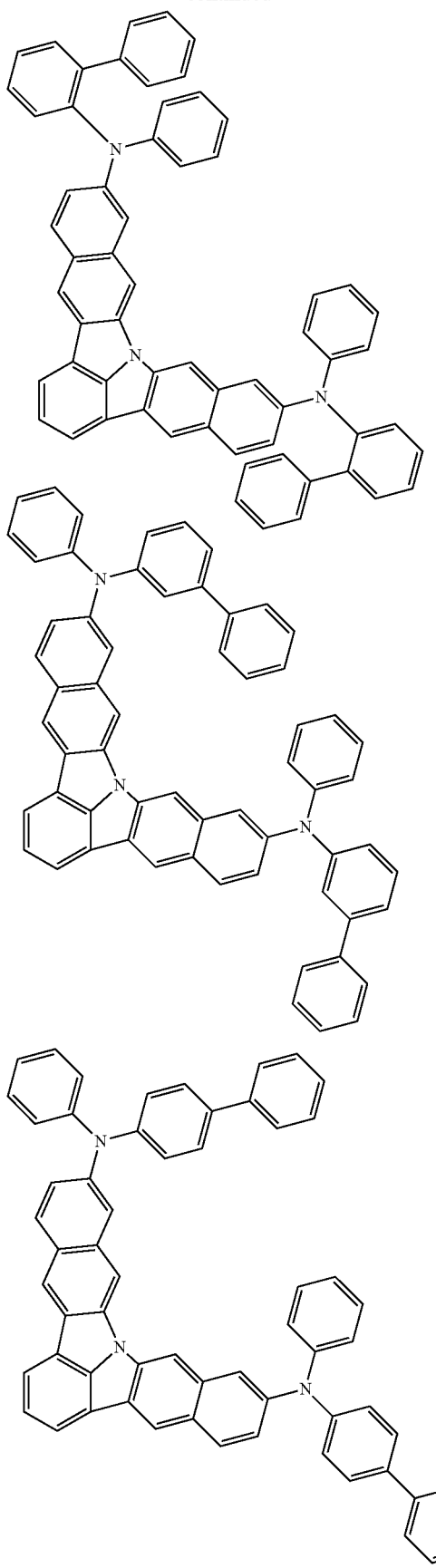
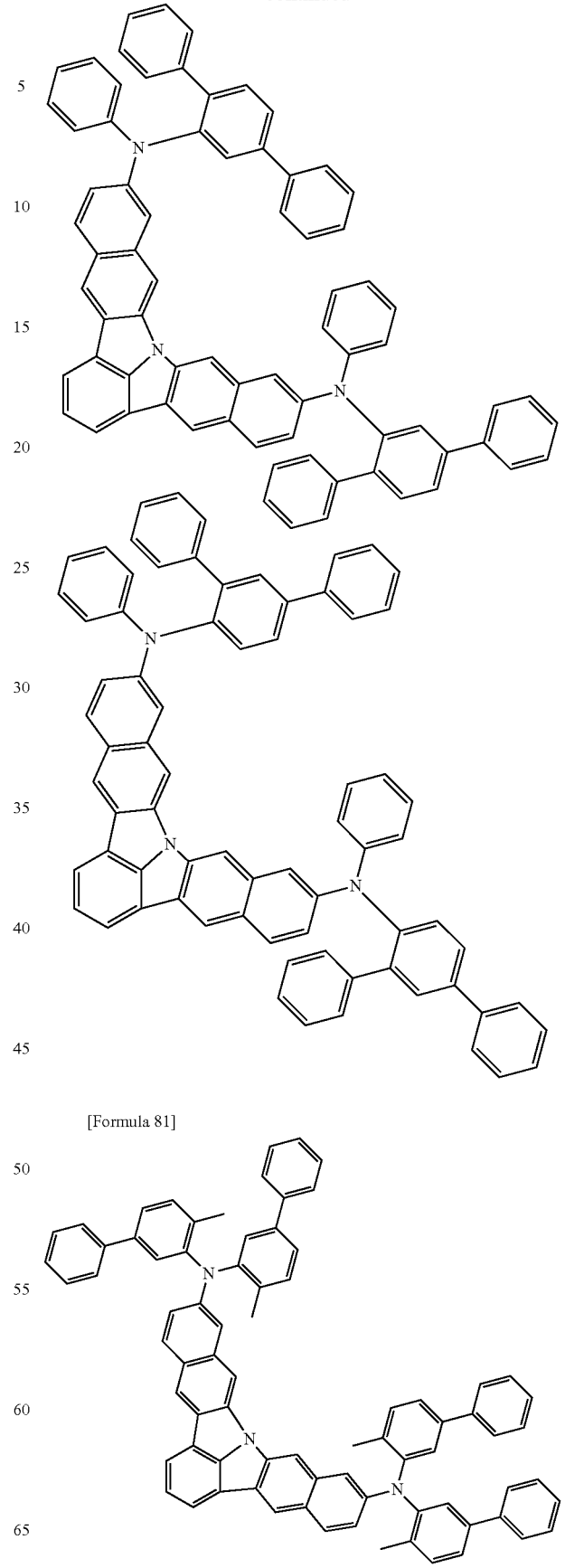
[Formula 81]

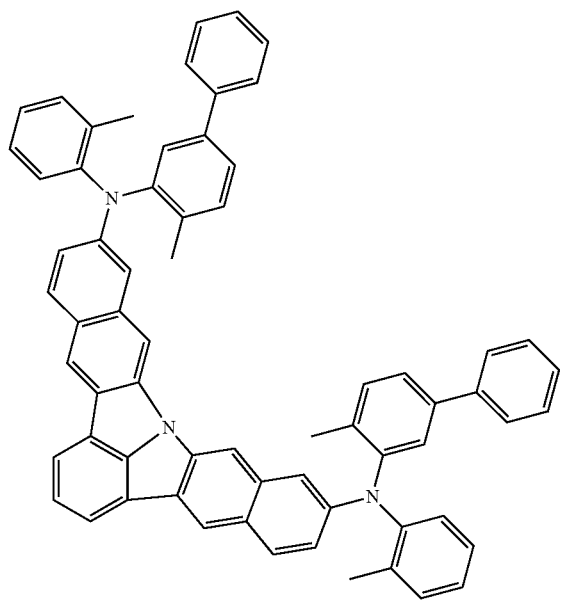
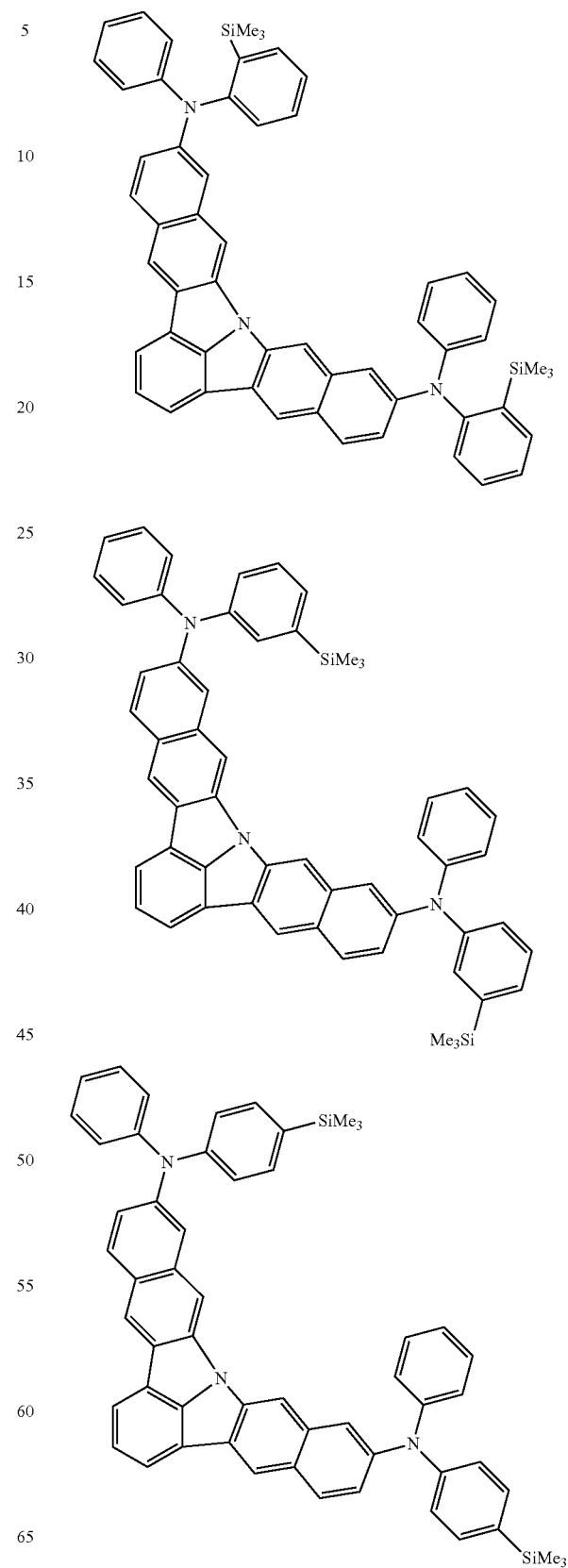

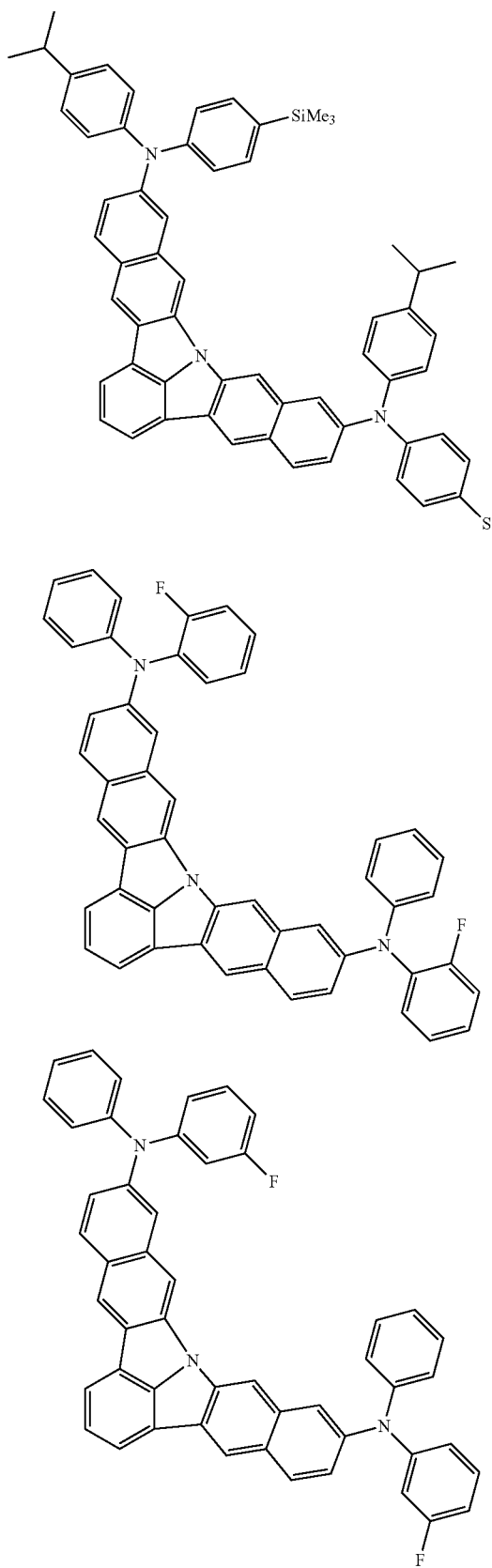
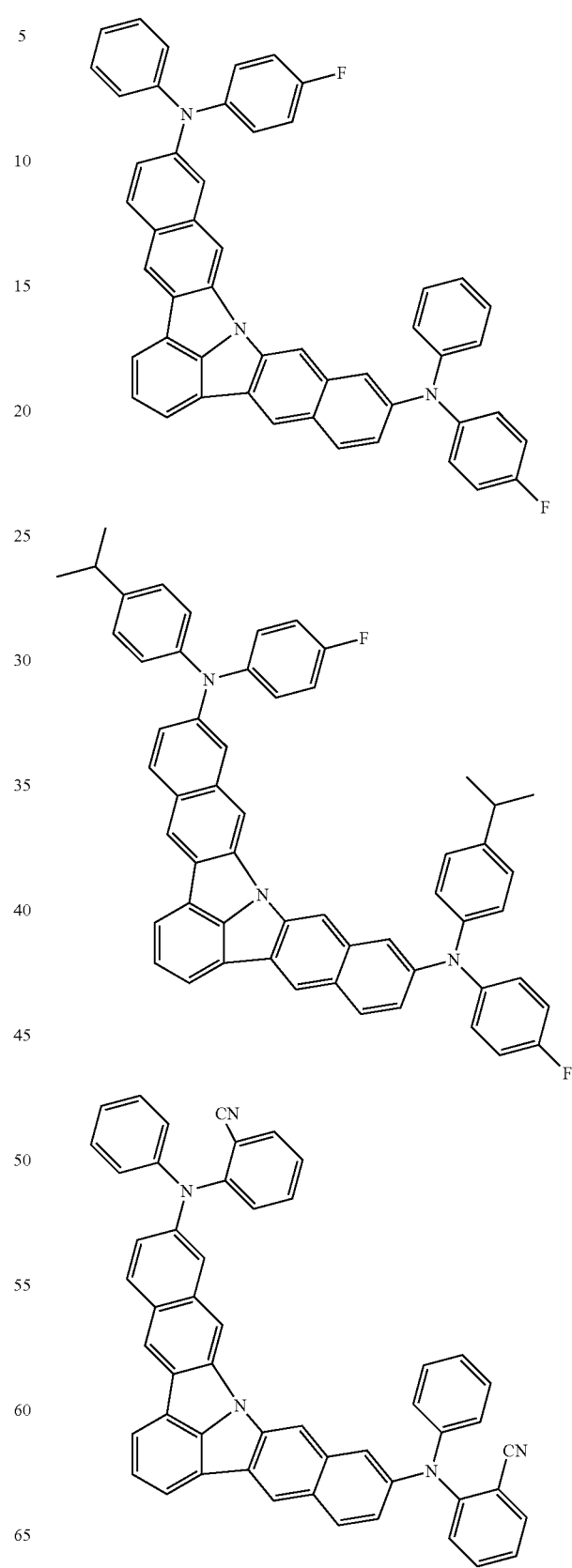

241
-continued
242
-continued
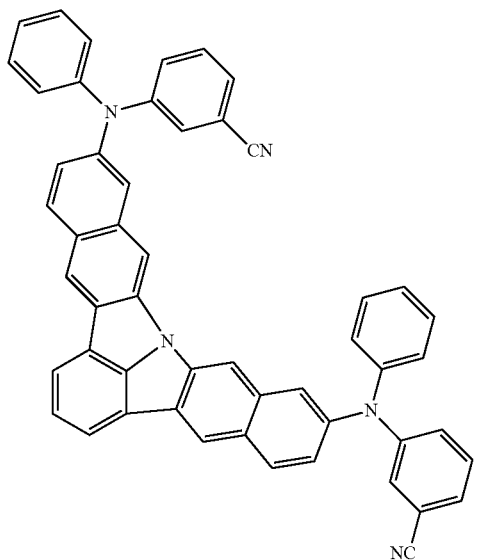
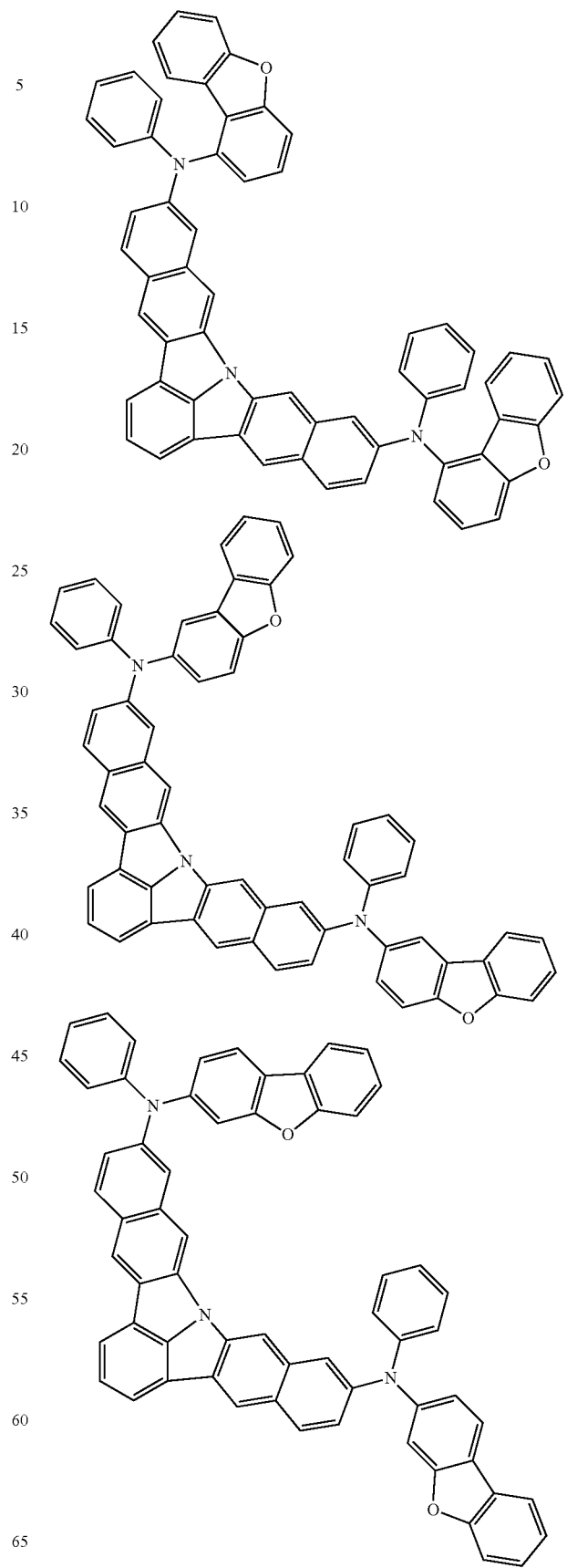

243
-continued
244
-continued
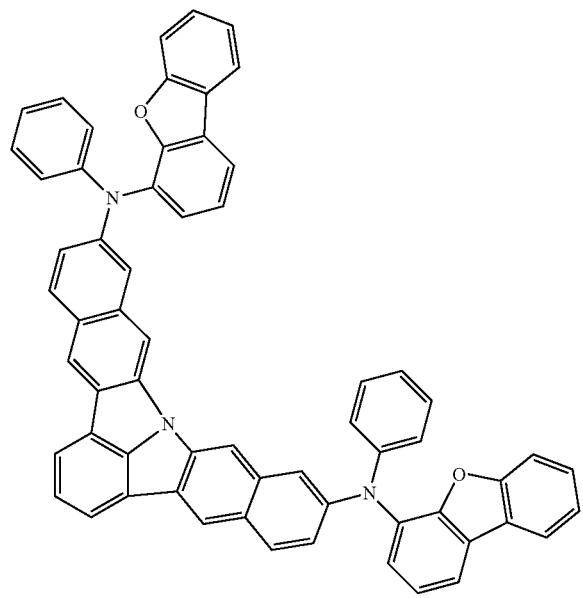
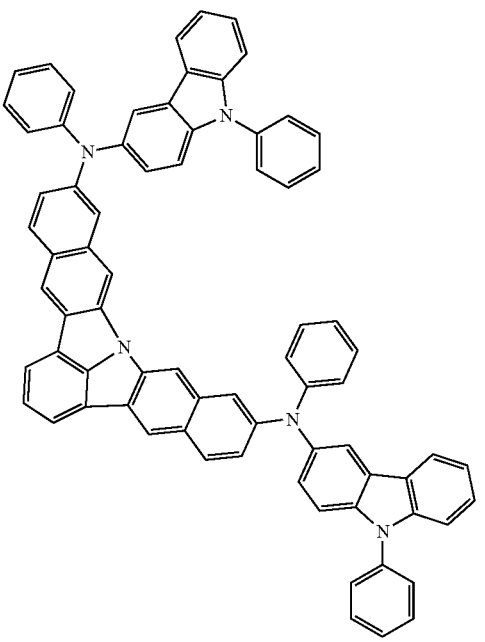
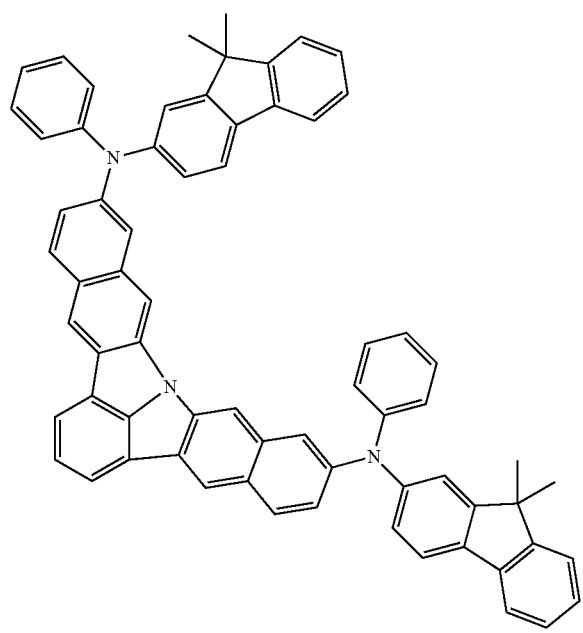

245
-continued
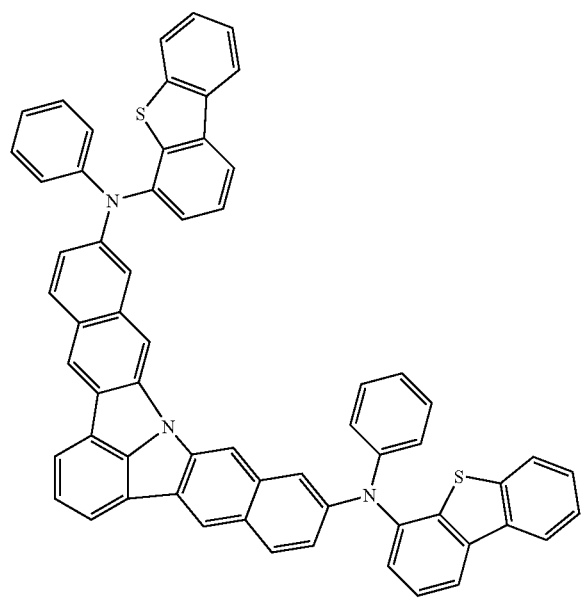
[Formula 82]
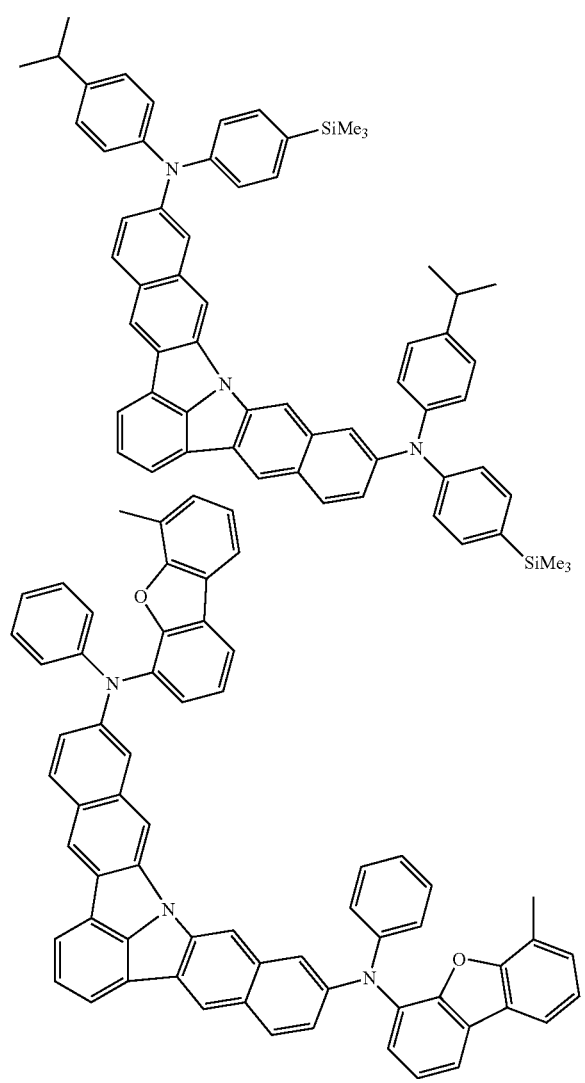
246
-continued
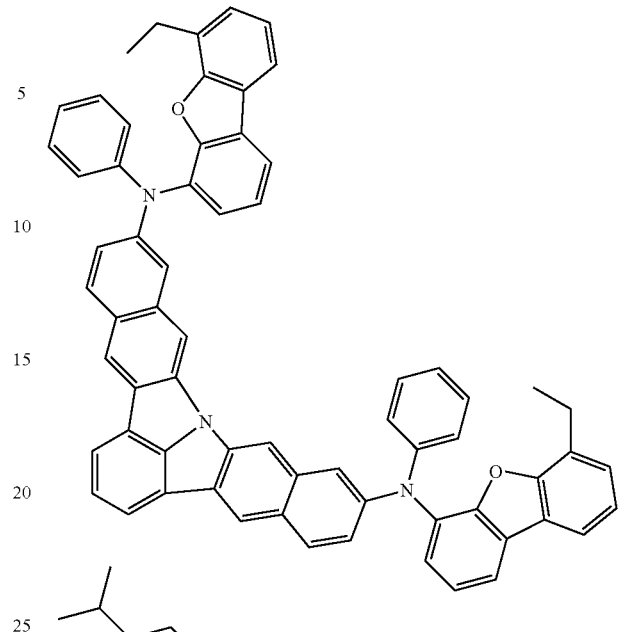
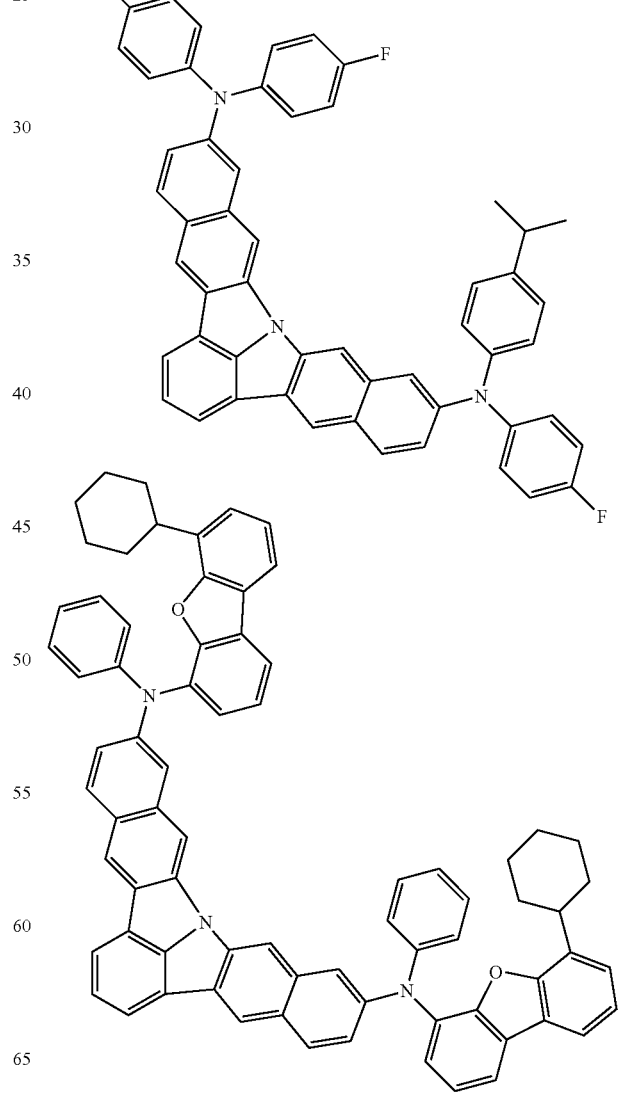

247
-continued
248
-continued
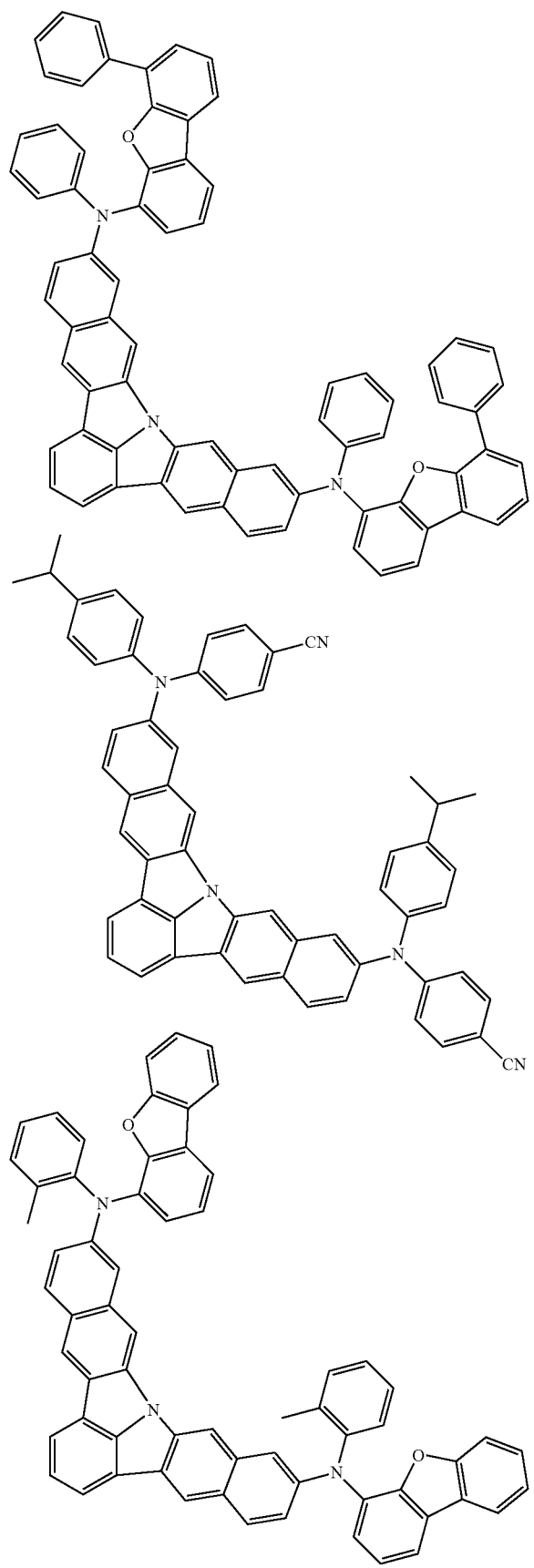
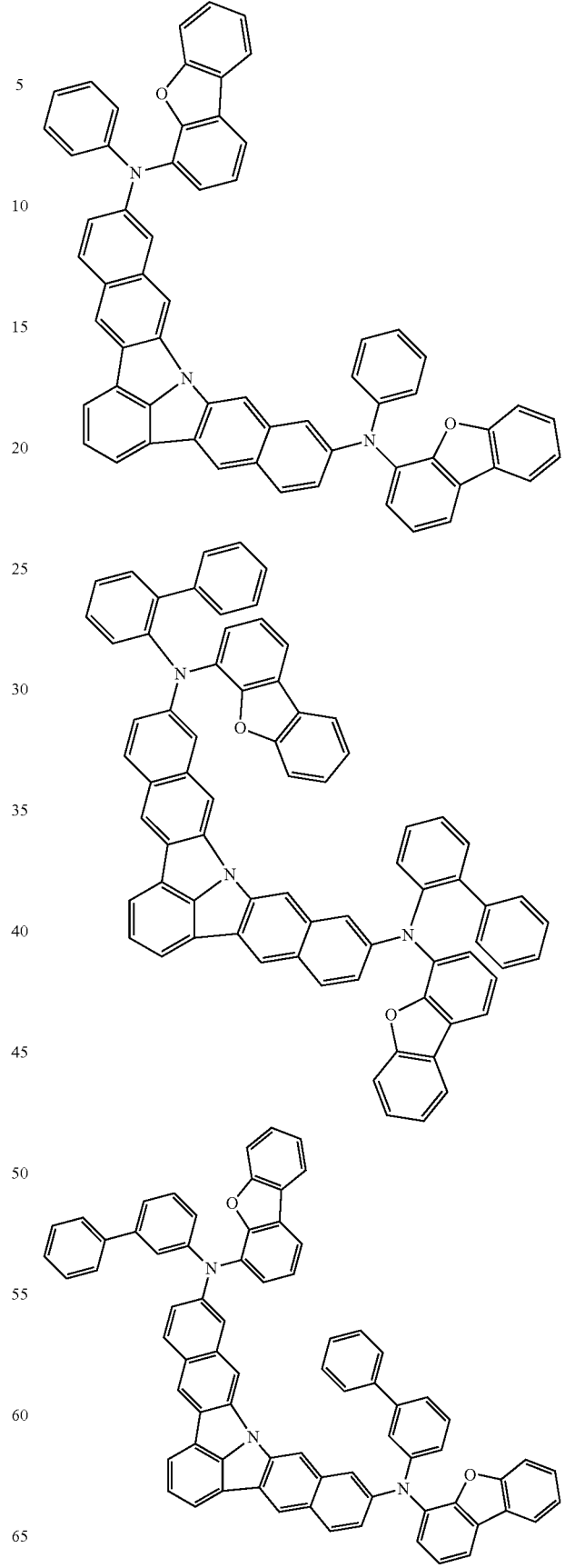

249
-continued
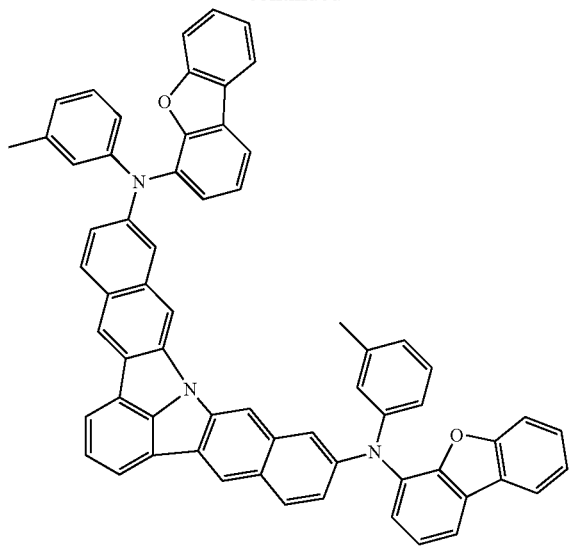
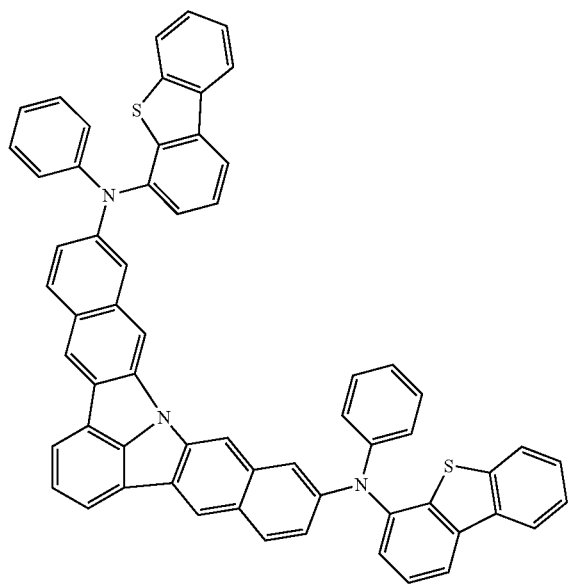
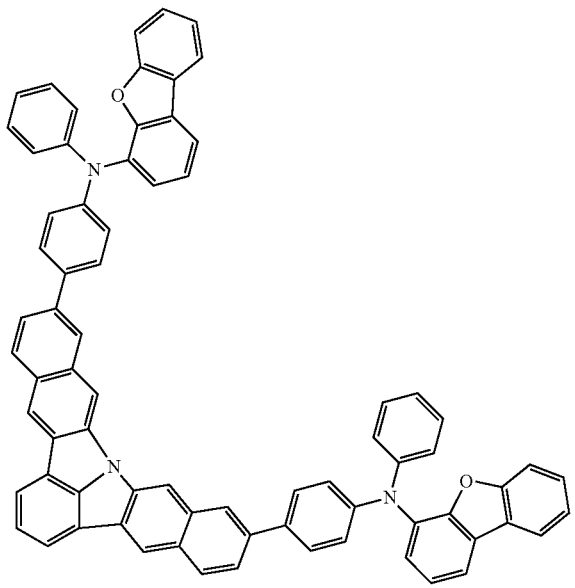
250
-continued
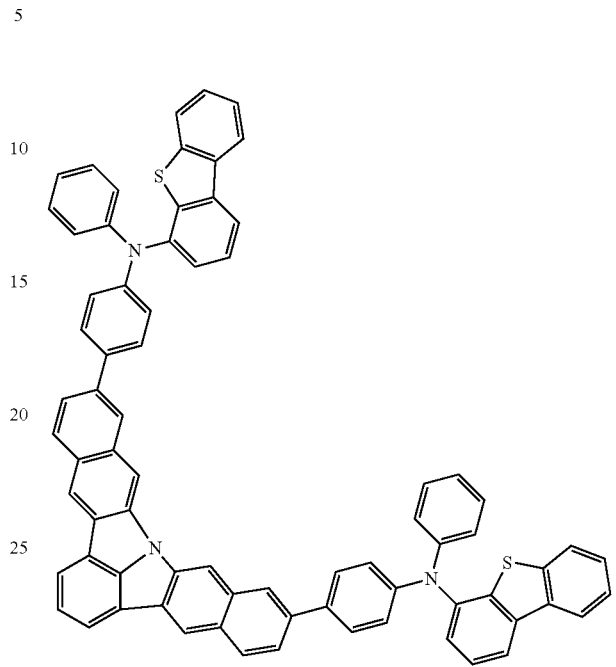
[Formula 83]
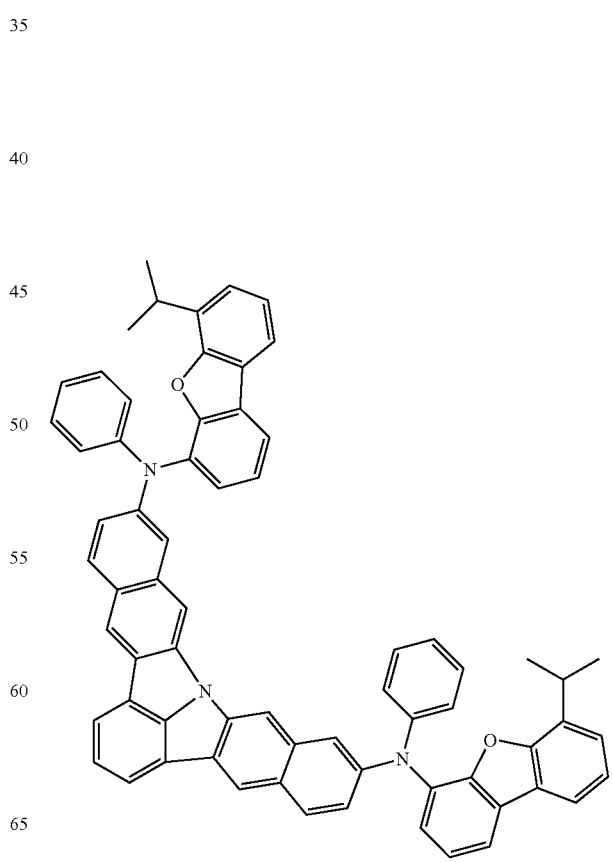

251
-continued
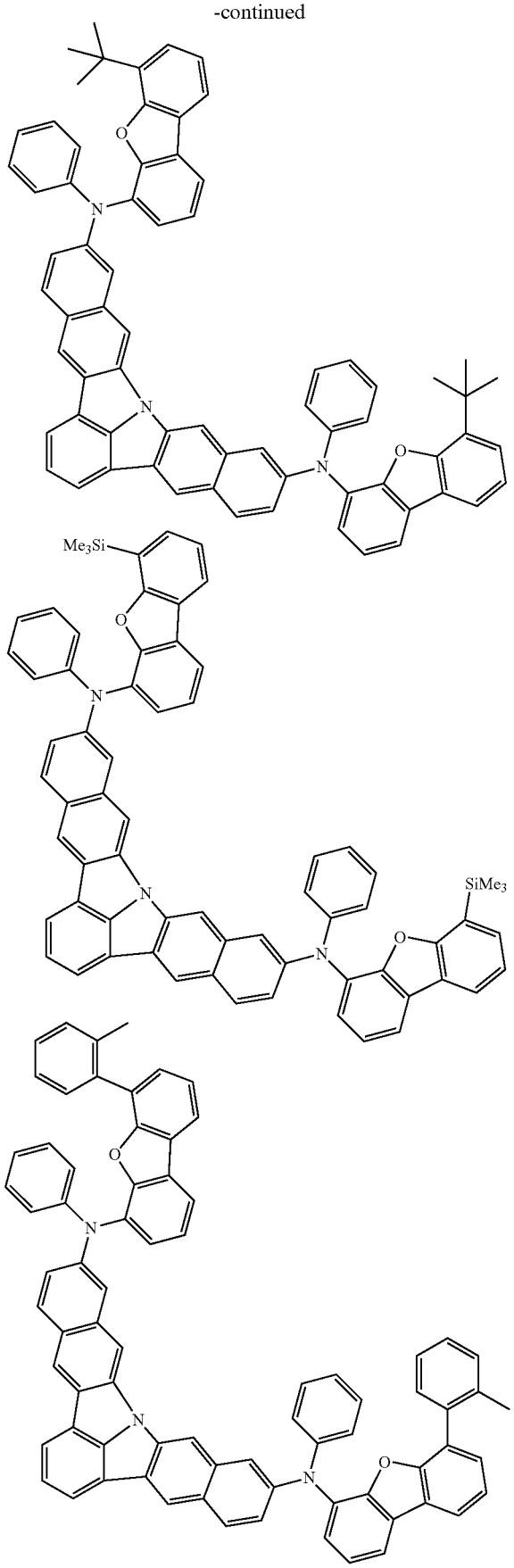
252
-continued
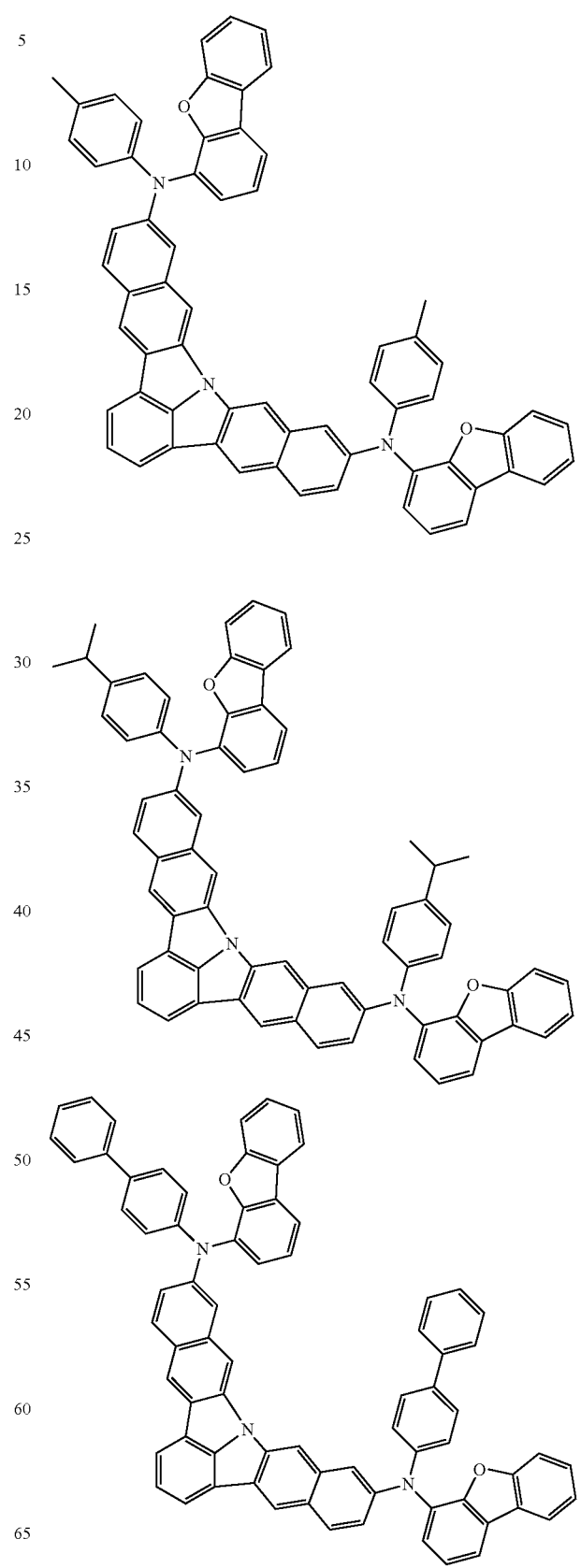

-continued
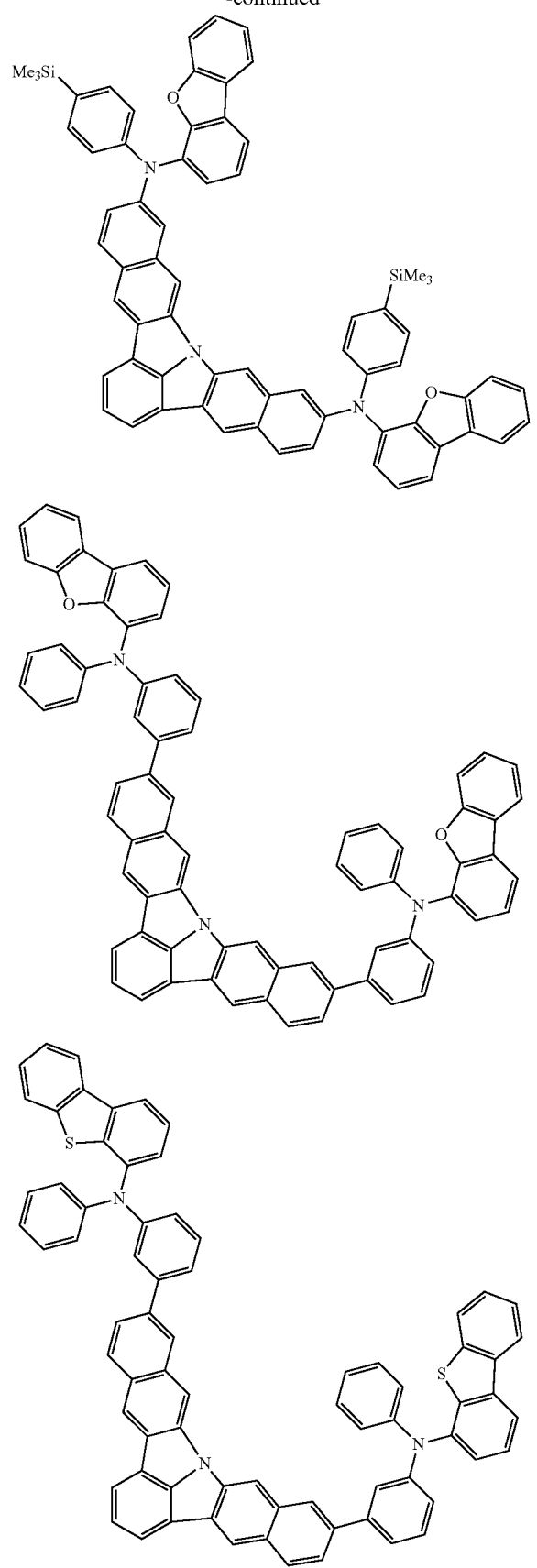
[Formula 84]
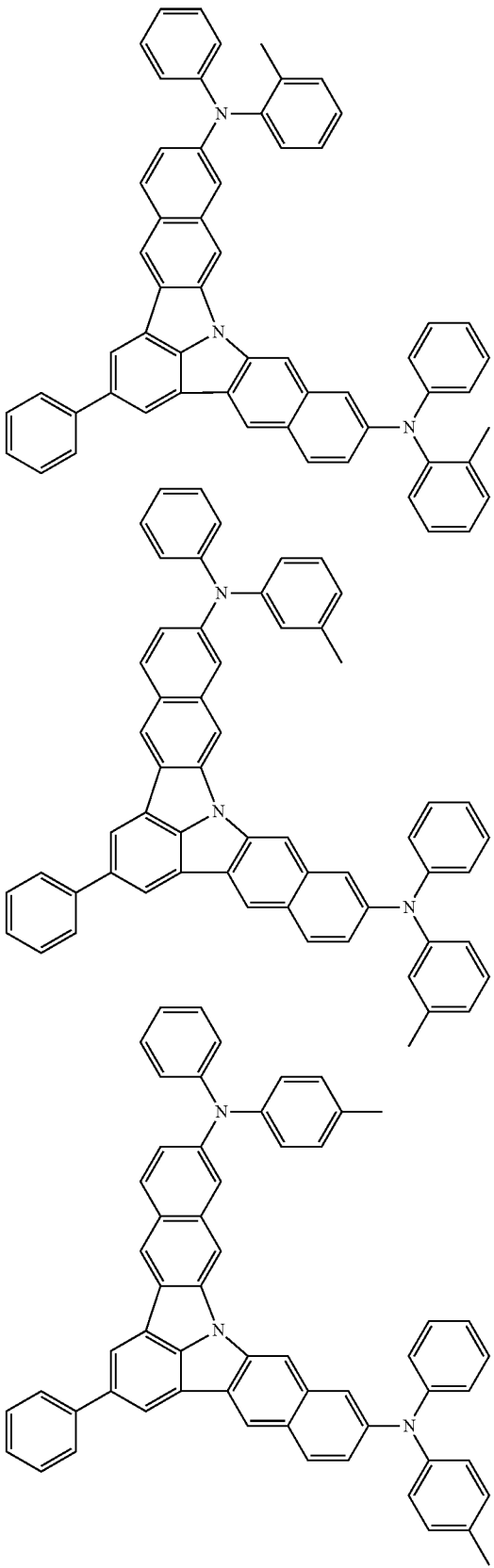

255
-continued
256
-continued
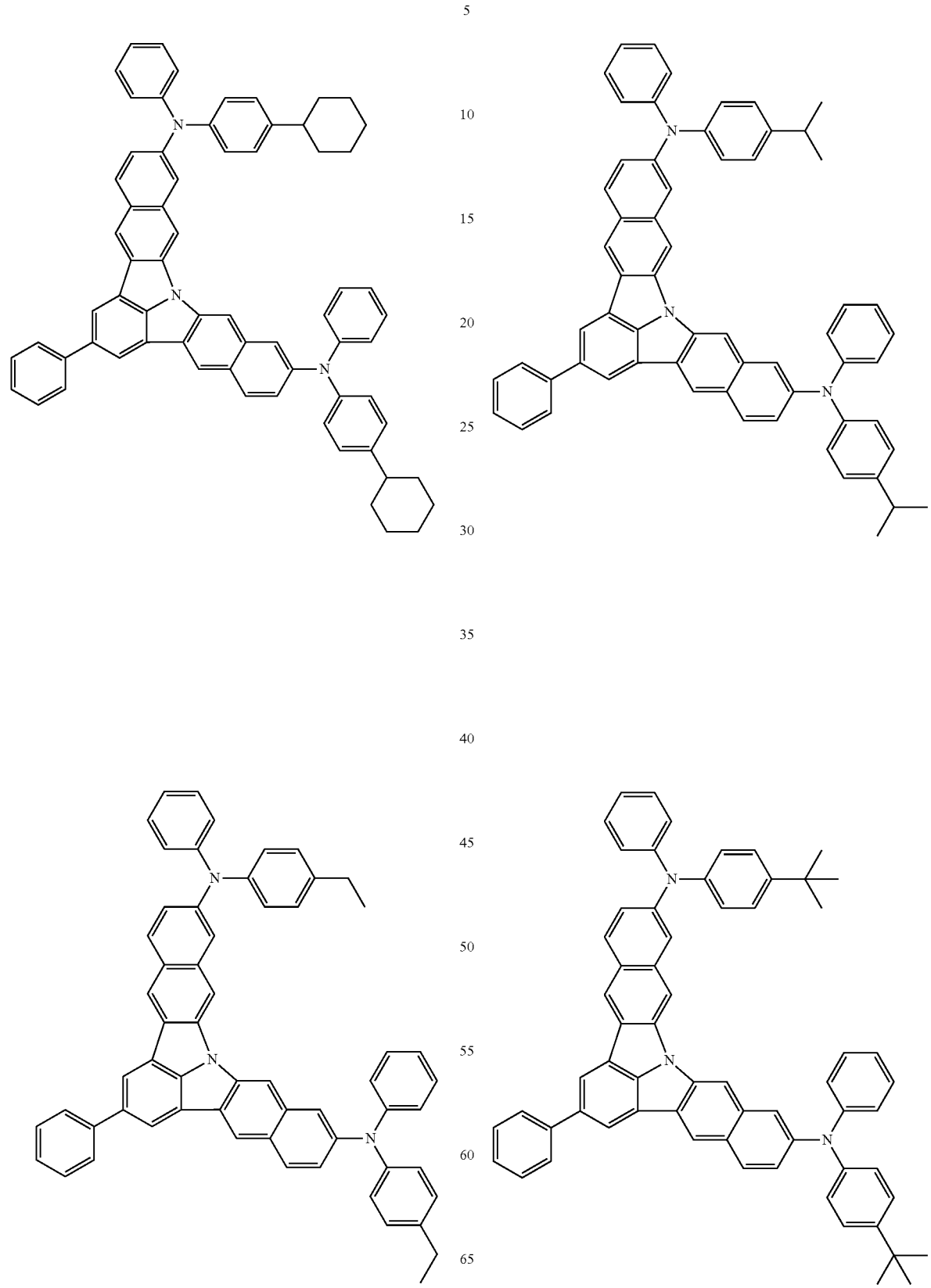

257
-continued
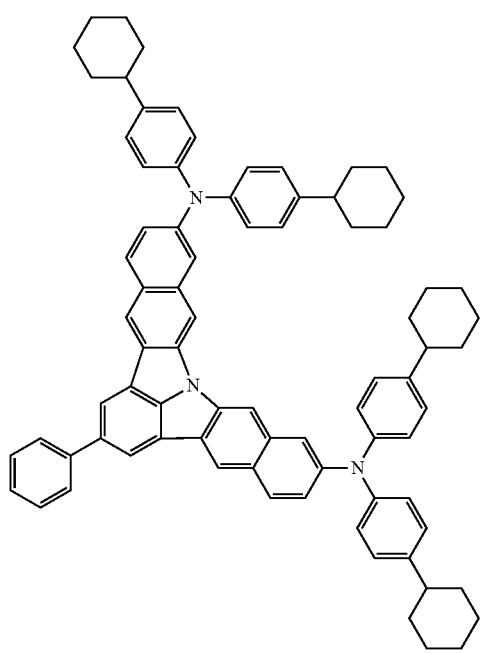
258
-continued
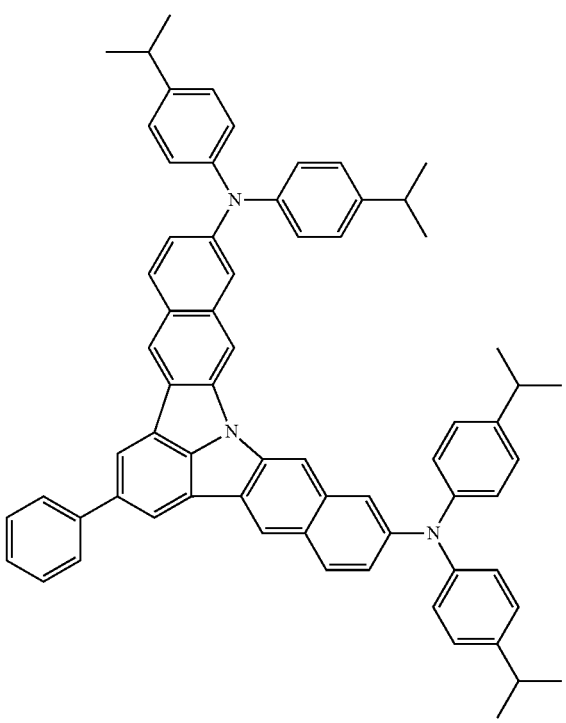
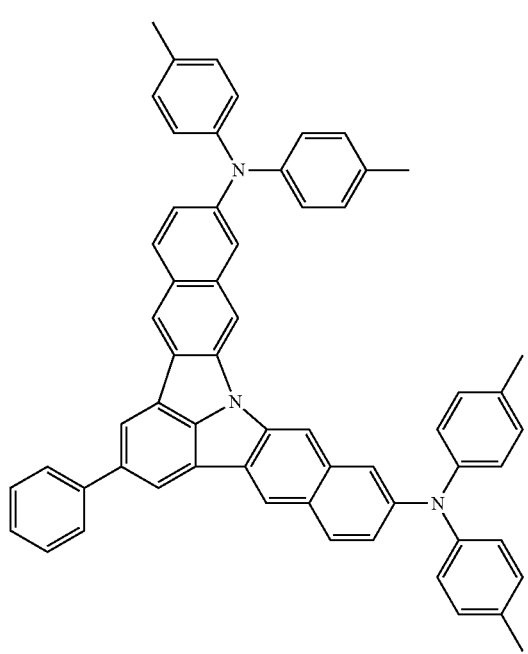
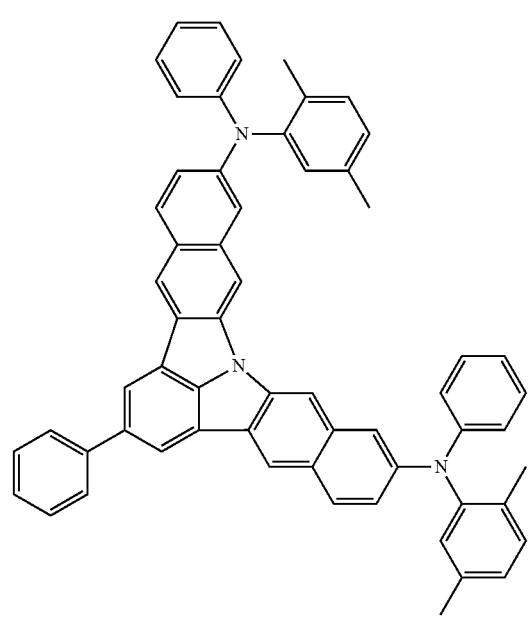

259
-continued
260
-continued
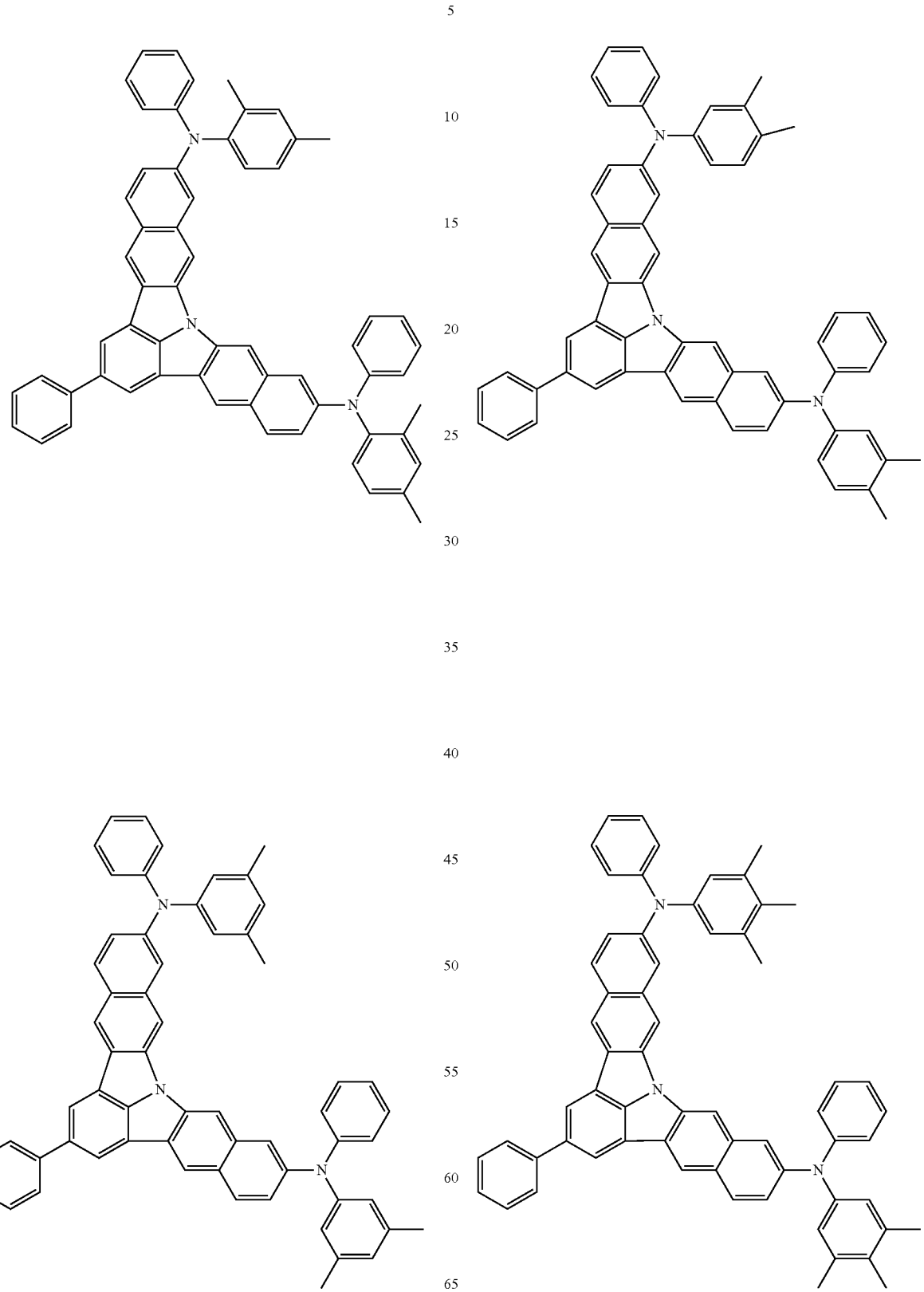

261
-continued
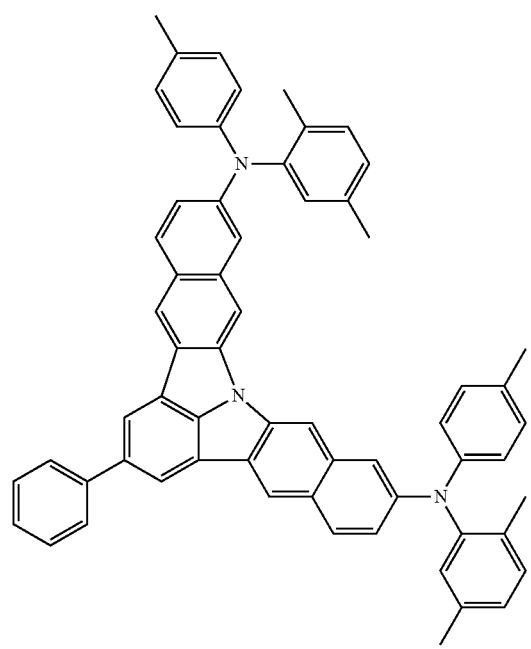
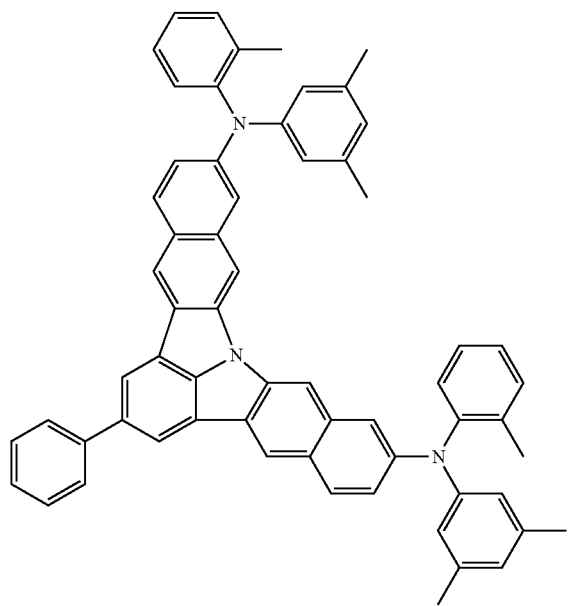
262
-continued
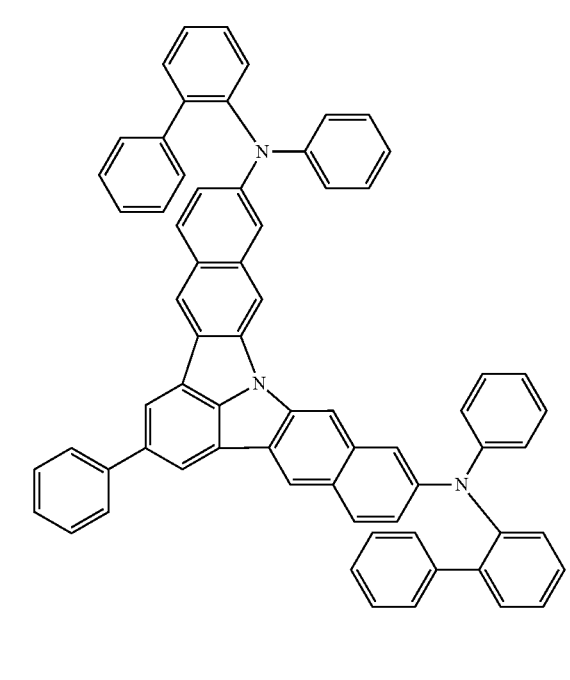
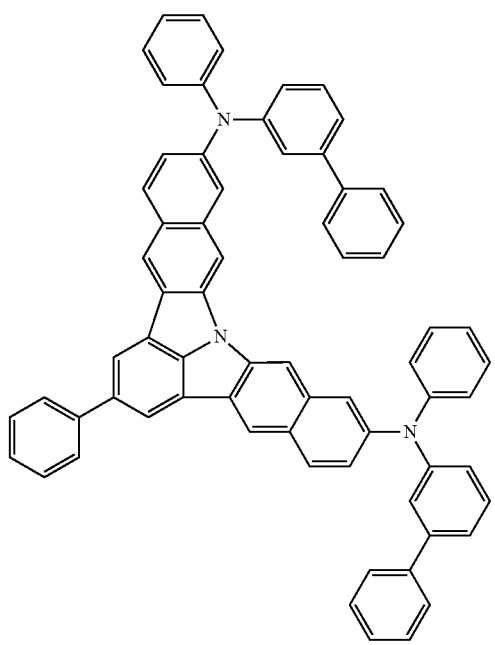

263
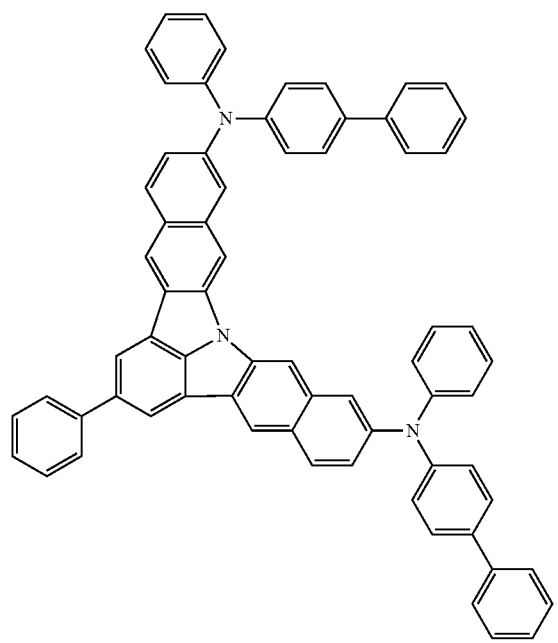
264
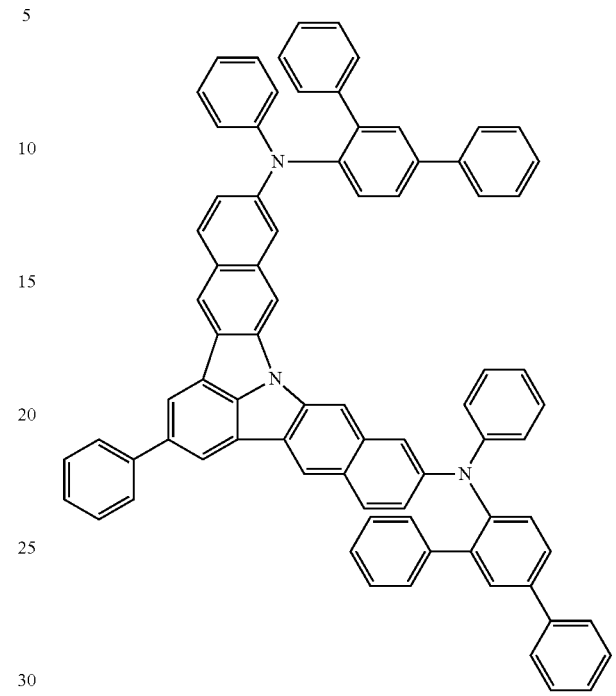
[Formula 85]
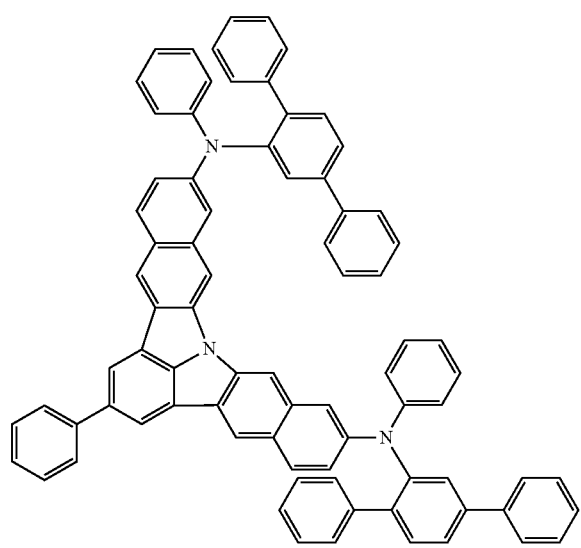
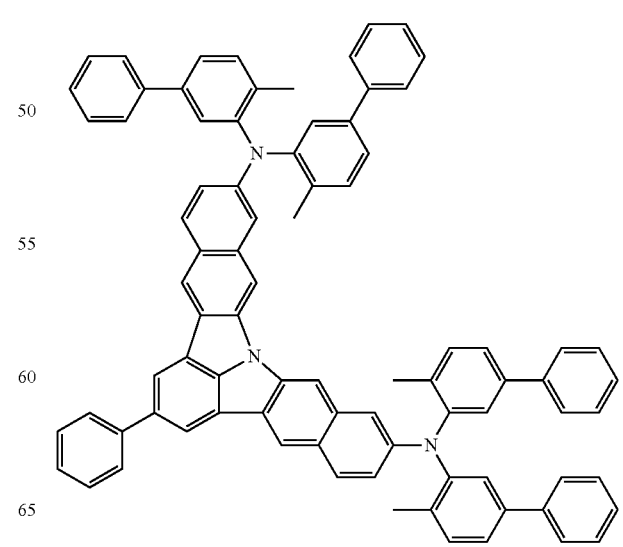

265
-continued
266
-continued
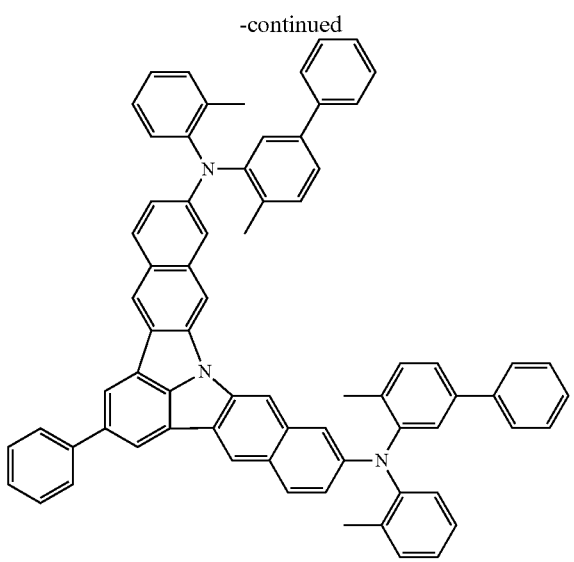
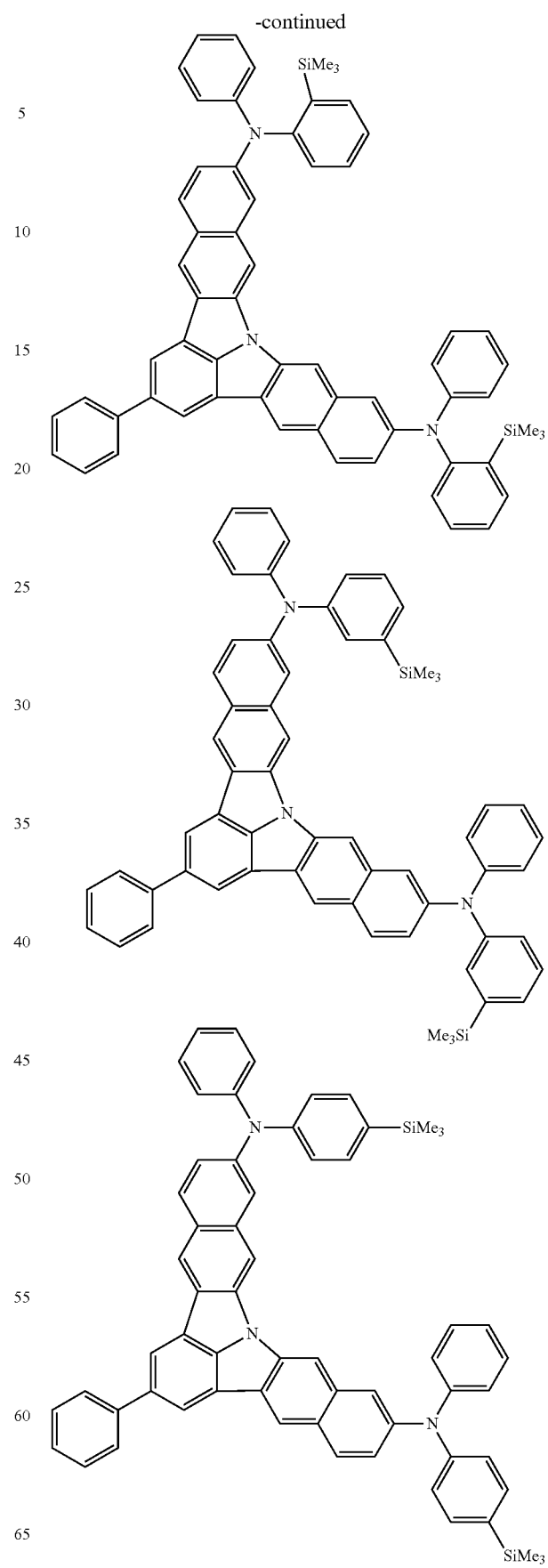

267
-continued
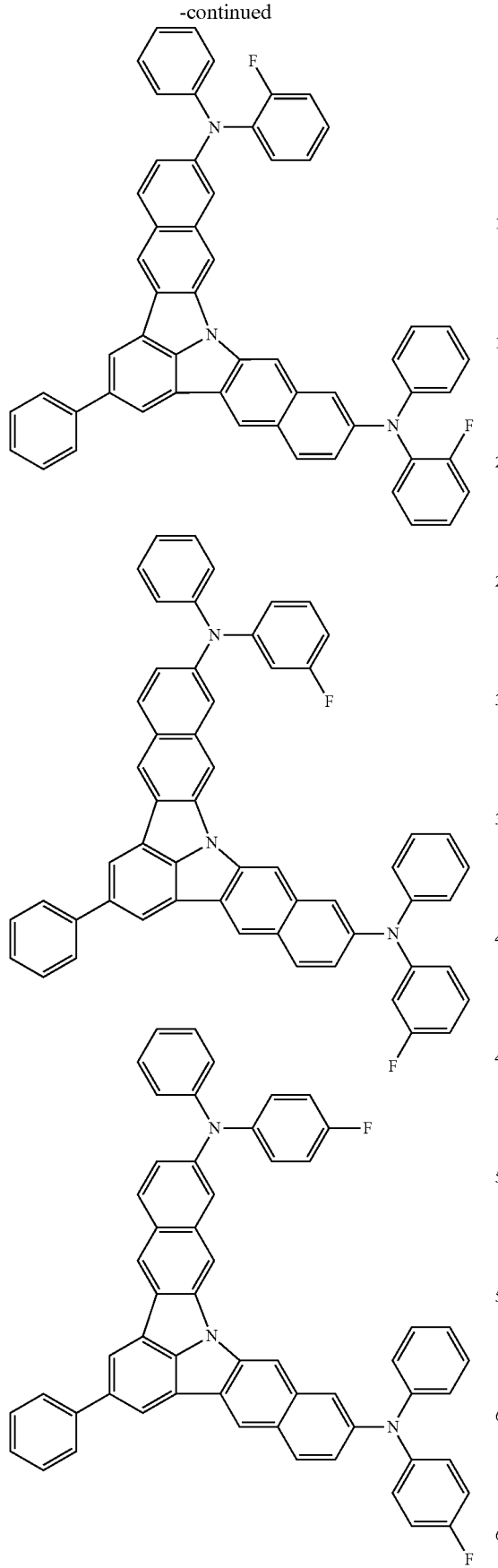
268
-continued
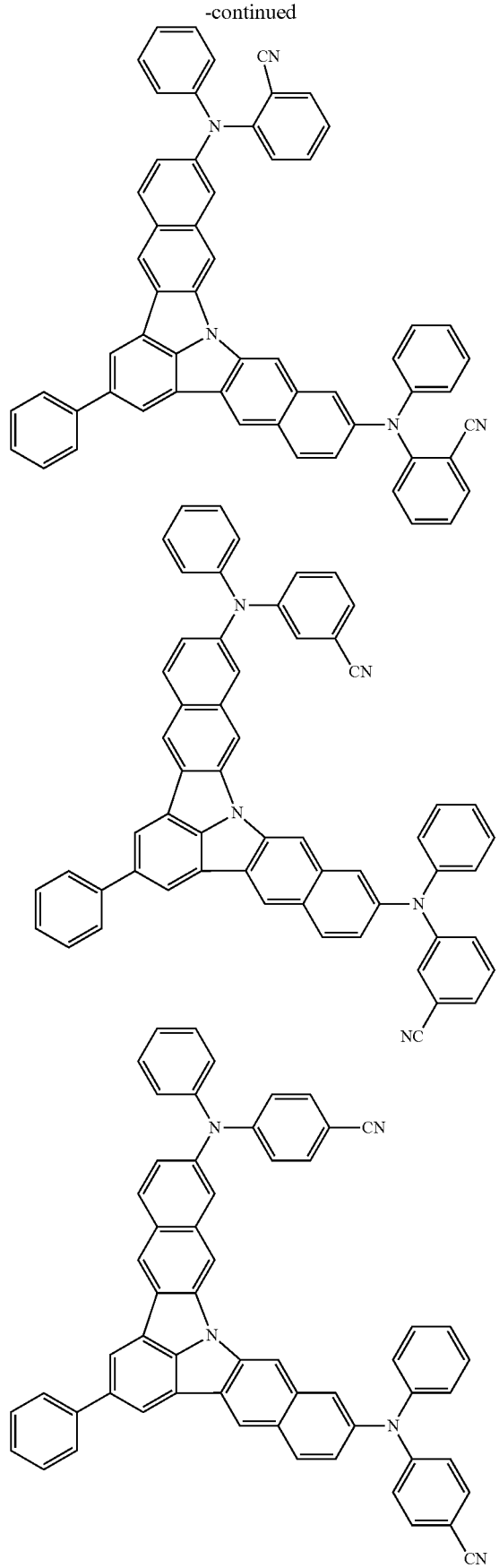

269
-continued
270
-continued
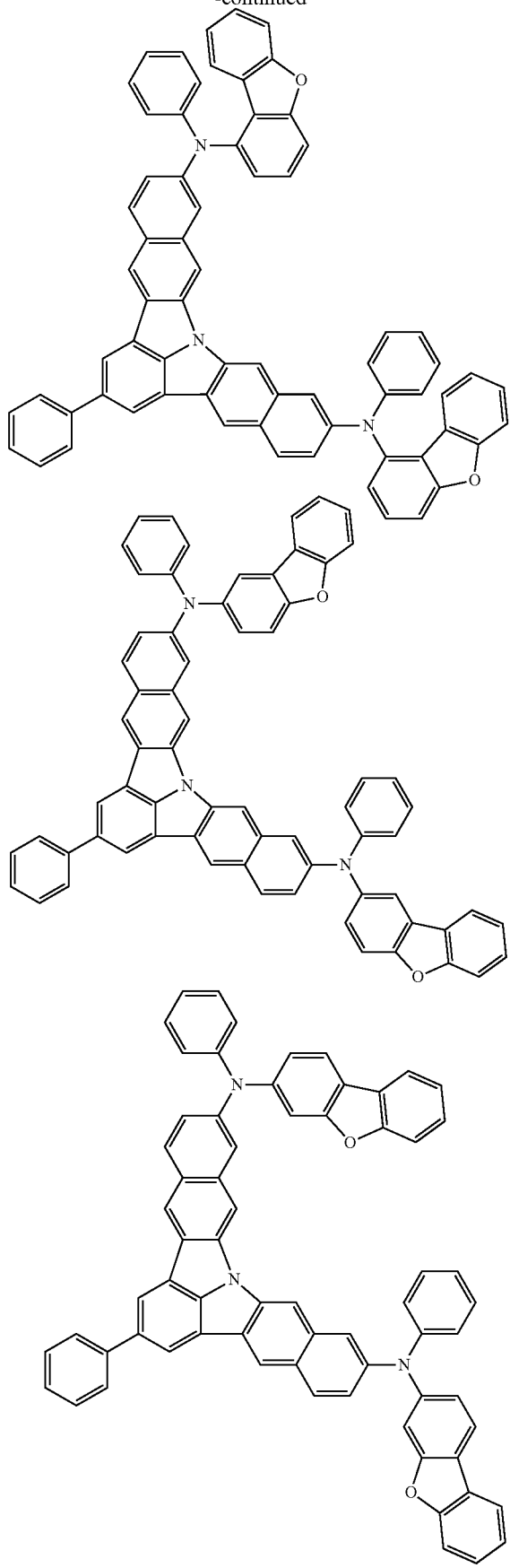
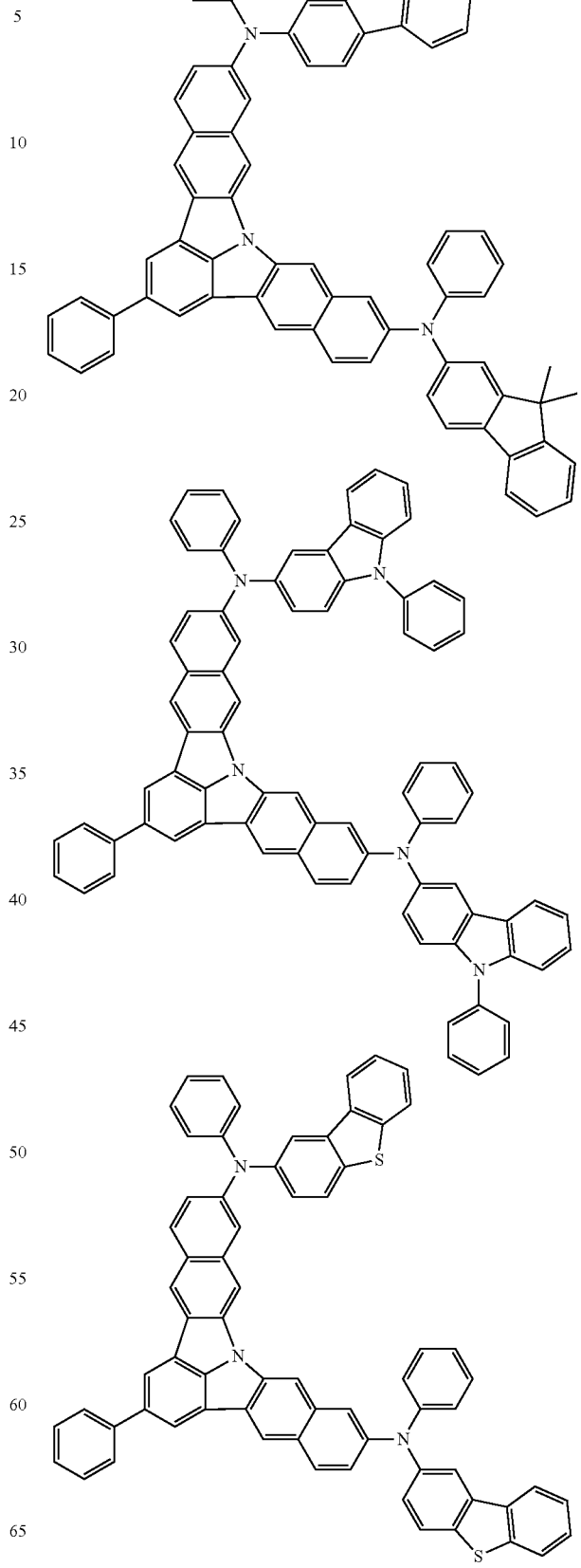

[Formula 86]
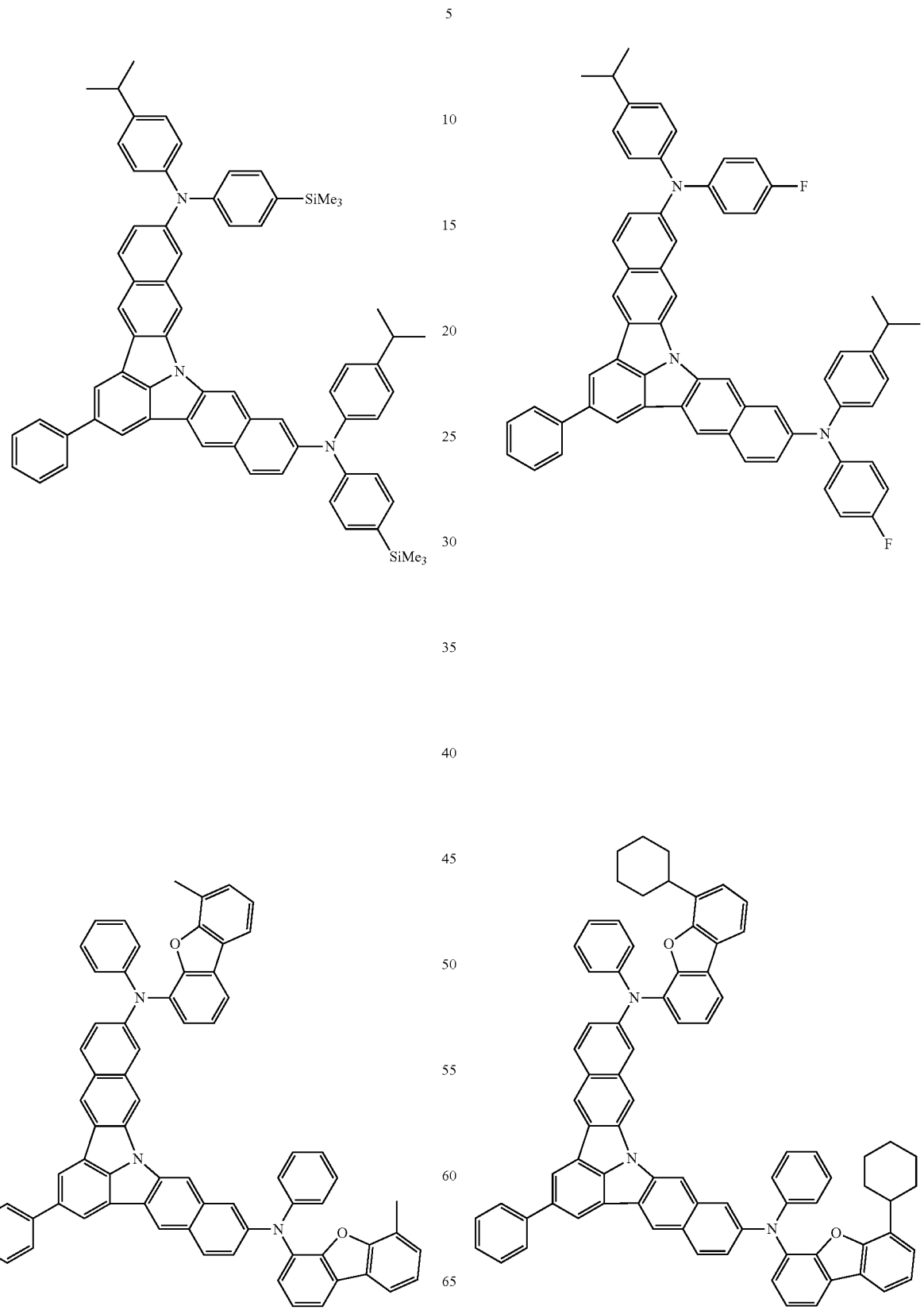

273
-continued
274
-continued
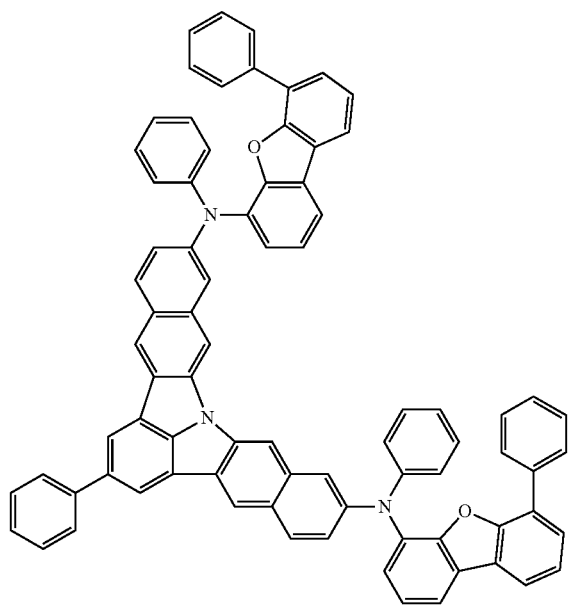
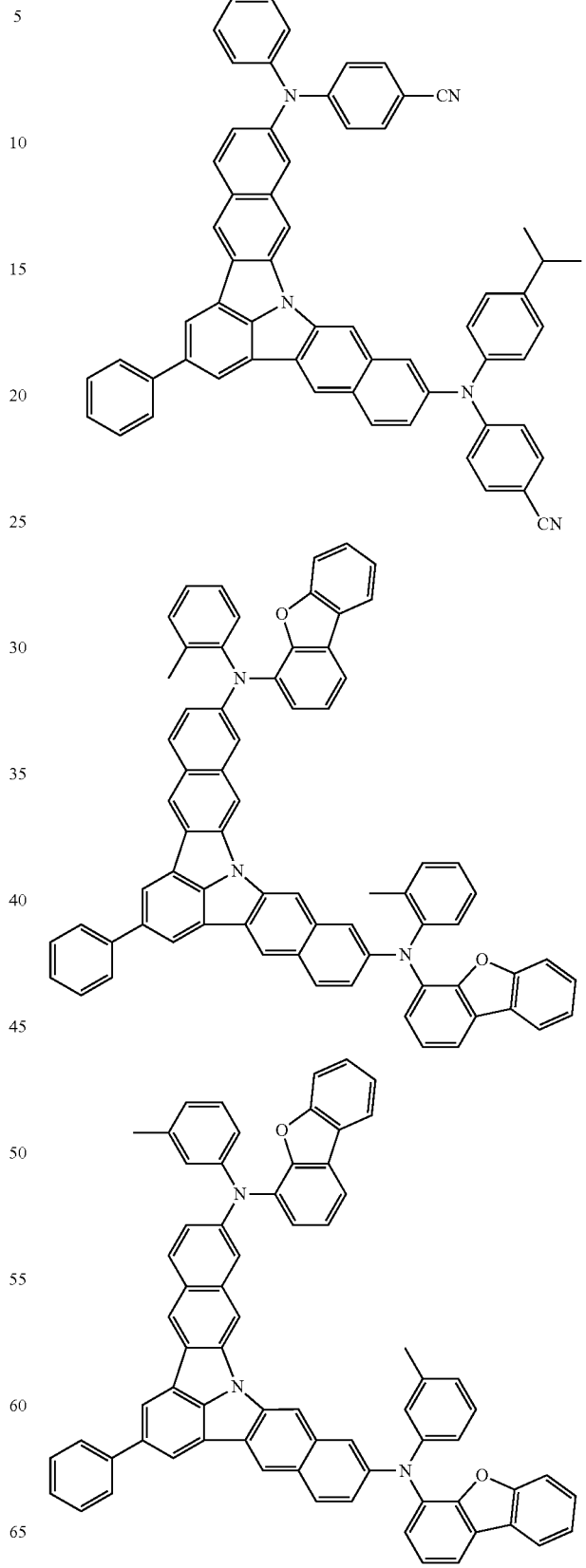

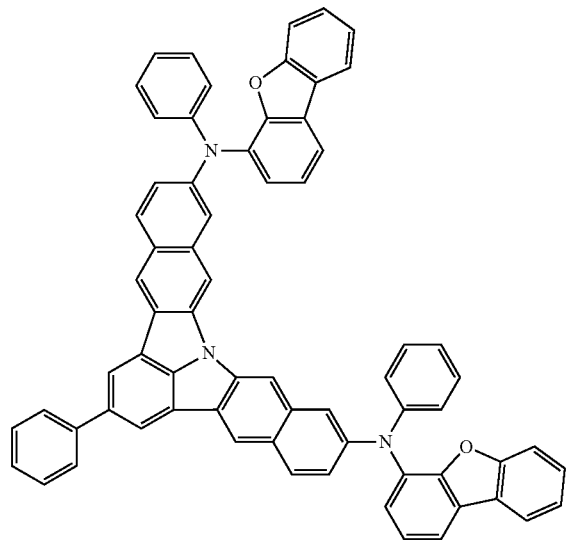
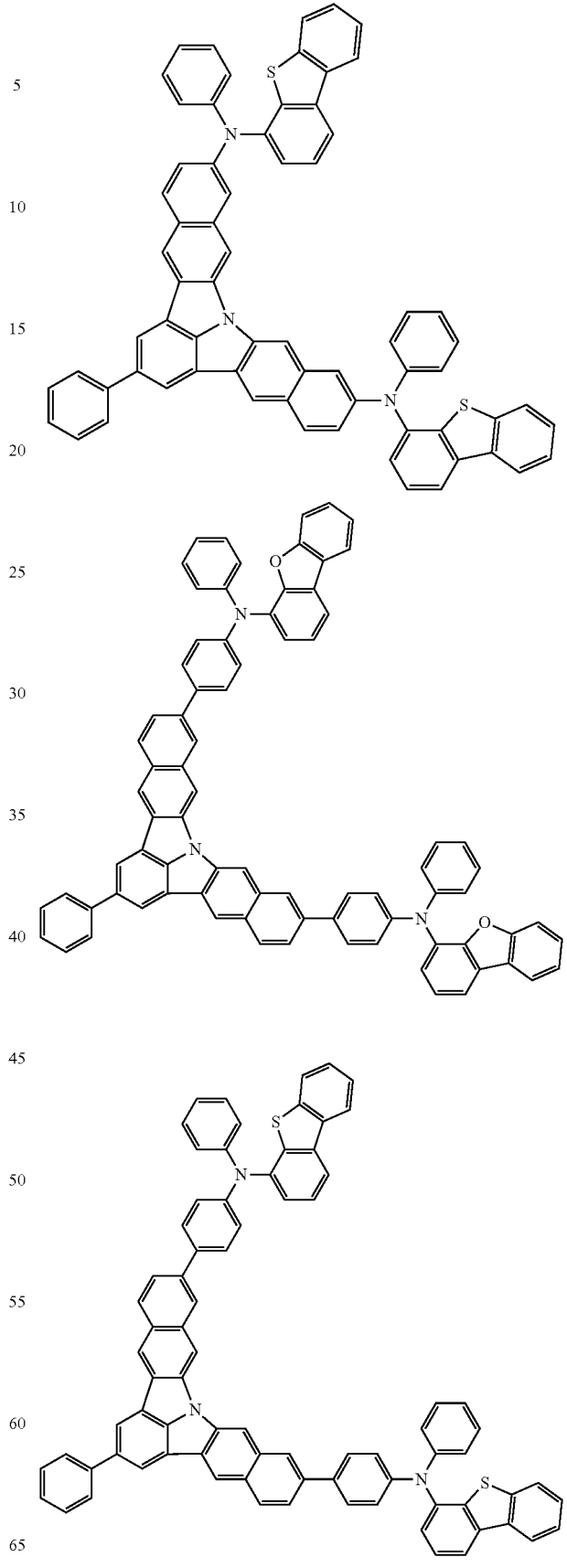

277
-continued
[Formula 87]
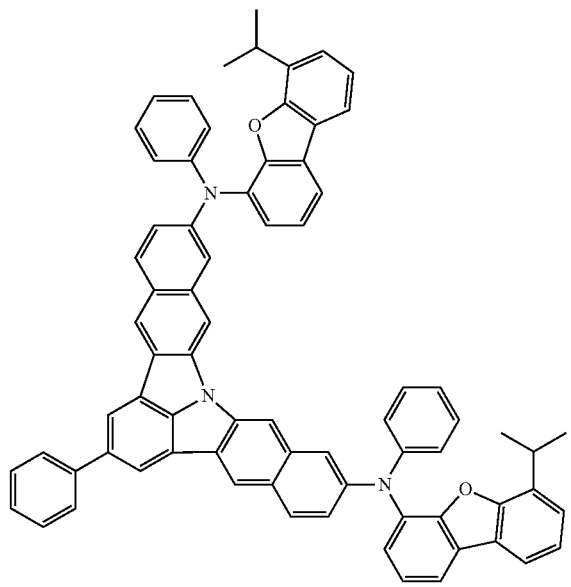
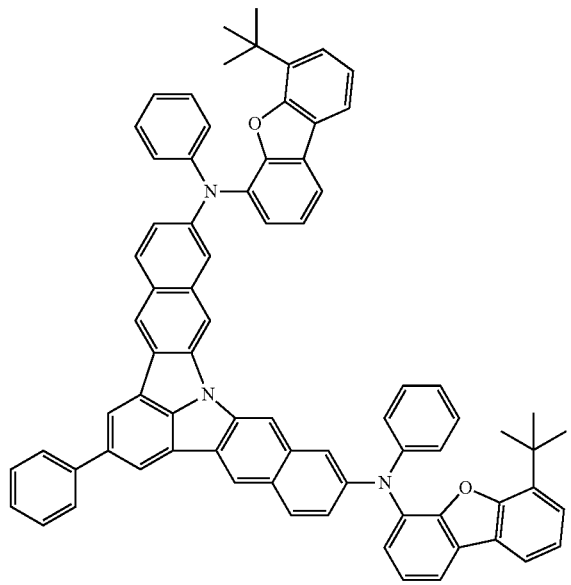
278
-continued
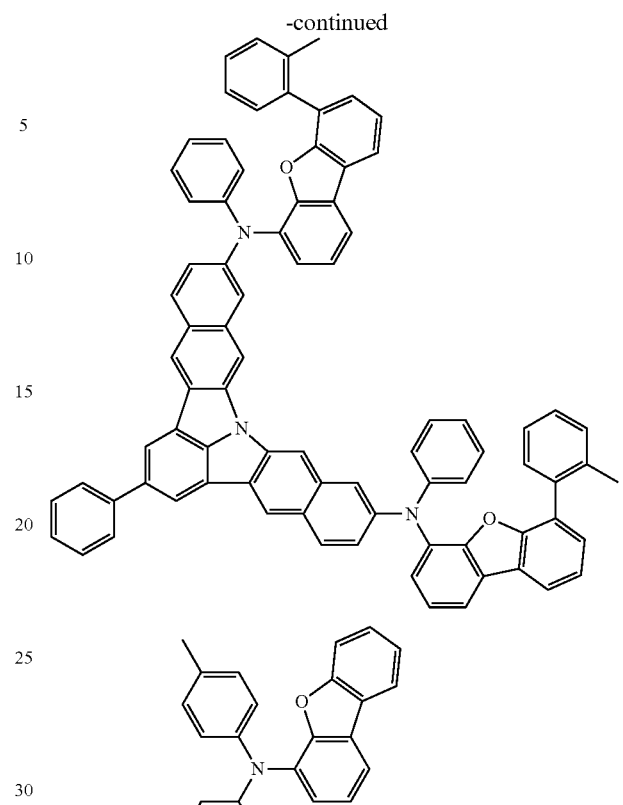
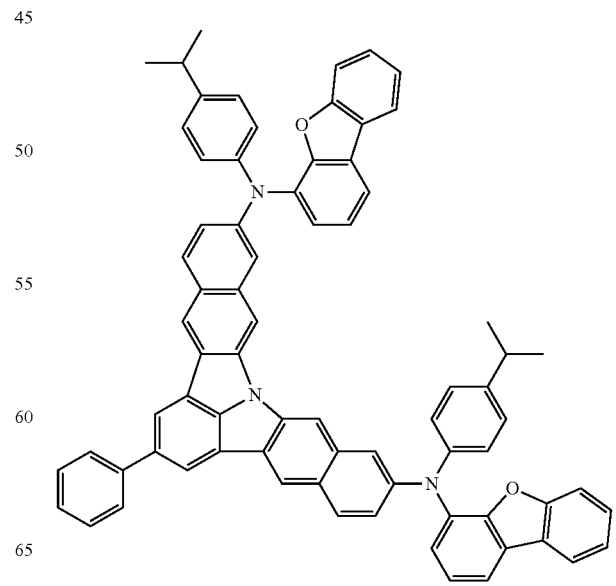

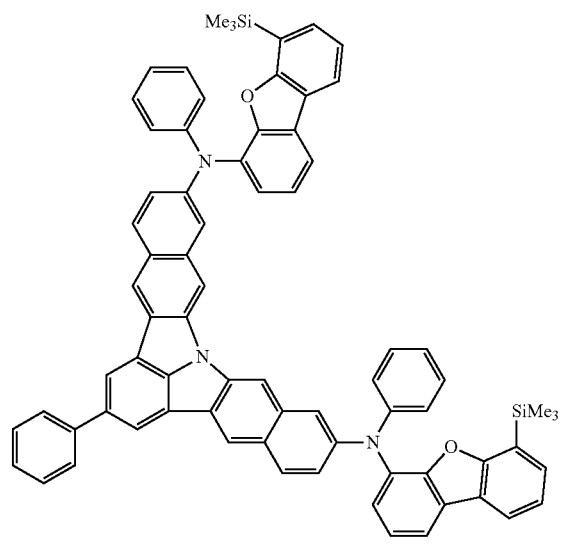
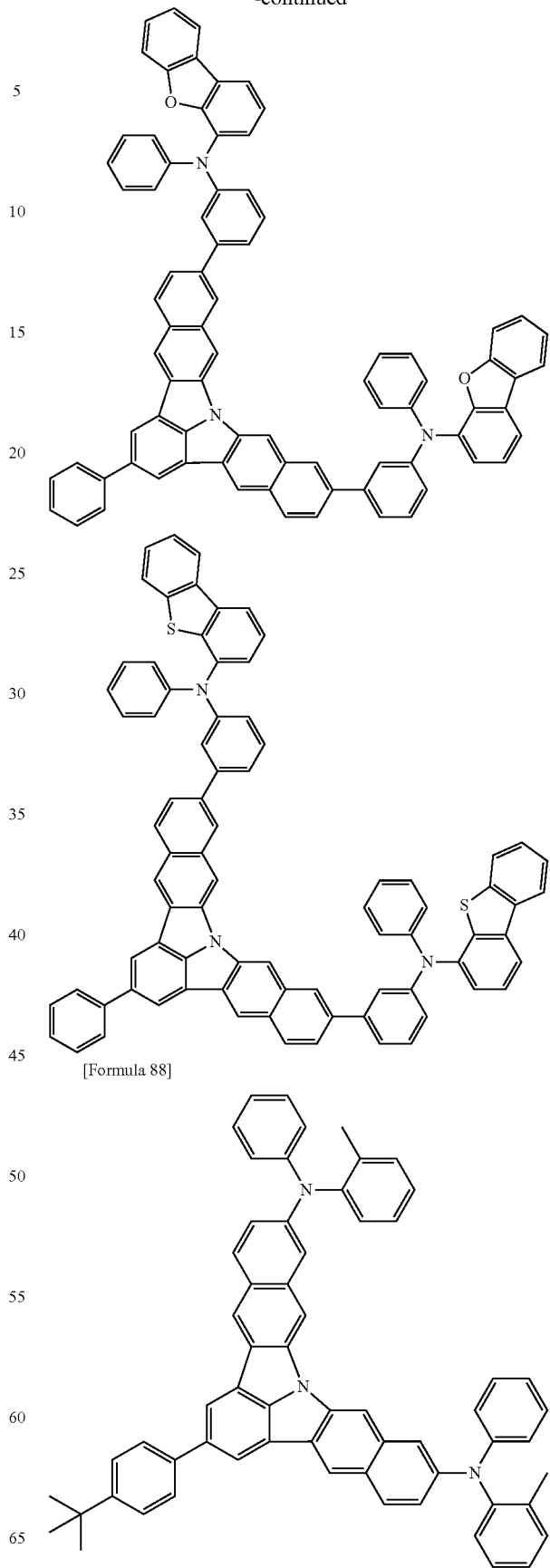

281
-continued
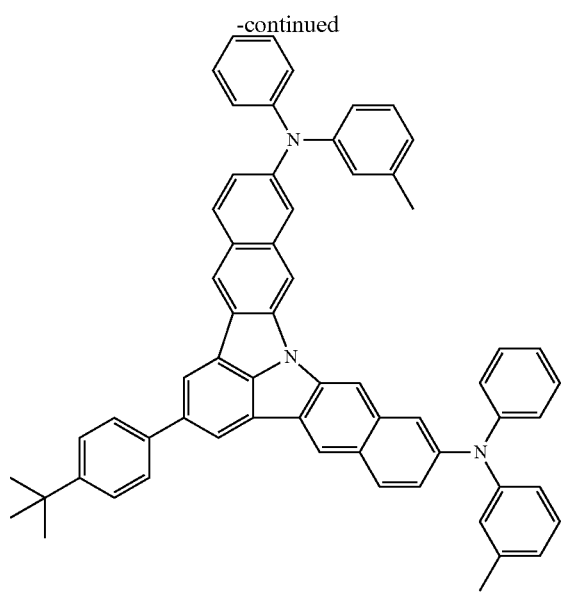
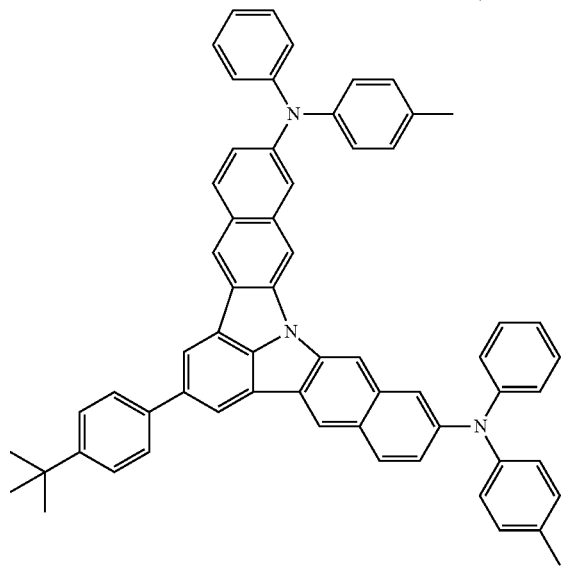
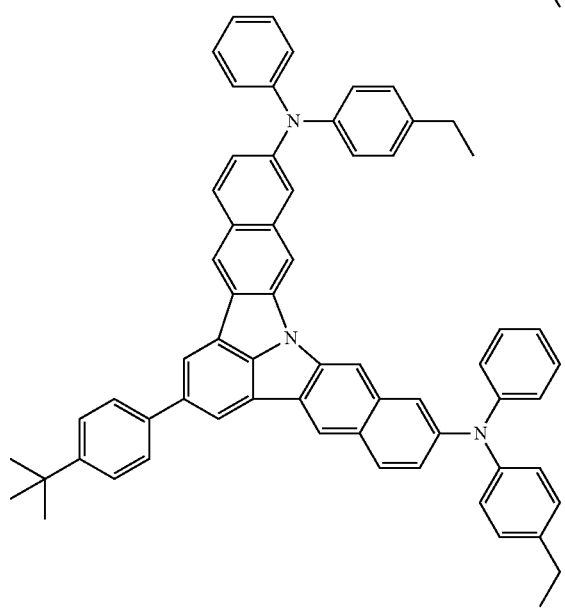
282
-continued
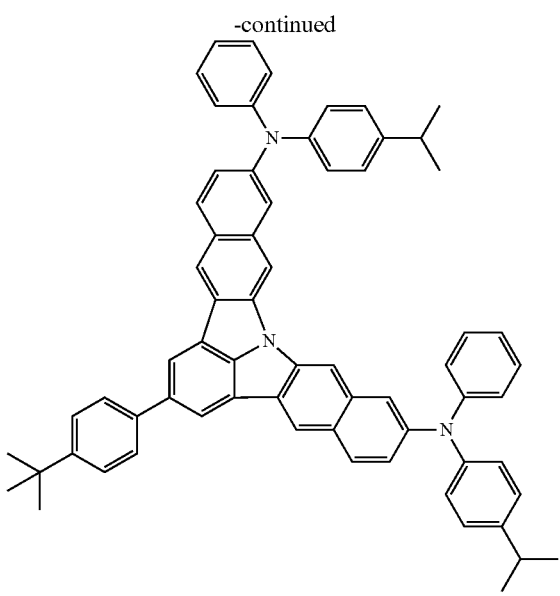
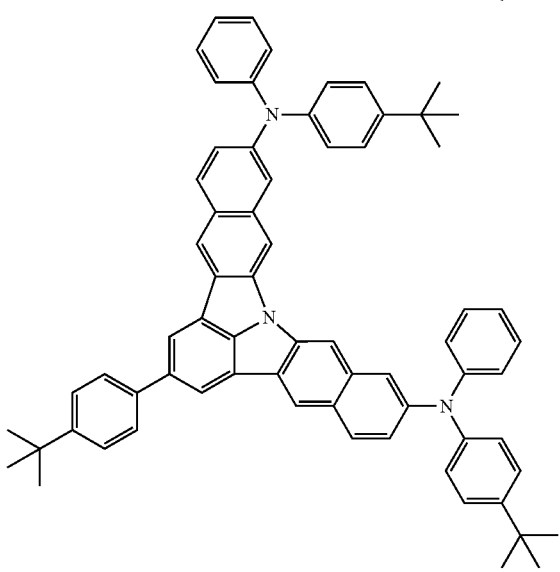
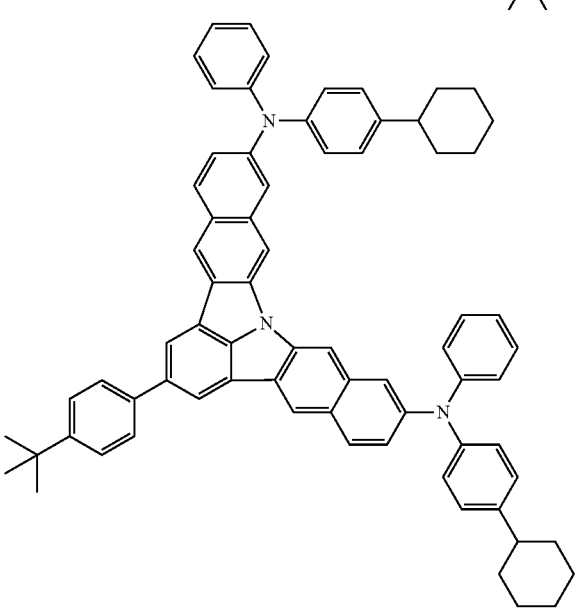

-continued

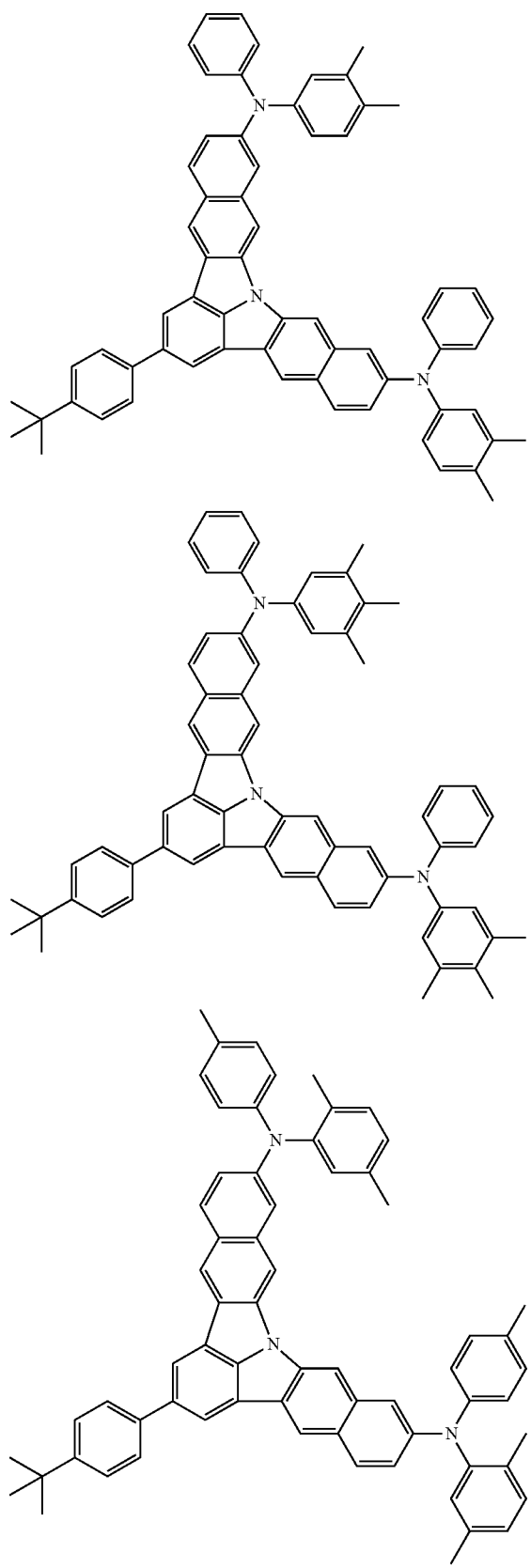
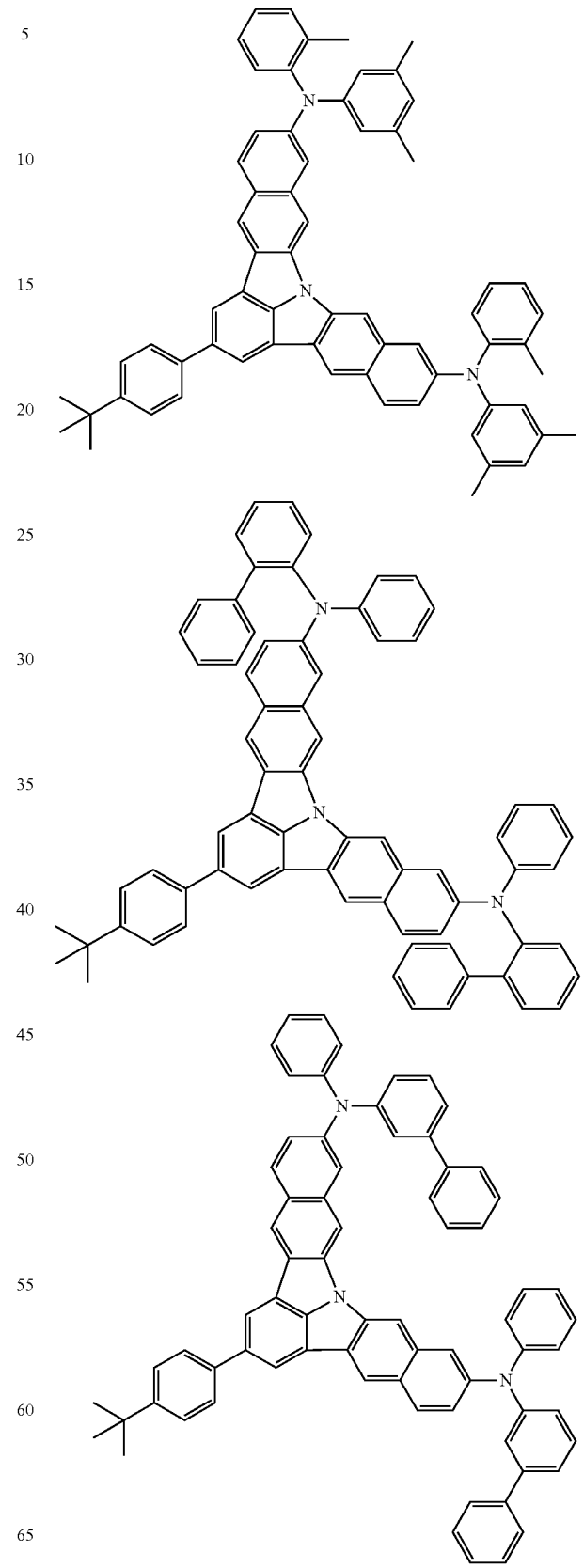

287
-continued
288
-continued
[Formula 89]
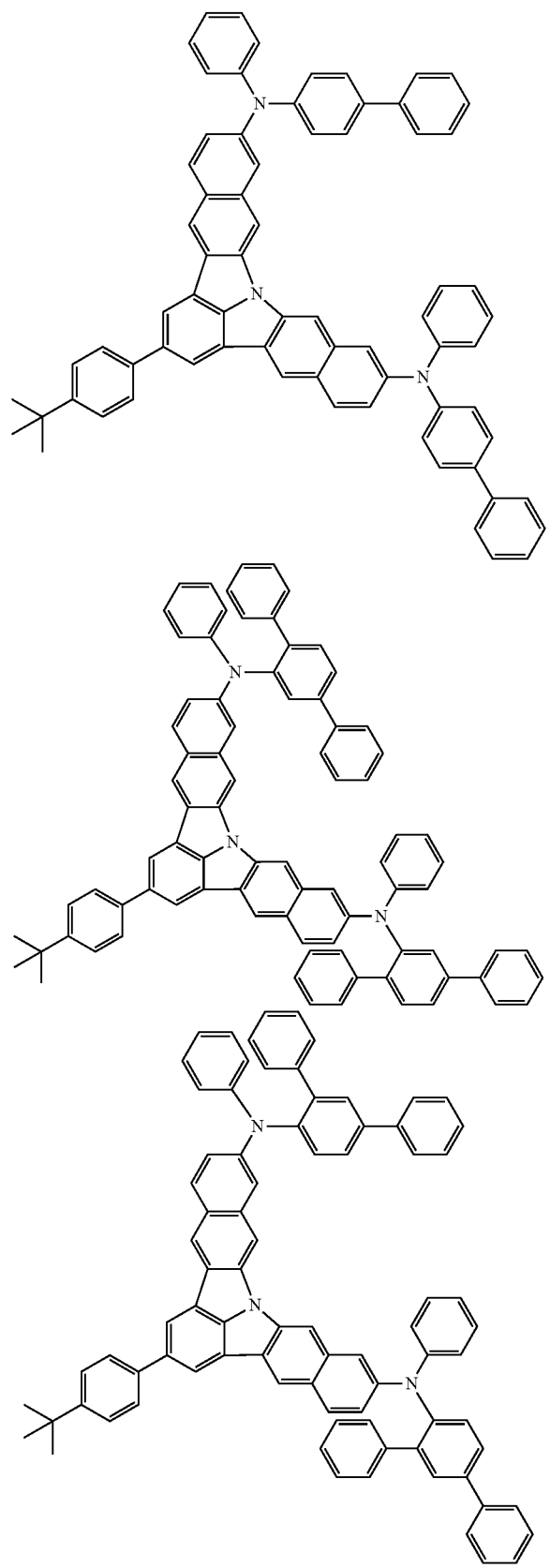
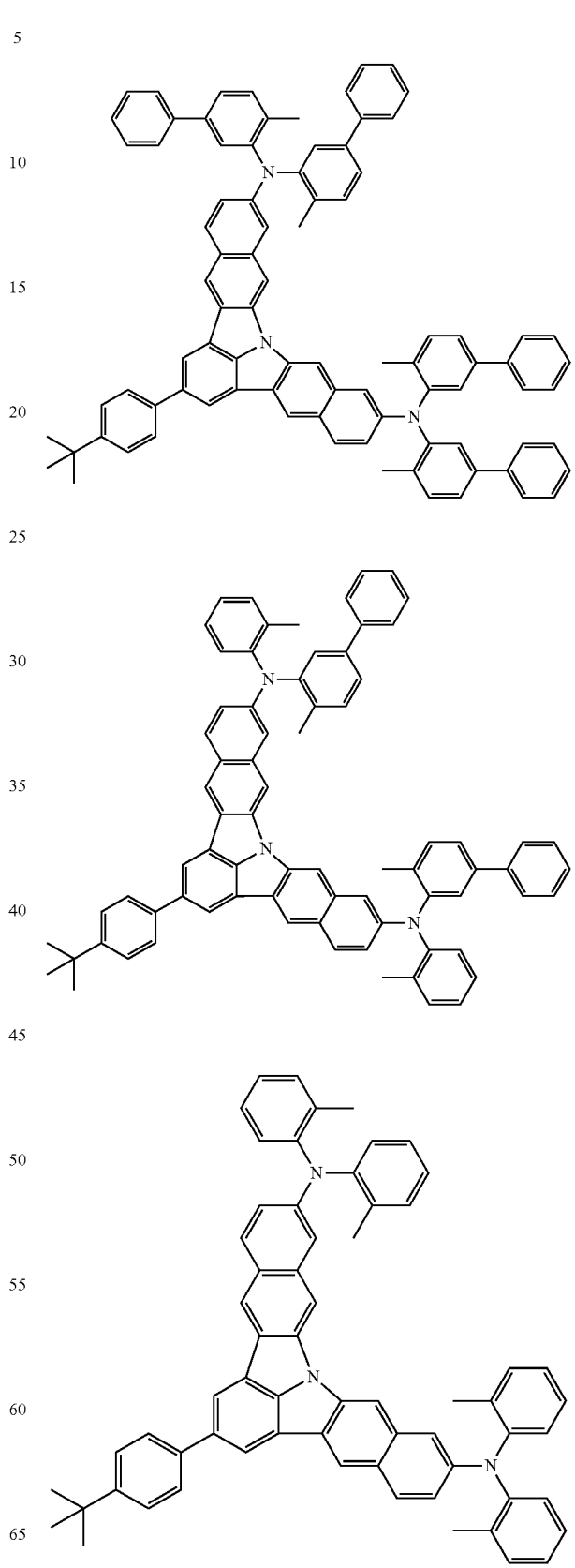

289 -continued
290 -continued
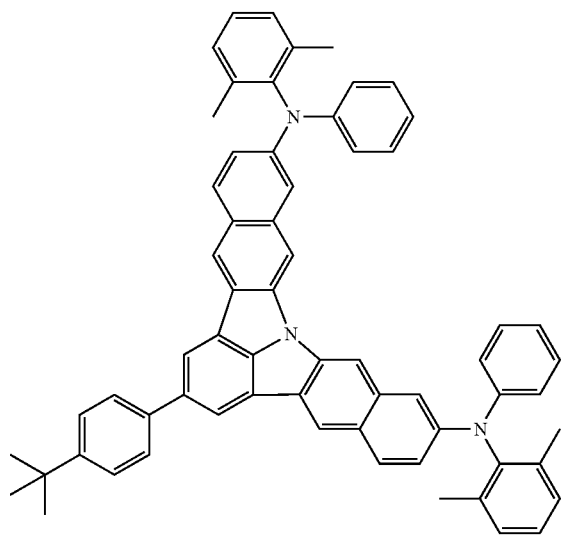
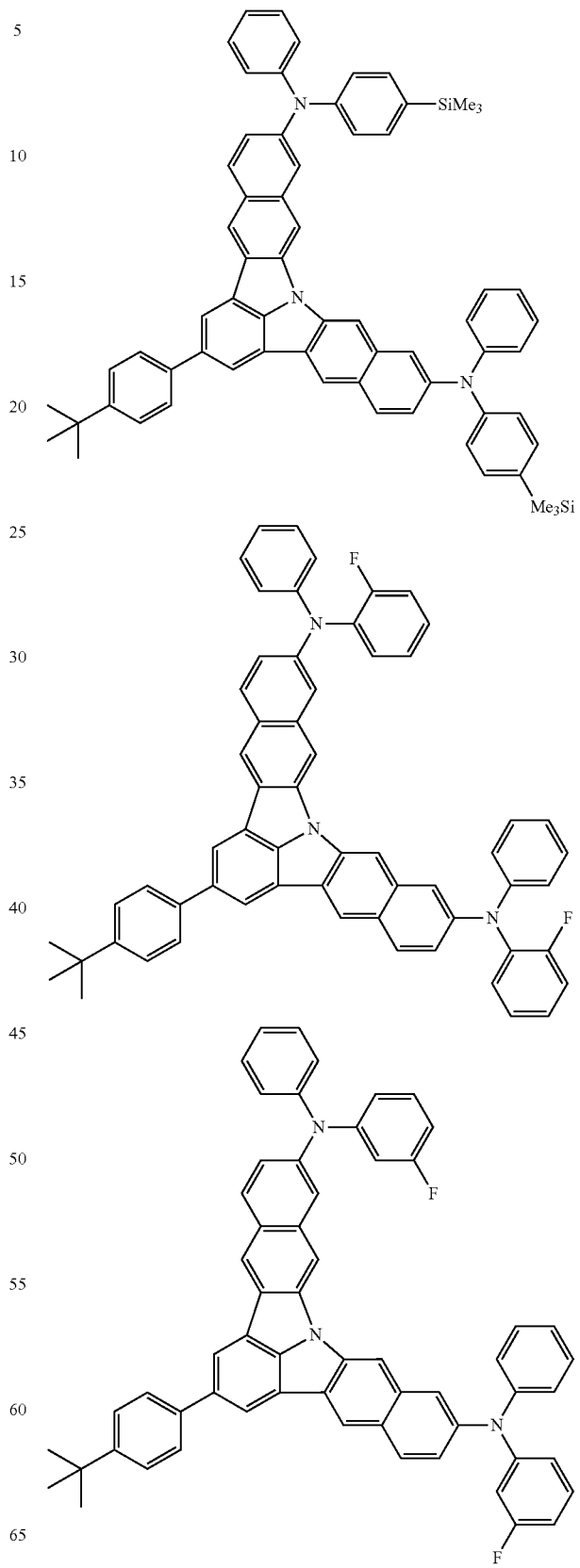

291
-continued
292
-continued
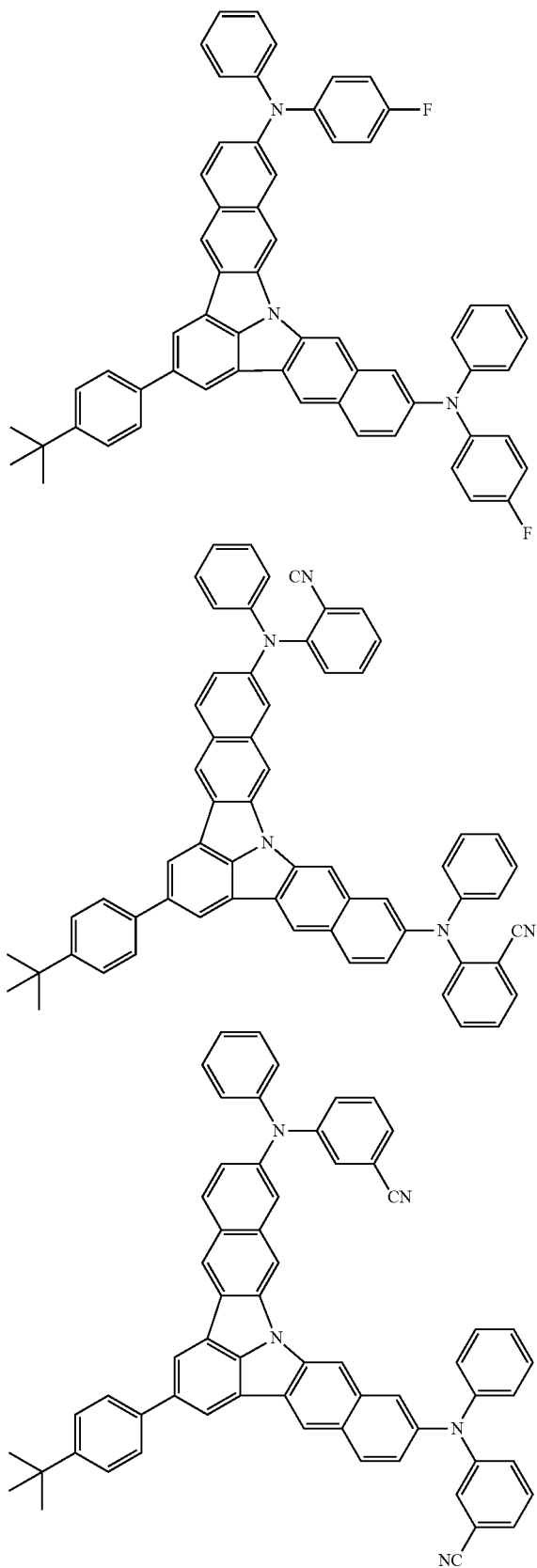
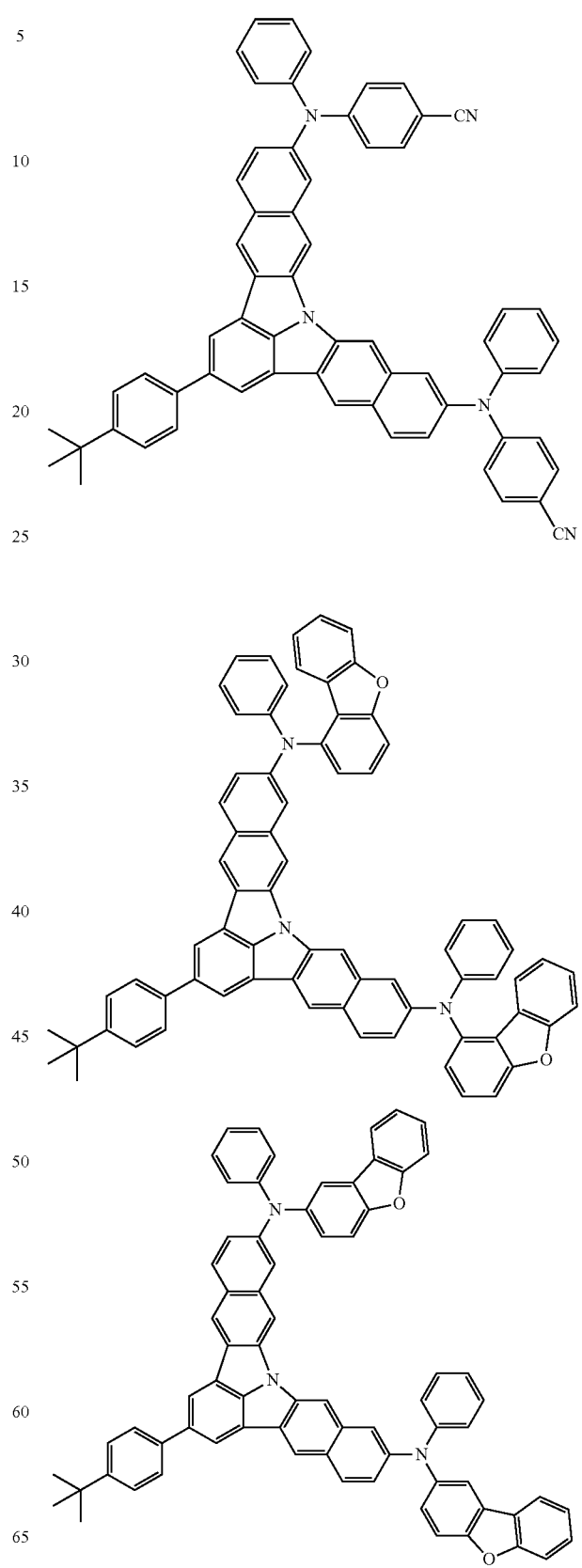

293
-continued
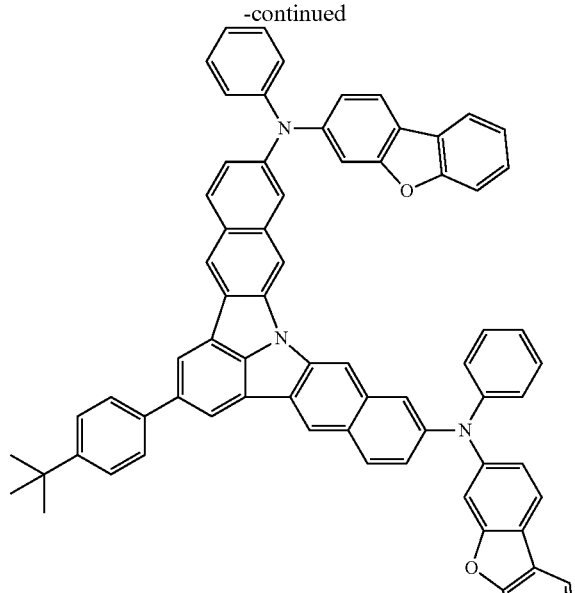
294
-continued
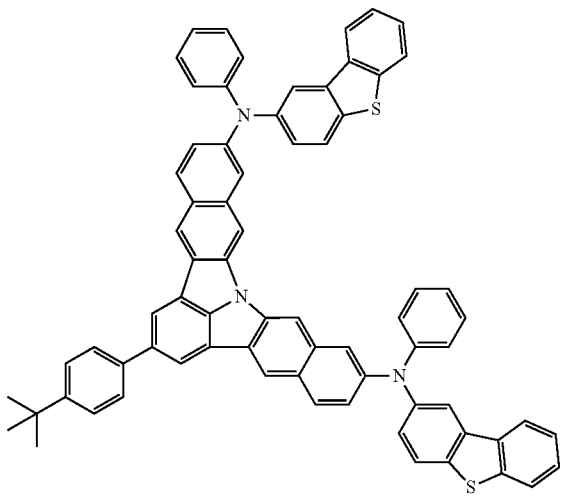
[Formula 90]
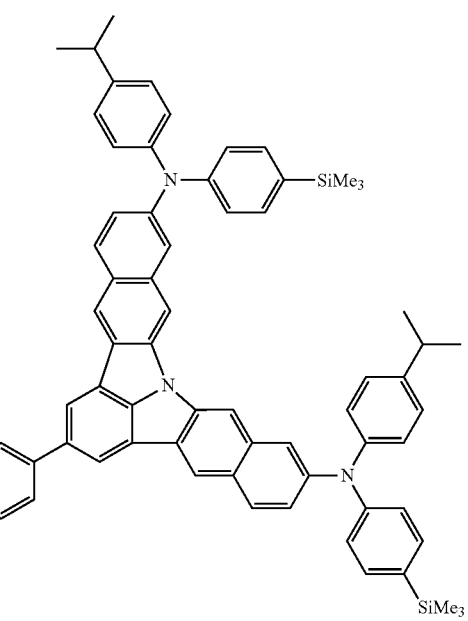
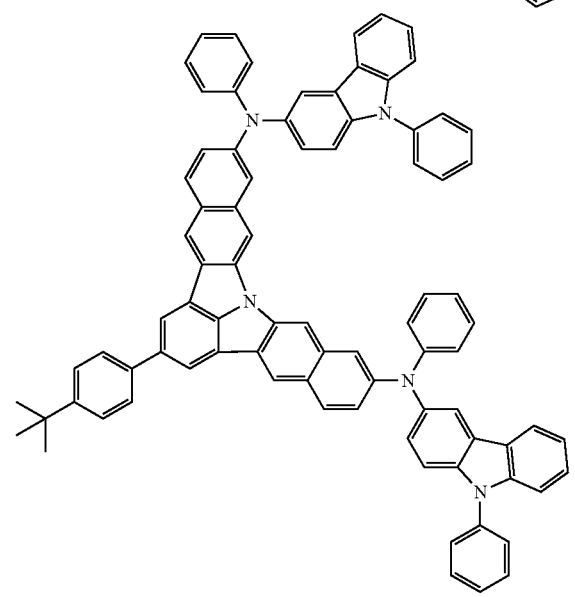
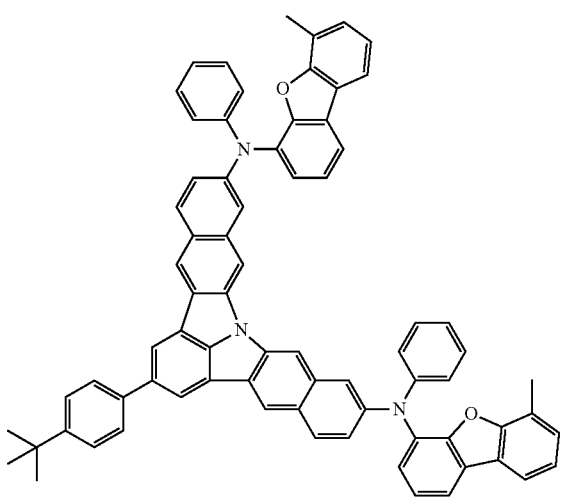

295
-continued
296
-continued
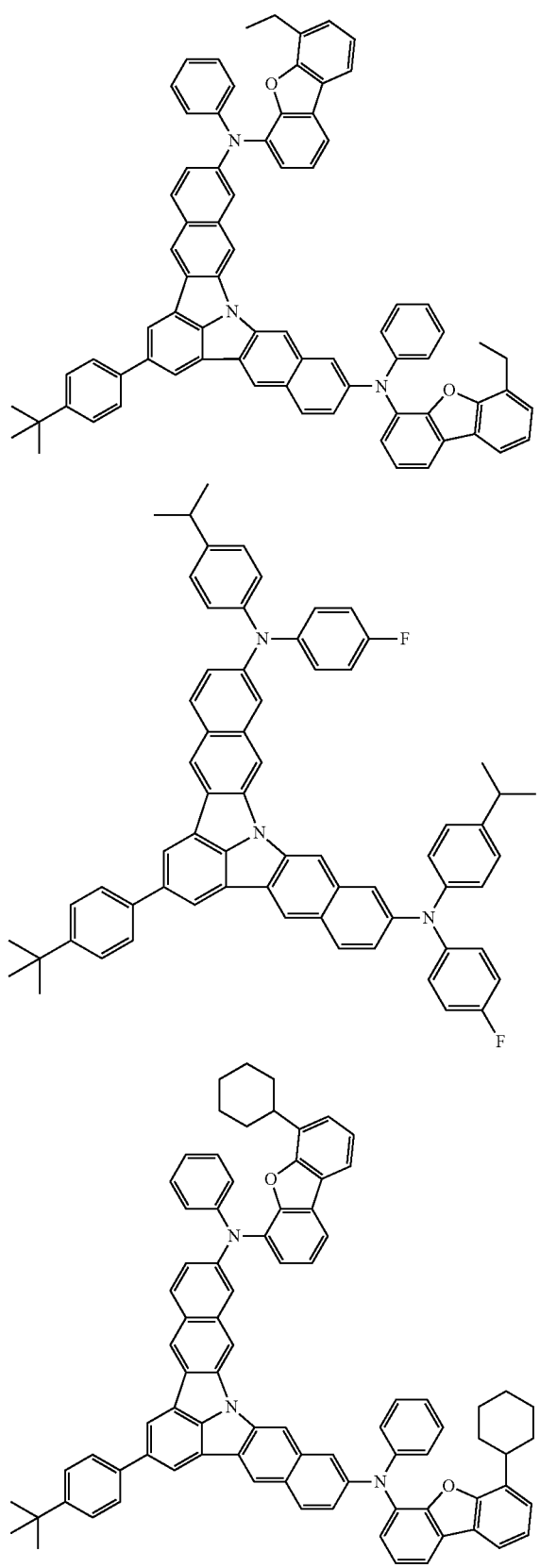
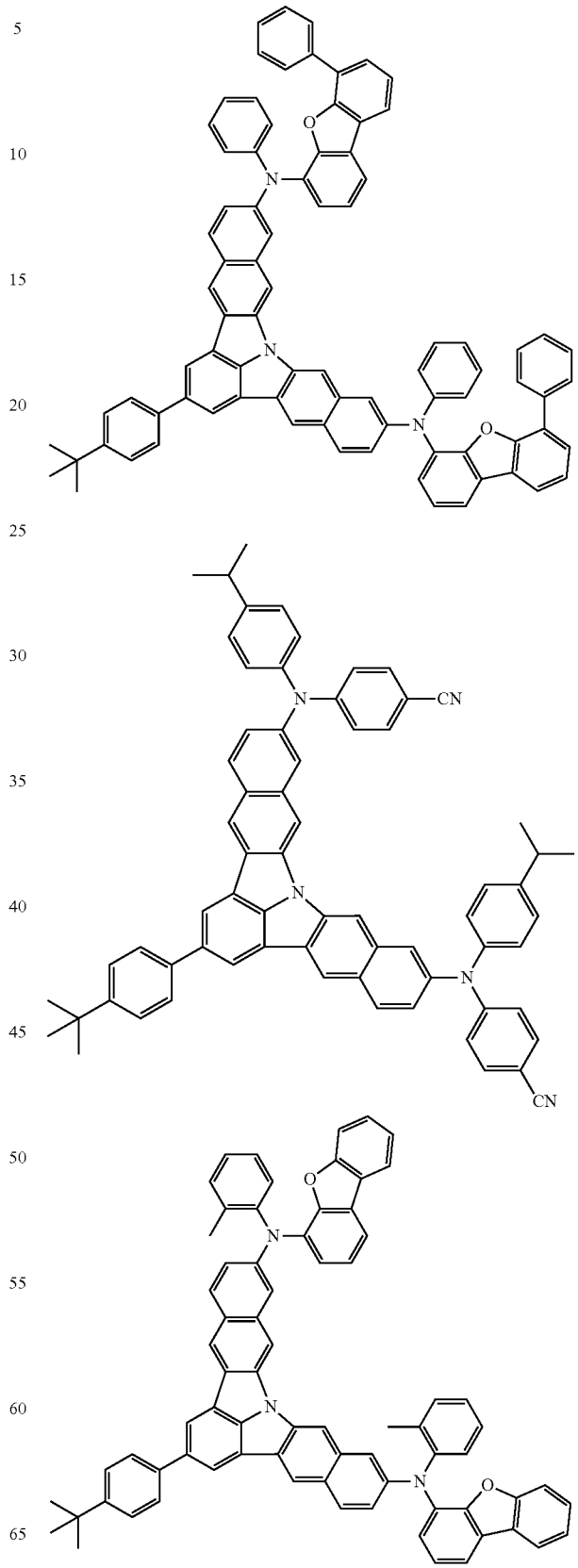

297
-continued
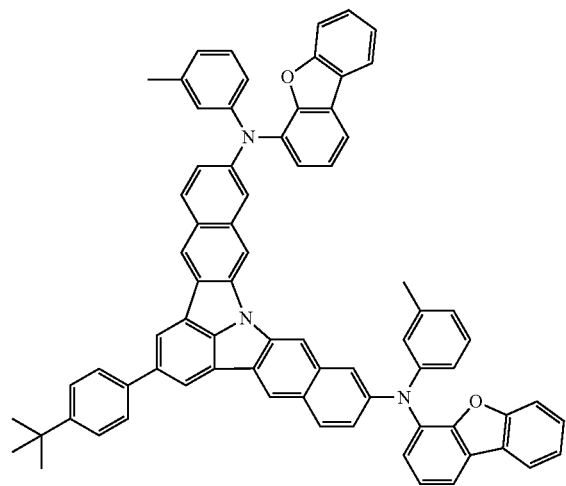
298
-continued
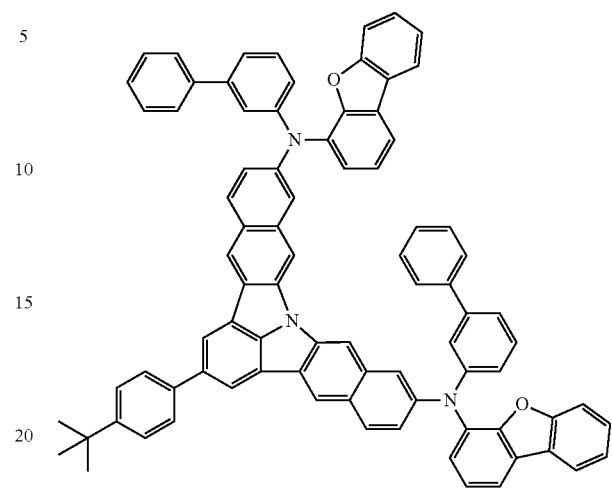
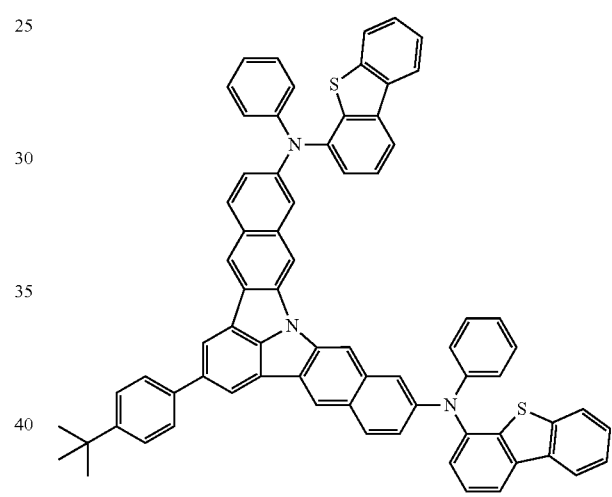
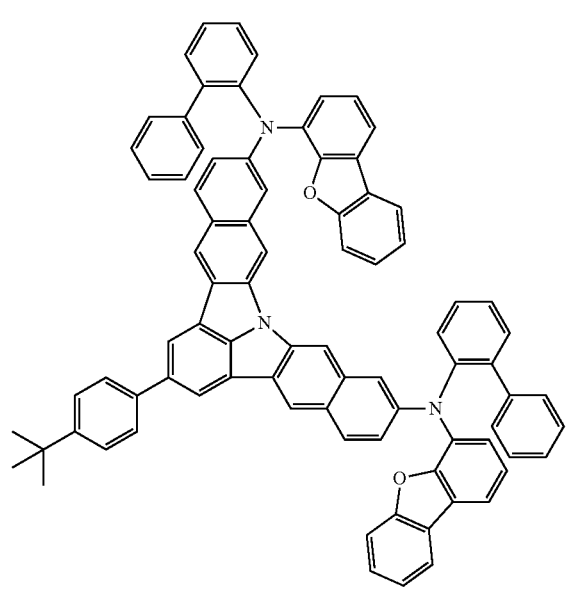
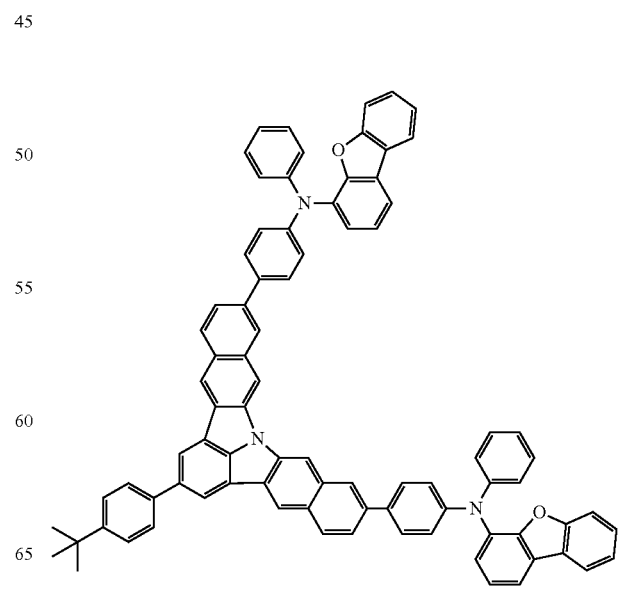

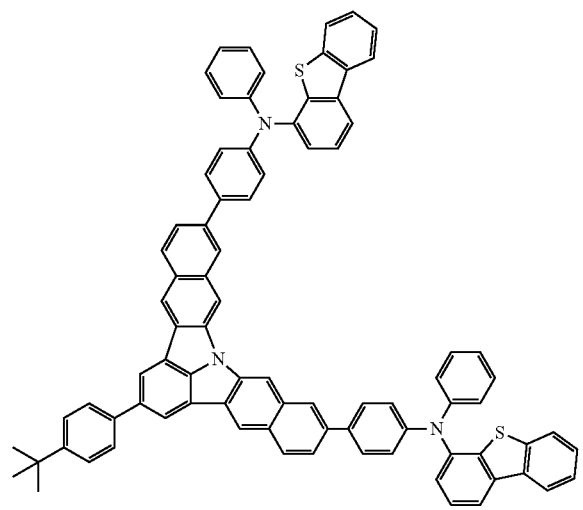
[Formula 91]
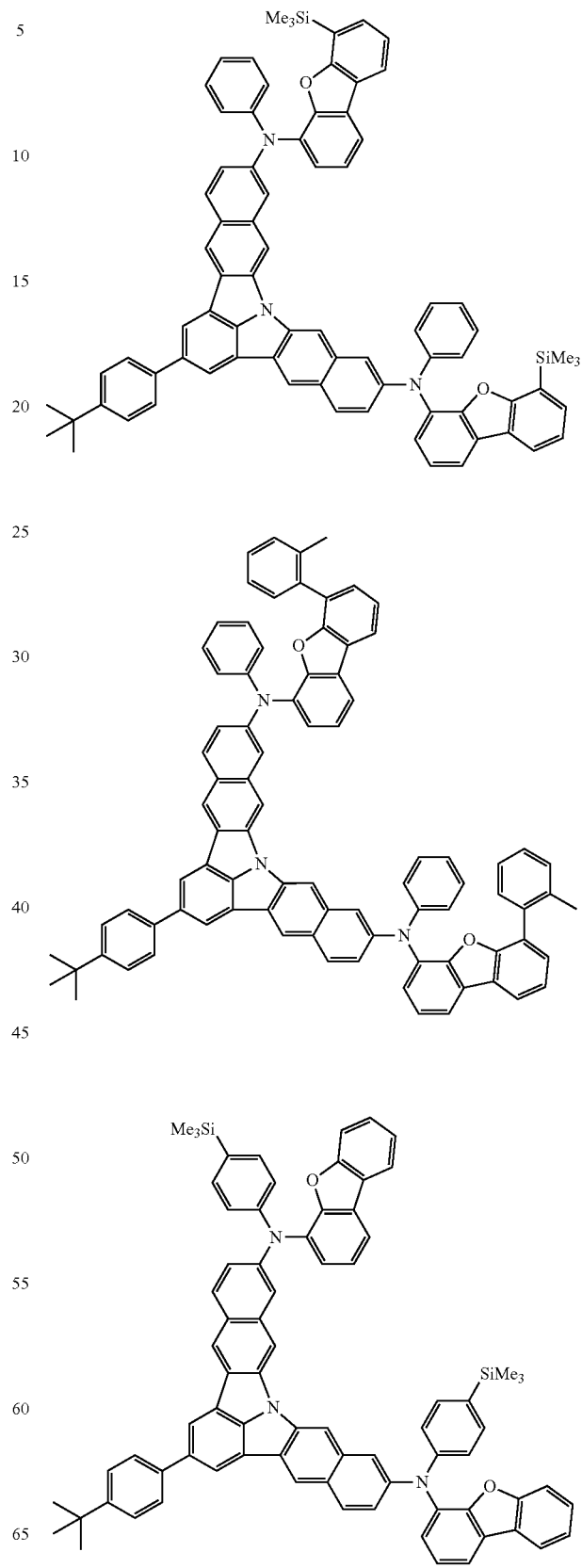

301
-continued

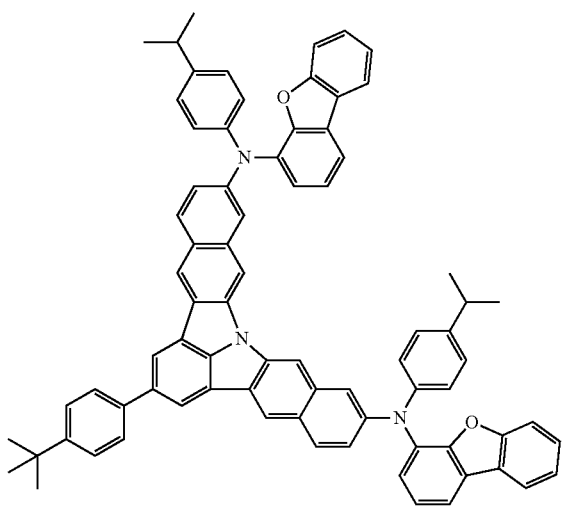

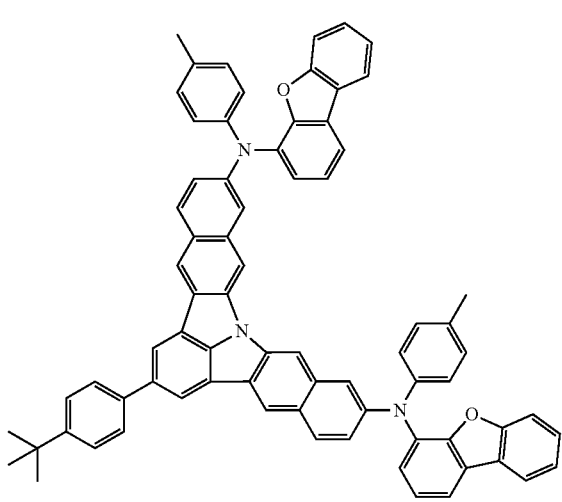

302
-continued

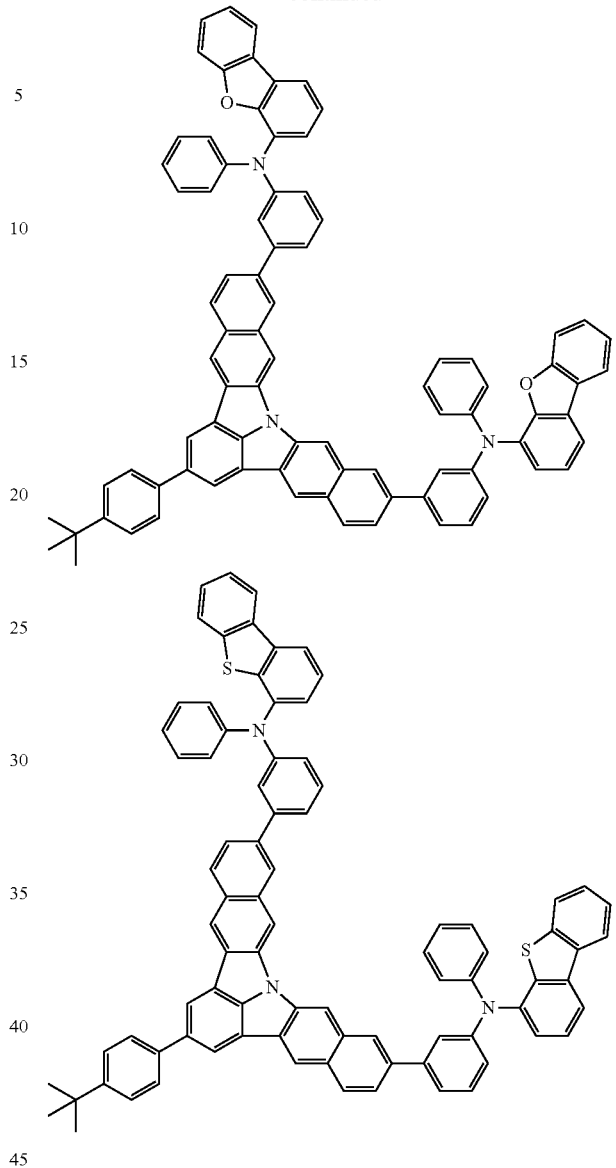

Relationship between First Compound and Second Compound in Emitting Layer

In the organic EL device 1 of the first exemplary embodiment, a singlet energy $S_1(M1)$ of the (delayed fluorescent) first compound and a singlet energy $S_1(M2)$ of the second compound preferably satisfy a relationship of a numerical formula (Numerical Formula 1) below.

$$S_1(M1) > S_1(M2) \quad \text{(Numerical Formula 1)}.$$

An energy gap $T_{77K}(M1)$ at 77 [K] of the first compound is preferably larger than an energy gap $T_{77K}(M2)$ at 77 [K] of the second compound. In other words, a relationship represented by a numerical formula below (Numerical Formula 4) is preferably satisfied.

$$T_{77K}(M1) > T_{77K}(M2) \quad \text{(Numerical Formula 4)}$$

When the organic EL device 1 in the first exemplary embodiment emits light, it is preferable that the second compound mainly emits light in the emitting layer 5.

In the organic EL device 1 of the first exemplary embodiment, the main peak wavelength of the second compound is preferably in a range from 430 nm to 480 nm, more preferably in a range from 445 nm to 480 nm.

The main peak wavelength herein means a peak wavelength of emission spectrum exhibiting a maximum luminous intensity among emission spectra measured in a toluene solution in which a target compound is dissolved at a concentration ranging from $10^{-6}$ mol/L to $10^{-5}$ mol/L.

The second compound preferably emits a blue fluorescence.

The second compound is preferably a material with a high emission quantum efficiency.

Relationship Between Triplet Energy and Energy Gap at 77[K]

Description will be made on a relationship between a triplet energy and an energy gap at 77[K]. In the exemplary embodiment, the energy gap at 77[K] is different from a typical triplet energy in some aspects.

The triplet energy is measured as follows. Firstly, a solution in which a compound (measurement target) is dissolved in an appropriate solvent is encapsulated in a quartz glass tube to prepare a sample. A phosphorescent spectrum (ordinate axis: phosphorescent luminous intensity, abscissa axis: wavelength) of each of the samples was measured at a low temperature (77[K]). A tangent is drawn to the rise of the phosphorescent spectrum on the short-wavelength side. Triplet energy is calculated according to a predetermined conversion equation based on a wavelength value at an intersection of the tangent and the abscissa axis.

The delayed fluorescent compound usable in the first exemplary embodiment is preferably a compound having a small ΔST. When ΔST is small, intersystem crossing and inverse intersystem crossing are likely to occur even at a low temperature (77[K]), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the first exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. The compound to be measured is dissolved in EPA (diethylether:isopentane:ethanol=5:5:2 in volume ratio) at a concentration of 10 μmol/L, and the resulting solution is set in a quartz cell to provide a measurement sample. A phosphorescent spectrum (ordinate axis: phosphorescent luminous intensity, abscissa axis: wavelength) of the sample is measured at a low temperature (77[K]). A tangent is drawn to the rise of the phosphorescent spectrum on the short-wavelength side. An energy amount is calculated as the energy gap $T_{77K}$ at 77[K] according to a conversion equation (F1) below based on a wavelength value $\lambda_{edge}$ (nm) at an intersection of the tangent and the abscissa axis.

$$T_{77K} [eV]=1239.85/\lambda_{edge} \quad \text{Conversion equation (F1):}$$

The above-described method for measuring the energy gap $T_{77K}$ will be sometimes referred to as a solution method.

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis was increased). A tangent drawn at a point of the maximum inclination (i.e., a tangent at an inflection point) is defined as the tangent to the rise of the phosphorescence spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the phosphorescence spectrum on the short-wavelength side.

For phosphorescence measurement, a spectrophotofluorometer body F-4500 (manufactured by Hitachi High-Technologies Corporation) is usable. The measurement machine is not limited to the above-described machine. A combination of a cooling unit, a low temperature container, an excitation light source and a light-receiving unit may be used for measurement.

In the organic EL device according to the first exemplary embodiment, a difference ΔST(M1) between the singlet energy $S_1$(M1) of the first compound and the energy gap $T_{77K}$(M1) at 77[K] of the first compound preferably satisfies a relationship of a numerical formula (Numerical Formula 10) below, more preferably a relationship of a numerical formula (Numerical Formula 10A) below, further preferably a relationship of a numerical formula (Numerical Formula 10B) below, furthermore preferably a relationship of a numerical formula (Numerical Formula 10C) below.

$$\Delta ST(M1)=S_1(M1)-T_{77K}(M1)<0.3 \text{ [eV]} \quad \text{(Numerical Formula 10)}$$

$$\Delta ST(M1)=S_1(M1)-T_{77K}(M1)<0.2 \text{ [eV]} \quad \text{(Numerical Formula 10A)}$$

$$\Delta ST(M1)=S_1(M1)-T_{77K}(M1)<0.1 \text{ [eV]} \quad \text{(Numerical Formula 10B)}$$

$$\Delta ST(M1)=S_1(M1)-T_{77K}(M1)\leq 0.03 \text{ [eV]} \quad \text{(Numerical Formula 10C)}$$

Singlet Energy $S_1$

A method of measuring a singlet energy $S_1$ with use of a solution (occasionally referred to as a solution method) is exemplified by a method below.

10 μmol/L of a toluene solution of the measurement target compound is prepared and put in a quartz cell to prepare a sample. An absorption spectrum (ordinate axis: luminous intensity, abscissa axis: wavelength) of the sample is measured at a normal temperature (300K). A tangent is drawn to the fall of the absorption spectrum on the long-wavelength side, and a wavelength value λedge (nm) at an intersection of the tangent and the abscissa axis is assigned to a conversion equation (F2) below to calculate singlet energy.

$$S_1 \text{ [eV]}=1239.85/\lambda \text{edge} \quad \text{Conversion Equation (F2):}$$

Any device for measuring absorption spectrum is usable. For instance, a spectrophotometer (U3310 manufactured by Hitachi, Ltd.) is usable.

The tangent to the fall of the absorption spectrum on the long-wavelength side is drawn as follows. While moving on a curve of the absorption spectrum from the maximum spectral value closest to the long-wavelength side in a long-wavelength direction, a tangent at each point on the curve is checked. An inclination of the tangent is decreased and increased in a repeated manner as the curve fell (i.e., a value of the ordinate axis is decreased). A tangent drawn at a point of the minimum inclination closest to the long-wavelength side (except when absorbance is 0.1 or less) is defined as the tangent to the fall of the absorption spectrum on the long-wavelength side.

The maximum absorbance of 0.2 or less is not included in the above-mentioned maximum absorbance on the long-wavelength side.

Content Ratio of Compounds in Emitting Layer

A content ratio between the first compound and the second compound in the emitting layer 5 is preferably in an exemplary range below.

The content ratio of the first compound is preferably in a range from 10 mass % to 80 mass %, more preferably in a range from 10 mass % to 60 mass %, further preferably in a range from 20 mass % to 60 mass %.

The content ratio of the second compound is preferably in a range from 0.01 mass % to 10 mass %, more preferably in a range from 0.01 mass % to 5 mass %, further preferably in a range from 0.01 mass % to 1 mass %.

It should be noted that the emitting layer 5 of the exemplary embodiment may further contain material(s) other than the first and second compounds.

Film Thickness of Emitting Layer

A film thickness of the emitting layer 5 is preferably in a range from 5 nm to 50 nm, more preferably in a range from 7 nm to 50 nm, and further preferably in a range from 10 nm to 50 nm. At 5 nm or more of the film thickness, the emitting layer 5 is easily formable and chromaticity of the emitting layer 5 is easily adjustable. When the film thickness of the emitting layer 5 is 50 nm or less, an increase in the drive voltage is suppressible.

TADF Mechanism

Figure 4:
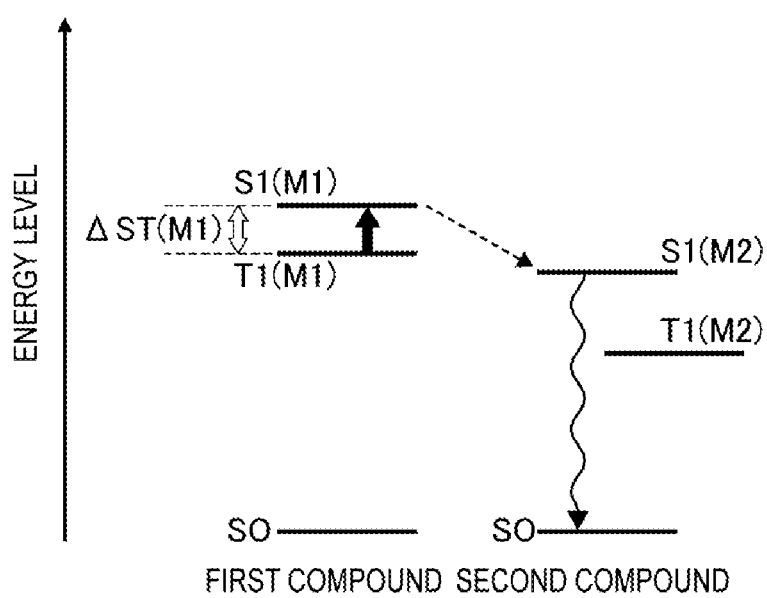
FIG. 4 shows a relationship between energy levels of a first compound and a second compound and an energy transfer between the first compound and the second compound in an exemplary emitting layer of the organic electroluminescence device according to the first exemplary embodiment of the invention.

FIG. 4 shows an example of a relationship between energy levels of the first compound and the second compound in the emitting layer. In FIG. 4, S0 represents a ground state. S1(M1) represents the lowest singlet state of the first compound. T1(M1) represents the lowest triplet state of the first compound. S1(M2) represents the lowest singlet state of the second compound. T1(M2) represents the lowest triplet state of the second compound.

A dashed arrow directed from S1(M1) to S1(M2) in FIG. 4 represents Förster energy transfer from the lowest singlet state of the first compound to the second compound.

As shown in FIG. 4, when a compound having a small ΔST(M1) is used as the first compound, inverse intersystem crossing from the lowest triplet state T1(M1) to the lowest singlet state S1(M1) can be caused by a heat energy. Accordingly, Förster energy transfer from the lowest singlet state S1(M1) of the first compound to the second compound is caused to generate the lowest singlet state S1(M2). As a result, fluorescence from the lowest singlet state S1(M2) of the second compound is observable. It is speculated that the internal quantum efficiency can be theoretically raised up to 100% also by using the delayed fluorescence by the TADF mechanism.

Substrate

A substrate 2 is used as a support for the organic EL device 1. For instance, glass, quartz, plastics and the like are usable for the substrate 2. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Preferable examples of a material for the anode 3 formed on the substrate 2 include metal, an alloy, an electroconductive compound, and a mixture thereof, which have a large work function (specifically, 4.0 eV or more). Specific examples of the material for the anode include ITO (Indium Tin Oxide), indium tin oxide containing silicon or silicon oxide, indium zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), or nitrides of the metal materials (e.g., titanium nitride) are usable.

The material is typically formed into a film by a sputtering method. For instance, the indium oxide-zinc oxide can be formed by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, vapor deposition, coating, ink jet printing, spin coating and the like may be used for forming a film.

Among the organic layers formed on the anode 3, the hole injecting layer 6 formed in contact with the anode 3 is formed using a composite material that facilitates injection of holes irrespective of the work function of the anode 3. Accordingly, a material usable as an electrode material (e.g., metal, alloy, an electrically conductive compound, a mixture thereof, and elements belonging to Groups 1 and 2 of the periodic table of the elements) is usable as the material for the anode 3.

The elements belonging to Groups 1 and 2 of the periodic table of the elements, which are materials having a small work function, a rare earth metal and alloy thereof are also usable as the material for the anode 3. The elements belonging to Group 1 of the periodic table of the elements are alkali metal. The elements belonging to Group 2 of the periodic table of the elements are alkaline earth metal. Examples of alkali metal are lithium (Li) and cesium (Cs). Examples of alkaline earth metal are magnesium (Mg), calcium (Ca), and strontium (Sr). Examples of the rare earth metal are europium (Eu) and ytterbium (Yb). Examples of the alloys including these metals are MgAg and AlLi.

It should be noted that the vacuum deposition method and the sputtering method are usable for forming the anode 3 using the alkali metal, alkaline earth metal and the alloy thereof. Further, when the anode is formed of silver paste and the like, coating, ink jet printing or the like is usable.

Hole Injecting Layer

The hole injecting layer 6 is a layer containing a highly hole-injectable substance. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule compound, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl(abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

Moreover, a high-molecular weight compound is also usable as the highly hole-injectable substance. Examples of the high-molecular weight compound are an oligomer, dendrimer and polymer. Specific examples of the high-molecular weight compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamido] (abbreviation: PTPDMA), and poly[N,N'-bis(4-butylphenyl)-N,N'-bis(phenyl)benzidine] (abbreviation: Poly-TPD). Moreover, an acid-added high-molecular weight compound such as poly(3,4-ethylenedioxythiophene)/poly (styrene sulfonate) (PEDOT/PSS) and polyaniline/poly (styrene sulfonate)(PAni/PSS) are also usable.

Hole Transporting Layer

The hole transporting layer 7 is a layer containing a highly hole-transportable substance. An aromatic amine compound, carbazole derivative, anthracene derivative and the like are usable for the hole transporting layer 7. Specific examples of a material for the hole transporting layer include 4,4'-bis[N-(1-naphthyl)-N-phenylamino]biphenyl (abbreviation: NPB), N, N'-bis(3-methylphenyl)-N, N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

A carbazole derivative (e.g., CBP, 9-[4-(N-carbazolyl)] phenyl-10-phenylanthracene (CzPA), and 9-phenyl-3-[4-(10-phenyl-9-anthryl)phenyl]-9H-carbazole (PCzPA)), an anthracene derivative (e.g., t-BuDNA, DNA, and DPAnth) and the like may be used for the hole transporting layer 7. A high-molecular weight compound such as poly(N-vinylcarbazole) (abbreviation: PVK) and poly(4-vinyltriphenylamine) (abbreviation: PVTPA) is also usable.

However, any substance having a hole transporting performance higher than an electron transporting performance may be used in addition to the above substances. A highly hole-transportable substance may be provided in the form of a single layer or a laminated layer of two or more layers of the above substance(s).

When the hole transporting layer includes two or more layers, one of the layers with a larger energy gap is preferably provided closer to the emitting layer 5.

Electron Transporting Layer

The electron transporting layer 8 is a layer containing a highly electron-transportable substance. As the electron transporting layer 8, (1) a metal complex such as an aluminum complex, beryllium complex and zinc complex, (2) a heteroaromatic compound such as an imidazole derivative, benzimidazole derivative, azine derivative, carbazole derivative, and phenanthroline derivative, and (3) a high-molecular weight compound are usable. Specifically, as a low-molecule organic compound, a metal complex such as Alq, tris(4-methyl-8-quinolinato)aluminum (abbreviation: Almq$_3$), bis(10-hydroxybenzo[h]quinolinato)beryllium (abbreviation: BeBq$_2$), BAlq, Znq, ZnPBO and ZnBTZ are usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the first exemplary embodiment, a benzimidazole compound is suitably usable. The above-described substances mostly have an electron mobility of $10^{-6}$ cm$^2$/(V·s) or more. However, any substance having an electron transporting performance higher than a hole transporting performance may be used for the electron transporting layer 8 in addition to the above substances. The electron transporting layer 8 may be provided in the form of a single layer or a laminated layer of two or more layers of the above substance(s).

Moreover, a high-molecular weight compound is also usable for the electron transporting layer 8. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) and the like are usable.

Electron Injecting Layer

The electron injecting layer 9 is a layer containing a highly electron-injectable substance. For the electron injecting layer 9, an alkali metal, alkaline earth metal or a compound thereof are usable, examples of which include lithium (Li), cesium (Cs), calcium (Ca), lithium fluoride (LiF), cesium fluoride (CsF), calcium fluoride (CaF$_2$), and lithium oxide (LiOx). In addition, a substance obtained by blending an alkali metal, alkaline earth metal or a compound thereof in the electron transportable substance, specifically, for instance, a substance obtained by blending magnesium (Mg) in Alq may be used. With this substance, electrons can be more efficiently injected from the cathode 4.

Alternatively, a composite material provided by mixing an organic compound with an electron donor may be used for the electron injecting layer 9. Such a composite material exhibits excellent electron injectability and electron transportability since electrons are generated in the organic compound by the electron donor. In this arrangement, the organic compound is preferably a material exhibiting excellent transporting performance of the generated electrons. Specifically, for instance, the above-described substance for the electron transporting layer 8 (e.g., the metal complex and heteroaromatic compound) is usable. As the electron donor, any substance exhibiting electron donating property to the organic compound is usable. Specifically, an alkali metal, an alkaline earth metal and a rare earth metal are preferable, examples of which include lithium, cesium, magnesium, calcium, erbium and ytterbium. Moreover, an alkali metal oxide or alkaline earth metal oxide is preferably used as the electron donor, examples of which include lithium oxide, calcium oxide, and barium oxide. Moreover, a Lewis base such as magnesium oxide is usable. Further, the organic compound such as tetrathiafulvalene (abbreviation: TTF) is usable.

Cathode

Metal, alloy, an electrically conductive compound, a mixture thereof and the like, which have a small work function, specifically, of 3.8 eV or less, are preferably usable as a material for the cathode 4. Specific examples of the material for the cathode are the elements belonging to Groups 1 and 2 of the periodic table of the elements, a rare earth metal and alloys thereof. The elements belonging to Group 1 of the periodic table of the elements are alkali metal. The elements belonging to Group 2 of the periodic table of the elements are alkaline earth metal. Examples of alkali metal are lithium (Li) and cesium (Cs). Examples of alkaline earth metal are magnesium (Mg), calcium (Ca), and strontium (Sr). Examples of the rare earth metal are europium (Eu) and ytterbium (Yb). Examples of the alloys including these metals are MgAg and AlLi.

It should be noted that the vacuum deposition method and the sputtering method are usable for forming the cathode 4 using the alkali metal, alkaline earth metal and the alloy thereof. Further, when the cathode is formed of silver paste and the like, coating, ink jet printing or the like is usable.

By providing the electron injecting layer 9, various conductive materials such as Al, Ag, ITO, graphene and indium tin oxide containing silicon or silicon oxide are usable for forming the cathode 4 irrespective of the magnitude of the work function. The conductive materials can be deposited as a film by sputtering, ink jet printing, spin coating and the like.

Layer Formation Method(s)

A method for forming each layer of the organic EL device 1 in the exemplary embodiment is subject to no limitation except for the above particular description, where known methods such as dry film-forming and wet film-forming are applicable. Examples of the dry film-forming include vacuum deposition, sputtering, plasma and ion plating. Examples of the wet film-forming include spin coating, dipping, flow coating and ink-jet.

Film Thickness

There is no restriction except for the above particular description for a film thickness of each of the organic layers of the organic EL device 1 in the first exemplary embodiment. The thickness is usually preferably in a range from several nanometers to 1 μm in order to cause less defects (e.g., pin holes) and prevent deterioration in the efficiency due to the necessity in applying high voltage.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group.

Further, "XX to YY atoms" in the description of "substituted or unsubstituted ZZ group having XX to YY atoms" herein represent atoms of an unsubstituted ZZ group and does not include atoms of a substituent(s) of the substituted ZZ group.

Herein, the ring carbon atoms refer to the number of carbon atoms among atoms forming a ring of a compound (e.g., a monocyclic compound, fused-ring compound, crosslinking compound, carbon ring compound, and heterocyclic compound) in which the atoms are bonded with each other to form the ring. When the ring is substituted by a substituent(s), carbon atom(s) contained in the substituent(s) is not counted in the ring carbon atoms. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring and/or a naphthalene ring is substituted by a substituent (e.g., an alkyl group), the number of carbon atoms of the alkyl group is not counted in the number of the ring carbon atoms. When a fluorene ring is substituted by a substituent (e.g., a fluorene ring) (i.e., a spirofluorene ring is included), the number of carbon atoms of the fluorene ring as the substituent is not counted in the number of the ring carbon atoms of the fluorene ring.

Herein, the ring atoms refer to the number of atoms forming a ring of a compound (e.g., a monocyclic compound, fused-ring compound, crosslinking compound, carbon ring compound, and heterocyclic compound) in which the atoms are bonded with each other to form the ring (e.g., monocyclic ring, fused ring, ring assembly). Atom(s) not involved in the formation of a ring and atom(s) included in a substituent when the ring is substituted by the substituent are not counted in the number of the ring atoms. Unless specifically described, the same applies to the "ring atoms" described later. For instance, a pyridine ring has six ring atoms, a quinazoline ring has ten ring atoms, and a furan ring has five ring atoms. A hydrogen atom(s) and/or an atom(s) of a substituent which are bonded with carbon atoms of a pyridine ring and/or quinazoline ring are not counted in the ring atoms. When a fluorene ring is substituted by a substituent (e.g., a fluorene ring) (i.e., a spirofluorene ring is included), the number of atoms of the fluorene ring as the substituent is not counted in the number of the ring atoms of the fluorene ring.

Herein, a hydrogen atom includes isotope having different numbers of neutrons, specifically, protium, deuterium and tritium.

Herein, "heteroaryl group", "heteroarylene group" and "heterocyclic group" refer to a group having at least one hetero atom as a ring atom. As the hetero atom, at least one atom selected from a nitrogen atom, oxygen atom, sulfur atom, silicon atom, and selenium atom is preferable.

Herein, the "substituted or unsubstituted carbazolyl group" refers to the following carbazolyl group,

[Formula 92]

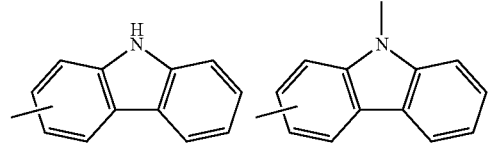

and a substituted carbazolyl group, which is the above carbazolyl group substituted by a substituent.

It should be noted that the substituted carbazolyl group may have substituents that are mutually bonded to form a fused ring, and may have a hetero atom such as a nitrogen atom, oxygen atom, sulfur atom, silicon atom, and selenium atom. Further, the bonding position of the substituent may be any one of positions 1 to 9. Specific examples of the substituted carbazolyl group are shown below.

[Formula 93]

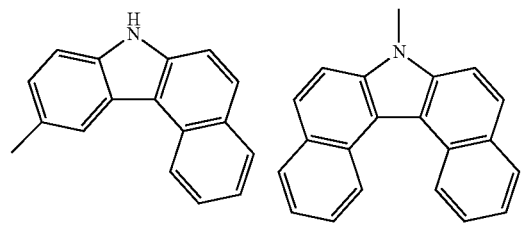

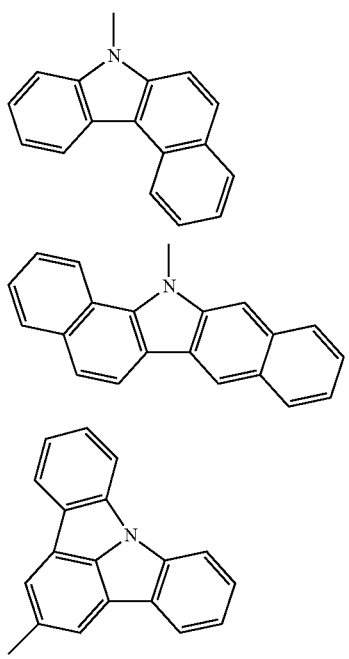

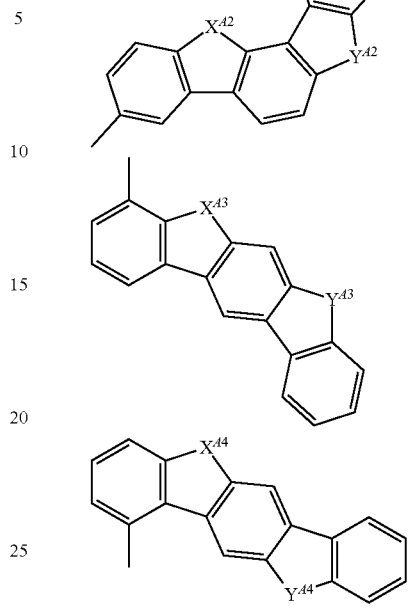

Herein, the "substituted or unsubstituted dibenzofuranyl group" and "substituted or unsubstituted dibenzothienyl group" respectively refer to the following dibenzofuranyl group and dibenzothienyl group,

[Formula 94]

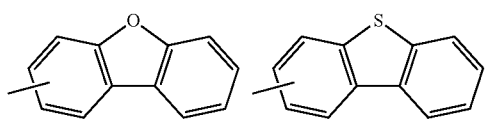

and a substituted dibenzofuranyl group and a substituted dibenzothienyl group, which are the above dibenzofuranyl group and dibenzothienyl group substituted by a substituent.

It should be noted that the substituted dibenzofuranyl group and the substituted dibenzothienyl may have substituents that are mutually bonded to form a fused ring, and may have a hetero atom such as a nitrogen atom, oxygen atom, sulfur atom, silicon atom, and selenium atom. Further, the bonding position of the substituent may be any one of positions 1 to 8.

Specific examples of the substituted dibenzofuranyl group and the substituted dibenzothienyl group are, for instance, shown below.

[Formula 95]

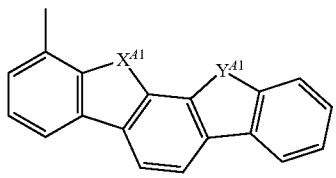

[Formula 96]

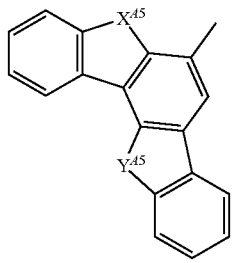

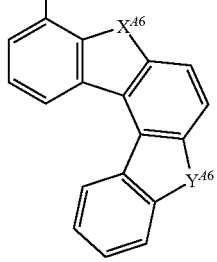

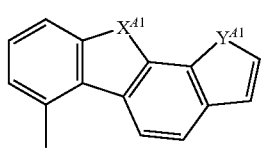

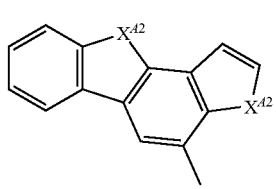

313

-continued

[Formula 97]

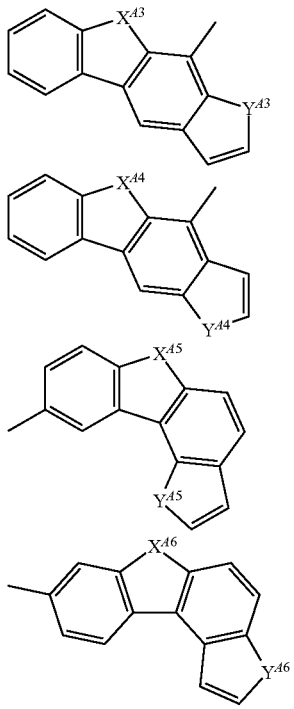

In the above formulae, $X^{41}$ to $X^{46}$ each represent an oxygen atom or a sulfur atom, $Y^{41}$ to $Y^{46}$ each represent an oxygen atom, a sulfur atom, NH, NRa (Ra being an alkyl group or an aryl group), $CH_2$, or $CR^b{}_2$ ($R^b$ being an alkyl group or an aryl group).

The substituent (sometimes referred to as a substituent $R_F$) meant by "substituent," or implied by the phrase "substituted or unsubstituted" is, unless otherwise specified, preferably at least one group selected from the group consisting of: an alkyl group having 1 to 50 (preferably 1 to 18, more preferably 1 to 8) carbon atoms; a cycloalkyl group having 3 to 50 (preferably 3 to 10, more preferably 3 to 8, further preferably 5 or 6) ring carbon atoms; an aryl group having 6 to 50 (preferably 6 to 25, more preferably 6 to 18) ring carbon atoms; an aralkyl group having 7 to 51 (preferably 7 to 30, more preferably 7 to 20) carbon atoms and having an aryl group ring having 6 to 50 (preferably 6 to 25, more preferably 6 to 18) carbon atoms; an amino group; a mono- or di-substituted amino group having a substituent selected from an alkyl group having 1 to 50 (preferably 1 to 18, more preferably 1 to 8) carbon atoms and an aryl group having 6 to 50 (preferably 6 to 25, more preferably 6 to 18) ring carbon atoms; an alkoxy group having an alkyl group having 1 to 50 (preferably 1 to 18, more preferably 1 to 8) carbon atoms; an aryloxy group having an aryl group having 6 to 50 (preferably 6 to 25, more preferably 6 to 18) ring carbon atoms; a mono-substituted, di-substituted or tri-substituted silyl group having an alkyl group having 1 to 50 (preferably 1 to 18, more preferably 1 to 8) carbon atoms and an aryl group having 6 to 50 (preferably 6 to 25, more preferably 6 to 18) ring carbon atoms; a heteroaryl group having 5 to 50 (preferably 5 to 24, more preferably 5 to 13) ring atoms; a haloalkyl group having 1 to 50 (preferably 1 to 18, more preferably 1 to 8) carbon atoms; a halogen atom (a fluorine atom, chlorine atom, bromine atom, or iodine atom); a cyano group; a nitro group; a sulfonyl group having

314 a substituent selected from an alkyl group having 1 to 50 (preferably 1 to 18, more preferably 1 to 8) carbon atoms and an aryl group having 6 to 50 (preferably 6 to 25, more preferably 6 to 18) ring carbon atoms; a di-substituted phosphoryl group having a substituent selected from an alkyl group having 1 to 50 (preferably 1 to 18, more preferably 1 to 8) carbon atoms and an aryl group having 6 to 50 (preferably 6 to 25, more preferably 6 to 18) ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth)acryloyl group; an epoxy group; and an oxetanyl group. However, the substituent is not limited to these specific examples.

These substituents $R_F$ may further be substituted by any one of the above substituents $R_F$. In addition, a plurality of the substituents $R_F$ may be bonded with each other to form a ring.

"Unsubstituted" in "substituted or unsubstituted" means that a group is not substituted by the above-described substituents $R_F$ but bonded with a hydrogen atom.

The substituent $R_F$ is more preferably a substituted or unsubstituted alkyl group having 1 to 50 (preferably 1 to 18, more preferably 1 to 8) carbon atoms, a substituted or unsubstituted cycloalkyl group having 3 to 50 (preferably 3 to 10, more preferably 3 to 8, further preferably 5 or 6) ring carbon atoms, a substituted or unsubstituted aryl group having 6 to 50 (preferably 6 to 25, more preferably 6 to 18) ring carbon atoms, a mono- or di-substituted amino group having a substituent selected from a substituted or unsubstituted alkyl group having 1 to 50 (preferably 1 to 18, more preferably 1 to 8) carbon atoms and a substituted or unsubstituted aryl group having 6 to 50 (preferably 6 to 25, more preferably 6 to 18) ring carbon atoms, a substituted or unsubstituted heteroaryl group having 5 to 50 (preferably 5 to 24, more preferably 5 to 13) ring atoms, a halogen atom, and a cyano group.

Examples of the alkyl group having 1 to 50 carbon atoms include a methyl group, ethyl group, n-propyl group, isopropyl group, n-butyl group, isobutyl group, s-butyl group, t-butyl group, pentyl group (including isomeric group thereof), hexyl group (including isomeric group thereof), heptyl group (including isomeric group thereof), octyl group (including isomeric group thereof), nonyl group (including isomeric group thereof), decyl group (including isomeric group thereof), undecyl group (including isomeric group thereof, and dodecyl group (including isomeric group thereof). Among the above, a methyl group, ethyl group, n-propyl group, isopropyl group, n-butyl group, isobutyl group, s-butyl group, t-butyl group, and pentyl group (including isomeric group thereof) are preferable, a methyl group, ethyl group, n-propyl group, isopropyl group, n-butyl group, isobutyl group, s-butyl group, and t-butyl group are more preferable, and a methyl group, ethyl group, isopropyl group and t-butyl group are especially preferable.

Examples of the cycloalkyl group having 3 to 50 ring carbon atoms include a cyclopropyl group, cyclobutyl group, cyclopentyl group, cyclohexyl group, cycloheptyl group, cyclooctyl group, and adamantyl group. Among the above, a cyclopentyl group or a cyclohexyl group is preferable.

Examples of the aryl group having 6 to 50 ring carbon atoms include a phenyl group, biphenylyl group, terphenylyl group, naphthyl group, acenaphthylenyl group, anthryl group, benzoanthryl group, aceanthryl group, phenanthryl group, benzo[c]phenanthryl group, phenalenyl group, fluorenyl group, picenyl group, pentaphenyl group, pyrenyl group, chrysenyl group, benzo[g]chrysenyl group, s-indecenyl group, as-indecenyl group, fluoranthenyl group, benzo[k]fluoranthenyl group, triphenylenyl group, benzo[b]triphenylenyl group and perylenyl group. Among the above, a phenyl group, biphenylyl group, terphenylyl group, naphthyl group, anthryl group, pyrenyl group, and fluoranthenyl group are preferable, a phenyl group, biphenylyl group, and terphenylyl group are more preferable, and a phenyl group is further preferable.

Specific examples of the aralkyl group having 7 to 51 ring carbon atoms and having an aryl group having 6 to 50 ring carbon atoms include a group whose aryl-group moiety is one of the specific examples of the aryl group having 6 to 50 ring carbon atoms and whose alkyl-group moiety is one of the specific examples of the alkyl group having 1 to 50 carbon atoms. Preferable examples of the aralkyl group having 7 to 51 ring carbon atoms include an aralkyl group whose aryl-group moiety is one of the preferable examples of the aryl group having 6 to 50 ring carbon atoms and whose alkyl-group moiety is one of the preferable examples of the alkyl group having 1 to 50 carbon atoms. The same applies to more preferable specific examples and further preferable specific examples of aralkyl group.

Specific examples of the mono- or di-substituted amino group having a substituent selected from an alkyl group having 1 to 50 carbon atoms and an aryl group having 6 to 50 ring carbon atoms include a mono- or di-substituted amino group whose aryl-group moiety is one of the specific examples of the aryl group having 6 to 50 ring carbon atoms and whose alkyl-group moiety is one of the specific examples of the alkyl group having 1 to 50 carbon atoms. Preferable examples of the mono- or di-substituted amino group having a substituent selected from an alkyl group having 1 to 50 carbon atoms and an aryl group having 6 to 50 ring carbon atoms include a mono- or di-substituted amino group whose aryl-group moiety is one of the preferable examples of the aryl group having 6 to 50 ring carbon atoms and whose alkyl-group moiety is one of the preferable examples of the alkyl group having 1 to 50 carbon atoms. The same applies to more preferable specific examples, further preferable specific examples, and especially preferable examples of the mono- or di-substituted amino group.

Specific examples of the alkoxy group having an alkyl group having 1 to 50 carbon atoms include an alkoxy group whose alkyl-group moiety is one of the specific examples of the alkyl group having 1 to 50 carbon atoms. Preferable examples of the alkoxy group having an alkyl group having 1 to 50 carbon atoms include an alkoxy group whose alkyl-group moiety is one of the preferable examples of the alkyl group having 1 to 50 carbon atoms. The same applies to more preferable specific examples, further preferable specific examples, and especially preferable examples of the alkoxy group.

Specific examples of the aryloxy group having an aryl group having 6 to 50 ring carbon atoms include an aryloxy group whose aryl-group moiety is one of the specific examples of the aryl group having 6 to 50 ring carbon atoms. Preferable examples of the aryloxy group having an aryl group having 6 to 50 ring carbon atoms include an aryloxy group whose aryl-group moiety is one of the preferable examples of the aryl group having 6 to 50 ring carbon atoms. The same applies to more preferable specific examples and further preferable specific examples of the aryloxy group.

Examples of the mono-substituted, di-substituted, or tri-substituted silyl group having a substituent selected from an alkyl group having 1 to 50 carbon atoms and an aryl group having 6 to 50 ring carbon atoms include monoalkylsilyl group, dialkylsilyl group, trialkylsilyl group; monoarylsilyl group, diarylsilyl group, triarylsilyl group; monoalkyldiarylsilyl group, and dialkylmonoarylsilyl group, the alkyl-group moiety and the aryl-group moiety of these examples being the specific examples of the above-described alkyl group having 1 to 50 carbon atoms and the aryl group having 6 to 50 ring carbon atoms, respectively. Preferable examples of the mono-substituted, di-substituted, or tri-substituted silyl group having a substituent selected from an alkyl group having 1 to 50 carbon atoms and an aryl group having 6 to 50 ring carbon atoms include monoalkylsilyl group, dialkylsilyl group, trialkylsilyl group; monoarylsilyl group, diarylsilyl group, triarylsilyl group; monoalkyldiarylsilyl group, and dialkylmonoarylsilyl group, the alkyl-group moiety and the aryl-group moiety of these examples being the preferable examples of the above-described alkyl group having 1 to 50 carbon atoms and the aryl group having 6 to 50 ring carbon atoms, respectively. The same applies to more preferable specific examples, further preferable specific examples, and especially preferable examples of the mono-substituted, di-substituted, or tri-substituted silyl group.

Examples of the heteroaryl group having 5 to 50 ring carbon atoms include a pyrrolyl group, furyl group, thienyl group, pyridyl group, imidazopyridyl group, pyridazinyl group, pyrimidinyl group, pyrazinyl group, triazinyl group, imidazolyl group, oxazolyl group, thiazolyl group, pyrazolyl group, isoxazolyl group, isothiazolyl group, oxadiazolyl group, thiadiazole group, triazolyl group, tetrazolyl group, indolyl group, isoindolyl group, benzofuranyl group, isobenzofuranyl group, benzothienyl group, isobenzothienyl group, indolizinyl group, quinolizinyl group, quinolyl group, isoquinolyl group, cinnolyl group, phthalazinyl group, quinazolinyl group, quinoxalinyl group, benzimidazolyl group, benzoxazolyl group, benzothiazolyl group, indazolyl group, benzisoxazolyl group, benzisothiazolyl group, dibenzofuranyl group, dibenzothienyl group, carbazolyl group, 9-phenylcarbazolyl group, phenanthridinyl group, acridinyl group, phenanthrolinyl group, phenazinyl group, phenothiazinyl group, phenoxazinyl group and xanthenyl group. Among the above, a pyridyl group, imidazopyridyl group, pyridazinyl group, pyrimidinyl group, pyrazinyl group, triazinyl group, benzimidazolyl group, dibenzofuranyl group, dibenzothienyl group, carbazolyl group, 9-phenylcarbazolyl group, phenanthrolinyl group, and quinazolinyl group are preferable.

Examples of the halogen atom include a fluorine atom, a chlorine atom, a bromine atom, and an iodine atom.

Specific examples of the haloalkyl group having 1 to 50 carbon atoms include a haloalkyl group, in which a hydrogen atom of an alkyl group having 1 to 50 carbon atoms is substituted by the halogen atom, preferable example of the alkyl group being one of the preferable examples of the alkyl group having 1 to 50 carbon atoms. The same applies to more preferable specific examples, further preferable specific examples, and especially preferable examples of the mono-substituted, di-substituted, or tri-substituted haloalkyl group.

Examples of the sulfonyl having a substituent selected from an alkyl group having 1 to 50 carbon atoms and an aryl group having 6 to 50 ring carbon atoms, a disubstituted phosphoryl group having a substituent selected from an alkyl group having 1 to 50 carbon atoms and an aryl group having 6 to 50 ring carbon atoms, an alkylsulfonyloxy group, an arylsulfonyloxy group, an alkylcarbonyloxy group, an arylcarbonyloxy group, and alkyl-substituted or aryl-substituted carbonyl group include a group whose aryl-group moiety and/or alkyl-group moiety is one of the specific examples of the aryl group having 6 to 50 ring carbon atoms and alkyl group having 1 to 50 carbon atoms. Preferable examples of the sulfonyl having a substituent selected from an alkyl group having 1 to 50 carbon atoms and an aryl group having 6 to 50 ring carbon atoms, a disubstituted phosphoryl group having a substituent selected from an alkyl group having 1 to 50 carbon atoms and an aryl group having 6 to 50 ring carbon atoms, an alkylsulfonyloxy group, an arylsulfonyloxy group, an alkylcarbonyloxy group, an arylcarbonyloxy group, and alkyl-substituted or aryl-substituted carbonyl group include a group whose aryl-group moiety and/or alkyl-group moiety is one of the preferable examples of the aryl group having 6 to 50 ring carbon atoms and alkyl group having 1 to 50 carbon atoms. The same applies to more preferable specific examples, further preferable specific examples, and especially preferable examples of the above groups.

Herein, the preferable arrangement (e.g. compound, various groups, numerical range and the like) is combinable with any other arrangement (compound, various groups, numerical range and the like) as desired, among which the combination with the preferable arrangements (including more preferable arrangement, further preferable arrangement and especially preferable arrangement) is further preferable.

Typically, it is difficult to narrow the full width at half maximum in an organic EL device using the TADF mechanism. According to the organic EL device of the first exemplary embodiment, the full width at half maximum can be narrowed as compared with typical organic EL devices. Consequently, the color purity of the organic EL device can also be improved.

In addition, according to the organic EL device of the first exemplary embodiment, the full width at half maximum can be narrowed as compared with typical organic EL devices in a blue wavelength region.

Electronic Device

An electronic device of the exemplary embodiment is provided with the organic EL device according to the first exemplary embodiment. Examples of the electronic device include a display device and a light-emitting unit. Examples of the display device include a display component (e.g., an organic EL panel module), TV, mobile phone, tablet and personal computer. Examples of the light-emitting unit include an illuminator and a vehicle light.

Second Exemplary Embodiment

An arrangement of an organic EL device according to a second exemplary embodiment will be described below. In the description of the second exemplary embodiment, the same components as those in the first exemplary embodiment are denoted by the same reference signs and names to simplify or omit explanation of the components. In the second exemplary embodiment, the same materials and compounds as described in the first exemplary embodiment are usable, unless otherwise specified.

The organic EL device according to the second exemplary embodiment is different from the organic EL device according to the first exemplary embodiment in that the emitting layer further contains a third compound. Other components are the same as those in the first exemplary embodiment.

Third Compound

A singlet energy $S_1(M3)$ of the third compound and the singlet energy $S_1(M1)$ of the first compound preferably satisfy a relationship of a numerical formula (Numerical Formula 2) below.

$$S_1(M3) > S_1(M1) \quad \text{(Numerical Formula 2)}.$$

The third compound may be a compound exhibiting delayed fluorescence or a compound exhibiting no delayed fluorescence.

The third compound is also preferably a host material (occasionally referred to as a matrix material). When the first compound and the third compound are the host materials, one of the compounds may be referred to as a first host material and the other of the compounds may be referred to as a second host material.

The third compound is not particularly limited, but is preferably a compound other than an amine compound. For instance, a carbazole derivative, dibenzofuran derivative or dibenzothiophene derivative is usable as the third compound. However, the third compound is not limited thereto.

The third compound is also preferably a compound that has at least one of the moiety represented by the formula (31) and the moiety represented by the formula (32) in one molecule.

[Formula 98]

(31)

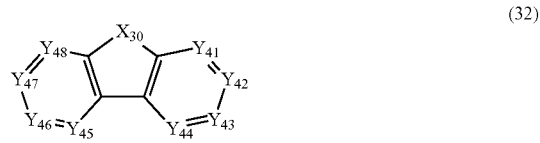

(32)

In the formula (31), $Y_{31}$ to $Y_{36}$ each independently represent a nitrogen atom or a carbon atom bonded with another atom in the molecule of the third compound, where at least one of $Y_{31}$ to $Y_{36}$ is a carbon atom bonded with another atom in the molecule of the third compound.

In the formula (32), $Y_{41}$ to $Y_{48}$ each independently represent a nitrogen atom or a carbon atom bonded with another atom in the molecule of the third compound, where at least one of $Y_{41}$ to $Y_{48}$ is a carbon atom bonded with another atom in the molecule of the third compound.

$X_{30}$ represents a nitrogen atom, oxygen atom or sulfur atom.

In the formula (32), it is also preferable that at least two of $Y_{41}$ to $Y_{48}$ are carbon atoms bonded with other atoms in the molecule of the third compound; and a cyclic structure including the carbon atoms is formed.

For instance, the moiety represented by the formula (32) is preferably any one selected from the group consisting of moieties represented by formulae (321), (322), (323), (324), (325) and (326).

[Formula 99]

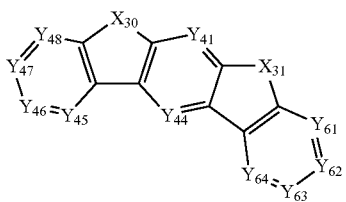
(321)

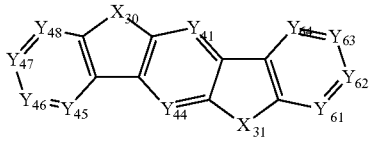
(322)

[Formula 100]

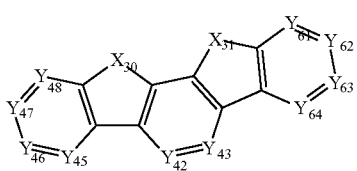
(323)

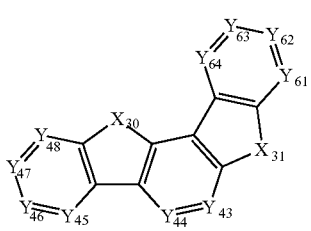
(324)

[Formula 101]

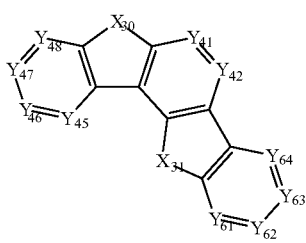
(325)

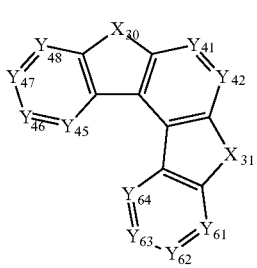
(326)

In the formulae (321) to (326): $X_{30}$ each independently represents a nitrogen atom, oxygen atom or sulfur atom;

$Y_{41}$ to $Y_{48}$ each independently represent a nitrogen atom or a carbon atom bonded with another atom in the molecule of the third compound;

$X_{31}$ each independently represents a nitrogen atom, oxygen atom, sulfur atom or carbon atom; and $Y_{61}$ to $Y_{64}$ each independently represent a nitrogen atom or a carbon atom bonded with another atom in the molecule of the third compound.

In the second exemplary embodiment, the third compound preferably includes the moiety represented by the formula (323) among the formulae (321) to (326).

The moiety represented by the formula (31) is preferably contained in the third compound in a form of at least one group selected from the group consisting of groups represented by formulae (33) and (34) below.

It is also preferable that the third compound has at least one of the moieties represented by the formulae (33) and (34). The moieties represented by the formulae (33) and (34), whose bonding positions are situated in meta positions, can keep an energy gap $T_{77K}(M3)$ at 77 [K] of the third compound at a high level.

[Formula 102]

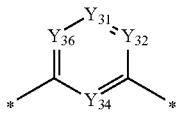
(33)

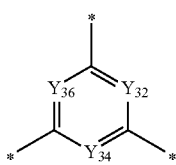
(34)

In the formula (33), $Y_{31}$, $Y_{32}$, $Y_{34}$ and $Y_{36}$ each independently represent a nitrogen atom or $CR_{31}$.

In the formula (34), $Y_{32}$, $Y_{34}$ and $Y_{36}$ each independently represent a nitrogen atom or $CR_{31}$.

In the formulae (33) and (34): $R_{31}$ is each independently a hydrogen atom or a substituent;

$R_{31}$ serving as the substituent is each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group, with a proviso that the substituted or unsubstituted aryl group having 6 to 30 ring carbon atoms in $R_{31}$ is preferably a non-fused ring.

in the formulae (33) to (34) represent a bonding position with another atom or another structure in the molecule of the third compound.

In the formula (33), $Y_{31}$, $Y_{32}$, $Y_{34}$ and $Y_{36}$ are preferably each independently $CR_{31}$, in which a plurality of $R_{31}$ are the same or different.

In the formula (34), $Y_{32}$, $Y_{34}$ and $Y_{36}$ are preferably each independently $CR_{31}$, in which a plurality of $R_{31}$ are the same or different.

The substituted germanium group is preferably represented by —Ge($R_{301}$)$_3$. $R_{301}$ are each independently a substituent. The substituent $R_{301}$ is preferably a substituted or unsubstituted alkyl group having 1 to 30 carbon atoms or a substituted or unsubstituted aryl group having 6 to 30 ring carbon atoms. A plurality of $R_{301}$ are mutually the same or different.

The moiety represented by the formula (32) is preferably included in the third compound as at least one group selected from the group consisting of groups represented by formulae (35) to (39) and (30a) below.

[Formula 103]

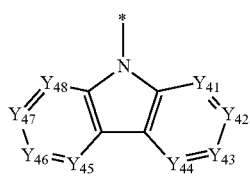
(35)

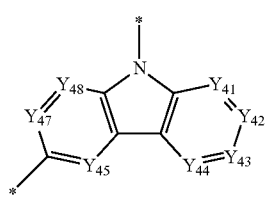
(36)

[Formula 104]

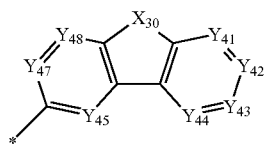
(37)

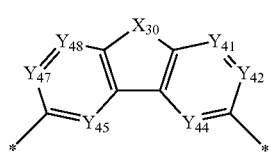
(38)

[Formula 105]

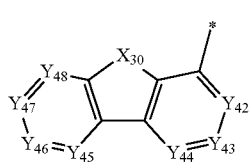
(39)

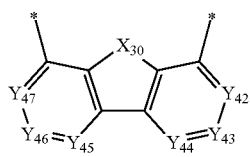
(30a)

In the formula (35), $Y_{41}$ to $Y_{48}$ each independently represent a nitrogen atom or $CR_{32}$.

In the formulae (36) and (37), $Y_{41}$ to $Y_{45}$, $Y_{47}$ and $Y_{48}$ each independently represent a nitrogen atom or $CR_{32}$.

In the formula (38), $Y_{41}$, $Y_{42}$, $Y_{44}$, $Y_{45}$, $Y_{47}$, and $Y_{48}$ each independently represent a nitrogen atom or $CR_{32}$.

In the formula (39), $Y_{42}$ to $Y_{48}$ each independently represent a nitrogen atom or $CR_{32}$.

In the formula (30a), $Y_{42}$ to $Y_{47}$ each independently represent a nitrogen atom or $CR_{32}$.

In the formulae (35) to (39) and (30a): $R_{32}$ is each independently a hydrogen atom or a substituent;

$R_{32}$ serving as the substituent is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group; and a plurality of $R_{32}$ are mutually the same or different.

In the formulae (37) to (39) and (30a): $X_{30}$ represents $NR_{33}$, an oxygen atom or a sulfur atom;

$R_{33}$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a fluorine atom, a cyano group, a nitro group, and a substituted or unsubstituted carboxy group; a plurality of $R_{33}$ are mutually the same or different; with a proviso that the substituted or unsubstituted aryl group having 6 to 30 ring carbon atoms in $R_{33}$ is preferably a non-fused ring.

* in the formulae (35) to (39) and (30a) represents a bonding position with another atom or another structure in the molecule of the third compound.

$Y_{41}$ to $Y_{48}$ in the formula (35) are preferably each independently $CR_{32}$. $Y_{41}$ to $Y_{45}$, $Y_{47}$ and $Y_{48}$ in the formula (36) and the formula (37) are preferably each independently $CR_{32}$. $Y_{41}$, $Y_{42}$, $Y_{44}$, $Y_{45}$, $Y_{47}$ and $Y_{48}$ in the formula (38) are preferably each independently $CR_{32}$. $Y_{42}$ to $Y_{48}$ in the formula (39) are preferably each independently $CR_{32}$. $Y_{42}$ to $Y_{47}$ in the formula (30a) are preferably each independently $CR_{32}$. A plurality of $R_{32}$ are optionally mutually the same or different.

In the third compound, $X_{30}$ is preferably an oxygen atom or a sulfur atom, more preferably an oxygen atom.

In the third compound, $R_{31}$ and $R_{32}$ each independently represent a hydrogen atom or a substituent. $R_{31}$ and $R_{32}$ as the substituents are preferably each independently a group selected from the group consisting of a fluorine atom, a cyano group, a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms. $R_{31}$ and $R_{32}$ are more preferably a hydrogen atom, a cyano group, a substituted or unsubstituted aryl group having 6 to 30 ring carbon atoms, or a substituted or unsubstituted heteroaryl group having 5 to 30 ring atoms. When $R_{31}$ and $R_{32}$ as the substituents are each a substituted or unsubstituted aryl group having 6 to 30 ring carbon atoms, the aryl group is preferably a non-fused ring.

The third compound is also preferably an aromatic hydrocarbon compound or an aromatic heterocyclic compound.

The third compound preferably contains no fused aromatic hydrocarbon ring in a molecule.

Method of Preparing Third Compound

The third compound can be prepared by methods disclosed in International Publication No. WO2012/153780, International Publication No. WO2013/038650, and the like. Furthermore, the third compound can be prepared, for instance, by application of known substitution reactions and/or materials depending on a target compound.

Examples of the substituent for the third compound are shown below, but the invention is not limited thereto.

Specific examples of the aryl group (occasionally referred to as an aromatic hydrocarbonl group) include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarterphenyl group and fluoranthenyl group, among which a phenyl group, biphenyl group, terphenyl group, quarterphenyl group, naphthyl group, triphenylenyl group, fluorenyl group and the like are preferable.

Specific examples of the aryl group having a substituent include a tolyl group, xylyl group and 9,9-dimethylfluorenyl group.

As is understood from the specific examples, the aryl group includes both fused aryl group and non-fused aryl group.

Preferable examples of the aryl group include a phenyl group, biphenyl group, terphenyl group, quarterphenyl group, naphthyl group, triphenylenyl group and fluorenyl group.

Specific examples of the heteroaryl group (occasionally referred to as a heterocyclic group, heteroaromatic ring group or aromatic heterocyclic group) include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thienyl group, benzothienyl group, dibenzothienyl group, azadibenzothienyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazolyl group, among which a dibenzofuranyl group, dibenzothienyl group, carbazolyl group, pyridyl group, pyrimidinyl group, triazinyl group, azadibenzofuranyl group, azadibenzothienyl group and the like are preferable.

Preferable heteroaryl groups are a dibenzofuranyl group, dibenzothienyl group, carbazolyl group, pyridyl group, pyrimidinyl group, triazinyl group, azadibenzofuranyl group and azadibenzothienyl group, and further preferable heteroaryl groups a dibenzofuranyl group, dibenzothienyl group, azadibenzofuranyl group and azadibenzothienyl group.

In the third compound, it is also preferable that the substituted silyl group is selected from the group consisting of a substituted or unsubstituted trialkylsilyl group, a substituted or unsubstituted arylalkylsilyl group, or a substituted or unsubstituted triarylsilyl group.

Specific examples of the substituted or unsubstituted trialkylsilyl group include trimethylsilyl group and triethylsilyl group.

Specific examples of the substituted or unsubstituted arylalkylsilyl group include diphenylmethylsilyl group, ditolylmethylsilyl group, and phenyldimethylsilyl group.

Specific examples of the substituted or unsubstituted triarylsilyl group include triphenylsilyl group and tritolylsilyl group.

In the third compound, the substituted phosphine oxide group is also preferably a substituted or unsubstituted diarylphosphine oxide group.

Specific examples of the substituted or unsubstituted diaryl phosphine oxide group include a diphenyl phosphine oxide group and ditolyl phosphine oxide group.

In the third compound, a substituted carboxy group is exemplified by a benzoyloxy group.

Relationship between First Compound, Second Compound and Third Compound in Emitting Layer The first compound, the second compound, and the third compound in the emitting layer preferably satisfy the relationships represented by the above numerical formulae (Numerical Formulae 1 and 2). Specifically, a relationship represented by a numerical formula below (Numerical Formula 3) is preferably satisfied.

$$S_1(M3) > S_1(M1) > S_1(M2) \quad \text{(Numerical Formula 3)}$$

The energy gap $T_{77K}(M3)$ at 77 [K] of the third compound is preferably larger than the energy gap $T_{77K}(M1)$ at 77 [K] of the first compound. Specifically, a relationship represented by a numerical formula below (Numerical Formula 5) is preferably satisfied.

$$T_{77K}(M3) > T_{77K}(M1) \quad \text{(Numerical Formula 5)}$$

The energy gap $T_{77K}(M3)$ at 77 [K] of the third compound is preferably larger than the energy gap $T_{77K}(M2)$ at 77 [K] of the second compound. Specifically, a relationship represented by a numerical formula below (Numerical Formula 6) is preferably satisfied.

$$T_{77K}(M3) > T_{77K}(M2) \quad \text{(Numerical Formula 6)}$$

The first compound, the second compound, and the third compound in the emitting layer preferably satisfy the relationships represented by the above numerical formulae (Numerical Formulae 4 and 5). Specifically, a relationship represented by a numerical formula below (Numerical Formula 7) is preferably satisfied.

$$T_{77K}(M3) > T_{77K}(M1) > T_{77K}(M2) \quad \text{(Numerical Formula 7)}$$

When the organic EL device in the second exemplary embodiment emits light, it is preferable that the second compound mainly emits light in the emitting layer.

Content Ratio of Compounds in Emitting Layer

A content ratio between the first compound, the second compound and the third compound in the emitting layer is preferably in an exemplary range below.

The content ratio of the first compound is preferably in a range from 10 mass % to 80 mass %, more preferably in a range from 10 mass % to 60 mass %, further preferably in a range from 20 mass % to 60 mass %.

The content ratio of the second compound is preferably in a range from 0.01 mass % to 10 mass %, more preferably in a range from 0.01 mass % to 5 mass %, further preferably in a range from 0.01 mass % to 1 mass %.

A content ratio of the third compound is preferably in a range from 10 mass % to 80 mass %.

An upper limit of the total of the respective content ratios of the first, second and third compounds in the emitting layer is 100 mass %. It should be noted that the emitting layer of the exemplary embodiment may further contain a material other than the first, second and third compounds.

Figure 5:
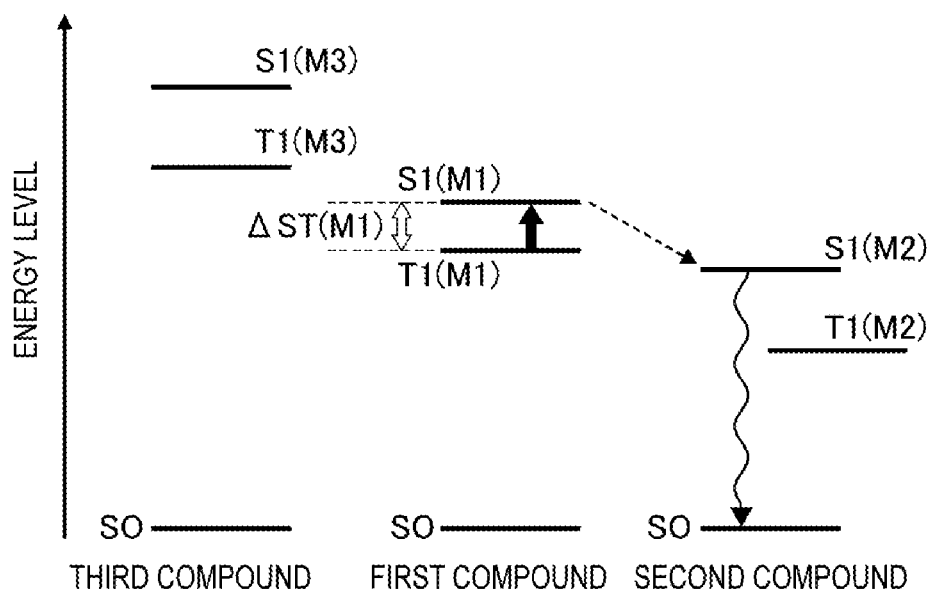
FIG. 5 shows a relationship between energy levels of a first compound, a second compound, and a third compound and an energy transfer between the first compound, the second compound, and the third compound in an exemplary emitting layer of an organic electroluminescence device according to a second exemplary embodiment of the invention.

FIG. 5 shows an example of a relationship among energy levels of the first compound, the second compound and the third compound in the emitting layer. In FIG. 5, S0 represents a ground state. S1(M1) represents the lowest singlet state of the first compound. T1(M1) represents the lowest triplet state of the first compound. S1(M2) represents the lowest singlet state of the second compound. T1(M2) represents the lowest triplet state of the second compound. S1(M3) represents the lowest singlet state of the third compound. T1(M3) represents the lowest triplet state of the third compound. A dashed arrow directed from S1(M1) to S1(M2) in FIG. 5 represents Förster energy transfer from the lowest singlet state of the first compound to the lowest singlet state of the second compound.

As shown in FIG. 5, when a compound having a small ΔST(M1) is used as the first compound, inverse intersystem crossing from the lowest triplet state T1(M1) to the lowest singlet state S1(M1) can be caused by a heat energy. Accordingly, Förster energy transfer from the lowest singlet state S1(M1) of the first compound to the second compound is caused to generate the lowest singlet state S1(M2). As a result, fluorescence from the lowest singlet state S1(M2) of the second compound is observable. It is speculated that the internal quantum efficiency can be theoretically raised up to 100% also by using the delayed fluorescence by the TADF mechanism.

According to the organic EL device of the second exemplary embodiment, the full width at half maximum can be narrowed as compared with typical organic EL devices. Consequently, the color purity of the organic EL device can also be improved.

In addition, according to the organic EL device of the second exemplary embodiment, the full width at half maximum can be narrowed as compared with typical organic EL devices in a blue wavelength region.

As in the organic EL device according to the first exemplary embodiment, the organic EL device according to the second exemplary embodiment is applicable to an electronic device such as a display device and a light-emitting device.

Modification of Embodiment(s)

It should be noted that the invention is not limited to the above exemplary embodiments but may include any modification and improvement as long as such modification and improvement are compatible with the invention.

For instance, the emitting layer is not limited to a single layer, but may be provided by laminating a plurality of emitting layers.

When the organic EL device includes the plurality of emitting layers, the plurality of emitting layers may be adjacent to each other, or provide a so-called tandem-type organic EL device in which a plurality of emitting units are layered through an intermediate layer.

Specific structure and shape of the components in the present invention may be designed in any manner as long as the object of the present invention can be achieved.

EXAMPLES

Example(s) of the invention will be described below. However, the invention is not limited to Example(s).

Compounds

Compounds used for preparing an organic EL device will be shown below.

[Formula 106]

Compound 1

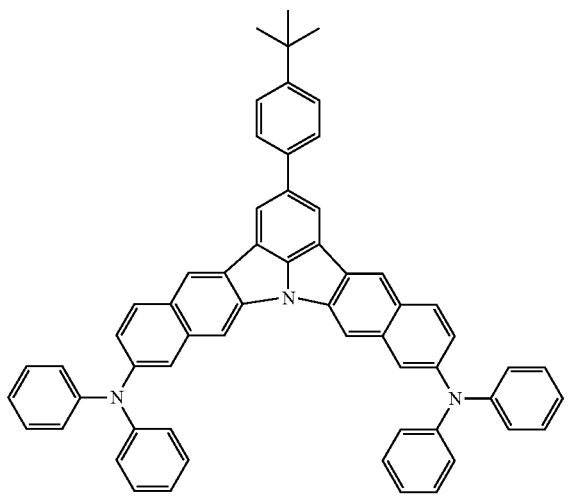

Compound 2

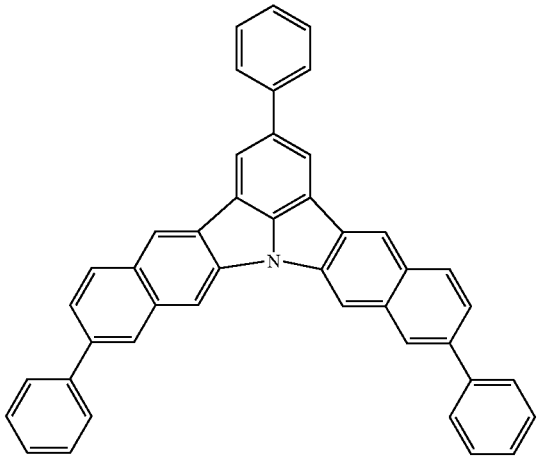

[Formula 107]

HI-1

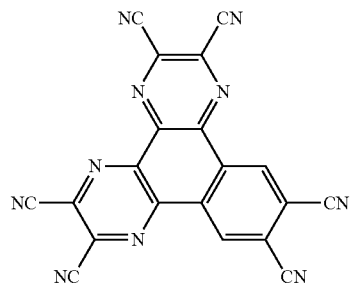

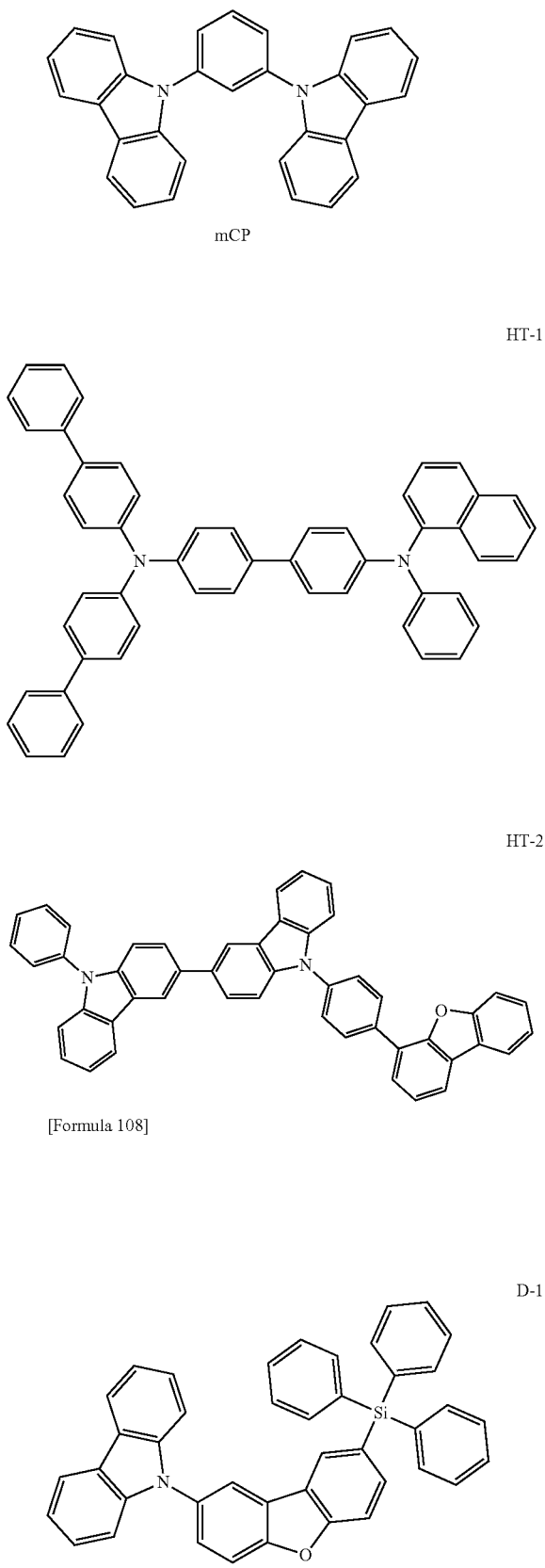
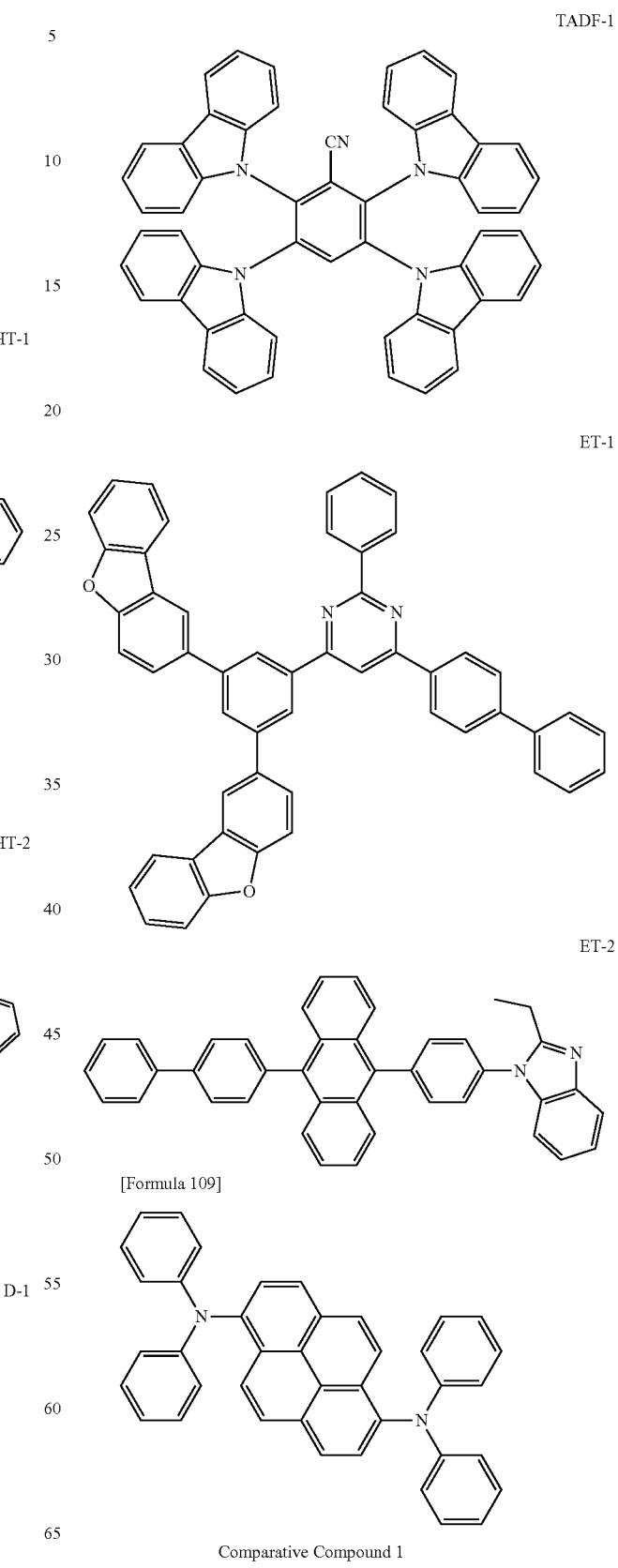

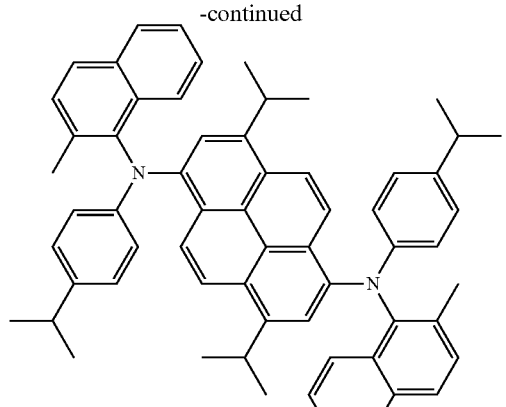

Comparative Compound 2

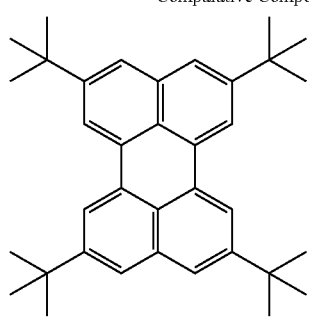

Comparative Compound 3

Synthesis of Compound(s)

Synthesis Example 1: Synthesis of Compound 1

[Formula 110]

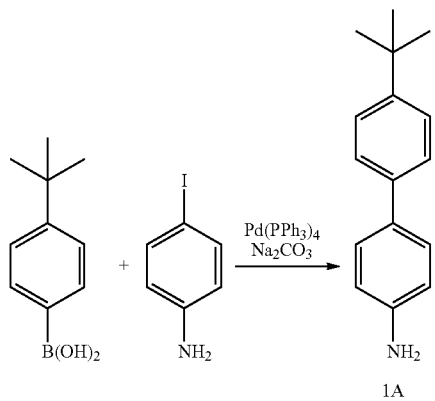

(1-1) Synthesis of Intermediate 1A

Under argon atmosphere, 4-tert-butylphenyl boronate (11.7 g, 66 mmol, 1.2eq), 4-iodoaniline (12 g, 55 mmol), and Pd(PPh$_3$)$_4$ (1.3 g, 1.1 mmol, 2% Pd) were added with 1,2-dimethoxyethane (150 mL) and 2M Na$_2$CO$_3$ aqueous solution (100 mL) for reflux for 11 hours. After being cooled, the reaction solution was celite-filtered to separate and condense an organic layer. The resultant oil was purified using a silica-gel column chromatography to obtain 6.1 g white solid (yield rate 49%).

The resultant white solid was an intermediate 1A (target substance). As a result of mass spectroscopy, m/e=225 relative to a molecular weight of 225.

[Formula 111]

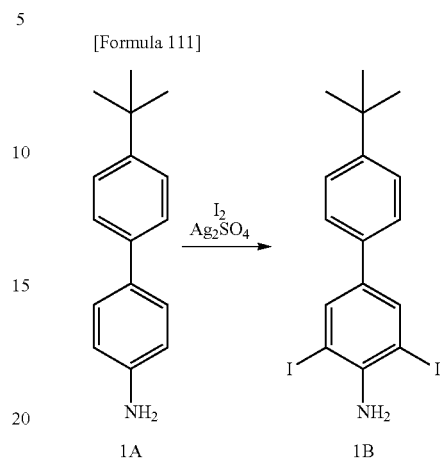

(1-2) Synthesis of Intermediate 1B

I$_2$ (15.1 g, 59 mmol, 2.2 eq) was dissolved in ethanol (300 mL), added with Ag$_2$SO$_4$ (18.4 g, 59 mmol) and, subsequently, the intermediate 1A (6.1 g, 27 mmol), and was agitated at a room temperature for 11 hours. After completion of the reaction, the reaction solution was celite-filtered. Then, an organic layer was washed with Na$_2$S$_2$O$_3$ aqueous solution and further with saturated salt solution, and was dried with magnesium sulfate. Subsequently, the organic layer was condensed. The condensed organic layer was purified using silica-gel column chromatography to obtain a red-brown sticky paste of 4.5 g (yield rate 35%).

The resultant red-brown sticky paste was an intermediate 1B (target substance). As a result of mass spectroscopy, m/e=477 relative to a molecular weight of 477.

[Formula 112]

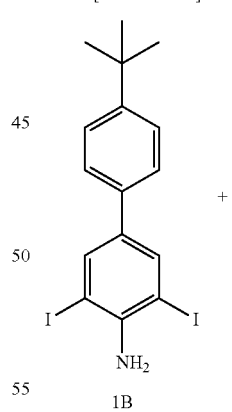

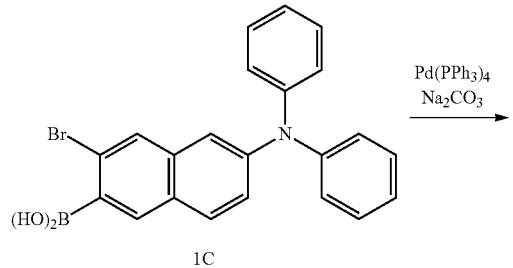

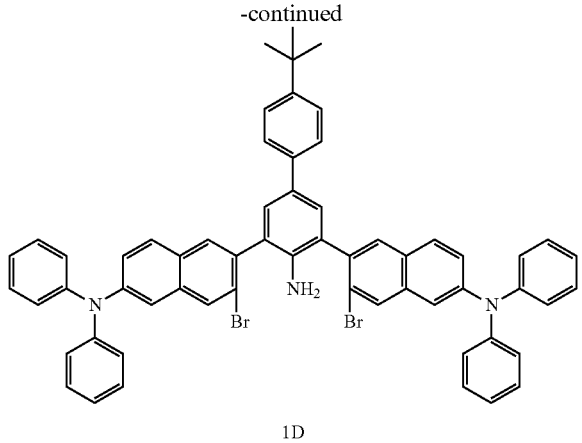

1D (1-3) Synthesis of Intermediate 1D

Under argon atmosphere, the intermediate 1B (3.05 g, 6.4 mmol), boronate compound 1C (5.9 g, 14 mmol), Pd(PPh$_3$)$_4$ (0.74 g, 0.64 mmol, 5% Pd), and NaHCO$_3$ (4.3 g, 51 mmol) were suspended in 1,2-dimethoxyethane. Water (40 mL) was added to the suspension for reflux for 11 hours. After completion of the reaction, an organic layer was extracted using dichloromethane, and was dried with magnesium sulfate. Subsequently, the organic layer was condensed. The condensed organic layer was purified using a silica-gel column chromatography to obtain 4.8 g yellow solid (yield rate 77%).

The resultant yellow solid was an intermediate 1D (target substance), which showed $^1$H-NMR measurement results as follows.

$^1$H-NMR (CDCl$_3$, TMS), 1.34 (9H, s), 3.53 (2H, bs), 7.08 (4H, t, J=7 Hz), 7.15 (8H, d, J=7 Hz), 7.28-7.32 (12H, m), 7.40 (2H, s), 7.43 (2H, s), 7.56 (2H, d, J=9 Hz), 7.68 (2H, d, J=9 Hz), 7.82 (2H, s), 7.86 (2H, s), 7.97 (2H, s)

[Formula 113]

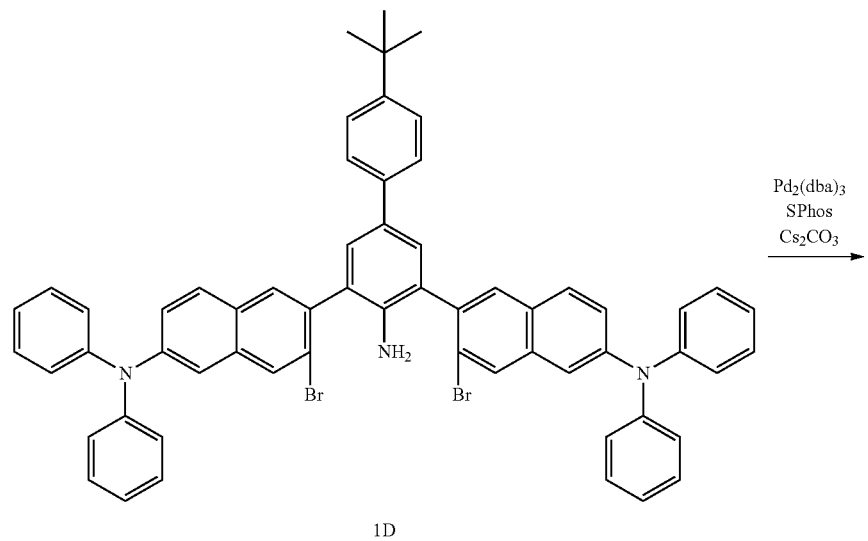

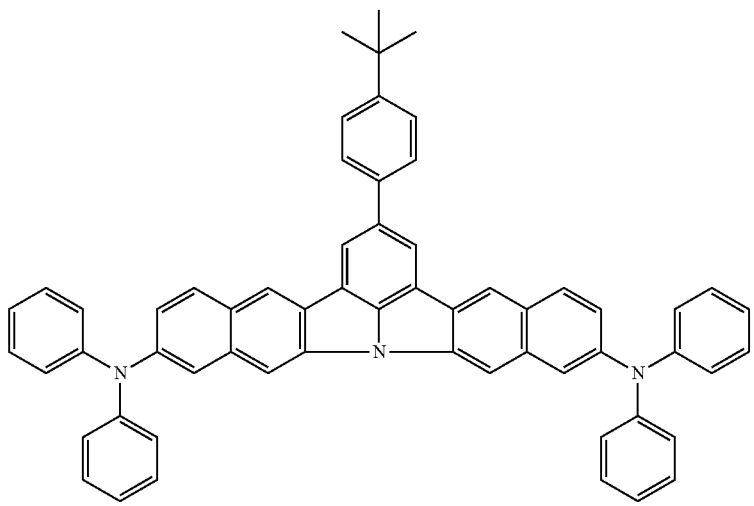

1

(1-4) Synthesis of Compound 1

Under argon atmosphere, the intermediate 1D (4.8 g, 4.95 mmol), Pd$_2$(dba)$_3$ (0.18 g, 0.20 mmol, 4% Pd), SPhos (0.32 g, 0.78 mmol), and Cs$_2$CO$_3$ (9.7 g, 29.8 mmol) were suspended in xylene anhydride (500 mL) for reflux for 11 hours. After the reaction mixture was passed through a silica-gel column chromatography, eluate was condensed. After the concentrate was mixed with ethanol, a resultant solid was filtered, which was dried in vacuum to obtain 3.32 g yellow solid (yield rate 84%).

The resultant yellow solid was a compound 1 (target substance). As a result of mass spectroscopy, m/e=808 relative to a molecular weight of 808.

Synthesis Example 2: Synthesis of Compound 2

[Formula 114]

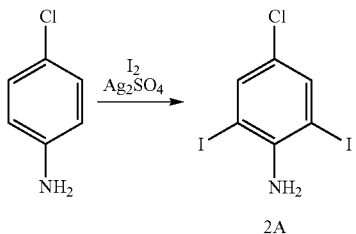

2A (2-1) Synthesis of Intermediate 2A

I$_2$ (15.1 g, 59 mmol, 2.2 eq) was dissolved in ethanol (300 mL), added with Ag$_2$SO$_4$ (18.4 g, 59 mmol) and, subsequently, 4-chloroaniline (6.1 g, 27 mmol), and was agitated at a room temperature for 6 hours. After completion of the reaction, the reaction solution was celite-filtered. Then, an organic layer was washed with Na$_2$S$_2$O$_3$ aqueous solution and further with saturated salt solution, and was dried with sodium sulfate. Subsequently, the organic layer was condensed. The condensed organic layer was purified using a silica-gel column chromatography to obtain 2.7 g white solid (yield rate 45%).

The resultant white solid was an intermediate 2A (target substance). As a result of mass spectroscopy, m/e=379 relative to a molecular weight of 379.

[Formula 115]

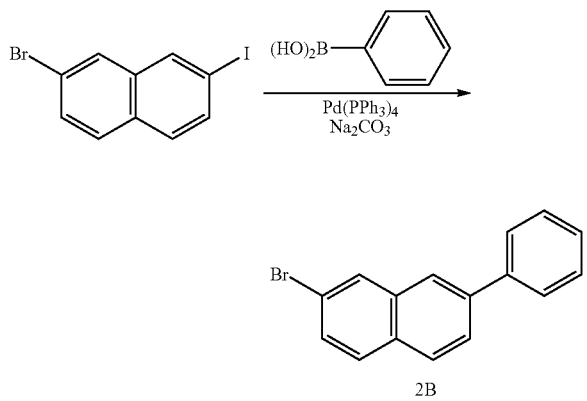

2B (2-2) Synthesis of Intermediate 2B

Under argon atmosphere, 2-bromo-7-iodonaphthalene (12.8 g, 38.4 mmol), phenyl boronate (4.7 g, 38 mmol), and Pd(PPh$_3$)$_4$ (0.888 g, 0.77 mmol) were added with 1,2-dimethoxyethane (150 mL) and 2M Na$_2$CO$_3$ aqueous solution (58 mL) for reflux for 8 hours. After completion of the reaction, an organic layer was extracted and collected using ethyl acetate, and was dried with magnesium sulfate. The magnesium sulfate was filtrated and a solvent was distilled away by adding silica gel. Subsequently, the resultant substance was purified using a silica-gel column chromatography to obtain 8.4 g white solid (yield rate 76%).

The resultant white solid was an intermediate 2B (target substance). As a result of mass spectroscopy, m/e=283 relative to a molecular weight of 283.

[Formula 116]

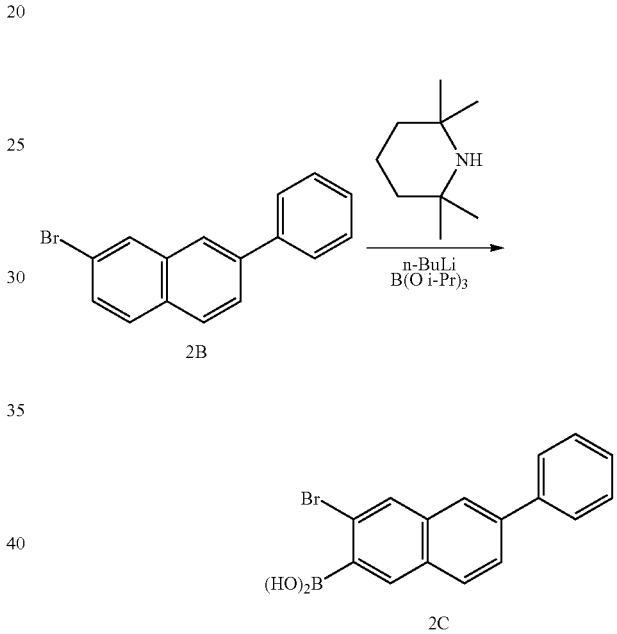

(2-3) Synthesis of Intermediate 2C

Under argon atmosphere, 2,2,6,6-tetramethylpiperidine (7.5 mL, 45 mmol) was dissolved in anhydrous THF (66 mL), which was cooled to −35 degrees C. in a dry ice/acetone bath. n-BuLi/hexane (1.64 mol/L, 29 mL, 45 mmol) was added to the solution, which was cooled to −67 degrees C. after being agitated at −50 degrees C. for 40 minutes. B(Oi-Pr)$_3$ (13.7 mL, 59 mmol) was dropped on the reaction mixture. After elapse of 5 minutes, an intermediate 2B/THF solution (8.4 g, 29.7 mmol/44 mL) was added, which was agitated for 6 hours in a cooling bath. 4M HCl aqueous solution (100 mL) was added to the reaction mixture and was agitated at a room temperature for 40 minutes. Subsequently, an organic layer was collected through extraction using toluene. The organic layer was washed with saturated salt solution (30 mL) and was dried with magnesium sulfate. After being dried, a solvent was distilled away from a separated solid component. The resultant solid component was purified using a silica-gel column chromatography to obtain a white solid (5.9 g, yield rate 60%).

The resultant white solid was an intermediate 2C (target substance). As a result of mass spectroscopy, m/e=327 relative to a molecular weight of 326.98.

[Formula 117]

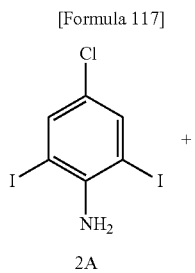

2A

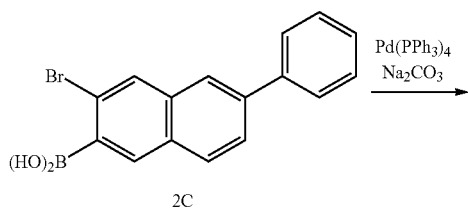

2C

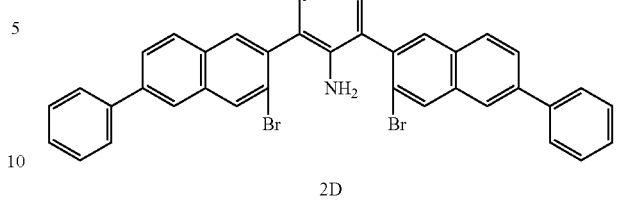

2D (2-4) Synthesis of Intermediate 2D

Under argon atmosphere, the intermediate 2A (3.70 g, 9.75 mmol), the intermediate 2C (7.02 g, 21.5 mmol), and Pd(PPh$_3$)$_4$ (0.56 g, 0.49 mmol) were suspended in 1,2-dimethoxyethane. 2M Na$_2$CO$_3$ aqueous solution (35 mL, 70 mmol) was added to the suspension for reflux for 24 hours. After the reaction, the reaction solution was celite-filtered and was extracted using toluene. The organic layer was collected and a solvent was distilled away from the organic layer. The organic layer was then purified using a silica-gel column chromatography to obtain 5.5 g yellow solid (yield rate 78%).

The resultant yellow solid was an intermediate 2D (target substance). As a result of mass spectroscopy, m/e=689 relative to a molecular weight of 689.

[Formula 118]

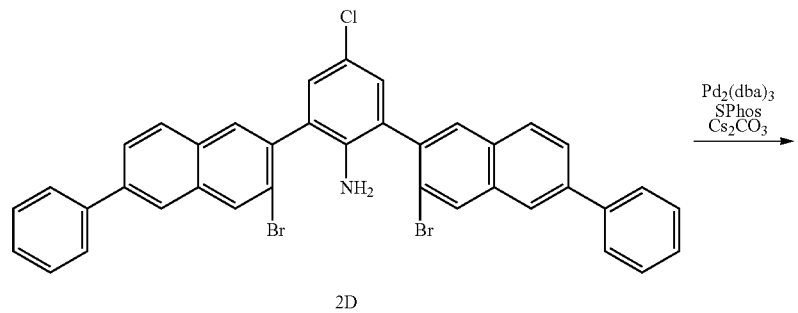

2D

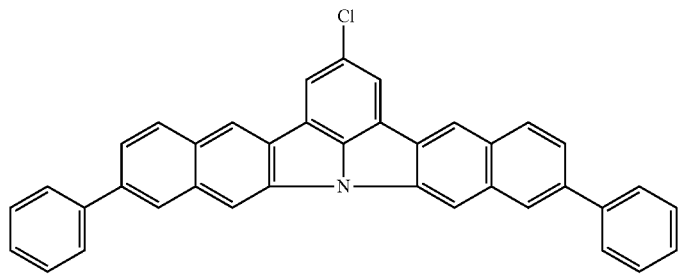

2E (2-5) Synthesis of Intermediate 2E

Under argon atmosphere, the intermediate 2D (5.1 g, 7.4 mmol), $Pd_2(dba)_3$ (0.27 g, 0.30 mmol), SPhos (0.49 g, 1.2 mmol), and $Cs_2CO_3$ (14.5 g, 29.8 mmol) were suspended in xylene anhydride (600 mL) for reflux for 24 hours. Solvent was distilled away from the reaction solution. Then, the remaining solid was washed with ethyl acetate and water. The resultant solid was dissolved in heated chlorobenzene and was then celite-filtered. Under reduced pressure, chlorobenzene was removed. The remaining solid was washed with toluene and methanol to obtain 2.35 g yellow solid (yield rate 60%).

The resultant solid was an intermediate 2E (target substance). As a result of mass spectroscopy, m/e=528 relative to a molecular weight of 528.

shown in FIG. 2. A sample was prepared by co-depositing the compound TADF-1 and the compound TH-2 on a quartz substrate at a ratio of the compound TADF-1 of 12 mass % to form a 100-nm-thick thin film. Emission from the compound TADF-1 include: Prompt emission observed immediately when the excited state is achieved by exciting the compound TADF-1 with a pulse beam (i.e., a beam emitted from a pulse laser unit) having an absorbable wavelength; and Delayed emission observed not immediately when but after the excited state is achieved. The delayed fluorescence in Examples means that an amount of Delay Emission is 5% or more based on an amount of Prompt Emission. Specifically, provided that the amount of Prompt emission is denoted by $X_P$ and the amount of Delay emission is denoted by $X_D$, a value of $X_D/X_P$ is 0.05 or more.

[Formula 119]

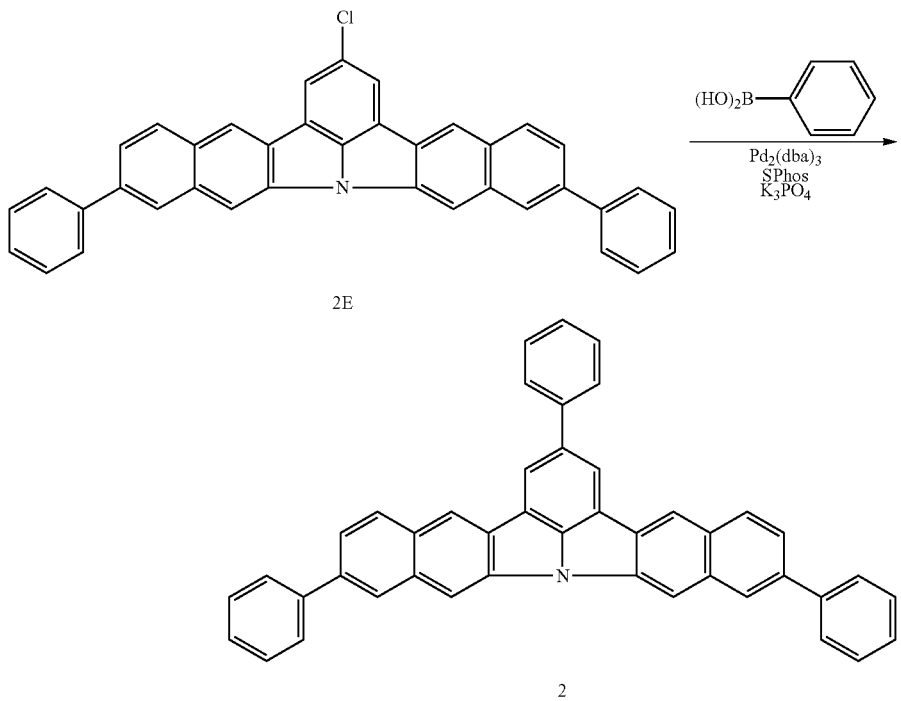

(2-6) Synthesis of Compound 2

Under argon atmosphere, the intermediate 2E (2.5 g, 4.73 mmol), phenyl boronate (5.13 g, 42 mmol), $Pd_2(dba)_3$ (0.15 g, 0.16 mmol), SPhos (0.27 g, 0.66 mmol), and $K_3PO_4$ (17.9 g, 84.4 mmol) were suspended in xylene anhydride (500 mL) for reflux for 24 hours. Solvent was distilled away from the reaction solution. The remaining solid was dissolved in heated chlorobenzene and was then celite-filtered. Under reduced pressure, chlorobenzene was removed. The remaining solid was washed with toluene to obtain 2.44 g yellow solid (yield rate 87%).

The obtained yellow solid was a compound 2 (target compound). As a result of mass spectroscopy, it was found m/e=569 relative to molecular weight of 569.

Evaluation of Compounds

A method of measuring characteristics of the compounds is shown below.

Delayed Fluorescence

Occurrence of delayed fluorescence was determined by measuring transient PL (PhotoLuminescence) using a device It was found that the amount of Delay Emission was 5% or more based on the amount of Prompt Emission in the compound TADF-1. Specifically, it was found that the value of $X_D/X_P$ was 0.05 or more in the compound TADF-1.

The amount of Prompt emission and the amount of Delay emission can be obtained according to the same method as a method described in "Nature 492, 234-238, 2012." A device used for calculating the amounts of Prompt Emission and Delay Emission is not limited to the device of FIG. 2 and a device described in the above document.

Singlet Energy S1

Singlet energies $S_1$ of the compound TADF-1, the compound 1, the compound 2, and the compound D-1 were measured according to the above-described solution method.

The singlet energy $S_1$ of the compound TADF-1 was 2.90 eV.

The singlet energy $S_1$ of the compound 1 was 2.75 eV.

The singlet energy $S_1$ of the compound 2 was 2.75 eV.

The singlet energy $S_1$ of the compound D-1 was 3.54 eV.

Energy Gap $T_{77K}$ at 77 [K]

$T_{77K}$ of the compound TADF-1 was measured by the above-described solution method.

$T_{77K}$ of the compound TADF-1 was 2.87 eV. Accordingly, $\Delta ST$ of the compound TADF-1 was 0.03 eV.

Preparation of Organic EL Device

The organic EL device was prepared and evaluated as follows.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130 nm thick.

After the glass substrate having the transparent electrode line was cleaned, the glass substrate was mounted on a substrate holder of a vacuum evaporation apparatus. Initially, a compound H1-1 was vapor-deposited on a surface of the glass substrate where the transparent electrode line was provided in a manner to cover the transparent electrode, thereby forming a 5-nm-thick hole injecting layer.

Next, the compound HT-1 was vapor-deposited on the hole injecting layer to form an 80-nm-thick first hole transporting layer on the H1-1 film.

Subsequently, the compound HT-2 was vapor-deposited on the first hole transporting layer to form a 10-nm-thick second hole transporting layer.

Then, a compound mCP was vapor-deposited on the second hole transporting layer to form a 5-nm-thick third hole transporting layer.

Further, the compound D-1, the compound TADF-1, and the compound 1 were co-deposited on the third hole transporting layer to form a 25-nm-thick emitting layer. A concentration of the compound D-1 was 75 mass %, a concentration of the compound TADF-1 was 24 mass %, and a concentration of the compound 1 was 1 mass % in the emitting layer.

The compound ET-1 was then vapor-deposited on the emitting layer to form a 5-nm-thick first electron transporting layer.

The compound ET-2 was then vapor-deposited on the first electron transporting layer to form a 20-nm-thick second electron transporting layer.

Next, lithium fluoride (LiF) was vapor-deposited on the second electron transporting layer to form a 1-nm-thick electron injecting electrode (cathode).

A metal aluminum (Al) was then deposited on the electron injecting electrode to form an 80-nm-thick metal Al cathode.

A device arrangement of the organic EL device in Example 1 is schematically shown as follows.

ITO (130)/HI (5)/HT-1 (80)/HT-2 (10)/mCP (5)/D-1:TADF-1:compound 1 (25, 75%:24%:1%)/ET-1 (5): ET-2 (20)/LiF (1)/Al (80)

Numerals in parentheses represent a film thickness (unit: nm). The numerals in the form of percentage in parentheses indicate ratios (mass %) of the compounds in the emitting layer.

Example 2

An organic EL device of Example 2 was prepared in the same manner as the organic EL device of Example 1 except that a compound 2 was used in place of the compound 1 in the emitting layer of Example 1.

A device arrangement of the organic EL device in Example 2 is schematically shown as follows.

ITO (130)/HI (5)/HT-1 (80)/HT-2 (10)/mCP (5)/D-1:TADF-1:compound 2 (25, 75%:24%:1%)/ET-1 (5): ET-2 (20)/LiF (1)/Al (80)

Comparative 1

An organic EL device of Comparative 1 was prepared in the same manner as the organic EL device of Example 1 except that a comparative compound 1 was used in place of the compound 1 in the emitting layer of Example 1.

A device arrangement of the organic EL device in Comparative 1 is schematically shown as follows.

ITO (130)/HI (5)/HT-1 (80)/HT-2 (10)/mCP (5)/D-1:TADF-1:comparative compound 1 (25, 75%:24%:1%)/ET-1 (5): ET-2 (20)/LiF (1)/Al (80)

Comparative 2

An organic EL device of Comparative 2 was prepared in the same manner as the organic EL device of Example 1 except that a comparative compound 2 was used in place of the compound 1 in the emitting layer of Example 1.

A device arrangement of the organic EL device in Comparative 2 is schematically shown as follows.

ITO (130)/HI (5)/HT-1 (80)/HT-2 (10)/mCP (5)/D-1:TADF-1:comparative compound 2 (25, 75%:24%:1%)/ET-1 (5): ET-2 (20)/LiF (1)/Al (80)

Comparative 3

An organic EL device of Comparative 3 was prepared in the same manner as the organic EL device of Example 1 except that a comparative compound 3 was used in place of the compound 1 in the emitting layer of Example 1.

A device arrangement of the organic EL device of Comparative 3 is schematically shown as follows.

ITO (130)/HI (5)/HT-1 (80)/HT-2 (10)/mCP (5)/D-1:TADF-1:comparative compound 3 (25, 75%:24%:1%)/ET-1 (5): ET-2 (20)/LiF (1)/Al (80)

Evaluation of Organic EL Devices

The prepared organic EL devices of Examples 1 and 2 and Comparatives 1 to 3 were evaluated as follows. The evaluation results are shown in Table 1.

EQE Relative Value

Voltage was applied on each of the organic EL devices such that a current density was 0.1 mA/cm$^2$, where spectral radiance spectra were measured by a spectroradiometer CS-2000 (manufactured by Konica Minolta, Inc.).

The external quantum efficiency EQE (EQE$_{(0.1)}$) at 0.1 mA/cm$^2$ current density was calculated based on the obtained spectral-radiance spectra, assuming that the spectra were provided under a Lambertian radiation.

Further, voltage was applied on each of the organic EL devices such that a current density was 10 mA/cm$^2$, where spectral radiance spectra were measured by a spectroradiometer CS-2000 (manufactured by Konica Minolta, Inc.).

The external quantum efficiency EQE (EQE$_{(10)}$) at 10 mA/cm$^2$ current density was calculated based on the obtained spectral-radiance spectra, assuming that the spectra were provided under a Lambertian radiation.

An EQE relative value (EQE$_{(10)}$/EQE$_{(0.1)}$) was calculated as a ratio of the external quantum efficiency EQE(EQE$_{(10)}$) when the current density was 10 mA/cm$^2$ to the external quantum efficiency EQE (EQE$_{(0.1)}$) when the current density was 0.1 mA/cm$^2$.

Main Peak Wavelength λp and Full Width at Half Maximum FWHM

Voltage was applied on each of the organic EL devices such that a current density was 10 mA/cm$^2$, where spectral radiance spectra were measured by a spectroradiometer CS-2000 (manufactured by Konica Minolta, Inc.).

A main peak wavelength λp (unit: nm) was calculated based on the obtained spectral-radiance spectra.

A full width at half maximum (unit: nm) was calculated based on the obtained spectral-radiance spectra.

TABLE 1

|  |  | Components of Emitting Layer |  | $EQE_{(10)}/EQE_{(0.1)}$ | $\lambda p@10$ | FWHM@10 |
|---|---|---|---|---|---|---|
| Ex. 1 | D-1 | TADF-1 | Compound 1 | 0.69 | 454 | 24 |
| Ex. 2 | D-1 | TADF-1 | Compound 2 | 0.63 | 455 | 25 |
| Comp. 1 | D-1 | TADF-1 | Comparative Compound 1 | 0.67 | 460 | 41 |
| Comp. 2 | D-1 | TADF-1 | Comparative Compound 2 | 0.70 | 466 | 33 |
| Comp. 3 | D-1 | TADF-1 | Comparative Compound 3 | 0.64 | 463 | 45 |

According to the organic EL device of Examples 1 and 2, the full width at half maximum FWHM can be narrowed as compared with organic EL devices of Comparative Examples 1 to 3. It should be noted that the EQE relative value and the emission wavelength λp were approximately the same in the organic EL devices of Examples 1 and 2 and Comparative Examples 1 to 3.

The invention claimed is:
1. An organic electroluminescence device comprising:
an anode;
an emitting layer; and
a cathode, wherein
the emitting layer comprises a first compound and a second compound,
the first compound is a delayed fluorescent compound, and
the second compound is a compound represented by a formula (200) below,

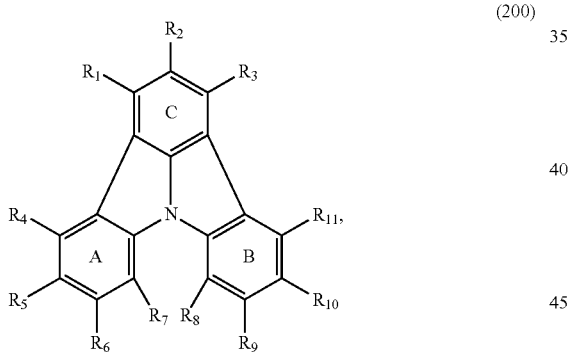

(200)

where, in the formula (200):
in each of one or more pairs selected from the pairs of $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$ with n representing an integer selected from 1, 2, 4 to 6, and 8 to 10 are mutually bonded to form a three-or-more-atom cyclic structure in combination with a carbon atom bonded with $R_n$ and a carbon atom bonded with $R_{n+1}$;
the three-or-more-atom cyclic structure comprises, as the atom for forming the cyclic structure, one or more atoms selected from a carbon atom, an oxygen atom, a sulfur atom, and a nitrogen atom in addition to the carbon atom bonded with $R_n$ and the carbon atom bonded with $R_{n+1}$;
at least one atom of the three-or-more-atom cyclic structure that is bondable with an atom other than the rest of atoms of the three-or-more-atom cyclic structure is bonded with a hydrogen atom or a substituent $R_X$, the substituent $R_X$ being each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by $-Si(R_{101})(R_{102})(R_{103})$, a group represented by $-N(R_{104})(R_{105})$, a substituted or unsubstituted aryl group having 6 to 50 ring carbon atoms, and a substituted or unsubstituted heteroaryl group having 5 to 50 ring atoms;
adjacent substituents $R_X$ are mutually bonded to form a cyclic structure or are not mutually bonded to form no cyclic structure, the number of the atoms of the three-or-more-atom cyclic structure not including the number of atoms of the substituent $R_X$;
$R_1$ to $R_{11}$ not involved in the formation of the three-or-more-atom cyclic structure each independently represent a hydrogen atom or a substituent, $R_1$ to $R_{11}$ as the substituent being each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by $-Si(R_{101})(R_{102})(R_{103})$, a group represented by $-N(R_{104})(R_{105})$, a substituted or unsubstituted aryl group having 6 to 50 ring carbon atoms, and a substituted or unsubstituted heteroaryl group having 5 to 50 ring atoms;
$R_{101}$ to $R_{105}$ are each independently a hydrogen atom or a substituent; and
$R_{101}$ to $R_{105}$ serving as the substituents are each independently selected from the group consisting of a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, and a substituted or unsubstituted heteroaryl group having 5 to 50 ring atoms.

2. The organic electroluminescence device according to claim 1, wherein in each of two or more pairs selected from the pairs of $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$ with n representing an integer selected from 1, 2, 4 to 6, and 8 to 10 are mutually bonded to form the three-or-more-atom cyclic structure in combination with the carbon atom bonded with $R_n$ and the carbon atom bonded with $R_{n+1}$.

3. The organic electroluminescence device according to claim 1, wherein the three-or-more-atom cyclic structure is a cyclic structure represented by a formula selected from formulae (2a) to (2g) below,

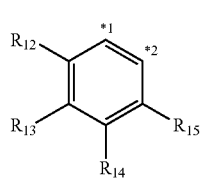

(2a)

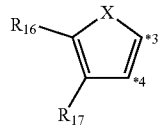

(2b)

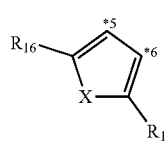

(2c)

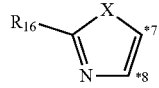

(2d)

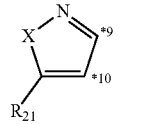

(2e)

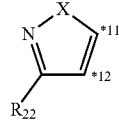

(2f)

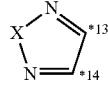

(2g)

where, in the formulae (2a) to (2g), one of *1 and *2, one of *3 and *4, one of *5 and *6, one of *7 and *8, one of *9 and *10, one of *11 and *12, and one of *13 and *14 are each a carbon atom bonded with $R_n$, and the other of *1 and *2, the other of *3 and *4, the other of *5 and *6, the other of *7 and *8, the other of *9 and *10, the other of *11 and *12, and the other of *13 and *14 are each a carbon atom bonded with $R_{n+1}$;

in the formulae (2b) to (2g), X is each independently selected from the group consisting of $C(R_{23})(R_{24})$, $NR_{25}$, an oxygen atom, and a sulfur atom;

$R_{12}$ to $R_{25}$ are each independently a hydrogen atom or a substituent;

$R_{12}$ to $R_{25}$ as the substituents are each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by $-Si(R_{101})(R_{102})(R_{103})$, a group represented by $-N(R_{104})(R_{105})$, a substituted or unsubstituted aryl group having 6 to 50 ring carbon atoms, and a substituted or unsubstituted heteroaryl group having 5 to 50 ring atoms;

$R_{12}$ and $R_{13}$ are mutually bonded to form a cyclic structure or are not mutually bonded to form no cyclic structure;

$R_{13}$ and $R_{14}$ are mutually bonded to form a cyclic structure or are not mutually bonded to form no cyclic structure;

$R_{14}$ and $R_{15}$ are mutually bonded to form a cyclic structure or are not mutually bonded to form no cyclic structure;

$R_{16}$ and $R_{17}$ are mutually bonded to form a cyclic structure or are not mutually bonded to form no cyclic structure;

$R_{23}$ and $R_{24}$ are mutually bonded to form a cyclic structure or are not mutually bonded to form no cyclic structure; and $R_{101}$ to $R_{105}$ represent the same as $R_{101}$ to $R_{105}$ in the formula (200), respectively.

4. The organic electroluminescence device according to claim 3, wherein at least one of $R_2$, $R_4$, $R_5$, $R_{10}$, or $R_{11}$ in the formula (200) is a group not involved in the formation of the three-or-more-atom cyclic structure, and is selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$) ($R_{101}$ to $R_{103}$ representing the same as $R_{101}$ to $R_{103}$ in the formula (200), respectively), a group represented by —N($R_{104}$)($R_{105}$) with $R_{104}$ and $R_{105}$ representing the same as $R_{104}$ and $R_{105}$ in the formula (200), respectively, a substituted or unsubstituted aryl group having 6 to 50 ring carbon atoms, and a substituted or unsubstituted heteroaryl group having 5 to 50 ring atoms.

5. The organic electroluminescence device according to claim 3, wherein the substituents $R_X$ in the formula (200) are each independently selected from the group consisting of a substituted or unsubstituted alkyl group having 1 to 20 carbon atoms, a group represented by —N($R_{104}$)($R_{105}$) with $R_{104}$ and $R_{105}$ representing the same as $R_{104}$ and $R_{105}$ in the formula (200), respectively, a substituted or unsubstituted aryl group having 6 to 50 ring carbon atoms, a substituted or unsubstituted heteroaryl group having 5 to 50 ring atoms, a group represented by a formula (s-1) below, a group represented by a formula (s-2) below, a group represented by a formula (s-3) below, and a group represented by a formula (s-4) below,

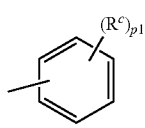

(s-1)

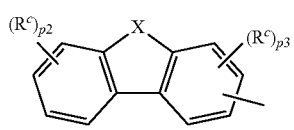

(s-2)

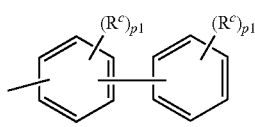

(s-3)

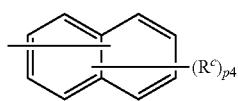

(s-4)

where, in the formulae (s-1) to (s-4):

$R^c$ is each independently a hydrogen atom or a substituent;

$R^c$ as the substituent is each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms;

p1 is 5;
p2 is 4;
p3 is 3;
p4 is 7;

$R_{101}$ to $R_{105}$ represent the same as $R_{101}$ to $R_{105}$ in the formula (200), respectively; and in the formula (s-2), X represents the same as X in the formulae (2b) to (2g).

6. The organic electroluminescence device according to claim 3, wherein $R_1$ to $R_{11}$ not involved in the formation of the three-or-more-atom cyclic structure in the formula (200) are each independently a hydrogen atom or a substituent;

$R_1$ to $R_{11}$ as the substituents are each independently selected from the group consisting of a substituted or unsubstituted alkyl group having 1 to 20 carbon atoms, a group represented by —N($R_{104}$)($R_{105}$) with $R_{104}$ and $R_{105}$ representing the same as $R_{104}$ and $R_{105}$ in the formula (200), respectively, a substituted or unsubstituted aryl group having 6 to 50 ring carbon atoms, a substituted or unsubstituted heteroaryl group having 5 to 50 ring atoms, a group represented by a formula (s-1) below, a group represented by a formula (s-2) below, a group represented by a formula (s-3) below, and a group represented by a formula (s-4) below;

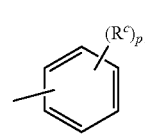

(s-1)

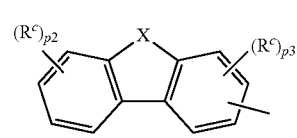

(s-2)

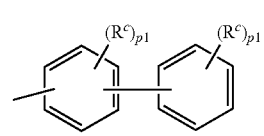

(s-3)

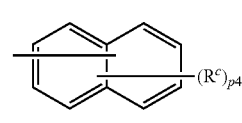

(s-4)

where, in the formulae (s-1) to (s-4):

$R^c$ is each independently a hydrogen atom or a substituent;

$R^c$ as the substituent is each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by $-Si(R_{101})(R_{102})(R_{103})$, a group represented by $-N(R_{104})(R_{105})$, a substituted or unsubstituted aryl group having 6 to 50 ring carbon atoms, and a substituted or unsubstituted heteroaryl group having 5 to 50 ring atoms;

p1 is 5;
p2 is 4;
p3 is 3;
p4 is 7;
$R_{101}$ to $R_{105}$ represent the same as $R_{101}$ to $R_{105}$ in the formula (200), respectively; and
in the formula (s-2), X represents the same as X in the formulae (2b) to (2g).

7. The organic electroluminescence device according to claim 3, wherein
$R_{12}$ to $R_{22}$ in the formulae (2a) to (2g) each independently represent a hydrogen atom or a substituent; $R_{12}$ to $R_{22}$ as the substituents are each independently selected from the group consisting of a substituted or unsubstituted alkyl group having 1 to 20 carbon atoms, a group represented by $-N(R_{104})(R_{105})$ ($R_{104}$ and $R_{105}$ representing the same as $R_{104}$ and $R_{105}$ in the formula (200), respectively), a substituted or unsubstituted aryl group having 6 to 50 ring carbon atoms, a substituted or unsubstituted heteroaryl group having 5 to 50 ring atoms, a group represented by a formula (s-1) below, a group represented by a formula (s-2) below, a group represented by a formula (s-3) below, and a group represented by a formula (s-4) below;

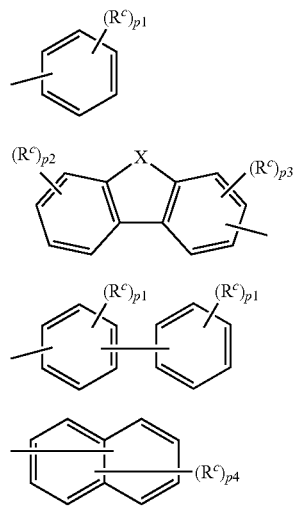

where, in the formulae (s-1) to (s-4):
$R^c$ is each independently a hydrogen atom or a substituent;
$R^c$ as the substituent is each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by $-Si(R_{101})(R_{102})(R_{103})$, a group represented by $-N(R_{104})(R_{105})$, a substituted or unsubstituted aryl group having 6 to 50 ring carbon atoms, and a substituted or unsubstituted heteroaryl group having 5 to 50 ring atoms;

p1 is 5;
p2 is 4;
p3 is 3;
p4 is 7;
$R_{101}$ to $R_{105}$ represent the same as $R_{101}$ to $R_{105}$ in the formula (200), respectively; and
in the formula (s-2), X represents the same as X in the formulae (2b) to (2g).

8. The organic electroluminescence device according to claim 1, wherein
the second compound represented by the formula (200) is a compound represented by any one of formulae (201) to (204) below,

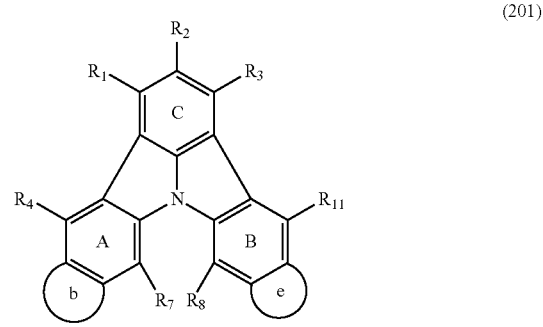

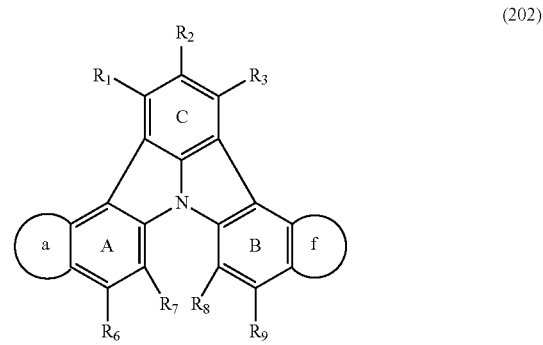

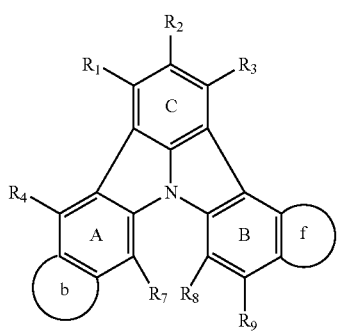

(203)

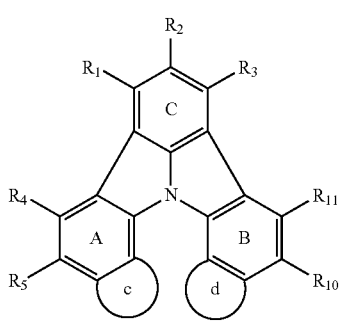

(204)

where, in the formulae (201) to (204):
rings a to f each independently represent the three-or-more-atom cyclic structure,
the rings a to f each independently comprise at least one substituent Ry or are unsubstituted, the substituent Ry being mutually bonded to form a cyclic structure or not mutually bonded to form no cyclic structure;
the substituent Ry is each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by $-Si(R_{101})(R_{102})(R_{103})$, a group represented by $-N(R_{104})(R_{105})$, a substituted or unsubstituted aryl group having 6 to 50 ring carbon atoms, and a substituted or unsubstituted heteroaryl group having 5 to 50 ring atoms,
the number of the atoms of the three-or-more-atom cyclic structure not including the number of atoms of the substituent Ry; and
$R_1$ to $R_{11}$, and $R_{101}$ to $R_{105}$ represent the same as $R_1$ to $R_{11}$, and $R_{101}$ to $R_{105}$ in the formula (200), respectively.

9. The organic electroluminescence device according to claim 8, wherein:
the substituent Ry in the formulae (201) to (204) each independently selected from the group consisting of a substituted or unsubstituted alkyl group having 1 to 20 carbon atoms, a group represented by $-N(R_{104})(R_{105})$ with $R_{104}$ and $R_{105}$ representing the same as $R_{104}$ and $R_{105}$ in the formula (200), respectively, a substituted or unsubstituted aryl group having 6 to 50 ring carbon atoms, a substituted or unsubstituted heteroaryl group having 5 to 50 ring atoms, a group represented by a formula (s-1) below, a group represented by a formula (s-2) below, a group represented by a formula (s-3) below, and a group represented by a formula (s-4) below;

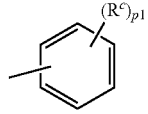

(s-1)

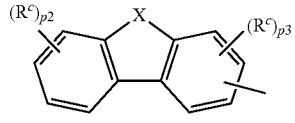

(s-2)

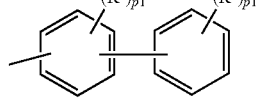

(s-3)

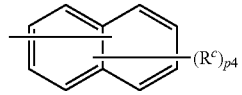

(s-4)

where, in the formulae (s-1) to (s-4):
$R^c$ is each independently a hydrogen atom or a substituent;
$R^c$ as the substituent is each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by $-Si(R_{101})(R_{102})(R_{103})$, a group represented by $-N(R_{104})(R_{105})$, a substituted or unsubstituted aryl group having 6 to 50 ring carbon atoms, and a substituted or unsubstituted heteroaryl group having 5 to 50 ring atoms;
p1 is 5;
p2 is 4;
p3 is 3;
p4 is 7;
$R_{101}$ to $R_{105}$ represent the same as $R_{101}$ to $R_{105}$ in the formula (200), respectively; and
in the formula (s-2), X represents the same as X in the formulae (2b) to (2g).

10. The organic electroluminescence device according to claim 1, wherein the second compound represented by the formula (200) is a compound represented by any one of formulae (201-1), (202-1), (203-1), and (204-1) below,

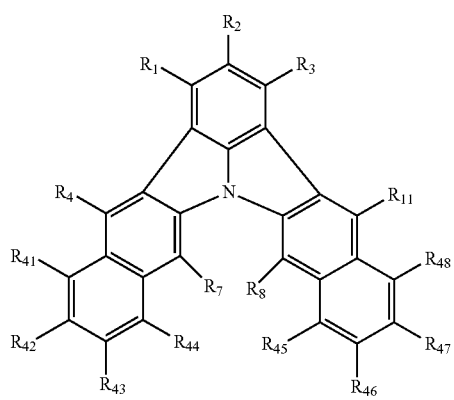
(201-1)

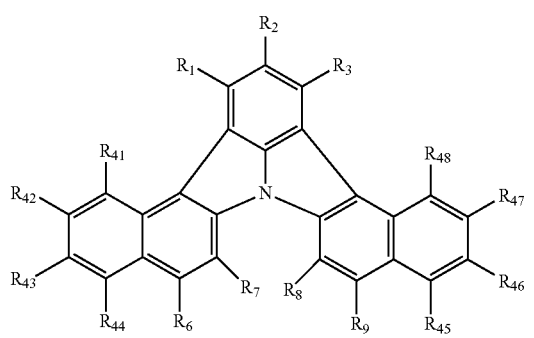
(202-1)

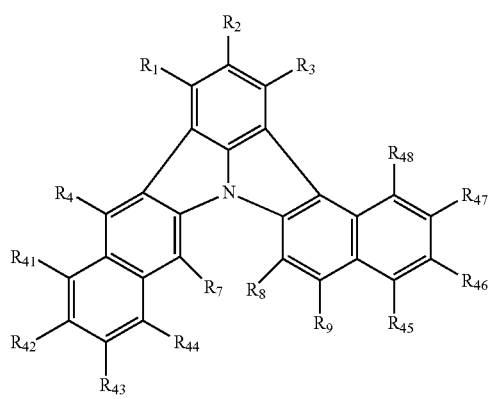
(203-1)

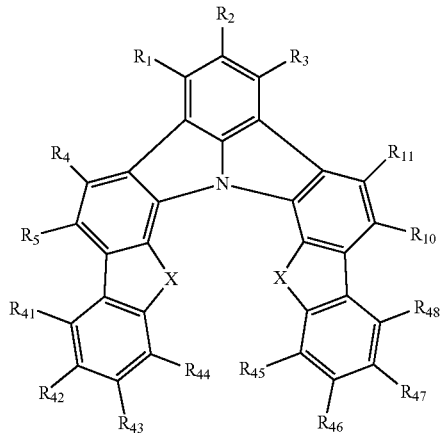
(204-1)

where, in the formulae (201-1), (202-1), (203-1), and (204-1):

X is selected from the group consisting of $C(R_{23})(R_{24})$, $NR_{25}$, an oxygen atom, and a sulfur atom;

$R_{23}$ to $R_{25}$ and $R_{41}$ to $R_{48}$ each independently represent a hydrogen atom or a substituent, $R_{23}$ to $R_{25}$ and $R_{41}$ to $R_{48}$ as the substituents being each independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si$(R_{101})(R_{102})(R_{103})$, a group represented by —N$(R_{104})(R_{105})$, a substituted or unsubstituted aryl group having 6 to 50 ring carbon atoms, and a substituted or unsubstituted heteroaryl group having 5 to 50 ring atoms; and $R_1$ to $R_{11}$, and $R_{101}$ to $R_{105}$ represent the same as $R_1$ to $R_{11}$, and $R_{101}$ to $R_{105}$ in the formula (200), respectively.

11. The organic electroluminescence device according to claim 1, wherein In the formula (200): the pairs of $R_1$ and $R_2$ and $R_2$ and $R_3$ do not simultaneously form the cyclic structure;

the pairs of $R_4$ and $R_5$ and $R_5$ and $R_6$ do not simultaneously form the cyclic structure;

the pairs of $R_5$ and $R_6$ and $R_6$ and $R_7$ do not simultaneously form the cyclic structure;

the pairs of $R_8$ and $R_9$ and $R_9$ and $R_{10}$ do not simultaneously form the cyclic structure; and the pairs of $R_9$ and $R_{10}$ and $R_{10}$ and $R_{11}$ do not simultaneously form the cyclic structure.

12. The organic electroluminescence device according to claim 1, wherein the second compound represented by the formula (200) is a dopant material contained in the emitting layer.

13. The organic electroluminescence device according to claim 1, wherein
the first compound is a compound represented by a formula (102) below,

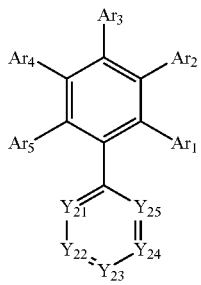
(102)

where, in the formula (102):
$Y_{21}$ to $Y_{25}$ are each independently a nitrogen atom, C—CN, or C—$R_{310}$, with a proviso that at least one of $Y_{21}$ to $Y_{25}$ is a nitrogen atom or C—CN;
$R_{310}$ is each independently a hydrogen atom or a substituent, $R_{310}$ as the substituent being each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;
$Ar_1$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, a group represented by a formula (12a) below, a group represented by a formula (12b) below, and a group represented by a formula (12c) below;
$Ar_2$ to $Ar_5$ are each independently a hydrogen atom or a substituent, and
$Ar_2$ to $Ar_5$ serving as the substituents are each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, a group represented by the formula (12a) below, a group represented by the formula (12b) below, and a group represented by the formula (12c) below, at least one of $Ar_1$ to $Ar_5$ is a group selected from the group consisting of groups represented by the formulae (12a) to (12c),

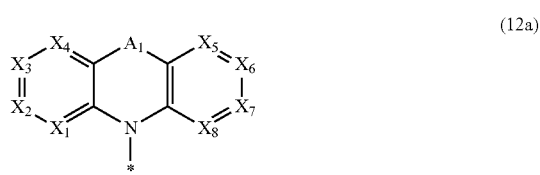
(12a)

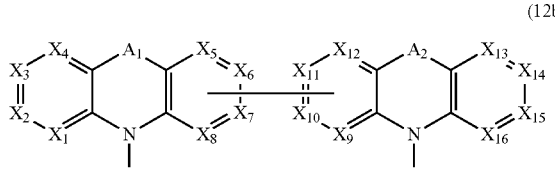
(12b)

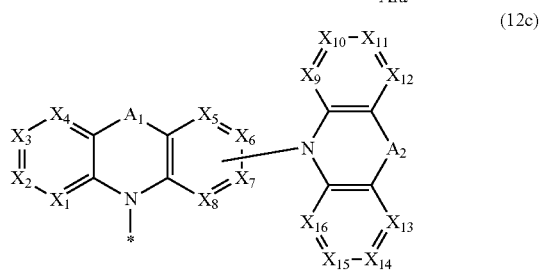
(12c)

where, in the formulae (12a) to (12c): $X_1$ to $X_{16}$ are each independently a nitrogen atom or C—$R_{300}$ with a proviso that, in the formula (12b), one of $X_5$ to $X_8$ is a carbon atom bonded to one of $X_9$ to $X_{12}$ and one of $X_9$ to $X_{12}$ is a carbon atom bonded to one of $X_5$ to $X_8$, and in the formula (12c), one of $X_5$ to $X_8$ is a carbon atom bonded to a nitrogen atom of a six-membered ring in a fused ring comprising $X_9$ to $X_{12}$, $X_{13}$ to $X_{16}$ and $A_2$;
$R_{300}$ is each independently a hydrogen atom or a substituent;
$R_{300}$ as the substituent is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; and
a plurality of $R_{300}$ as the substituents are mutually the same or different;
the plurality of $R_{300}$ as the substituents are mutually directly bonded to form a ring, are bonded through a hetero atom to form a ring, or are not bonded;
$A_1$ and $A_2$ are each independently a single bond, an oxygen atom, a sulfur atom, C($R_{301}$)($R_{302}$), Si($R_{303}$)($R_{304}$), C(=O), S(=O), SO$_2$, or N($R_{305}$);
$R_{301}$ to $R_{305}$ are each independently a hydrogen atom or a substituent;
$R_{301}$, $R_{302}$, $R_{303}$, $R_{304}$, and $R_{305}$ as the substituents are each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; and Ara is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group.

14. The organic electroluminescence device according to claim 1, wherein
the first compound is a compound represented by a formula (121) below,

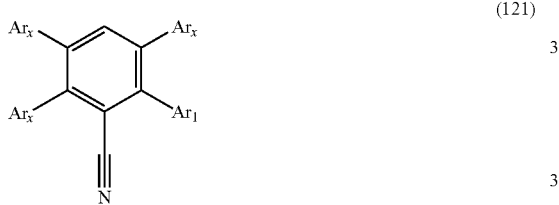

(121)

where, in the formulae (121): $Ar_1$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and a group represented by any one of formulae (12a) to (12j) below;

$Ar_X$ is each independently a hydrogen atom or a substituent;

$Ar_X$ as the substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, a group represented by a formula (12a) below, a group represented by a formula (12b) below, a group represented by a formula (12c) below, a group represented by a formula (12d) below, a group represented by a formula (12e) below, a group represented by a formula (12f) below, a group represented by a formula (12g) below, a group represented by a formula (12h) below, a group represented by a formula (12i) below, and a group represented by a formula (12j) below;

at least one of $Ar_1$ and $Ar_X$ is a group selected from the group consisting of the groups represented by the formulae (12a) to (12j) below;

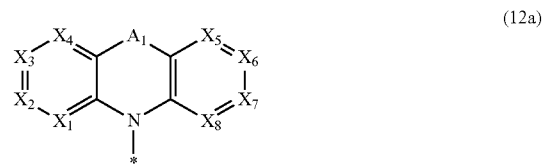

(12a)

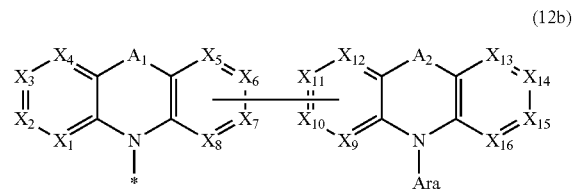

(12b)

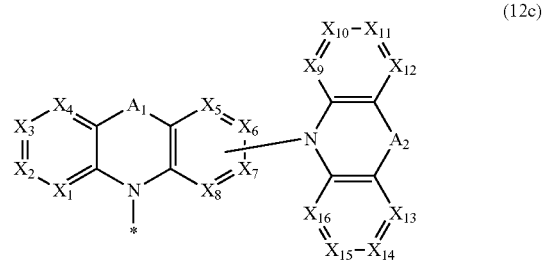

(12c)

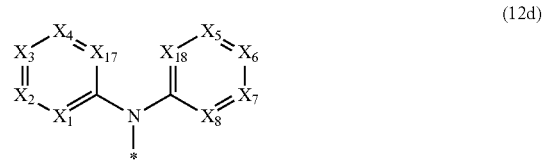

(12d)

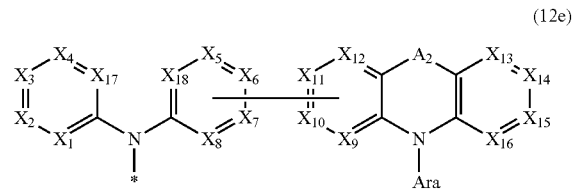

(12e)

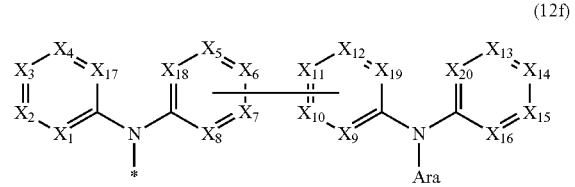

(12f)

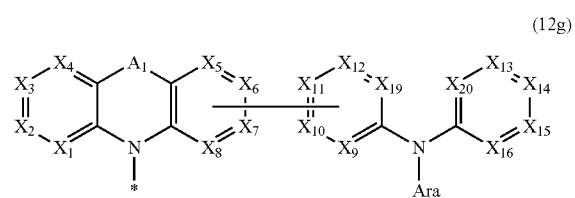

(12g)

-continued

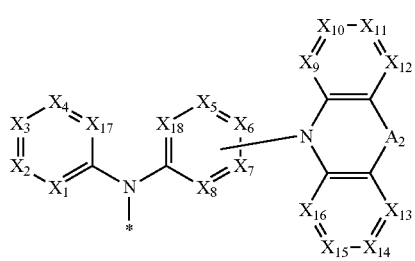

(12h)

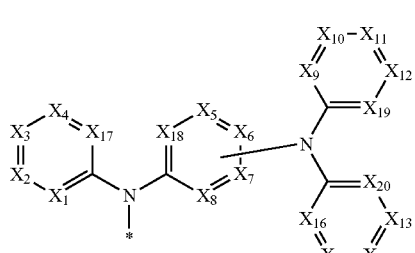

(12i)

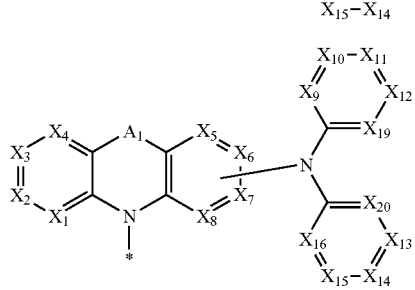

(12j)

where, in the formulae (12a) to (12j): $X_1$ to $X_{20}$ are each independently a nitrogen atom or C—$R_{300}$;

with a proviso that, in the formula (12b), one of $X_5$ to $X_8$ is a carbon atom bonded with one of $X_9$ to $X_{12}$, and one of $X_9$ to $X_{12}$ is a carbon atom bonded with one of $X_5$ to $X_8$; in the formula (12c), one of one of $X_5$ to $X_8$ is a carbon atom bonded with a nitrogen atom in the six-membered ring of the fused ring including $X_9$ to $X_{12}$, $X_{13}$ to $X_{16}$ and $A_2$; in the formula (12e), one of $X_5$ to $X_8$ and $X_{18}$ is a carbon atom bonded with one of $X_9$ to $X_{12}$, and one of $X_9$ to $X_{12}$ is a carbon atom bonded with one of $X_5$ to $X_8$ and $X_{18}$; in the formula (12f), one of $X_5$ to $X_8$ and $X_{18}$ is a carbon atom bonded with one of $X_9$ to $X_{12}$ and $X_{19}$ and one of $X_9$ to $X_{12}$ and $X_{19}$ is a carbon atom bonded with one of $X_5$ to $X_8$ and $X_{18}$; in the formula (12g), one of $X_5$ to $X_8$ is a carbon atom bonded with one of $X_9$ to $X_{12}$ and $X_{19}$, and one of $X_9$ to $X_{12}$ and $X_{19}$ is a carbon atom bonded with one of $X_5$ to $X_8$; in the formula (12h), one of $X_5$ to $X_8$ and $X_{18}$ is a carbon atom bonded with the nitrogen atom in the six-membered ring of the fused ring including $X_9$ to $X_{12}$, $X_{13}$ to $X_{16}$ and $A_2$; in the formula (12i), one of $X_5$ to $X_8$ and $X_{18}$ is a carbon atom bonded with the nitrogen atom connecting the ring including $X_9$ to $X_{12}$ and $X_{19}$ and the ring including $X_{13}$ to $X_{16}$ and $X_{20}$; and in the formula (12j), one of $X_5$ to $X_8$ is a carbon atom bonded with the nitrogen atom connecting the ring including $X_9$ to $X_{12}$ and $X_{19}$ and the ring including $X_{13}$ to $X_{16}$ and $X_{20}$;

$R_{300}$ is each independently a hydrogen atom or a substituent;

$R_{300}$ as the substituent is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;

a plurality of $R_{300}$ as the substituents are mutually the same or different;

the plurality of $R_{300}$ as the substituents are mutually directly bonded to form a ring, are bonded through a hetero atom to form a ring, or are not bonded;

$A_1$ and $A_2$ are each independently a single bond, an oxygen atom, a sulfur atom, $C(R_{301})(R_{302})$, $Si(R_{303})(R_{304})$, $C(=O)$, $S(=O)$, $SO_2$, or $N(R_{305})$;

$R_{301}$ to $R_{305}$ are each independently a hydrogen atom or a substituent;

$R_{301}$ to $R_{305}$ as the substituents are each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; and Ara is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group.

15. The organic electroluminescence device according to claim 1, wherein
the emitting layer comprises the second compound represented by the formula (200) in an amount ranging from 0.01 mass % to 10 mass %.

16. The organic electroluminescence device according to claim 1, wherein
a difference $\Delta ST(M1)$ between a singlet energy $S_1(M1)$ of the first compound and an energy gap $T_{77K}(M1)$ at 77[K] of the first compound satisfies a relationship of a Numerical Formula 10 below, $$\Delta ST(M1)=S_1(M1)-T_{77K}(M1)<0.3 \text{ [eV]} \quad \text{(Numerical Formula 10)}.$$

17. The organic electroluminescence device according to claim 1, wherein
the emitting layer does not comprise a heavy metal complex.

18. The organic electroluminescence device according to claim 1, wherein
the emitting layer further comprises a third compound.

19. The organic electroluminescence device according to claim 1, further comprising:
a hole transporting layer between the anode and the emitting layer.

20. The organic electroluminescence device according to claim 1, further comprising:
   an electron transporting layer between the cathode and the emitting layer.

21. An electronic device comprising the organic electroluminescence device according to claim 1.

* * * * *